US011359209B2

(12) United States Patent
Seguin et al.

(10) Patent No.: US 11,359,209 B2
(45) Date of Patent: Jun. 14, 2022

(54) COMPOSITIONS AND METHODS FOR CONTROL OF INSECT PESTS

(71) Applicant: Syngenta Participations AG, Basel (CH)

(72) Inventors: Katherine Seguin, Research Triangle Park, NC (US); Mark Scott Rose, Research Triangle Park, NC (US); Milan Jucovic, Research Triangle Park, NC (US); Matthew Richard Bramlett, Gent-Zwijnaarde (BE); Christopher Fleming, Research Triangle Park, NC (US)

(73) Assignee: Syngenta Participations AG, Basel (CH)

(*) Notice: Subject to any disclaimer, the term of this patent is extended or adjusted under 35 U.S.C. 154(b) by 289 days.

(21) Appl. No.: 16/473,467

(22) PCT Filed: Dec. 6, 2017

(86) PCT No.: PCT/US2017/064897
§ 371 (c)(1),
(2) Date: Jun. 25, 2019

(87) PCT Pub. No.: WO2018/128744
PCT Pub. Date: Jul. 12, 2018

(65) Prior Publication Data
US 2021/0261631 A1    Aug. 26, 2021

Related U.S. Application Data

(60) Provisional application No. 62/442,155, filed on Jan. 4, 2017.

(51) Int. Cl.
*C12N 15/82* (2006.01)
*C07K 14/325* (2006.01)

(52) U.S. Cl.
CPC ........ *C12N 15/8286* (2013.01); *C07K 14/325* (2013.01); *Y02A 40/146* (2018.01)

(58) Field of Classification Search
None
See application file for complete search history.

(56) References Cited

U.S. PATENT DOCUMENTS

| 5,322,687 A * | 6/1994 | Donovan | C12N 1/205 424/93.461 |
|---|---|---|---|
| 2013/0254933 A1 | 9/2013 | Kramer | |
| 2016/0108428 A1 | 4/2016 | Baum et al. | |

FOREIGN PATENT DOCUMENTS

| CN | 104673706 A | 6/2015 |
|---|---|---|
| WO | 2001047952 A2 | 7/2001 |
| WO | 2014138339 A2 | 9/2014 |
| WO | 2016061208 A1 | 4/2016 |

OTHER PUBLICATIONS

GenBank Accession No. AAA22341 (1994, https://www.ncbi.nlm.nih.gov/protein/AAA22341).*
Argolo-Filho et al, 2014, Insects 5:62-91.*
Bravo et al, 2001, Insect Biochem. Mol. Biol. 41:423-431.*
Extended EP Search Report for EP Application No. 17890754.9 dated Dec. 18, 2020.
Lucena, Wagner et al: "Molecular Approaches to Improve the Insecticidal Activity of Bacillus thuringiensis Cry Toxins", Toxins, vol. 6(8), Aug. 13, 2014, pp. 2393-2423.
Alejandra Bravo et al., "Bacillus Thuringiensis: A story of a successful bioinsecticide", Insects Biochemistry and Molecular Biology, vol. 41, No. 7, Jul. 1, 2011, pp. 423-431, XP055281787, Amsterdam, NL, Issn: 0965-1748, DOI: 10.1016/j.ibmb.2011.02.006.
"Revision of the Nomenciature for the Bacillus Thuringiensis Pesticidal Crystal Proteinds", Crickmore et al., Microbiology and Molecular Biology Reviews, Sep. 1998, pp. 807-813, p. 809, Table 1.
Notification of Transmittal of the International Search Report dated Apr. 9, 2018, mailed in Application No. PCT/US2017/064897 filed Dec. 6, 2017.

* cited by examiner

*Primary Examiner* — Anne Kubelik
(74) *Attorney, Agent, or Firm* — Amy Krom

(57) ABSTRACT

Novel insecticidal proteins that are toxic to lepidopteran pests are disclosed. The polynucleotides encoding the insecticidal proteins can be used to transform prokaryotic and eukaryotic organisms to express the insecticidal proteins. The recombinant organisms or compositions containing the recombinant organisms or the insecticidal proteins alone or in combination with other pest control agents and an appropriate agricultural carrier can be used to control lepidopteran pests in various environments.

13 Claims, 11 Drawing Sheets

Specification includes a Sequence Listing.

```
BT2                1 MEINNQKQCIPYNCLSNPEEVLLDGERILPDIDPLEVSLSLLQFLLNNFV
mBT2BLK-1          1 MEINNQKQCIPYNCLSNPEEVLLDGERILPDIDPLEVSLSLLQFLLNNFV
mBT2BLK-2          1 MEINNQKQCIPYNCLSNPEEVLLDGERILPDIDPLEVSLSLLQFLLNNFV
mBT2BLK-3          1 MEINNQKQCIPYNCLSNPEEVLLDGERILPDIDPLEVSLSLLQFLLNNFV
mBT2BLK-1&2        1 MEINNQKQCIPYNCLSNPEEVLLDGERILPDIDPLEVSLSLLQFLLNNFV
mBT2BLK-2&3        1 MEINNQKQCIPYNCLSNPEEVLLDGERILPDIDPLEVSLSLLQFLLNNFV
mBT2Blk-1&3        1 MEINNQKQCIPYNCLSNPEEVLLDGERILPDIDPLEVSLSLLQFLLNNFV
mBT2BLK-123        1 MEINNQKQCIPYNCLSNPEEVLLDGERILPDIDPLEVSLSLLQFLLNNFV
mBT2pro            1 MEINNQKQCIPYNCLSNPEEVLLDGERILPDIDPLEVSLSLLQFLLNNFV

                                                          α-helix 3
BT2               51 PGGGFISGLVDKIWGALRPSEWDLFLAQIERLIDQRIEATVRAKAIAELE
mBT2BLK-1         51 PGGGFISGLVDKIWGALRPSEWDLFLAQIERLIDQRIEATVRAKAITELE
mBT2BLK-2         51 PGGGFISGLVDKIWGALRPSEWDLFLAQIERLIDQRIEATVRAKAIAELE
mBT2BLK-3         51 PGGGFISGLVDKIWGALRPSEWDLFLAQIERLIDQRIEATVRAKAIAELE
mBT2BLK-1&2       51 PGGGFISGLVDKIWGALRPSEWDLFLAQIERLIDQRIEATVRAKAITELE
mBT2BLK-2&3       51 PGGGFISGLVDKIWGALRPSEWDLFLAQIERLIDQRIEATVRAKAIAELE
mBT2Blk-1&3       51 PGGGFISGLVDKIWGALRPSEWDLFLAQIERLIDQRIEATVRAKAITELE
mBT2BLK-123       51 PGGGFISGLVDKIWGALRPSEWDLFLAQIERLIDQRIEATVRAKAITELE
mBT2pro           51 PGGGFISGLVDKIWGALRPSEWDLFLAQIERLIDQRIEATVRAKAIAELE

                          α-helix 3               α-helix 4
BT2              101 GLGRSYQLYGEAFKEWEKTPDNTAARSRVTERFRIIDAQIEANIPSFRVS
mBT2BLK-1        101 GLGRNYQIYAEAFKEWESDPDNTAARSRVTERFRIIDAQIEANIPSFRVS
mBT2BLK-2        101 GLGRSYQLYGEAFKEWEKTPDNEAAKSRVIDRFRILDGIIEANIPSFRII
mBT2BLK-3        101 GLGRSYQLYGEAFKEWEKTPDNTAARSRVTERFRIIDAQIEANIPSFRVS
mBT2BLK-1&2      101 GLGRNYQIYAEAFKEWESDPDNEAAKSRVIDRFRILDGIIEANIPSFRII
mBT2BLK-2&3      101 GLGRSYQLYGEAFKEWEKTPDNEAAKSRVIDRFRILDGIIEANIPSFRII
mBT2Blk-1&3      101 GLGRNYQIYAEAFKEWESDPDNTAARSRVTERFRIIDAQIEANIPSFRVS
mBT2BLK-123      101 GLGRNYQIYAEAFKEWESDPDNEAAKSRVIDRFRILDGIIEANIPSFRII
mBT2pro          101 GLGRSYQLYGEAFKEWEKTPDNTAARSRVTERFRIIDAQIEANIPSFRVS

                               α-helix 5                  α-helix 6
BT-0002          151 GFEVPLLLVYTQAANLHLALLRDSVVFGERWGLTTTNVNDIYNRQVNRIG
mBT02BLK-1       151 GFEVPLLLVYTQAANLHLALLRDSVVFGERWGLTTTNVNDIYNRQVNRIG
mBT0002BLK-2     151 GFEVPLLLVYTQAANLHLALLRDSVVFGERWGLTTTNVNDIYNRQVNRIG
mBT02BLK-3       151 GFEVPLLSVYVQAANLHLALLRDSVIFGERWGLTTKNVNDIYNRQIREIH
mBT02BLK-1&2     151 GFEVPLLLVYTQAANLHLALLRDSVVFGERWGLTTTNVNDIYNRQVNRIG
mBT02BLK-2&3     151 GFEVPLLSVYVQAANLHLALLRDSVIFGERWGLTTKNVNDIYNRQIREIH
mBT02Blk-1&3     151 GFEVPLLSVYVQAANLHLALLRDSVIFGERWGLTTKNVNDIYNRQIREIH
mBT02BLK-1-2     151 GFEVPLLSVYVQAANLHLALLRDSVIFGERWGLTTKNVNDIYNRQIREIH
mBT-0002pro      151 GFEVPLLLVYTQAANLHLALLRDSVVFGERWGLTTTNVNDIYNRQVNRIG
```

Fig. 1A

```
                   α-helix 6
BT-0002         201 EYSNHCVDTYNTELERLGFRSIAQWRIYNQFRRELTLTVLDIVALFPNYD
mBT02BLK-1      201 EYSNHCVDTYNTELERLGFRSIAQWRIYNQFRRELTLTVLDIVALFPNYD
mBT0002BLK-2    201 EYSNHCVDTYNTELERLGFRSIAQWRIYNQFRRELTLTVLDIVALFPNYD
mBT02BLK-3      201 EYSNHCVDTYNTELERLGFRSIAQWRIYNQFRRELTLTVLDIVALFPNYD
mBT02BLK-1&2    201 EYSNHCVDTYNTELERLGFRSIAQWRIYNQFRRELTLTVLDIVALFPNYD
mBT02BLK-2&3    201 EYSNHCVDTYNTELERLGFRSIAQWRIYNQFRRELTLTVLDIVALFPNYD
mBT02Blk-1&3    201 EYSNHCVDTYNTELERLGFRSIAQWRIYNQFRRELTLTVLDIVALFPNYD
mBT02BLK-1-2    201 EYSNHCVDTYNTELERLGFRSIAQWRIYNQFRRELTLTVLDIVALFPNYD
mBT-0002pro     201 EYSNHCVDTYNTELERLGFRSIAQWRIYNQFRRELTLTVLDIVALFPNYD

BT-0002         251 SRLYPIQTFSQLTREIVTSPVSEFYYGVINSGNINGTLTEQQIRRPHLMD
mBT02BLK-1      251 SRLYPIQTFSQLTREIVTSPVSEFYYGVINSGNINGTLTEQQIRRPHLMD
mBT0002BLK-2    251 SRLYPIQTFSQLTREIVTSPVSEFYYGVINSGNINGTLTEQQIRRPHLMD
mBT02BLK-3      251 SRLYPIQTFSQLTREIVTSPVSEFYYGVINSGNINGTLTEQQIRRPHLMD
mBT02BLK-1&2    251 SRLYPIQTFSQLTREIVTSPVSEFYYGVINSGNINGTLTEQQIRRPHLMD
mBT02BLK-2&3    251 SRLYPIQTFSQLTREIVTSPVSEFYYGVINSGNINGTLTEQQIRRPHLMD
mBT02Blk-1&3    251 SRLYPIQTFSQLTREIVTSPVSEFYYGVINSGNINGTLTEQQIRRPHLMD
mBT02BLK-1-2    251 SRLYPIQTFSQLTREIVTSPVSEFYYGVINSGNINGTLTEQQIRRPHLMD
mBT-0002pro     251 SRLYPIQTFSQLTREIVTSPVSEFYYGVINSGNINGTLTEQQIRRPHLMD

BT-0002         301 FFNSMIMYTSDNRREHYWSGLEMTAYFTGFAGAQVSFPLVGTRGESAPPL
mBT02BLK-1      301 FFNSMIMYTSDNRREHYWSGLEMTAYFTGFAGAQVSFPLVGTRGESAPPL
mBT0002BLK-2    301 FFNSMIMYTSDNRREHYWSGLEMTAYFTGFAGAQVSFPLVGTRGESAPPL
mBT02BLK-3      301 FFNSMIMYTSDNRREHYWSGLEMTAYFTGFAGAQVSFPLVGTRGESAPPL
mBT02BLK-1&2    301 FFNSMIMYTSDNRREHYWSGLEMTAYFTGFAGAQVSFPLVGTRGESAPPL
mBT02BLK-2&3    301 FFNSMIMYTSDNRREHYWSGLEMTAYFTGFAGAQVSFPLVGTRGESAPPL
mBT02Blk-1&3    301 FFNSMIMYTSDNRREHYWSGLEMTAYFTGFAGAQVSFPLVGTRGESAPPL
mBT02BLK-1-2    301 FFNSMIMYTSDNRREHYWSGLEMTAYFTGFAGAQVSFPLVGTRGESAPPL
mBT-0002pro     301 FFNSMIMYTSDNRREHYWSGLEMTAYFTGFAGAQVSFPLVGTRGESAPPL

BT-0002         351 TVRSVNDGIYRILSAPFYSAPFLGTIVLGSRGEKFDFALNNISPPPSTIY
mBT02BLK-1      351 TVRSVNDGIYRILSAPFYSAPFLGTIVLGSRGEKFDFALNNISPPPSTIY
mBT0002BLK-2    351 TVRSVNDGIYRILSAPFYSAPFLGTIVLGSRGEKFDFALNNISPPPSTIY
mBT02BLK-3      351 TVRSVNDGIYRILSAPFYSAPFLGTIVLGSRGEKFDFALNNISPPPSTIY
mBT02BLK-1&2    351 TVRSVNDGIYRILSAPFYSAPFLGTIVLGSRGEKFDFALNNISPPPSTIY
mBT02BLK-2&3    351 TVRSVNDGIYRILSAPFYSAPFLGTIVLGSRGEKFDFALNNISPPPSTIY
mBT02Blk-1&3    351 TVRSVNDGIYRILSAPFYSAPFLGTIVLGSRGEKFDFALNNISPPPSTIY
mBT02BLK-1-2    351 TVRSVNDGIYRILSAPFYSAPFLGTIVLGSRGEKFDFALNNISPPPSTIY
mBT-0002pro     351 TVRSVNDGIYRILSAPFYSAPFLGTIVLGSRGEKFDFALNNISPPPSTIY

BT-0002         401 RHPGTVDSLVSIPPQDNSVPPHRGSSHRLSHVTMRASSPIFHWTHRSATT
mBT02BLK-1      401 RHPGTVDSLVSIPPQDNSVPPHRGSSHRLSHVTMRASSPIFHWTHRSATT
mBT0002BLK-2    401 RHPGTVDSLVSIPPQDNSVPPHRGSSHRLSHVTMRASSPIFHWTHRSATT
mBT02BLK-3      401 RHPGTVDSLVSIPPQDNSVPPHRGSSHRLSHVTMRASSPIFHWTHRSATT
mBT02BLK-1&2    401 RHPGTVDSLVSIPPQDNSVPPHRGSSHRLSHVTMRASSPIFHWTHRSATT
mBT02BLK-2&3    401 RHPGTVDSLVSIPPQDNSVPPHRGSSHRLSHVTMRASSPIFHWTHRSATT
mBT02Blk-1&3    401 RHPGTVDSLVSIPPQDNSVPPHRGSSHRLSHVTMRASSPIFHWTHRSATT
mBT02BLK-1-2    401 RHPGTVDSLVSIPPQDNSVPPHRGSSHRLSHVTMRASSPIFHWTHRSATT
mBT-0002pro     401 RHPGTVDSLVSIPPQDNSVPPHRGSSHRLSHVTMRASSPIFHWTHRSATT
```

Fig. 1B

```
BT-0002          451 TNTINPNAIIQIPLVKAFNLHSGATVVRGPGFTGGDILRRTNTGTFADMR
mBT02BLK-1       451 TNTINPNAIIQIPLVKAFNLHSGATVVRGPGFTGGDILRRTNTGTFADMR
mBT0002BLK-2     451 TNTINPNAIIQIPLVKAFNLHSGATVVRGPGFTGGDILRRTNTGTFADMR
mBT02BLK-3       451 TNTINPNAIIQIPLVKAFNLHSGATVVRGPGFTGGDILRRTNTGTFADMR
mBT02BLK-1&2     451 TNTINPNAIIQIPLVKAFNLHSGATVVRGPGFTGGDILRRTNTGTFADMR
mBT02BLK-2&3     451 TNTINPNAIIQIPLVKAFNLHSGATVVRGPGFTGGDILRRTNTGTFADMR
mBT02Blk-1&3     451 TNTINPNAIIQIPLVKAFNLHSGATVVRGPGFTGGDILRRTNTGTFADMR
mBT02BLK-1-2     451 TNTINPNAIIQIPLVKAFNLHSGATVVRGPGFTGGDILRRTNTGTFADMR
mBT-0002pro      451 TNTINPNAIIQIPLVKAFNLHSGATVVRGPGFTGGDILRRTNTGTFADMR

BT-0002          501 VNITGPLSQRYRVRIRYASTTDLQFFTRINGTSVNQGNFQRTMNRGDNLE
mBT02BLK-1       501 VNITGPLSQRYRVRIRYASTTDLQFFTRINGTSVNQGNFQRTMNRGDNLE
mBT0002BLK-2     501 VNITGPLSQRYRVRIRYASTTDLQFFTRINGTSVNQGNFQRTMNRGDNLE
mBT02BLK-3       501 VNITGPLSQRYRVRIRYASTTDLQFFTRINGTSVNQGNFQRTMNRGDNLE
mBT02BLK-1&2     501 VNITGPLSQRYRVRIRYASTTDLQFFTRINGTSVNQGNFQRTMNRGDNLE
mBT02BLK-2&3     501 VNITGPLSQRYRVRIRYASTTDLQFFTRINGTSVNQGNFQRTMNRGDNLE
mBT02Blk-1&3     501 VNITGPLSQRYRVRIRYASTTDLQFFTRINGTSVNQGNFQRTMNRGDNLE
mBT02BLK-1-2     501 VNITGPLSQRYRVRIRYASTTDLQFFTRINGTSVNQGNFQRTMNRGDNLE
mBT-0002pro      501 VNITGPLSQRYRVRIRYASTTDLQFFTRINGTSVNQGNFQRTMNRGDNLE

BT-0002          551 SGNFRTAGFSTPFSFSNAQSTFTLGTQAFSNQEVYIDRIEFVPAEVTFEA
mBT02BLK-1       551 SGNFRTAGFSTPFSFSNAQSTFTLGTQAFSNQEVYIDRIEFVPAEVTFEA
mBT0002BLK-2     551 SGNFRTAGFSTPFSFSNAQSTFTLGTQAFSNQEVYIDRIEFVPAEVTFEA
mBT02BLK-3       551 SGNFRTAGFSTPFSFSNAQSTFTLGTQAFSNQEVYIDRIEFVPAEVTFEA
mBT02BLK-1&2     551 SGNFRTAGFSTPFSFSNAQSTFTLGTQAFSNQEVYIDRIEFVPAEVTFEA
mBT02BLK-2&3     551 SGNFRTAGFSTPFSFSNAQSTFTLGTQAFSNQEVYIDRIEFVPAEVTFEA
mBT02Blk-1&3     551 SGNFRTAGFSTPFSFSNAQSTFTLGTQAFSNQEVYIDRIEFVPAEVTFEA
mBT02BLK-1-2     551 SGNFRTAGFSTPFSFSNAQSTFTLGTQAFSNQEVYIDRIEFVPAEVTFEA
mBT-0002pro      551 SGNFRTAGFSTPFSFSNAQSTFTLGTQAFSNQEVYIDRIEFVPAEVTFEA

BT-0002          601 ESDLERAQKAVNALFTSTNQLGLKTDVTDYQIDQVSNLVECLSDEFCLDE
mBT02BLK-1       601 ESDLERAQKAVNALFTSTNQLGLKTDVTDYQIDQVSNLVECLSDEFCLDE
mBT0002BLK-2     601 ESDLERAQKAVNALFTSTNQLGLKTDVTDYQIDQVSNLVECLSDEFCLDE
mBT02BLK-3       601 ESDLERAQKAVNALFTSTNQLGLKTDVTDYQIDQVSNLVECLSDEFCLDE
mBT02BLK-1&2     601 ESDLERAQKAVNALFTSTNQLGLKTDVTDYQIDQVSNLVECLSDEFCLDE
mBT02BLK-2&3     601 ESDLERAQKAVNALFTSTNQLGLKTDVTDYQIDQVSNLVECLSDEFCLDE
mBT02Blk-1&3     601 ESDLERAQKAVNALFTSTNQLGLKTDVTDYQIDQVSNLVECLSDEFCLDE
mBT02BLK-1-2     601 ESDLERAQKAVNALFTSTNQLGLKTDVTDYQIDQVSNLVECLSDEFCLDE
mBT-0002pro      601 ESDLERAQKAVNALFTSTNQLGLKTDVTDYQIDQVSNLVECLSDEFCLDE

BT-0002          651 KRELSEKVKHAKRLSDKRNLLQDPNFTSINRQLDRGWRGSTDITIQGGND
mBT02BLK-1       651 KRELSEKVKHAKRLSDKRNLLQDPNFTSINRQLDRGWRGSTDITIQGGND
mBT0002BLK-2     651 KRELSEKVKHAKRLSDKRNLLQDPNFTSINRQLDRGWRGSTDITIQGGND
mBT02BLK-3       651 KRELSEKVKHAKRLSDKRNLLQDPNFTSINRQLDRGWRGSTDITIQGGND
mBT02BLK-1&2     651 KRELSEKVKHAKRLSDKRNLLQDPNFTSINRQLDRGWRGSTDITIQGGND
mBT02BLK-2&3     651 KRELSEKVKHAKRLSDKRNLLQDPNFTSINRQLDRGWRGSTDITIQGGND
mBT02Blk-1&3     651 KRELSEKVKHAKRLSDKRNLLQDPNFTSINRQLDRGWRGSTDITIQGGND
mBT02BLK-1-2     651 KRELSEKVKHAKRLSDKRNLLQDPNFTSINRQLDRGWRGSTDITIQGGND
mBT-0002pro      651 KRELSEKVKHAKRLSDKRNLLQDPNFTSINRQLDRGWRGSTDITIQGGND
```

Fig. 1C

```
BT-0002          701 VFKENYVTLPGTFDECYPTYLYQKIDESKLKAYTRYELRGYIEDSQDLEV
mBT02BLK-1       701 VFKENYVTLPGTFDECYPTYLYQKIDESKLKAYTRYELRGYIEDSQDLEV
mBT0002BLK-2     701 VFKENYVTLPGTFDECYPTYLYQKIDESKLKAYTRYELRGYIEDSQDLEV
mBT02BLK-3       701 VFKENYVTLPGTFDECYPTYLYQKIDESKLKAYTRYELRGYIEDSQDLEV
mBT02BLK-1&2     701 VFKENYVTLPGTFDECYPTYLYQKIDESKLKAYTRYELRGYIEDSQDLEV
mBT02BLK-2&3     701 VFKENYVTLPGTFDECYPTYLYQKIDESKLKAYTRYELRGYIEDSQDLEV
mBT02Blk-1&3     701 VFKENYVTLPGTFDECYPTYLYQKIDESKLKAYTRYELRGYIEDSQDLEV
mBT02BLK-1-2     701 VFKENYVTLPGTFDECYPTYLYQKIDESKLKAYTRYELRGYIEDSQDLEV
mBT-0002pro      701 VFKENYVTLPGTFDECYPTYLYQKIDESKLKAYTRYELRGYIEDSQDLEV

BT-0002          751 YLIRYNAKHETVNVPGTGSLWPLSVESPIGRCGEPNRCVPHIEWNPDLDC
mBT02BLK-1       751 YLIRYNAKHETVNVPGTGSLWPLSVESPIGRCGEPNRCVPHIEWNPDLDC
mBT0002BLK-2     751 YLIRYNAKHETVNVPGTGSLWPLSVESPIGRCGEPNRCVPHIEWNPDLDC
mBT02BLK-3       751 YLIRYNAKHETVNVPGTGSLWPLSVESPIGRCGEPNRCVPHIEWNPDLDC
mBT02BLK-1&2     751 YLIRYNAKHETVNVPGTGSLWPLSVESPIGRCGEPNRCVPHIEWNPDLDC
mBT02BLK-2&3     751 YLIRYNAKHETVNVPGTGSLWPLSVESPIGRCGEPNRCVPHIEWNPDLDC
mBT02Blk-1&3     751 YLIRYNAKHETVNVPGTGSLWPLSVESPIGRCGEPNRCVPHIEWNPDLDC
mBT02BLK-1-2     751 YLIRYNAKHETVNVPGTGSLWPLSVESPIGRCGEPNRCVPHIEWNPDLDC
mBT-0002pro      751 YLIRYNAKHETVNVPGTGSLWPLSVESPIGRCGEPNRCVPHIEWNPDLDC

BT-0002          801 SCRDGEKCAHHSHHFSLDIDVGCTDLNEDLGVWVIFKIKTQDGHARLGNL
mBT02BLK-1       801 SCRDGEKCAHHSHHFSLDIDVGCTDLNEDLGVWVIFKIKTQDGHARLGNL
mBT0002BLK-2     801 SCRDGEKCAHHSHHFSLDIDVGCTDLNEDLGVWVIFKIKTQDGHARLGNL
mBT02BLK-3       801 SCRDGEKCAHHSHHFSLDIDVGCTDLNEDLGVWVIFKIKTQDGHARLGNL
mBT02BLK-1&2     801 SCRDGEKCAHHSHHFSLDIDVGCTDLNEDLGVWVIFKIKTQDGHARLGNL
mBT02BLK-2&3     801 SCRDGEKCAHHSHHFSLDIDVGCTDLNEDLGVWVIFKIKTQDGHARLGNL
mBT02Blk-1&3     801 SCRDGEKCAHHSHHFSLDIDVGCTDLNEDLGVWVIFKIKTQDGHARLGNL
mBT02BLK-1-2     801 SCRDGEKCAHHSHHFSLDIDVGCTDLNEDLGVWVIFKIKTQDGHARLGNL
mBT-0002pro      801 SCRDGEKCAHHSHHFSLDIDVGCTDLNEDLGVWVIFKIKTQDGHARLGNL

BT-0002          851 EFLEEKPLLGEALARVKRAEKKWRDKREQLQFETNIVYKEAKESVDALFV
mBT02BLK-1       851 EFLEEKPLLGEALARVKRAEKKWRDKREQLQFETNIVYKEAKESVDALFV
mBT0002BLK-2     851 EFLEEKPLLGEALARVKRAEKKWRDKREQLQFETNIVYKEAKESVDALFV
mBT02BLK-3       851 EFLEEKPLLGEALARVKRAEKKWRDKREQLQFETNIVYKEAKESVDALFV
mBT02BLK-1&2     851 EFLEEKPLLGEALARVKRAEKKWRDKREQLQFETNIVYKEAKESVDALFV
mBT02BLK-2&3     851 EFLEEKPLLGEALARVKRAEKKWRDKREQLQFETNIVYKEAKESVDALFV
mBT02Blk-1&3     851 EFLEEKPLLGEALARVKRAEKKWRDKREQLQFETNIVYKEAKESVDALFV
mBT02BLK-1-2     851 EFLEEKPLLGEALARVKRAEKKWRDKREQLQFETNIVYKEAKESVDALFV
mBT-0002pro      851 EFLEEKPLLGEALARVKRAEKKWRDKREQLQFETNIVYKEAKESVDALFV

BT-0002          901 DSHYNRLQADTNITMIHAADKRVHRIREAYLPELSVIPGVNADIFEELEG
mBT02BLK-1       901 DSHYNRLQADTNITMIHAADKRVHRIREAYLPELSVIPGVNADIFEELEG
mBT0002BLK-2     901 DSHYNRLQADTNITMIHAADKRVHRIREAYLPELSVIPGVNADIFEELEG
mBT02BLK-3       901 DSHYNRLQADTNITMIHAADKRVHRIREAYLPELSVIPGVNADIFEELEG
mBT02BLK-1&2     901 DSHYNRLQADTNITMIHAADKRVHRIREAYLPELSVIPGVNADIFEELEG
mBT02BLK-2&3     901 DSHYNRLQADTNITMIHAADKRVHRIREAYLPELSVIPGVNADIFEELEG
mBT02Blk-1&3     901 DSHYNRLQADTNITMIHAADKRVHRIREAYLPELSVIPGVNADIFEELEG
mBT02BLK-1-2     901 DSHYNRLQADTNITMIHAADKRVHRIREAYLPELSVIPGVNADIFEELEG
mBT-0002pro      901 DSHYNRLQADTNITMIHAADKRVHRIREAYLPELSVIPGVNADIFEELEG
```

Fig. 1D

```
BT-0002          951 LIFTAFSLYDARNIIKNGDFNNGLSCWNVKGHVDIQQNDHRSVLVVPEWE
mBT02BLK-1       951 LIFTAFSLYDARNIIKNGDFNNGLSCWNVKGHVDIQQNDHRSVLVVPEWE
mBT0002BLK-2     951 LIFTAFSLYDARNIIKNGDFNNGLSCWNVKGHVDIQQNDHRSVLVVPEWE
mBT02BLK-3       951 LIFTAFSLYDARNIIKNGDFNNGLSCWNVKGHVDIQQNDHRSVLVVPEWE
mBT02BLK-1&2     951 LIFTAFSLYDARNIIKNGDFNNGLSCWNVKGHVDIQQNDHRSVLVVPEWE
mBT02BLK-2&3     951 LIFTAFSLYDARNIIKNGDFNNGLSCWNVKGHVDIQQNDHRSVLVVPEWE
mBT02Blk-1&3     951 LIFTAFSLYDARNIIKNGDFNNGLSCWNVKGHVDIQQNDHRSVLVVPEWE
mBT02BLK-1-2     951 LIFTAFSLYDARNIIKNGDFNNGLSCWNVKGHVDIQQNDHRSVLVVPEWE
mBT-0002pro      951 LIFTAFSLYDARNIIKNGDFNNGLSCWNVKGHVDIQQNDHRSVLVVPEWE

BT-0002         1001 SEVSQEVRVCPGRGYILRVTAYKEGYGEGCVTIHEIEDNTDELKFSNCIE
mBT02BLK-1      1001 SEVSQEVRVCPGRGYILRVTAYKEGYGEGCVTIHEIEDNTDELKFSNCIE
mBT0002BLK-2    1001 SEVSQEVRVCPGRGYILRVTAYKEGYGEGCVTIHEIEDNTDELKFSNCIE
mBT02BLK-3      1001 SEVSQEVRVCPGRGYILRVTAYKEGYGEGCVTIHEIEDNTDELKFSNCIE
mBT02BLK-1&2    1001 SEVSQEVRVCPGRGYILRVTAYKEGYGEGCVTIHEIEDNTDELKFSNCIE
mBT02BLK-2&3    1001 SEVSQEVRVCPGRGYILRVTAYKEGYGEGCVTIHEIEDNTDELKFSNCIE
mBT02Blk-1&3    1001 SEVSQEVRVCPGRGYILRVTAYKEGYGEGCVTIHEIEDNTDELKFSNCIE
mBT02BLK-1-2    1001 SEVSQEVRVCPGRGYILRVTAYKEGYGEGCVTIHEIEDNTDELKFSNCIE
mBT-0002pro     1001 SEVSQEVRVCPGRGYILRVTAYKEGYGEGCVTIHEIEDNTDELKFSNCIE

BT-0002         1051 EEVYPTDTGNDYTAHQGTTGCADACNSRNVGYEDGYEINTTASVNYKPTY
mBT02BLK-1      1051 EEVYPTDTGNDYTAHQGTTGCADACNSRNVGYEDGYEINTTASVNYKPTY
mBT0002BLK-2    1051 EEVYPTDTGNDYTAHQGTTGCADACNSRNVGYEDGYEINTTASVNYKPTY
mBT02BLK-3      1051 EEVYPTDTGNDYTAHQGTTGCADACNSRNVGYEDGYEINTTASVNYKPTY
mBT02BLK-1&2    1051 EEVYPTDTGNDYTAHQGTTGCADACNSRNVGYEDGYEINTTASVNYKPTY
mBT02BLK-2&3    1051 EEVYPTDTGNDYTAHQGTTGCADACNSRNVGYEDGYEINTTASVNYKPTY
mBT02Blk-1&3    1051 EEVYPTDTGNDYTAHQGTTGCADACNSRNVGYEDGYEINTTASVNYKPTY
mBT02BLK-1-2    1051 EEVYPTDTGNDYTAHQGTTGCADACNSRNVGYEDGYEINTTASVNYKPTY
mBT-0002pro     1051 EEVYPTDTGNDYTAHQGTTGCADACNSRNVGYEDGYEINTTASVNYKPTY

BT-0002         1101 EEEMYTDVRRDNHCEYDRGYGNHTPLPAGYVTKELEYFPETDTVWIEIGE
mBT02BLK-1      1101 EEEMYTDVRRDNHCEYDRGYGNHTPLPAGYVTKELEYFPETDTVWIEIGE
mBT0002BLK-2    1101 EEEMYTDVRRDNHCEYDRGYGNHTPLPAGYVTKELEYFPETDTVWIEIGE
mBT02BLK-3      1101 EEEMYTDVRRDNHCEYDRGYGNHTPLPAGYVTKELEYFPETDTVWIEIGE
mBT02BLK-1&2    1101 EEEMYTDVRRDNHCEYDRGYGNHTPLPAGYVTKELEYFPETDTVWIEIGE
mBT02BLK-2&3    1101 EEEMYTDVRRDNHCEYDRGYGNHTPLPAGYVTKELEYFPETDTVWIEIGE
mBT02Blk-1&3    1101 EEEMYTDVRRDNHCEYDRGYGNHTPLPAGYVTKELEYFPETDTVWIEIGE
mBT02BLK-1-2    1101 EEEMYTDVRRDNHCEYDRGYGNHTPLPAGYVTKELEYFPETDTVWIEIGE
mBT-0002pro     1101 EEEMYTDVRRDNHCEYDRGYGNHTPLPAGYVTKELEYFPETDTVWLEIGE

BT-0002         1151 TEGTFIVDSVELLLMEE
mBT02BLK-1      1151 TEGTFIVDSVELLLMEE
mBT0002BLK-2    1151 TEGTFIVDSVELLLMEE
mBT02BLK-3      1151 TEGTFIVDSVELLLMEE
mBT02BLK-1&2    1151 TEGTFIVDSVELLLMEE
mBT02BLK-2&3    1151 TEGTFIVDSVELLLMEE
mBT02Blk-1&3    1151 TEGTFIVDSVELLLMEE
mBT02BLK-1-2    1151 TEGTFIVDSVELLLMEE
mBT-0002pro     1151 TEGTFIVDSVELILMEE
```

Fig. 1E

```
Cry1Ig1      1 MKLKNQDKHQSFSSNAKVDKISTDSLKNETDIELQNINHEDCLKMSEYEN
BT-0025      1 ..S...NM...L.N..T...NF.G..E.N.NT....F..---------.G
vBT25pro     1 ..S...NM...L.N..T...NF.G..E.N.NT....F..---------.G

Cry1Ig1     51 VEPFVSVSTIQTGIGIAGKILGNLGVPFAGQVASLYSFILGELWPKGKSQ
BT-0025     42 I.................................................
vBT25pro    42 I.................................................

Cry1Ig1    101 WEIFMEHVEELINQKISTYARNKALADLKGLGDALAVYHESLESWIKNRN
BT-0025     92 ..................................................
vBT25pro    92 ..................................................

Cry1Ig1    151 NTRTRSVVKSQYITLELMFVQSLPSFAVSGEEVPLLPIYAQAANLHLLLL
BT-0025    142 ..................................................
vBT25pro   142 ..................................................

Cry1Ig1    201 RDASIFGKEWGLSDSEISTFYNRQVERTSDYSDHCTKWFDTGLNRLKGSN
BT-0025    192 ..................................................
vBT25pro   192 ..................................................

Cry1Ig1    251 AEIWVKYNQFRRDMTLMVLDLVALFQSYDTHMYPIKTTAQLTREVYTNAI
BT-0025    242 .................................................L
vBT25pro   242 .................................................L

Cry1Ig1    301 GTVHPHPSFASTTWYNNNAPSFSAIEAAVIRSPHLLDFLEQVTIYSLLSR
BT-0025    292 .........T........................................
vBT25pro   292 .........T........................................

Cry1Ig1    351 WSNTQYMNMWGGHKLEFRTIGGTLNTSTQGSTNTSINPVTLPFTSRDIYR
BT-0025    342 ..................................................
vBT25pro   342 ..................................................

Cry1Ig1    401 TESLAGLNLFLTQPVNGVPRVDFHWKFVTHPIASDNFYYPGYAGIGTQLQ
BT-0025    392 ..................................................
vBT25pro   392 ..................................................

Cry1Ig1    451 DSENELPPETTGQPNYESYSHRLSHIGLISASHVKALVYSWTHRSADRTN
BT-0025    442 .........A........................................
vBT25pro   442 .........A........................................
```

Fig. 2A

```
Cry1Ig1      501 TIHSDSITQIPLVKAHTLQSGTTVVKGPGFTGGDILRRTSGGPFAFSNVN
BT-0025      492 ..................................................
vBT25pro     492 ..................................................

Cry1Ig1      551 LDWNLSQRYRARIRYASTTNLRMYVTIAGERIFAGQFNKTMNTGDPLTFQ
BT-0025      542 ..................................................
vBT25pro     542 ..................................................

Cry1Ig1      601 SFSYATIDTAFTFPTKASSLTVGADTFSSGNEVYVDRFELIPVTATLEAV
BT-0025      592 ..................................................
vBT25pro     592 ..................................................

Cry1Ig1      651 TDLERAQKAVHELFTSTNPGGLKTDVKDYHIDQVSNLVESLSDEFYLDEK
BT-0025      642 ...........................................K......
vBT25pro     642 ..............................L............K......

Cry1Ig1      701 RELFEIVKYAKQLHIEPNM
BT-0025      692 ................R..
vBT25pro     692 .....L..........R..
```

Fig. 2B

```
Cry1Ja1      1 MEINNQKQCIPYNCLSNPEEVLLDGERILPDIDPLEVSLSLLQFLLNNFV
BT2pro       1 ..................................................
vBT2pro      1 ..................................................

Cry1Ja1     51 PGGGFISGLVDKIWGALRPSEWDLFLAQIERLIDQRIEATVRAKAITELE
BT2pro      51 ..............................................A...
vBT2pro     51 ..............................................A...

Cry1Ja1    101 GLGRNYQIYAEAFKEWESDPDNEAAKSRVIDRFRILDGLIEANIPSFRII
BT2pro     101 ....S..L.G.......KT...T..R...TE....I.AQ.........VS
vBT2pro    101 ....S..L.G.......KT...T..R...TE....I.AQ.........VS

Cry1Ja1    151 GFEVPLLSVYVQAANLHLALLRDSVIFGERWGLTTKNVNDIYNRQIREIH
BT2pro     151 .......L..T..............V.........T.........VNR.G
vBT2pro    151 .......L..T..............V.........T.........VNR.G

Cry1Ja1    201 EYSNHCVDTYNTELERLGFRSIAQWRIYNQFRRELTLTVLDIVALFPNYD
BT2pro     201 ..................................................
vBT2pro    201 ..................................................

Cry1Ja1    251 SRLYPIQTFSQLTREIVTSPVSEFYYGVINSGNIIGTLTEQQIRRPHLMD
BT2pro     251 ..................................N...............
vBT2pro    251 ..................................N...............

Cry1Ja1    301 FFNSMIMYTSDNRREHYWSGLEMTAYFTGFAGAQVSFPLVGTRGESAPPL
BT2pro     301 ..................................................
vBT2pro    301 ..................................................

Cry1Ja1    351 TVRSVNDGIYRILSAPFYSAPFLGTIVLGSRGEKFDFALNNISPPPSTIY
BT2pro     351 ..................................................
vBT2pro    351 ..................................................

Cry1Ja1    401 RHPGTVDSLVSIPPQDNSVPPHRGSSHRLSHVTMRASSPIFHWTHRSATT
BT2pro     401 ..................................................
vBT2pro    401 ..................................................

Cry1Ja1    451 TNTINPNAIIQIPLVKAFNLHSGATVVRGPGFTGGDILRRTNTGTFADMR
BT2pro     451 ..................................................
vBT2pro    451 ..................................................

Cry1Ja1    501 VNITGPLSQRYRVRIRYASTTDLQFFTRINGTSVNQGNFQRTMNRGDNLE
BT2pro     501 ..................................................
vBT2pro    501 ..................................................

Cry1Ja1    551 SGNFRTAGFSTPFSFSNAQSTFTLGTQAFSNQEVYIDRIEFVPAEVTFEA
BT2pro     551 ..................................................
vBT2pro    551 ..................................................
```

Fig. 3A

```
Cry1Ja1    601 ESDLERAQKAVNALFTSTNQLGLKTDVTDYQIDQVSNLVECLSDEFCLDE
BT2pro     601 ..................................................
vBT2pro    601 ..................................................

Cry1Ja1    651 KRELSEKVKHAKRLSDKRNLLQDPNFTSINRQLDRGWRGSTDITIQGGND
BT2pro     651 ..................................................
vBT2pro    651 ..................................................

Cry1Ja1    701 VFKENYVTLPGTFDECYPTYLYQKIDESKLKAYTRYELRGYIEDSQDLEV
BT2pro     701 ..................................................
vBT2pro    701 ..................................................

Cry1Ja1    751 YLIRYNAKHETVNVPGTGSLWPLSVESPIGRCGEPNRCVPHIEWNPDLDC
BT2pro     751 ..................................................
vBT2pro    751 ..................................................

Cry1Ja1    801 SCRDGEKCAHHSHHFSLDIDVGCTDLNEDLGVWVIFKIKTQDGHARLGNL
BT2pro     801 ..................................................
vBT2pro    801 ..................................................

Cry1Ja1    851 EFLEEKPLLGEALARVKRAEKKWRDKREQLQFETNIVYKEAKESVDALFV
BT2pro     851 ..................................................
vBT2pro    851 ..................................................

Cry1Ja1    901 DSHYNRLQADTNITMIHAADKRVHRIREAYLPELSVIPGVNADIFEELEG
BT2pro     901 ..................................................
vBT2pro    901 ..................................................

Cry1Ja1    951 LIFTAFSLYDARNIIKNGDFNNGLSCWNVKGHVDIQQNDHRSVLVVPEWE
BT2pro     951 ..................................................
vBT2pro    951 ..................................................

Cry1Ja1   1001 SEVSQEVRVCPGRGYILRVTAYKEGYGEGCVTIHEIEDNTDELKFSNCIE
BT2pro    1001 ..................................................
vBT2pro   1001 ..................................................

Cry1Ja1   1051 EEVYPTDTGNDYTAHQGTTGCADACNSRNVGYEDGYEINTTASVNYKPTY
BT2pro    1051 ..................................................
vBT2pro   1051 ..................................................

Cry1Ja1   1101 EEEMYTDVRRDNHCEYDRGYGNHTPLPAGYVTKELEYFPETDTVWIEIGE
BT2pro    1101 ..................................................
vBT2pro   1101 .............................................L....

Cry1Ja1   1151 TEGTFIVDSVELLLMEE
BT2pro    1151 .................
vBT2pro   1151 ............I....
```

Fig. 3B

```
Cry1Jc1      1 MEINNQNQCIPYNCLSNPEEVFLDGERILPDIDPLEVSLSLLQFLLNNFV
BT53pro      1 ..................................................
vBT53pro     1 .A................................................

Cry1Jc1     51 PGGGFISGLLDKIWGALRPSDWELFLEQIEQLIDRRIERTVRAKAIAELE
BT53pro     51 ..................................................
vBT53pro    51 ..................................................

Cry1Jc1    101 GLGRSYQLYGEAFKEWEKTPDNTXARSRVTERFRIIDAXIEANIPSFRVS
BT53pro    101 .......................A..............Q...........
vBT53pro   101 .......................A..............Q...........

Cry1Jc1    151 GFEVPLLLVYTQAANLHLALLRDSVVFGERWGLTTTNVNDIYNRQVNRIG
BT53pro    151 ..................................................
vBT53pro   151 ..................................................

Cry1Jc1    201 EYSKHCVDTYKTELERLGFRSIAQWRIYNQFRRELTLTVLDIVAVFPNYD
BT53pro    201 ..................................................
vBT53pro   201 ..................................................

Cry1Jc1    251 SRLYPIRTISQLTREIYTSPVSEFYYGVINSNNIIGTLTEQQIRRPHLMD
BT53pro    251 ..................................................
vBT53pro   251 ..................................................

Cry1Jc1    301 FFNSMIMYTSDNRREHYWSGLEMTATNTEGHQRSFPLAGTIGNSAPPVTV
BT53pro    301 ..................................................
vBT53pro   301 ..................................................

Cry1Jc1    351 RNNGEGIYRILSEPFYSAPFLGTSVLGSRGEEFAFASNTTTSLPSTIYRN
BT53pro    351 ..................................................
vBT53pro   351 ..................................................

Cry1Jc1    401 RGTVDSLVSIPPQDYSVPPHRGYSHLLSHVTMRNSSPIFHWTHRSATPRN
BT53pro    401 ..................................................
vBT53pro   401 ..................................................

Cry1Jc1    451 TIDPDSITQIPAVKGAYIFNSPVITGPGHTGGDIIRFNPNTQNNIRIPFQ
BT53pro    451 ..................................................
vBT53pro   451 ..................................................

Cry1Jc1    501 SNAVQRYRIRMRYAAEADCILESGVNIVTGAGVTFRPIPIKATMTPGSPL
BT53pro    501 ..................................................
vBT53pro   501 ..................................................

Cry1Jc1    551 TYYSFQYADLNINLTAPIRPNNFVSIRRSNQPGNLYIDRIEFIPIDPIRE
BT53pro    551 ..................................................
vBT53pro   551 ..................................................
```

Fig. 4A

```
Cry1Jc1     601  AEHDLERAQKAVNALFTSSNQLGLKTDVTDYHIDQVSNLVACLSDKFCLD
BT53pro     601  .....................I............................
vBT53pro    601  .....................I............................

Cry1Jc1     651  EKRELSEKVKHAKRLSDERNLLQDQNFTGINRQVDRGWRGSTDITTQGGN
BT53pro     651  .............................................I....
vBT53pro    651  .............................................I....

Cry1Jc1     701  DVFKENYVTLPGTFDECYPTYLYQKIDESKLKPYTRYELRGYIEDSQDLE
BT53pro     701  ..................................................
vBT53pro    701  ..................................................

Cry1Jc1     751  VYLIRYNAKHETLNVPGTGSLWPLAAESSIGRCGEPNRCAPHIEWNPELD
BT53pro     751  ..................................................
vBT53pro    751  ..................................................

Cry1Jc1     801  CSCRDGEKCAHHSHHFSLDIDVGCTDLNEDLGVWVIFKIKTQDGYARLGN
BT53pro     801  ..................................................
vBT53pro    801  ..................................................

Cry1Jc1     851  LEFLEEKPLLGEALARVKRAEKKWRDKRDKLXWXTNIVYKEXKESVDALX
BT53pro     851  ...............................E.E.......A.......F
vBT53pro    851  ...............................E.E.......A.......F

Cry1Jc1     901  VDSQYNRLQPDTNIAMIHVADKRVHRIREAYLPELSVIPGVNAAIFEELE
BT53pro     901  .........T........................................
vBT53pro    901  .........T........................................

Cry1Jc1     951  GLIFTAFSLYDARNVIKNGDFNHGLSCWNVKGHVDVEEQNNHRSVLVVPE
BT53pro     951  ..................................................
vBT53pro    951  ..................................................

Cry1Jc1    1001  WEAEVSQEVRVCPGRGYILRVTAYKEGYGEGCVTIHEIEDHTDELKFRNC
BT53pro    1001  ..................................................
vBT53pro   1001  ..................................................

Cry1Jc1    1051  EEEEVYPNNTVTCNDYPANQEEYRAAETSRNRGYGESYESNSSIPAEYAP
BT53pro    1051  ..................................................
vBT53pro   1051  ..................................................

Cry1Jc1    1101  IYEKAYTDGRKENSCESNRGYGNYTPLPAGYVTKELEYFPETDKVWIEIG
BT53pro    1101  ..................................................
vBT53pro   1101  ..................................................

Cry1Jc1    1151  ETEGTFIVDSVELLLMEE
BT53pro    1151  ..................
vBT53pro   1151  ......L...........
```

Fig. 4B

SEQUENCE LISTING

<160> NUMBER OF SEQ ID NOS: 34

<210> SEQ ID NO 1
<211> LENGTH: 1167

<212> TYPE: PRT
<213> ORGANISM: Bacillus thuringiensis

<400> SEQUENCE: 1

```
Met Glu Ile Asn Asn Gln Lys Gln Cys Ile Pro Tyr Asn Cys Leu Ser
1               5                   10                  15

Asn Pro Glu Glu Val Leu Leu Asp Gly Glu Arg Ile Leu Pro Asp Ile
            20                  25                  30

Asp Pro Leu Glu Val Ser Leu Ser Leu Leu Gln Phe Leu Leu Asn Asn
        35                  40                  45

Phe Val Pro Gly Gly Gly Phe Ile Ser Gly Leu Val Asp Lys Ile Trp
    50                  55                  60

Gly Ala Leu Arg Pro Ser Glu Trp Asp Leu Phe Leu Ala Gln Ile Glu
65                  70                  75                  80

Arg Leu Ile Asp Gln Arg Ile Glu Ala Thr Val Arg Ala Lys Ala Ile
                85                  90                  95

Ala Glu Leu Glu Gly Leu Gly Arg Ser Tyr Gln Leu Tyr Gly Glu Ala
            100                 105                 110

Phe Lys Glu Trp Glu Lys Thr Pro Asp Asn Thr Ala Ala Arg Ser Arg
        115                 120                 125

Val Thr Glu Arg Phe Arg Ile Ile Asp Ala Gln Ile Glu Ala Asn Ile
    130                 135                 140

Pro Ser Phe Arg Val Ser Gly Phe Glu Val Pro Leu Leu Leu Val Tyr
145                 150                 155                 160

Thr Gln Ala Ala Asn Leu His Leu Ala Leu Leu Arg Asp Ser Val Val
                165                 170                 175

Phe Gly Glu Arg Trp Gly Leu Thr Thr Thr Asn Val Asn Asp Ile Tyr
            180                 185                 190

Asn Arg Gln Val Asn Arg Ile Gly Glu Tyr Ser Asn His Cys Val Asp
        195                 200                 205

Thr Tyr Asn Thr Glu Leu Glu Arg Leu Gly Phe Arg Ser Ile Ala Gln
    210                 215                 220

Trp Arg Ile Tyr Asn Gln Phe Arg Arg Glu Leu Thr Leu Thr Val Leu
225                 230                 235                 240

Asp Ile Val Ala Leu Phe Pro Asn Tyr Asp Ser Arg Leu Tyr Pro Ile
                245                 250                 255

Gln Thr Phe Ser Gln Leu Thr Arg Glu Ile Val Thr Ser Pro Val Ser
            260                 265                 270

Glu Phe Tyr Tyr Gly Val Ile Asn Ser Gly Asn Ile Asn Gly Thr Leu
        275                 280                 285

Thr Glu Gln Gln Ile Arg Arg Pro His Leu Met Asp Phe Phe Asn Ser
    290                 295                 300

Met Ile Met Tyr Thr Ser Asp Asn Arg Arg Glu His Tyr Trp Ser Gly
305                 310                 315                 320

Leu Glu Met Thr Ala Tyr Phe Thr Gly Phe Ala Gly Ala Gln Val Ser
                325                 330                 335

Phe Pro Leu Val Gly Thr Arg Gly Glu Ser Ala Pro Pro Leu Thr Val
            340                 345                 350

Arg Ser Val Asn Asp Gly Ile Tyr Arg Ile Leu Ser Ala Pro Phe Tyr
        355                 360                 365

Ser Ala Pro Phe Leu Gly Thr Ile Val Leu Gly Ser Arg Gly Glu Lys
    370                 375                 380

Phe Asp Phe Ala Leu Asn Asn Ile Ser Pro Pro Pro Ser Thr Ile Tyr
385                 390                 395                 400
```

-continued

```
Arg His Pro Gly Thr Val Asp Ser Leu Val Ser Ile Pro Pro Gln Asp
                405                 410                 415

Asn Ser Val Pro Pro His Arg Gly Ser Ser His Arg Leu Ser His Val
            420                 425                 430

Thr Met Arg Ala Ser Ser Pro Ile Phe His Trp Thr His Arg Ser Ala
        435                 440                 445

Thr Thr Thr Asn Thr Ile Asn Pro Asn Ala Ile Ile Gln Ile Pro Leu
    450                 455                 460

Val Lys Ala Phe Asn Leu His Ser Gly Ala Thr Val Val Arg Gly Pro
465                 470                 475                 480

Gly Phe Thr Gly Gly Asp Ile Leu Arg Arg Thr Asn Thr Gly Thr Phe
                485                 490                 495

Ala Asp Met Arg Val Asn Ile Thr Gly Pro Leu Ser Gln Arg Tyr Arg
            500                 505                 510

Val Arg Ile Arg Tyr Ala Ser Thr Thr Asp Leu Gln Phe Phe Thr Arg
        515                 520                 525

Ile Asn Gly Thr Ser Val Asn Gln Gly Asn Phe Gln Arg Thr Met Asn
    530                 535                 540

Arg Gly Asp Asn Leu Glu Ser Gly Asn Phe Arg Thr Ala Gly Phe Ser
545                 550                 555                 560

Thr Pro Phe Ser Phe Ser Asn Ala Gln Ser Thr Phe Thr Leu Gly Thr
                565                 570                 575

Gln Ala Phe Ser Asn Gln Glu Val Tyr Ile Asp Arg Ile Glu Phe Val
            580                 585                 590

Pro Ala Glu Val Thr Phe Glu Ala Glu Ser Asp Leu Glu Arg Ala Gln
        595                 600                 605

Lys Ala Val Asn Ala Leu Phe Thr Ser Thr Asn Gln Leu Gly Leu Lys
    610                 615                 620

Thr Asp Val Thr Asp Tyr Gln Ile Asp Gln Val Ser Asn Leu Val Glu
625                 630                 635                 640

Cys Leu Ser Asp Glu Phe Cys Leu Asp Glu Lys Arg Glu Leu Ser Glu
                645                 650                 655

Lys Val Lys His Ala Lys Arg Leu Ser Asp Lys Arg Asn Leu Leu Gln
            660                 665                 670

Asp Pro Asn Phe Thr Ser Ile Asn Arg Gln Leu Asp Arg Gly Trp Arg
        675                 680                 685

Gly Ser Thr Asp Ile Thr Ile Gln Gly Gly Asn Asp Val Phe Lys Glu
    690                 695                 700

Asn Tyr Val Thr Leu Pro Gly Thr Phe Asp Glu Cys Tyr Pro Thr Tyr
705                 710                 715                 720

Leu Tyr Gln Lys Ile Asp Glu Ser Lys Leu Lys Ala Tyr Thr Arg Tyr
                725                 730                 735

Glu Leu Arg Gly Tyr Ile Glu Asp Ser Gln Asp Leu Glu Val Tyr Leu
            740                 745                 750

Ile Arg Tyr Asn Ala Lys His Glu Thr Val Asn Val Pro Gly Thr Gly
        755                 760                 765

Ser Leu Trp Pro Leu Ser Val Glu Ser Pro Ile Gly Arg Cys Gly Glu
    770                 775                 780

Pro Asn Arg Cys Val Pro His Ile Glu Trp Asn Pro Asp Leu Asp Cys
785                 790                 795                 800

Ser Cys Arg Asp Gly Glu Lys Cys Ala His His Ser His His Phe Ser
                805                 810                 815
```

-continued

```
Leu Asp Ile Asp Val Gly Cys Thr Asp Leu Asn Glu Asp Leu Gly Val
            820                 825                 830

Trp Val Ile Phe Lys Ile Lys Thr Gln Asp Gly His Ala Arg Leu Gly
        835                 840                 845

Asn Leu Glu Phe Leu Glu Glu Lys Pro Leu Leu Gly Glu Ala Leu Ala
    850                 855                 860

Arg Val Lys Arg Ala Glu Lys Lys Trp Arg Asp Lys Arg Glu Gln Leu
865                 870                 875                 880

Gln Phe Glu Thr Asn Ile Val Tyr Lys Glu Ala Lys Glu Ser Val Asp
                885                 890                 895

Ala Leu Phe Val Asp Ser His Tyr Asn Arg Leu Gln Ala Asp Thr Asn
            900                 905                 910

Ile Thr Met Ile His Ala Ala Asp Lys Arg Val His Arg Ile Arg Glu
        915                 920                 925

Ala Tyr Leu Pro Glu Leu Ser Val Ile Pro Gly Val Asn Ala Asp Ile
    930                 935                 940

Phe Glu Glu Leu Glu Gly Leu Ile Phe Thr Ala Phe Ser Leu Tyr Asp
945                 950                 955                 960

Ala Arg Asn Ile Ile Lys Asn Gly Asp Phe Asn Asn Gly Leu Ser Cys
                965                 970                 975

Trp Asn Val Lys Gly His Val Asp Ile Gln Gln Asn Asp His Arg Ser
            980                 985                 990

Val Leu Val Val Pro Glu Trp Glu  Ser Glu Val Ser Gln  Glu Val Arg
        995                 1000                 1005

Val Cys  Pro Gly Arg Gly Tyr  Ile Leu Arg Val Thr  Ala Tyr Lys
    1010                 1015                 1020

Glu Gly  Tyr Gly Glu Gly Cys  Val Thr Ile His Glu  Ile Glu Asp
    1025                 1030                 1035

Asn Thr  Asp Glu Leu Lys Phe  Ser Asn Cys Ile Glu  Glu Glu Val
    1040                 1045                 1050

Tyr Pro  Thr Asp Thr Gly Asn  Asp Tyr Thr Ala His  Gln Gly Thr
    1055                 1060                 1065

Thr Gly  Cys Ala Asp Ala Cys  Asn Ser Arg Asn Val  Gly Tyr Glu
    1070                 1075                 1080

Asp Gly  Tyr Glu Ile Asn Thr  Thr Ala Ser Val Asn  Tyr Lys Pro
    1085                 1090                 1095

Thr Tyr  Glu Glu Glu Met Tyr  Thr Asp Val Arg Arg  Asp Asn His
    1100                 1105                 1110

Cys Glu  Tyr Asp Arg Gly Tyr  Gly Asn His Thr Pro  Leu Pro Ala
    1115                 1120                 1125

Gly Tyr  Val Thr Lys Glu Leu  Glu Tyr Phe Pro Glu  Thr Asp Thr
    1130                 1135                 1140

Val Trp  Ile Glu Ile Gly Glu  Thr Glu Gly Thr Phe  Ile Val Asp
    1145                 1150                 1155

Ser Val  Glu Leu Leu Leu Met  Glu Glu
    1160                 1165


<210> SEQ ID NO 2
<211> LENGTH: 710
<212> TYPE: PRT
<213> ORGANISM: Bacillus thuringiensis

<400> SEQUENCE: 2

Met Lys Ser Lys Asn Gln Asn Met His Gln Ser Leu Ser Asn Asn Ala
1               5                   10                  15
```

-continued

```
Thr Val Asp Lys Asn Phe Thr Gly Ser Leu Glu Asn Asn Thr Asn Thr
            20                  25                  30

Glu Leu Gln Asn Phe Asn His Glu Gly Ile Glu Pro Phe Val Ser Val
        35                  40                  45

Ser Thr Ile Gln Thr Gly Ile Gly Ile Ala Gly Lys Ile Leu Gly Asn
    50                  55                  60

Leu Gly Val Pro Phe Ala Gly Gln Val Ala Ser Leu Tyr Ser Phe Ile
65                  70                  75                  80

Leu Gly Glu Leu Trp Pro Lys Gly Lys Ser Gln Trp Glu Ile Phe Met
                85                  90                  95

Glu His Val Glu Glu Leu Ile Asn Gln Lys Ile Ser Thr Tyr Ala Arg
            100                 105                 110

Asn Lys Ala Leu Ala Asp Leu Lys Gly Leu Gly Asp Ala Leu Ala Val
        115                 120                 125

Tyr His Glu Ser Leu Glu Ser Trp Ile Lys Asn Arg Asn Asn Thr Arg
    130                 135                 140

Thr Arg Ser Val Val Lys Ser Gln Tyr Ile Thr Leu Glu Leu Met Phe
145                 150                 155                 160

Val Gln Ser Leu Pro Ser Phe Ala Val Ser Gly Glu Glu Val Pro Leu
                165                 170                 175

Leu Pro Ile Tyr Ala Gln Ala Ala Asn Leu His Leu Leu Leu Leu Arg
            180                 185                 190

Asp Ala Ser Ile Phe Gly Lys Glu Trp Gly Leu Ser Asp Ser Glu Ile
        195                 200                 205

Ser Thr Phe Tyr Asn Arg Gln Val Glu Arg Thr Ser Asp Tyr Ser Asp
    210                 215                 220

His Cys Thr Lys Trp Phe Asp Thr Gly Leu Asn Arg Leu Lys Gly Ser
225                 230                 235                 240

Asn Ala Glu Ile Trp Val Lys Tyr Asn Gln Phe Arg Arg Asp Met Thr
                245                 250                 255

Leu Met Val Leu Asp Leu Val Ala Leu Phe Gln Ser Tyr Asp Thr His
            260                 265                 270

Met Tyr Pro Ile Lys Thr Thr Ala Gln Leu Thr Arg Glu Val Tyr Thr
        275                 280                 285

Asn Ala Leu Gly Thr Val His Pro His Pro Ser Phe Thr Ser Thr Thr
    290                 295                 300

Trp Tyr Asn Asn Asn Ala Pro Ser Phe Ser Ala Ile Glu Ala Ala Val
305                 310                 315                 320

Ile Arg Ser Pro His Leu Leu Asp Phe Leu Glu Gln Val Thr Ile Tyr
                325                 330                 335

Ser Leu Leu Ser Arg Trp Ser Asn Thr Gln Tyr Met Asn Met Trp Gly
            340                 345                 350

Gly His Lys Leu Glu Phe Arg Thr Ile Gly Gly Thr Leu Asn Thr Ser
        355                 360                 365

Thr Gln Gly Ser Thr Asn Thr Ser Ile Asn Pro Val Thr Leu Pro Phe
    370                 375                 380

Thr Ser Arg Asp Ile Tyr Arg Thr Glu Ser Leu Ala Gly Leu Asn Leu
385                 390                 395                 400

Phe Leu Thr Gln Pro Val Asn Gly Val Pro Arg Val Asp Phe His Trp
                405                 410                 415

Lys Phe Val Thr His Pro Ile Ala Ser Asp Asn Phe Tyr Tyr Pro Gly
            420                 425                 430
```

```
Tyr Ala Gly Ile Gly Thr Gln Leu Gln Asp Ser Glu Asn Glu Leu Pro
        435                 440                 445

Pro Glu Ala Thr Gly Gln Pro Asn Tyr Glu Ser Tyr Ser His Arg Leu
    450                 455                 460

Ser His Ile Gly Leu Ile Ser Ala Ser His Val Lys Ala Leu Val Tyr
465                 470                 475                 480

Ser Trp Thr His Arg Ser Ala Asp Arg Thr Asn Thr Ile His Ser Asp
                485                 490                 495

Ser Ile Thr Gln Ile Pro Leu Val Lys Ala His Thr Leu Gln Ser Gly
            500                 505                 510

Thr Thr Val Val Lys Gly Pro Gly Phe Thr Gly Gly Asp Ile Leu Arg
        515                 520                 525

Arg Thr Ser Gly Gly Pro Phe Ala Phe Ser Asn Val Asn Leu Asp Trp
    530                 535                 540

Asn Leu Ser Gln Arg Tyr Arg Ala Arg Ile Arg Tyr Ala Ser Thr Thr
545                 550                 555                 560

Asn Leu Arg Met Tyr Val Thr Ile Ala Gly Glu Arg Ile Phe Ala Gly
                565                 570                 575

Gln Phe Asn Lys Thr Met Asn Thr Gly Asp Pro Leu Thr Phe Gln Ser
            580                 585                 590

Phe Ser Tyr Ala Thr Ile Asp Thr Ala Phe Thr Phe Pro Thr Lys Ala
        595                 600                 605

Ser Ser Leu Thr Val Gly Ala Asp Thr Phe Ser Ser Gly Asn Glu Val
    610                 615                 620

Tyr Val Asp Arg Phe Glu Leu Ile Pro Val Thr Ala Thr Leu Glu Ala
625                 630                 635                 640

Val Thr Asp Leu Glu Arg Ala Gln Lys Ala Val His Glu Leu Phe Thr
                645                 650                 655

Ser Thr Asn Pro Gly Gly Leu Lys Thr Asp Val Lys Asp Tyr His Ile
            660                 665                 670

Asp Gln Val Ser Asn Leu Val Glu Ser Leu Ser Asp Lys Phe Tyr Leu
        675                 680                 685

Asp Glu Lys Arg Glu Leu Phe Glu Ile Val Lys Tyr Ala Lys Gln Leu
    690                 695                 700

His Ile Glu Arg Asn Met
705                 710


<210> SEQ ID NO 3
<211> LENGTH: 1168
<212> TYPE: PRT
<213> ORGANISM: Bacillus thuringiensis

<400> SEQUENCE: 3

Met Glu Ile Asn Asn Gln Asn Gln Cys Ile Pro Tyr Asn Cys Leu Ser
1               5                   10                  15

Asn Pro Glu Glu Val Phe Leu Asp Gly Glu Arg Ile Leu Pro Asp Ile
            20                  25                  30

Asp Pro Leu Glu Val Ser Leu Ser Leu Leu Gln Phe Leu Leu Asn Asn
        35                  40                  45

Phe Val Pro Gly Gly Gly Phe Ile Ser Gly Leu Leu Asp Lys Ile Trp
    50                  55                  60

Gly Ala Leu Arg Pro Ser Asp Trp Glu Leu Phe Leu Glu Gln Ile Glu
65                  70                  75                  80

Gln Leu Ile Asp Arg Arg Ile Glu Arg Thr Val Arg Ala Lys Ala Ile
                85                  90                  95
```

-continued

```
Ala Glu Leu Glu Gly Leu Gly Arg Ser Tyr Gln Leu Tyr Gly Glu Ala
            100                 105                 110

Phe Lys Glu Trp Glu Lys Thr Pro Asp Asn Thr Ala Ala Arg Ser Arg
        115                 120                 125

Val Thr Glu Arg Phe Arg Ile Ile Asp Ala Gln Ile Glu Ala Asn Ile
    130                 135                 140

Pro Ser Phe Arg Val Ser Gly Phe Glu Val Pro Leu Leu Leu Val Tyr
145                 150                 155                 160

Thr Gln Ala Ala Asn Leu His Leu Ala Leu Leu Arg Asp Ser Val Val
                165                 170                 175

Phe Gly Glu Arg Trp Gly Leu Thr Thr Thr Asn Val Asn Asp Ile Tyr
            180                 185                 190

Asn Arg Gln Val Asn Arg Ile Gly Glu Tyr Ser Lys His Cys Val Asp
        195                 200                 205

Thr Tyr Lys Thr Glu Leu Glu Arg Leu Gly Phe Arg Ser Ile Ala Gln
    210                 215                 220

Trp Arg Ile Tyr Asn Gln Phe Arg Arg Glu Leu Thr Leu Thr Val Leu
225                 230                 235                 240

Asp Ile Val Ala Val Phe Pro Asn Tyr Asp Ser Arg Leu Tyr Pro Ile
                245                 250                 255

Arg Thr Ile Ser Gln Leu Thr Arg Glu Ile Tyr Thr Ser Pro Val Ser
            260                 265                 270

Glu Phe Tyr Tyr Gly Val Ile Asn Ser Asn Asn Ile Ile Gly Thr Leu
        275                 280                 285

Thr Glu Gln Gln Ile Arg Arg Pro His Leu Met Asp Phe Phe Asn Ser
    290                 295                 300

Met Ile Met Tyr Thr Ser Asp Asn Arg Arg Glu His Tyr Trp Ser Gly
305                 310                 315                 320

Leu Glu Met Thr Ala Thr Asn Thr Glu Gly His Gln Arg Ser Phe Pro
                325                 330                 335

Leu Ala Gly Thr Ile Gly Asn Ser Ala Pro Pro Val Thr Val Arg Asn
            340                 345                 350

Asn Gly Glu Gly Ile Tyr Arg Ile Leu Ser Glu Pro Phe Tyr Ser Ala
        355                 360                 365

Pro Phe Leu Gly Thr Ser Val Leu Gly Ser Arg Gly Glu Glu Phe Ala
    370                 375                 380

Phe Ala Ser Asn Thr Thr Thr Ser Leu Pro Ser Thr Ile Tyr Arg Asn
385                 390                 395                 400

Arg Gly Thr Val Asp Ser Leu Val Ser Ile Pro Pro Gln Asp Tyr Ser
                405                 410                 415

Val Pro Pro His Arg Gly Tyr Ser His Leu Leu Ser His Val Thr Met
            420                 425                 430

Arg Asn Ser Ser Pro Ile Phe His Trp Thr His Arg Ser Ala Thr Pro
        435                 440                 445

Arg Asn Thr Ile Asp Pro Asp Ser Ile Thr Gln Ile Pro Ala Val Lys
    450                 455                 460

Gly Ala Tyr Ile Phe Asn Ser Pro Val Ile Thr Gly Pro Gly His Thr
465                 470                 475                 480

Gly Gly Asp Ile Ile Arg Phe Asn Pro Asn Thr Gln Asn Asn Ile Arg
                485                 490                 495

Ile Pro Phe Gln Ser Asn Ala Val Gln Arg Tyr Arg Ile Arg Met Arg
            500                 505                 510
```

```
Tyr Ala Ala Glu Ala Asp Cys Ile Leu Glu Ser Gly Val Asn Ile Val
        515                 520                 525

Thr Gly Ala Gly Val Thr Phe Arg Pro Ile Pro Ile Lys Ala Thr Met
    530                 535                 540

Thr Pro Gly Ser Pro Leu Thr Tyr Tyr Ser Phe Gln Tyr Ala Asp Leu
545                 550                 555                 560

Asn Ile Asn Leu Thr Ala Pro Ile Arg Pro Asn Asn Phe Val Ser Ile
                565                 570                 575

Arg Arg Ser Asn Gln Pro Gly Asn Leu Tyr Ile Asp Arg Ile Glu Phe
            580                 585                 590

Ile Pro Ile Asp Pro Ile Arg Glu Ala Glu His Asp Leu Glu Arg Ala
        595                 600                 605

Gln Lys Ala Val Asn Ala Leu Phe Thr Ser Ser Asn Gln Ile Gly Leu
    610                 615                 620

Lys Thr Asp Val Thr Asp Tyr His Ile Asp Gln Val Ser Asn Leu Val
625                 630                 635                 640

Ala Cys Leu Ser Asp Lys Phe Cys Leu Asp Glu Lys Arg Glu Leu Ser
                645                 650                 655

Glu Lys Val Lys His Ala Lys Arg Leu Ser Asp Glu Arg Asn Leu Leu
            660                 665                 670

Gln Asp Gln Asn Phe Thr Gly Ile Asn Arg Gln Val Asp Arg Gly Trp
        675                 680                 685

Arg Gly Ser Thr Asp Ile Thr Ile Gln Gly Gly Asn Asp Val Phe Lys
    690                 695                 700

Glu Asn Tyr Val Thr Leu Pro Gly Thr Phe Asp Glu Cys Tyr Pro Thr
705                 710                 715                 720

Tyr Leu Tyr Gln Lys Ile Asp Glu Ser Lys Leu Lys Pro Tyr Thr Arg
                725                 730                 735

Tyr Glu Leu Arg Gly Tyr Ile Glu Asp Ser Gln Asp Leu Glu Val Tyr
            740                 745                 750

Leu Ile Arg Tyr Asn Ala Lys His Glu Thr Leu Asn Val Pro Gly Thr
        755                 760                 765

Gly Ser Leu Trp Pro Leu Ala Ala Glu Ser Ser Ile Gly Arg Cys Gly
    770                 775                 780

Glu Pro Asn Arg Cys Ala Pro His Ile Glu Trp Asn Pro Glu Leu Asp
785                 790                 795                 800

Cys Ser Cys Arg Asp Gly Glu Lys Cys Ala His His Ser His His Phe
                805                 810                 815

Ser Leu Asp Ile Asp Val Gly Cys Thr Asp Leu Asn Glu Asp Leu Gly
            820                 825                 830

Val Trp Val Ile Phe Lys Ile Lys Thr Gln Asp Gly Tyr Ala Arg Leu
        835                 840                 845

Gly Asn Leu Glu Phe Leu Glu Glu Lys Pro Leu Leu Gly Glu Ala Leu
    850                 855                 860

Ala Arg Val Lys Arg Ala Glu Lys Lys Trp Arg Asp Lys Arg Asp Lys
865                 870                 875                 880

Leu Glu Trp Glu Thr Asn Ile Val Tyr Lys Glu Ala Lys Glu Ser Val
                885                 890                 895

Asp Ala Leu Phe Val Asp Ser Gln Tyr Asn Arg Leu Gln Thr Asp Thr
            900                 905                 910

Asn Ile Ala Met Ile His Val Ala Asp Lys Arg Val His Arg Ile Arg
        915                 920                 925

Glu Ala Tyr Leu Pro Glu Leu Ser Val Ile Pro Gly Val Asn Ala Ala
```

```
    930                 935                 940

Ile Phe Glu Glu Leu Glu Gly Leu Ile Phe Thr Ala Phe Ser Leu Tyr
945                 950                 955                 960

Asp Ala Arg Asn Val Ile Lys Asn Gly Asp Phe Asn His Gly Leu Ser
                965                 970                 975

Cys Trp Asn Val Lys Gly His Val Asp Val Glu Glu Gln Asn Asn His
            980                 985                 990

Arg Ser Val Leu Val Val Pro Glu  Trp Glu Ala Glu Val  Ser Gln Glu
        995                 1000                1005

Val Arg  Val Cys Pro Gly Arg  Gly Tyr Ile Leu Arg  Val Thr Ala
    1010                1015                1020

Tyr Lys  Glu Gly Tyr Gly Glu  Gly Cys Val Thr Ile  His Glu Ile
    1025                1030                1035

Glu Asp  His Thr Asp Glu Leu  Lys Phe Arg Asn Cys  Glu Glu Glu
    1040                1045                1050

Glu Val  Tyr Pro Asn Asn Thr  Val Thr Cys Asn Asp  Tyr Pro Ala
    1055                1060                1065

Asn Gln  Glu Glu Tyr Arg Ala  Ala Glu Thr Ser Arg  Asn Arg Gly
    1070                1075                1080

Tyr Gly  Glu Ser Tyr Glu Ser  Asn Ser Ser Ile Pro  Ala Glu Tyr
    1085                1090                1095

Ala Pro  Ile Tyr Glu Lys Ala  Tyr Thr Asp Gly Arg  Lys Glu Asn
    1100                1105                1110

Ser Cys  Glu Ser Asn Arg Gly  Tyr Gly Asn Tyr Thr  Pro Leu Pro
    1115                1120                1125

Ala Gly  Tyr Val Thr Lys Glu  Leu Glu Tyr Phe Pro  Glu Thr Asp
    1130                1135                1140

Lys Val  Trp Ile Glu Ile Gly  Glu Thr Glu Gly Thr  Phe Ile Val
    1145                1150                1155

Asp Ser  Val Glu Leu Leu Leu  Met Glu Glu
    1160                1165


<210> SEQ ID NO 4
<211> LENGTH: 1167
<212> TYPE: PRT
<213> ORGANISM: Artificial Sequence
<220> FEATURE:
<223> OTHER INFORMATION: Variant BT0002 protein
<220> FEATURE:
<221> NAME/KEY: MISC_FEATURE
<223> OTHER INFORMATION: Amino acid substitutions: I1146L and L1163I

<400> SEQUENCE: 4

Met Glu Ile Asn Asn Gln Lys Gln Cys Ile Pro Tyr Asn Cys Leu Ser
1               5                   10                  15

Asn Pro Glu Glu Val Leu Leu Asp Gly Glu Arg Ile Leu Pro Asp Ile
            20                  25                  30

Asp Pro Leu Glu Val Ser Leu Ser Leu Leu Gln Phe Leu Leu Asn Asn
        35                  40                  45

Phe Val Pro Gly Gly Gly Phe Ile Ser Gly Leu Val Asp Lys Ile Trp
    50                  55                  60

Gly Ala Leu Arg Pro Ser Glu Trp Asp Leu Phe Leu Ala Gln Ile Glu
65                  70                  75                  80

Arg Leu Ile Asp Gln Arg Ile Glu Ala Thr Val Arg Ala Lys Ala Ile
                85                  90                  95

Ala Glu Leu Glu Gly Leu Gly Arg Ser Tyr Gln Leu Tyr Gly Glu Ala
```

-continued

```
            100                 105                 110

Phe Lys Glu Trp Glu Lys Thr Pro Asp Asn Thr Ala Ala Arg Ser Arg
        115                 120                 125

Val Thr Glu Arg Phe Arg Ile Ile Asp Ala Gln Ile Glu Ala Asn Ile
    130                 135                 140

Pro Ser Phe Arg Val Ser Gly Phe Glu Val Pro Leu Leu Leu Val Tyr
145                 150                 155                 160

Thr Gln Ala Ala Asn Leu His Leu Ala Leu Leu Arg Asp Ser Val Val
                165                 170                 175

Phe Gly Glu Arg Trp Gly Leu Thr Thr Thr Asn Val Asn Asp Ile Tyr
            180                 185                 190

Asn Arg Gln Val Asn Arg Ile Gly Glu Tyr Ser Asn His Cys Val Asp
        195                 200                 205

Thr Tyr Asn Thr Glu Leu Glu Arg Leu Gly Phe Arg Ser Ile Ala Gln
    210                 215                 220

Trp Arg Ile Tyr Asn Gln Phe Arg Arg Glu Leu Thr Leu Thr Val Leu
225                 230                 235                 240

Asp Ile Val Ala Leu Phe Pro Asn Tyr Asp Ser Arg Leu Tyr Pro Ile
                245                 250                 255

Gln Thr Phe Ser Gln Leu Thr Arg Glu Ile Val Thr Ser Pro Val Ser
            260                 265                 270

Glu Phe Tyr Tyr Gly Val Ile Asn Ser Gly Asn Ile Asn Gly Thr Leu
        275                 280                 285

Thr Glu Gln Gln Ile Arg Arg Pro His Leu Met Asp Phe Phe Asn Ser
    290                 295                 300

Met Ile Met Tyr Thr Ser Asp Asn Arg Arg Glu His Tyr Trp Ser Gly
305                 310                 315                 320

Leu Glu Met Thr Ala Tyr Phe Thr Gly Phe Ala Gly Ala Gln Val Ser
                325                 330                 335

Phe Pro Leu Val Gly Thr Arg Gly Glu Ser Ala Pro Pro Leu Thr Val
            340                 345                 350

Arg Ser Val Asn Asp Gly Ile Tyr Arg Ile Leu Ser Ala Pro Phe Tyr
        355                 360                 365

Ser Ala Pro Phe Leu Gly Thr Ile Val Leu Gly Ser Arg Gly Glu Lys
    370                 375                 380

Phe Asp Phe Ala Leu Asn Asn Ile Ser Pro Pro Pro Ser Thr Ile Tyr
385                 390                 395                 400

Arg His Pro Gly Thr Val Asp Ser Leu Val Ser Ile Pro Pro Gln Asp
                405                 410                 415

Asn Ser Val Pro Pro His Arg Gly Ser Ser His Arg Leu Ser His Val
            420                 425                 430

Thr Met Arg Ala Ser Ser Pro Ile Phe His Trp Thr His Arg Ser Ala
        435                 440                 445

Thr Thr Thr Asn Thr Ile Asn Pro Asn Ala Ile Ile Gln Ile Pro Leu
    450                 455                 460

Val Lys Ala Phe Asn Leu His Ser Gly Ala Thr Val Val Arg Gly Pro
465                 470                 475                 480

Gly Phe Thr Gly Gly Asp Ile Leu Arg Arg Thr Asn Thr Gly Thr Phe
                485                 490                 495

Ala Asp Met Arg Val Asn Ile Thr Gly Pro Leu Ser Gln Arg Tyr Arg
            500                 505                 510

Val Arg Ile Arg Tyr Ala Ser Thr Thr Asp Leu Gln Phe Phe Thr Arg
        515                 520                 525
```

-continued

```
Ile Asn Gly Thr Ser Val Asn Gln Gly Asn Phe Gln Arg Thr Met Asn
    530                 535                 540

Arg Gly Asp Asn Leu Glu Ser Gly Asn Phe Arg Thr Ala Gly Phe Ser
545                 550                 555                 560

Thr Pro Phe Ser Phe Ser Asn Ala Gln Ser Thr Phe Thr Leu Gly Thr
                565                 570                 575

Gln Ala Phe Ser Asn Gln Glu Val Tyr Ile Asp Arg Ile Glu Phe Val
            580                 585                 590

Pro Ala Glu Val Thr Phe Glu Ala Glu Ser Asp Leu Glu Arg Ala Gln
        595                 600                 605

Lys Ala Val Asn Ala Leu Phe Thr Ser Thr Asn Gln Leu Gly Leu Lys
    610                 615                 620

Thr Asp Val Thr Asp Tyr Gln Ile Asp Gln Val Ser Asn Leu Val Glu
625                 630                 635                 640

Cys Leu Ser Asp Glu Phe Cys Leu Asp Glu Lys Arg Glu Leu Ser Glu
                645                 650                 655

Lys Val Lys His Ala Lys Arg Leu Ser Asp Lys Arg Asn Leu Leu Gln
            660                 665                 670

Asp Pro Asn Phe Thr Ser Ile Asn Arg Gln Leu Asp Arg Gly Trp Arg
        675                 680                 685

Gly Ser Thr Asp Ile Thr Ile Gln Gly Gly Asn Asp Val Phe Lys Glu
    690                 695                 700

Asn Tyr Val Thr Leu Pro Gly Thr Phe Asp Glu Cys Tyr Pro Thr Tyr
705                 710                 715                 720

Leu Tyr Gln Lys Ile Asp Glu Ser Lys Leu Lys Ala Tyr Thr Arg Tyr
                725                 730                 735

Glu Leu Arg Gly Tyr Ile Glu Asp Ser Gln Asp Leu Glu Val Tyr Leu
            740                 745                 750

Ile Arg Tyr Asn Ala Lys His Glu Thr Val Asn Val Pro Gly Thr Gly
        755                 760                 765

Ser Leu Trp Pro Leu Ser Val Glu Ser Pro Ile Gly Arg Cys Gly Glu
    770                 775                 780

Pro Asn Arg Cys Val Pro His Ile Glu Trp Asn Pro Asp Leu Asp Cys
785                 790                 795                 800

Ser Cys Arg Asp Gly Glu Lys Cys Ala His His Ser His His Phe Ser
                805                 810                 815

Leu Asp Ile Asp Val Gly Cys Thr Asp Leu Asn Glu Asp Leu Gly Val
            820                 825                 830

Trp Val Ile Phe Lys Ile Lys Thr Gln Asp Gly His Ala Arg Leu Gly
        835                 840                 845

Asn Leu Glu Phe Leu Glu Glu Lys Pro Leu Leu Gly Glu Ala Leu Ala
    850                 855                 860

Arg Val Lys Arg Ala Glu Lys Lys Trp Arg Asp Lys Arg Glu Gln Leu
865                 870                 875                 880

Gln Phe Glu Thr Asn Ile Val Tyr Lys Glu Ala Lys Glu Ser Val Asp
                885                 890                 895

Ala Leu Phe Val Asp Ser His Tyr Asn Arg Leu Gln Ala Asp Thr Asn
            900                 905                 910

Ile Thr Met Ile His Ala Ala Asp Lys Arg Val His Arg Ile Arg Glu
        915                 920                 925

Ala Tyr Leu Pro Glu Leu Ser Val Ile Pro Gly Val Asn Ala Asp Ile
    930                 935                 940
```

Phe Glu Glu Leu Glu Gly Leu Ile Phe Thr Ala Phe Ser Leu Tyr Asp
945 950 955 960

Ala Arg Asn Ile Ile Lys Asn Gly Asp Phe Asn Asn Gly Leu Ser Cys
965 970 975

Trp Asn Val Lys Gly His Val Asp Ile Gln Gln Asn Asp His Arg Ser
980 985 990

Val Leu Val Val Pro Glu Trp Glu Ser Glu Val Ser Gln Glu Val Arg
995 1000 1005

Val Cys Pro Gly Arg Gly Tyr Ile Leu Arg Val Thr Ala Tyr Lys
1010 1015 1020

Glu Gly Tyr Gly Glu Gly Cys Val Thr Ile His Glu Ile Glu Asp
1025 1030 1035

Asn Thr Asp Glu Leu Lys Phe Ser Asn Cys Ile Glu Glu Glu Val
1040 1045 1050

Tyr Pro Thr Asp Thr Gly Asn Asp Tyr Thr Ala His Gln Gly Thr
1055 1060 1065

Thr Gly Cys Ala Asp Ala Cys Asn Ser Arg Asn Val Gly Tyr Glu
1070 1075 1080

Asp Gly Tyr Glu Ile Asn Thr Thr Ala Ser Val Asn Tyr Lys Pro
1085 1090 1095

Thr Tyr Glu Glu Glu Met Tyr Thr Asp Val Arg Arg Asp Asn His
1100 1105 1110

Cys Glu Tyr Asp Arg Gly Tyr Gly Asn His Thr Pro Leu Pro Ala
1115 1120 1125

Gly Tyr Val Thr Lys Glu Leu Glu Tyr Phe Pro Glu Thr Asp Thr
1130 1135 1140

Val Trp Leu Glu Ile Gly Glu Thr Glu Gly Thr Phe Ile Val Asp
1145 1150 1155

Ser Val Glu Leu Ile Leu Met Glu Glu
1160 1165

<210> SEQ ID NO 5
<211> LENGTH: 710
<212> TYPE: PRT
<213> ORGANISM: Artificial Sequence
<220> FEATURE:
<223> OTHER INFORMATION: Variant BT0025 protein
<220> FEATURE:
<221> NAME/KEY: MISC_FEATURE
<223> OTHER INFORMATION: Amino acid substitutions: I672L and I697L

<400> SEQUENCE: 5

Met Lys Ser Lys Asn Gln Asn Met His Gln Ser Leu Ser Asn Asn Ala
1 5 10 15

Thr Val Asp Lys Asn Phe Thr Gly Ser Leu Glu Asn Asn Thr Asn Thr
20 25 30

Glu Leu Gln Asn Phe Asn His Glu Gly Ile Glu Pro Phe Val Ser Val
35 40 45

Ser Thr Ile Gln Thr Gly Ile Gly Ile Ala Gly Lys Ile Leu Gly Asn
50 55 60

Leu Gly Val Pro Phe Ala Gly Gln Val Ala Ser Leu Tyr Ser Phe Ile
65 70 75 80

Leu Gly Glu Leu Trp Pro Lys Gly Lys Ser Gln Trp Glu Ile Phe Met
85 90 95

Glu His Val Glu Glu Leu Ile Asn Gln Lys Ile Ser Thr Tyr Ala Arg
100 105 110

-continued

Asn Lys Ala Leu Ala Asp Leu Lys Gly Leu Gly Asp Ala Leu Ala Val
115 120 125

Tyr His Glu Ser Leu Glu Ser Trp Ile Lys Asn Arg Asn Asn Thr Arg
130 135 140

Thr Arg Ser Val Val Lys Ser Gln Tyr Ile Thr Leu Glu Leu Met Phe
145 150 155 160

Val Gln Ser Leu Pro Ser Phe Ala Val Ser Gly Glu Glu Val Pro Leu
165 170 175

Leu Pro Ile Tyr Ala Gln Ala Ala Asn Leu His Leu Leu Leu Leu Arg
180 185 190

Asp Ala Ser Ile Phe Gly Lys Glu Trp Gly Leu Ser Asp Ser Glu Ile
195 200 205

Ser Thr Phe Tyr Asn Arg Gln Val Glu Arg Thr Ser Asp Tyr Ser Asp
210 215 220

His Cys Thr Lys Trp Phe Asp Thr Gly Leu Asn Arg Leu Lys Gly Ser
225 230 235 240

Asn Ala Glu Ile Trp Val Lys Tyr Asn Gln Phe Arg Arg Asp Met Thr
245 250 255

Leu Met Val Leu Asp Leu Val Ala Leu Phe Gln Ser Tyr Asp Thr His
260 265 270

Met Tyr Pro Ile Lys Thr Thr Ala Gln Leu Thr Arg Glu Val Tyr Thr
275 280 285

Asn Ala Leu Gly Thr Val His Pro His Pro Ser Phe Thr Ser Thr Thr
290 295 300

Trp Tyr Asn Asn Asn Ala Pro Ser Phe Ser Ala Ile Glu Ala Ala Val
305 310 315 320

Ile Arg Ser Pro His Leu Leu Asp Phe Leu Glu Gln Val Thr Ile Tyr
325 330 335

Ser Leu Leu Ser Arg Trp Ser Asn Thr Gln Tyr Met Asn Met Trp Gly
340 345 350

Gly His Lys Leu Glu Phe Arg Thr Ile Gly Gly Thr Leu Asn Thr Ser
355 360 365

Thr Gln Gly Ser Thr Asn Thr Ser Ile Asn Pro Val Thr Leu Pro Phe
370 375 380

Thr Ser Arg Asp Ile Tyr Arg Thr Glu Ser Leu Ala Gly Leu Asn Leu
385 390 395 400

Phe Leu Thr Gln Pro Val Asn Gly Val Pro Arg Val Asp Phe His Trp
405 410 415

Lys Phe Val Thr His Pro Ile Ala Ser Asp Asn Phe Tyr Tyr Pro Gly
420 425 430

Tyr Ala Gly Ile Gly Thr Gln Leu Gln Asp Ser Glu Asn Glu Leu Pro
435 440 445

Pro Glu Ala Thr Gly Gln Pro Asn Tyr Glu Ser Tyr Ser His Arg Leu
450 455 460

Ser His Ile Gly Leu Ile Ser Ala Ser His Val Lys Ala Leu Val Tyr
465 470 475 480

Ser Trp Thr His Arg Ser Ala Asp Arg Thr Asn Thr Ile His Ser Asp
485 490 495

Ser Ile Thr Gln Ile Pro Leu Val Lys Ala His Thr Leu Gln Ser Gly
500 505 510

Thr Thr Val Val Lys Gly Pro Gly Phe Thr Gly Gly Asp Ile Leu Arg
515 520 525

Arg Thr Ser Gly Gly Pro Phe Ala Phe Ser Asn Val Asn Leu Asp Trp

```
    530                 535                 540

Asn Leu Ser Gln Arg Tyr Arg Ala Arg Ile Arg Tyr Ala Ser Thr Thr
545                 550                 555                 560

Asn Leu Arg Met Tyr Val Thr Ile Ala Gly Glu Arg Ile Phe Ala Gly
                565                 570                 575

Gln Phe Asn Lys Thr Met Asn Thr Gly Asp Pro Leu Thr Phe Gln Ser
            580                 585                 590

Phe Ser Tyr Ala Thr Ile Asp Thr Ala Phe Thr Phe Pro Thr Lys Ala
        595                 600                 605

Ser Ser Leu Thr Val Gly Ala Asp Thr Phe Ser Ser Gly Asn Glu Val
    610                 615                 620

Tyr Val Asp Arg Phe Glu Leu Ile Pro Val Thr Ala Thr Leu Glu Ala
625                 630                 635                 640

Val Thr Asp Leu Glu Arg Ala Gln Lys Ala Val His Glu Leu Phe Thr
                645                 650                 655

Ser Thr Asn Pro Gly Gly Leu Lys Thr Asp Val Lys Asp Tyr His Leu
            660                 665                 670

Asp Gln Val Ser Asn Leu Val Glu Ser Leu Ser Asp Lys Phe Tyr Leu
        675                 680                 685

Asp Glu Lys Arg Glu Leu Phe Glu Leu Val Lys Tyr Ala Lys Gln Leu
    690                 695                 700

His Ile Glu Arg Asn Met
705                 710


<210> SEQ ID NO 6
<211> LENGTH: 1168
<212> TYPE: PRT
<213> ORGANISM: Artificial Sequence
<220> FEATURE:
<223> OTHER INFORMATION: Variant BT0053 protein
<220> FEATURE:
<221> NAME/KEY: MISC_FEATURE
<223> OTHER INFORMATION: Amino acid substitutions: E2A and I1157L

<400> SEQUENCE: 6

Met Ala Ile Asn Asn Gln Asn Gln Cys Ile Pro Tyr Asn Cys Leu Ser
1               5                   10                  15

Asn Pro Glu Glu Val Phe Leu Asp Gly Glu Arg Ile Leu Pro Asp Ile
            20                  25                  30

Asp Pro Leu Glu Val Ser Leu Ser Leu Leu Gln Phe Leu Leu Asn Asn
        35                  40                  45

Phe Val Pro Gly Gly Gly Phe Ile Ser Gly Leu Leu Asp Lys Ile Trp
    50                  55                  60

Gly Ala Leu Arg Pro Ser Asp Trp Glu Leu Phe Leu Glu Gln Ile Glu
65                  70                  75                  80

Gln Leu Ile Asp Arg Arg Ile Glu Arg Thr Val Arg Ala Lys Ala Ile
                85                  90                  95

Ala Glu Leu Glu Gly Leu Gly Arg Ser Tyr Gln Leu Tyr Gly Glu Ala
            100                 105                 110

Phe Lys Glu Trp Glu Lys Thr Pro Asp Asn Thr Ala Ala Arg Ser Arg
        115                 120                 125

Val Thr Glu Arg Phe Arg Ile Ile Asp Ala Gln Ile Glu Ala Asn Ile
    130                 135                 140

Pro Ser Phe Arg Val Ser Gly Phe Glu Val Pro Leu Leu Leu Val Tyr
145                 150                 155                 160

Thr Gln Ala Ala Asn Leu His Leu Ala Leu Leu Arg Asp Ser Val Val
```

-continued

```
                165                 170                 175

Phe Gly Glu Arg Trp Gly Leu Thr Thr Thr Asn Val Asn Asp Ile Tyr
            180                 185                 190

Asn Arg Gln Val Asn Arg Ile Gly Glu Tyr Ser Lys His Cys Val Asp
        195                 200                 205

Thr Tyr Lys Thr Glu Leu Glu Arg Leu Gly Phe Arg Ser Ile Ala Gln
    210                 215                 220

Trp Arg Ile Tyr Asn Gln Phe Arg Arg Glu Leu Thr Leu Thr Val Leu
225                 230                 235                 240

Asp Ile Val Ala Val Phe Pro Asn Tyr Asp Ser Arg Leu Tyr Pro Ile
                245                 250                 255

Arg Thr Ile Ser Gln Leu Thr Arg Glu Ile Tyr Thr Ser Pro Val Ser
            260                 265                 270

Glu Phe Tyr Tyr Gly Val Ile Asn Ser Asn Asn Ile Ile Gly Thr Leu
        275                 280                 285

Thr Glu Gln Gln Ile Arg Arg Pro His Leu Met Asp Phe Phe Asn Ser
    290                 295                 300

Met Ile Met Tyr Thr Ser Asp Asn Arg Arg Glu His Tyr Trp Ser Gly
305                 310                 315                 320

Leu Glu Met Thr Ala Thr Asn Thr Glu Gly His Gln Arg Ser Phe Pro
                325                 330                 335

Leu Ala Gly Thr Ile Gly Asn Ser Ala Pro Pro Val Thr Val Arg Asn
            340                 345                 350

Asn Gly Glu Gly Ile Tyr Arg Ile Leu Ser Glu Pro Phe Tyr Ser Ala
        355                 360                 365

Pro Phe Leu Gly Thr Ser Val Leu Gly Ser Arg Gly Glu Glu Phe Ala
    370                 375                 380

Phe Ala Ser Asn Thr Thr Thr Ser Leu Pro Ser Thr Ile Tyr Arg Asn
385                 390                 395                 400

Arg Gly Thr Val Asp Ser Leu Val Ser Ile Pro Pro Gln Asp Tyr Ser
                405                 410                 415

Val Pro Pro His Arg Gly Tyr Ser His Leu Leu Ser His Val Thr Met
            420                 425                 430

Arg Asn Ser Ser Pro Ile Phe His Trp Thr His Arg Ser Ala Thr Pro
        435                 440                 445

Arg Asn Thr Ile Asp Pro Asp Ser Ile Thr Gln Ile Pro Ala Val Lys
    450                 455                 460

Gly Ala Tyr Ile Phe Asn Ser Pro Val Ile Thr Gly Pro Gly His Thr
465                 470                 475                 480

Gly Gly Asp Ile Ile Arg Phe Asn Pro Asn Thr Gln Asn Asn Ile Arg
                485                 490                 495

Ile Pro Phe Gln Ser Asn Ala Val Gln Arg Tyr Arg Ile Arg Met Arg
            500                 505                 510

Tyr Ala Ala Glu Ala Asp Cys Ile Leu Glu Ser Gly Val Asn Ile Val
        515                 520                 525

Thr Gly Ala Gly Val Thr Phe Arg Pro Ile Pro Ile Lys Ala Thr Met
    530                 535                 540

Thr Pro Gly Ser Pro Leu Thr Tyr Tyr Ser Phe Gln Tyr Ala Asp Leu
545                 550                 555                 560

Asn Ile Asn Leu Thr Ala Pro Ile Arg Pro Asn Asn Phe Val Ser Ile
                565                 570                 575

Arg Arg Ser Asn Gln Pro Gly Asn Leu Tyr Ile Asp Arg Ile Glu Phe
            580                 585                 590
```

```
Ile Pro Ile Asp Pro Ile Arg Glu Ala Glu His Asp Leu Glu Arg Ala
        595                 600                 605

Gln Lys Ala Val Asn Ala Leu Phe Thr Ser Ser Asn Gln Ile Gly Leu
    610                 615                 620

Lys Thr Asp Val Thr Asp Tyr His Ile Asp Gln Val Ser Asn Leu Val
625                 630                 635                 640

Ala Cys Leu Ser Asp Lys Phe Cys Leu Asp Glu Lys Arg Glu Leu Ser
                645                 650                 655

Glu Lys Val Lys His Ala Lys Arg Leu Ser Asp Glu Arg Asn Leu Leu
            660                 665                 670

Gln Asp Gln Asn Phe Thr Gly Ile Asn Arg Gln Val Asp Arg Gly Trp
        675                 680                 685

Arg Gly Ser Thr Asp Ile Thr Ile Gln Gly Gly Asn Asp Val Phe Lys
    690                 695                 700

Glu Asn Tyr Val Thr Leu Pro Gly Thr Phe Asp Glu Cys Tyr Pro Thr
705                 710                 715                 720

Tyr Leu Tyr Gln Lys Ile Asp Glu Ser Lys Leu Lys Pro Tyr Thr Arg
                725                 730                 735

Tyr Glu Leu Arg Gly Tyr Ile Glu Asp Ser Gln Asp Leu Glu Val Tyr
            740                 745                 750

Leu Ile Arg Tyr Asn Ala Lys His Glu Thr Leu Asn Val Pro Gly Thr
        755                 760                 765

Gly Ser Leu Trp Pro Leu Ala Ala Glu Ser Ser Ile Gly Arg Cys Gly
    770                 775                 780

Glu Pro Asn Arg Cys Ala Pro His Ile Glu Trp Asn Pro Glu Leu Asp
785                 790                 795                 800

Cys Ser Cys Arg Asp Gly Glu Lys Cys Ala His His Ser His His Phe
                805                 810                 815

Ser Leu Asp Ile Asp Val Gly Cys Thr Asp Leu Asn Glu Asp Leu Gly
            820                 825                 830

Val Trp Val Ile Phe Lys Ile Lys Thr Gln Asp Gly Tyr Ala Arg Leu
        835                 840                 845

Gly Asn Leu Glu Phe Leu Glu Glu Lys Pro Leu Leu Gly Glu Ala Leu
    850                 855                 860

Ala Arg Val Lys Arg Ala Glu Lys Lys Trp Arg Asp Lys Arg Asp Lys
865                 870                 875                 880

Leu Glu Trp Glu Thr Asn Ile Val Tyr Lys Glu Ala Lys Glu Ser Val
                885                 890                 895

Asp Ala Leu Phe Val Asp Ser Gln Tyr Asn Arg Leu Gln Thr Asp Thr
            900                 905                 910

Asn Ile Ala Met Ile His Val Ala Asp Lys Arg Val His Arg Ile Arg
        915                 920                 925

Glu Ala Tyr Leu Pro Glu Leu Ser Val Ile Pro Gly Val Asn Ala Ala
    930                 935                 940

Ile Phe Glu Glu Leu Glu Gly Leu Ile Phe Thr Ala Phe Ser Leu Tyr
945                 950                 955                 960

Asp Ala Arg Asn Val Ile Lys Asn Gly Asp Phe Asn His Gly Leu Ser
                965                 970                 975

Cys Trp Asn Val Lys Gly His Val Asp Val Glu Glu Gln Asn Asn His
            980                 985                 990

Arg Ser Val Leu Val Val Pro Glu  Trp Glu Ala Glu Val  Ser Gln Glu
        995                 1000                1005
```

```
Val Arg  Val Cys Pro Gly Arg  Gly Tyr Ile Leu Arg  Val Thr Ala
    1010                 1015                 1020

Tyr Lys  Glu Gly Tyr Gly Glu  Gly Cys Val Thr Ile  His Glu Ile
    1025                 1030                 1035

Glu Asp  His Thr Asp Glu Leu  Lys Phe Arg Asn Cys  Glu Glu Glu
    1040                 1045                 1050

Glu Val  Tyr Pro Asn Asn Thr  Val Thr Cys Asn Asp  Tyr Pro Ala
    1055                 1060                 1065

Asn Gln  Glu Glu Tyr Arg Ala  Ala Glu Thr Ser Arg  Asn Arg Gly
    1070                 1075                 1080

Tyr Gly  Glu Ser Tyr Glu Ser  Asn Ser Ser Ile Pro  Ala Glu Tyr
    1085                 1090                 1095

Ala Pro  Ile Tyr Glu Lys Ala  Tyr Thr Asp Gly Arg  Lys Glu Asn
    1100                 1105                 1110

Ser Cys  Glu Ser Asn Arg Gly  Tyr Gly Asn Tyr Thr  Pro Leu Pro
    1115                 1120                 1125

Ala Gly  Tyr Val Thr Lys Glu  Leu Glu Tyr Phe Pro  Glu Thr Asp
    1130                 1135                 1140

Lys Val  Trp Ile Glu Ile Gly  Glu Thr Glu Gly Thr  Phe Leu Val
    1145                 1150                 1155

Asp Ser  Val Glu Leu Leu Leu  Met Glu Glu
    1160                 1165


<210> SEQ ID NO 7
<211> LENGTH: 1167
<212> TYPE: PRT
<213> ORGANISM: Artificial Sequence
<220> FEATURE:
<223> OTHER INFORMATION: Modified alpha-helix 3 BT0002
<220> FEATURE:
<221> NAME/KEY: MISC_FEATURE
<222> LOCATION: (97)..(119)
<223> OTHER INFORMATION: BT0002 block 1 mutations: A97T; S105N; L108I;
      G110A; K118S & T119D

<400> SEQUENCE: 7

Met Glu Ile Asn Asn Gln Lys Gln Cys Ile Pro Tyr Asn Cys Leu Ser
1               5                   10                  15

Asn Pro Glu Glu Val Leu Leu Asp Gly Glu Arg Ile Leu Pro Asp Ile
            20                  25                  30

Asp Pro Leu Glu Val Ser Leu Ser Leu Leu Gln Phe Leu Leu Asn Asn
        35                  40                  45

Phe Val Pro Gly Gly Gly Phe Ile Ser Gly Leu Val Asp Lys Ile Trp
    50                  55                  60

Gly Ala Leu Arg Pro Ser Glu Trp Asp Leu Phe Leu Ala Gln Ile Glu
65                  70                  75                  80

Arg Leu Ile Asp Gln Arg Ile Glu Ala Thr Val Arg Ala Lys Ala Ile
                85                  90                  95

Thr Glu Leu Glu Gly Leu Gly Arg Asn Tyr Gln Ile Tyr Ala Glu Ala
            100                 105                 110

Phe Lys Glu Trp Glu Ser Asp Pro Asp Asn Thr Ala Ala Arg Ser Arg
        115                 120                 125

Val Thr Glu Arg Phe Arg Ile Ile Asp Ala Gln Ile Glu Ala Asn Ile
    130                 135                 140

Pro Ser Phe Arg Val Ser Gly Phe Glu Val Pro Leu Leu Leu Val Tyr
145                 150                 155                 160

Thr Gln Ala Ala Asn Leu His Leu Ala Leu Leu Arg Asp Ser Val Val
```

-continued

```
                165                 170                 175

Phe Gly Glu Arg Trp Gly Leu Thr Thr Thr Asn Val Asn Asp Ile Tyr
            180                 185                 190

Asn Arg Gln Val Asn Arg Ile Gly Glu Tyr Ser Asn His Cys Val Asp
        195                 200                 205

Thr Tyr Asn Thr Glu Leu Glu Arg Leu Gly Phe Arg Ser Ile Ala Gln
    210                 215                 220

Trp Arg Ile Tyr Asn Gln Phe Arg Arg Glu Leu Thr Leu Thr Val Leu
225                 230                 235                 240

Asp Ile Val Ala Leu Phe Pro Asn Tyr Asp Ser Arg Leu Tyr Pro Ile
                245                 250                 255

Gln Thr Phe Ser Gln Leu Thr Arg Glu Ile Val Thr Ser Pro Val Ser
            260                 265                 270

Glu Phe Tyr Tyr Gly Val Ile Asn Ser Gly Asn Ile Asn Gly Thr Leu
        275                 280                 285

Thr Glu Gln Gln Ile Arg Arg Pro His Leu Met Asp Phe Phe Asn Ser
    290                 295                 300

Met Ile Met Tyr Thr Ser Asp Asn Arg Arg Glu His Tyr Trp Ser Gly
305                 310                 315                 320

Leu Glu Met Thr Ala Tyr Phe Thr Gly Phe Ala Gly Ala Gln Val Ser
                325                 330                 335

Phe Pro Leu Val Gly Thr Arg Gly Glu Ser Ala Pro Pro Leu Thr Val
            340                 345                 350

Arg Ser Val Asn Asp Gly Ile Tyr Arg Ile Leu Ser Ala Pro Phe Tyr
        355                 360                 365

Ser Ala Pro Phe Leu Gly Thr Ile Val Leu Gly Ser Arg Gly Glu Lys
    370                 375                 380

Phe Asp Phe Ala Leu Asn Asn Ile Ser Pro Pro Pro Ser Thr Ile Tyr
385                 390                 395                 400

Arg His Pro Gly Thr Val Asp Ser Leu Val Ser Ile Pro Pro Gln Asp
                405                 410                 415

Asn Ser Val Pro Pro His Arg Gly Ser Ser His Arg Leu Ser His Val
            420                 425                 430

Thr Met Arg Ala Ser Ser Pro Ile Phe His Trp Thr His Arg Ser Ala
        435                 440                 445

Thr Thr Thr Asn Thr Ile Asn Pro Asn Ala Ile Ile Gln Ile Pro Leu
    450                 455                 460

Val Lys Ala Phe Asn Leu His Ser Gly Ala Thr Val Val Arg Gly Pro
465                 470                 475                 480

Gly Phe Thr Gly Gly Asp Ile Leu Arg Arg Thr Asn Thr Gly Thr Phe
                485                 490                 495

Ala Asp Met Arg Val Asn Ile Thr Gly Pro Leu Ser Gln Arg Tyr Arg
            500                 505                 510

Val Arg Ile Arg Tyr Ala Ser Thr Thr Asp Leu Gln Phe Phe Thr Arg
        515                 520                 525

Ile Asn Gly Thr Ser Val Asn Gln Gly Asn Phe Gln Arg Thr Met Asn
    530                 535                 540

Arg Gly Asp Asn Leu Glu Ser Gly Asn Phe Arg Thr Ala Gly Phe Ser
545                 550                 555                 560

Thr Pro Phe Ser Phe Ser Asn Ala Gln Ser Thr Phe Thr Leu Gly Thr
                565                 570                 575

Gln Ala Phe Ser Asn Gln Glu Val Tyr Ile Asp Arg Ile Glu Phe Val
            580                 585                 590
```

```
Pro Ala Glu Val Thr Phe Glu Ala Glu Ser Asp Leu Glu Arg Ala Gln
        595                 600                 605

Lys Ala Val Asn Ala Leu Phe Thr Ser Thr Asn Gln Leu Gly Leu Lys
    610                 615                 620

Thr Asp Val Thr Asp Tyr Gln Ile Asp Gln Val Ser Asn Leu Val Glu
625                 630                 635                 640

Cys Leu Ser Asp Glu Phe Cys Leu Asp Glu Lys Arg Glu Leu Ser Glu
                645                 650                 655

Lys Val Lys His Ala Lys Arg Leu Ser Asp Lys Arg Asn Leu Leu Gln
            660                 665                 670

Asp Pro Asn Phe Thr Ser Ile Asn Arg Gln Leu Asp Arg Gly Trp Arg
        675                 680                 685

Gly Ser Thr Asp Ile Thr Ile Gln Gly Gly Asn Asp Val Phe Lys Glu
    690                 695                 700

Asn Tyr Val Thr Leu Pro Gly Thr Phe Asp Glu Cys Tyr Pro Thr Tyr
705                 710                 715                 720

Leu Tyr Gln Lys Ile Asp Glu Ser Lys Leu Lys Ala Tyr Thr Arg Tyr
                725                 730                 735

Glu Leu Arg Gly Tyr Ile Glu Asp Ser Gln Asp Leu Glu Val Tyr Leu
            740                 745                 750

Ile Arg Tyr Asn Ala Lys His Glu Thr Val Asn Val Pro Gly Thr Gly
        755                 760                 765

Ser Leu Trp Pro Leu Ser Val Glu Ser Pro Ile Gly Arg Cys Gly Glu
    770                 775                 780

Pro Asn Arg Cys Val Pro His Ile Glu Trp Asn Pro Asp Leu Asp Cys
785                 790                 795                 800

Ser Cys Arg Asp Gly Glu Lys Cys Ala His His Ser His His Phe Ser
                805                 810                 815

Leu Asp Ile Asp Val Gly Cys Thr Asp Leu Asn Glu Asp Leu Gly Val
            820                 825                 830

Trp Val Ile Phe Lys Ile Lys Thr Gln Asp Gly His Ala Arg Leu Gly
        835                 840                 845

Asn Leu Glu Phe Leu Glu Glu Lys Pro Leu Leu Gly Glu Ala Leu Ala
    850                 855                 860

Arg Val Lys Arg Ala Glu Lys Lys Trp Arg Asp Lys Arg Glu Gln Leu
865                 870                 875                 880

Gln Phe Glu Thr Asn Ile Val Tyr Lys Glu Ala Lys Glu Ser Val Asp
                885                 890                 895

Ala Leu Phe Val Asp Ser His Tyr Asn Arg Leu Gln Ala Asp Thr Asn
            900                 905                 910

Ile Thr Met Ile His Ala Ala Asp Lys Arg Val His Arg Ile Arg Glu
        915                 920                 925

Ala Tyr Leu Pro Glu Leu Ser Val Ile Pro Gly Val Asn Ala Asp Ile
    930                 935                 940

Phe Glu Glu Leu Glu Gly Leu Ile Phe Thr Ala Phe Ser Leu Tyr Asp
945                 950                 955                 960

Ala Arg Asn Ile Ile Lys Asn Gly Asp Phe Asn Asn Gly Leu Ser Cys
                965                 970                 975

Trp Asn Val Lys Gly His Val Asp Ile Gln Gln Asn Asp His Arg Ser
            980                 985                 990

Val Leu Val Val Pro Glu Trp Glu  Ser Glu Val Ser Gln  Glu Val Arg
        995                 1000                1005
```

```
Val Cys  Pro Gly Arg Gly Tyr  Ile Leu Arg Val Thr  Ala Tyr Lys
    1010                 1015                 1020

Glu Gly  Tyr Gly Glu Gly Cys  Val Thr Ile His Glu  Ile Glu Asp
    1025                 1030                 1035

Asn Thr  Asp Glu Leu Lys Phe  Ser Asn Cys Ile Glu  Glu Glu Val
    1040                 1045                 1050

Tyr Pro  Thr Asp Thr Gly Asn  Asp Tyr Thr Ala His  Gln Gly Thr
    1055                 1060                 1065

Thr Gly  Cys Ala Asp Ala Cys  Asn Ser Arg Asn Val  Gly Tyr Glu
    1070                 1075                 1080

Asp Gly  Tyr Glu Ile Asn Thr  Thr Ala Ser Val Asn  Tyr Lys Pro
    1085                 1090                 1095

Thr Tyr  Glu Glu Glu Met Tyr  Thr Asp Val Arg Arg  Asp Asn His
    1100                 1105                 1110

Cys Glu  Tyr Asp Arg Gly Tyr  Gly Asn His Thr Pro  Leu Pro Ala
    1115                 1120                 1125

Gly Tyr  Val Thr Lys Glu Leu  Glu Tyr Phe Pro Glu  Thr Asp Thr
    1130                 1135                 1140

Val Trp  Ile Glu Ile Gly Glu  Thr Glu Gly Thr Phe  Ile Val Asp
    1145                 1150                 1155

Ser Val  Glu Leu Leu Leu Met  Glu Glu
    1160                 1165


<210> SEQ ID NO 8
<211> LENGTH: 1167
<212> TYPE: PRT
<213> ORGANISM: Artificial Sequence
<220> FEATURE:
<223> OTHER INFORMATION: Modified alpha-helix 4 BT0002
<220> FEATURE:
<221> NAME/KEY: MISC_FEATURE
<222> LOCATION: (123)..(150)
<223> OTHER INFORMATION: BT0002 block 2 mutations: T123E; R126K; T130I;
      E131D; I136L; A138G; Q139L; V149I & V150I

<400> SEQUENCE: 8

Met Glu Ile Asn Asn Gln Lys Gln Cys Ile Pro Tyr Asn Cys Leu Ser
1               5                   10                  15

Asn Pro Glu Glu Val Leu Leu Asp Gly Glu Arg Ile Leu Pro Asp Ile
            20                  25                  30

Asp Pro Leu Glu Val Ser Leu Ser Leu Leu Gln Phe Leu Leu Asn Asn
        35                  40                  45

Phe Val Pro Gly Gly Gly Phe Ile Ser Gly Leu Val Asp Lys Ile Trp
    50                  55                  60

Gly Ala Leu Arg Pro Ser Glu Trp Asp Leu Phe Leu Ala Gln Ile Glu
65                  70                  75                  80

Arg Leu Ile Asp Gln Arg Ile Glu Ala Thr Val Arg Ala Lys Ala Ile
                85                  90                  95

Ala Glu Leu Glu Gly Leu Gly Arg Ser Tyr Gln Leu Tyr Gly Glu Ala
            100                 105                 110

Phe Lys Glu Trp Glu Lys Thr Pro Asp Asn Glu Ala Ala Lys Ser Arg
        115                 120                 125

Val Ile Asp Arg Phe Arg Ile Leu Asp Gly Ile Ile Glu Ala Asn Ile
    130                 135                 140

Pro Ser Phe Arg Ile Ile Gly Phe Glu Val Pro Leu Leu Leu Val Tyr
145                 150                 155                 160

Thr Gln Ala Ala Asn Leu His Leu Ala Leu Leu Arg Asp Ser Val Val
```

-continued

```
                165                 170                 175

Phe Gly Glu Arg Trp Gly Leu Thr Thr Thr Asn Val Asn Asp Ile Tyr
            180                 185                 190

Asn Arg Gln Val Asn Arg Ile Gly Glu Tyr Ser Asn His Cys Val Asp
        195                 200                 205

Thr Tyr Asn Thr Glu Leu Glu Arg Leu Gly Phe Arg Ser Ile Ala Gln
    210                 215                 220

Trp Arg Ile Tyr Asn Gln Phe Arg Arg Glu Leu Thr Leu Thr Val Leu
225                 230                 235                 240

Asp Ile Val Ala Leu Phe Pro Asn Tyr Asp Ser Arg Leu Tyr Pro Ile
                245                 250                 255

Gln Thr Phe Ser Gln Leu Thr Arg Glu Ile Val Thr Ser Pro Val Ser
            260                 265                 270

Glu Phe Tyr Tyr Gly Val Ile Asn Ser Gly Asn Ile Asn Gly Thr Leu
        275                 280                 285

Thr Glu Gln Gln Ile Arg Arg Pro His Leu Met Asp Phe Phe Asn Ser
    290                 295                 300

Met Ile Met Tyr Thr Ser Asp Asn Arg Arg Glu His Tyr Trp Ser Gly
305                 310                 315                 320

Leu Glu Met Thr Ala Tyr Phe Thr Gly Phe Ala Gly Ala Gln Val Ser
                325                 330                 335

Phe Pro Leu Val Gly Thr Arg Gly Glu Ser Ala Pro Pro Leu Thr Val
            340                 345                 350

Arg Ser Val Asn Asp Gly Ile Tyr Arg Ile Leu Ser Ala Pro Phe Tyr
        355                 360                 365

Ser Ala Pro Phe Leu Gly Thr Ile Val Leu Gly Ser Arg Gly Glu Lys
    370                 375                 380

Phe Asp Phe Ala Leu Asn Asn Ile Ser Pro Pro Pro Ser Thr Ile Tyr
385                 390                 395                 400

Arg His Pro Gly Thr Val Asp Ser Leu Val Ser Ile Pro Pro Gln Asp
                405                 410                 415

Asn Ser Val Pro Pro His Arg Gly Ser Ser His Arg Leu Ser His Val
            420                 425                 430

Thr Met Arg Ala Ser Ser Pro Ile Phe His Trp Thr His Arg Ser Ala
        435                 440                 445

Thr Thr Thr Asn Thr Ile Asn Pro Asn Ala Ile Ile Gln Ile Pro Leu
    450                 455                 460

Val Lys Ala Phe Asn Leu His Ser Gly Ala Thr Val Val Arg Gly Pro
465                 470                 475                 480

Gly Phe Thr Gly Gly Asp Ile Leu Arg Arg Thr Asn Thr Gly Thr Phe
                485                 490                 495

Ala Asp Met Arg Val Asn Ile Thr Gly Pro Leu Ser Gln Arg Tyr Arg
            500                 505                 510

Val Arg Ile Arg Tyr Ala Ser Thr Thr Asp Leu Gln Phe Phe Thr Arg
        515                 520                 525

Ile Asn Gly Thr Ser Val Asn Gln Gly Asn Phe Gln Arg Thr Met Asn
    530                 535                 540

Arg Gly Asp Asn Leu Glu Ser Gly Asn Phe Arg Thr Ala Gly Phe Ser
545                 550                 555                 560

Thr Pro Phe Ser Phe Ser Asn Ala Gln Ser Thr Phe Thr Leu Gly Thr
                565                 570                 575

Gln Ala Phe Ser Asn Gln Glu Val Tyr Ile Asp Arg Ile Glu Phe Val
            580                 585                 590
```

-continued

```
Pro Ala Glu Val Thr Phe Glu Ala Glu Ser Asp Leu Glu Arg Ala Gln
        595                 600                 605

Lys Ala Val Asn Ala Leu Phe Thr Ser Thr Asn Gln Leu Gly Leu Lys
    610                 615                 620

Thr Asp Val Thr Asp Tyr Gln Ile Asp Gln Val Ser Asn Leu Val Glu
625                 630                 635                 640

Cys Leu Ser Asp Glu Phe Cys Leu Asp Glu Lys Arg Glu Leu Ser Glu
                645                 650                 655

Lys Val Lys His Ala Lys Arg Leu Ser Asp Lys Arg Asn Leu Leu Gln
            660                 665                 670

Asp Pro Asn Phe Thr Ser Ile Asn Arg Gln Leu Asp Arg Gly Trp Arg
        675                 680                 685

Gly Ser Thr Asp Ile Thr Ile Gln Gly Gly Asn Asp Val Phe Lys Glu
    690                 695                 700

Asn Tyr Val Thr Leu Pro Gly Thr Phe Asp Glu Cys Tyr Pro Thr Tyr
705                 710                 715                 720

Leu Tyr Gln Lys Ile Asp Glu Ser Lys Leu Lys Ala Tyr Thr Arg Tyr
                725                 730                 735

Glu Leu Arg Gly Tyr Ile Glu Asp Ser Gln Asp Leu Glu Val Tyr Leu
            740                 745                 750

Ile Arg Tyr Asn Ala Lys His Glu Thr Val Asn Val Pro Gly Thr Gly
        755                 760                 765

Ser Leu Trp Pro Leu Ser Val Glu Ser Pro Ile Gly Arg Cys Gly Glu
    770                 775                 780

Pro Asn Arg Cys Val Pro His Ile Glu Trp Asn Pro Asp Leu Asp Cys
785                 790                 795                 800

Ser Cys Arg Asp Gly Glu Lys Cys Ala His His Ser His His Phe Ser
                805                 810                 815

Leu Asp Ile Asp Val Gly Cys Thr Asp Leu Asn Glu Asp Leu Gly Val
            820                 825                 830

Trp Val Ile Phe Lys Ile Lys Thr Gln Asp Gly His Ala Arg Leu Gly
        835                 840                 845

Asn Leu Glu Phe Leu Glu Glu Lys Pro Leu Leu Gly Glu Ala Leu Ala
    850                 855                 860

Arg Val Lys Arg Ala Glu Lys Lys Trp Arg Asp Lys Arg Glu Gln Leu
865                 870                 875                 880

Gln Phe Glu Thr Asn Ile Val Tyr Lys Glu Ala Lys Glu Ser Val Asp
                885                 890                 895

Ala Leu Phe Val Asp Ser His Tyr Asn Arg Leu Gln Ala Asp Thr Asn
            900                 905                 910

Ile Thr Met Ile His Ala Ala Asp Lys Arg Val His Arg Ile Arg Glu
        915                 920                 925

Ala Tyr Leu Pro Glu Leu Ser Val Ile Pro Gly Val Asn Ala Asp Ile
    930                 935                 940

Phe Glu Glu Leu Glu Gly Leu Ile Phe Thr Ala Phe Ser Leu Tyr Asp
945                 950                 955                 960

Ala Arg Asn Ile Ile Lys Asn Gly Asp Phe Asn Asn Gly Leu Ser Cys
                965                 970                 975

Trp Asn Val Lys Gly His Val Asp Ile Gln Gln Asn Asp His Arg Ser
            980                 985                 990

Val Leu Val Val Pro Glu Trp Glu  Ser Glu Val Ser Gln  Glu Val Arg
        995                 1000                1005
```

Val Cys Pro Gly Arg Gly Tyr Ile Leu Arg Val Thr Ala Tyr Lys
1010 1015 1020

Glu Gly Tyr Gly Glu Gly Cys Val Thr Ile His Glu Ile Glu Asp
1025 1030 1035

Asn Thr Asp Glu Leu Lys Phe Ser Asn Cys Ile Glu Glu Glu Val
1040 1045 1050

Tyr Pro Thr Asp Thr Gly Asn Asp Tyr Thr Ala His Gln Gly Thr
1055 1060 1065

Thr Gly Cys Ala Asp Ala Cys Asn Ser Arg Asn Val Gly Tyr Glu
1070 1075 1080

Asp Gly Tyr Glu Ile Asn Thr Thr Ala Ser Val Asn Tyr Lys Pro
1085 1090 1095

Thr Tyr Glu Glu Glu Met Tyr Thr Asp Val Arg Arg Asp Asn His
1100 1105 1110

Cys Glu Tyr Asp Arg Gly Tyr Gly Asn His Thr Pro Leu Pro Ala
1115 1120 1125

Gly Tyr Val Thr Lys Glu Leu Glu Tyr Phe Pro Glu Thr Asp Thr
1130 1135 1140

Val Trp Ile Glu Ile Gly Glu Thr Glu Gly Thr Phe Ile Val Asp
1145 1150 1155

Ser Val Glu Leu Leu Leu Met Glu Glu
1160 1165

<210> SEQ ID NO 9
<211> LENGTH: 1167
<212> TYPE: PRT
<213> ORGANISM: Artificial Sequence
<220> FEATURE:
<223> OTHER INFORMATION: Modified alpha-helix 5/6 BT0002
<220> FEATURE:
<221> NAME/KEY: MISC_FEATURE
<222> LOCATION: (158)..(200)
<223> OTHER INFORMATION: BT0002 block 3 mutations: L158S; T161V; V176I; T186K; V196I; N197R; R198E & G200H

<400> SEQUENCE: 9

Met Glu Ile Asn Asn Gln Lys Gln Cys Ile Pro Tyr Asn Cys Leu Ser
1 5 10 15

Asn Pro Glu Glu Val Leu Leu Asp Gly Glu Arg Ile Leu Pro Asp Ile
20 25 30

Asp Pro Leu Glu Val Ser Leu Ser Leu Leu Gln Phe Leu Leu Asn Asn
35 40 45

Phe Val Pro Gly Gly Gly Phe Ile Ser Gly Leu Val Asp Lys Ile Trp
50 55 60

Gly Ala Leu Arg Pro Ser Glu Trp Asp Leu Phe Leu Ala Gln Ile Glu
65 70 75 80

Arg Leu Ile Asp Gln Arg Ile Glu Ala Thr Val Arg Ala Lys Ala Ile
85 90 95

Ala Glu Leu Glu Gly Leu Gly Arg Ser Tyr Gln Leu Tyr Gly Glu Ala
100 105 110

Phe Lys Glu Trp Glu Lys Thr Pro Asp Asn Thr Ala Ala Arg Ser Arg
115 120 125

Val Thr Glu Arg Phe Arg Ile Ile Asp Ala Gln Ile Glu Ala Asn Ile
130 135 140

Pro Ser Phe Arg Val Ser Gly Phe Glu Val Pro Leu Leu Ser Val Tyr
145 150 155 160

Val Gln Ala Ala Asn Leu His Leu Ala Leu Leu Arg Asp Ser Val Ile

```
                165                 170                 175

Phe Gly Glu Arg Trp Gly Leu Thr Thr Lys Asn Val Asn Asp Ile Tyr
            180                 185                 190

Asn Arg Gln Ile Arg Glu Ile His Glu Tyr Ser Asn His Cys Val Asp
        195                 200                 205

Thr Tyr Asn Thr Glu Leu Glu Arg Leu Gly Phe Arg Ser Ile Ala Gln
    210                 215                 220

Trp Arg Ile Tyr Asn Gln Phe Arg Arg Glu Leu Thr Leu Thr Val Leu
225                 230                 235                 240

Asp Ile Val Ala Leu Phe Pro Asn Tyr Asp Ser Arg Leu Tyr Pro Ile
                245                 250                 255

Gln Thr Phe Ser Gln Leu Thr Arg Glu Ile Val Thr Ser Pro Val Ser
            260                 265                 270

Glu Phe Tyr Tyr Gly Val Ile Asn Ser Gly Asn Ile Asn Gly Thr Leu
        275                 280                 285

Thr Glu Gln Gln Ile Arg Arg Pro His Leu Met Asp Phe Phe Asn Ser
    290                 295                 300

Met Ile Met Tyr Thr Ser Asp Asn Arg Arg Glu His Tyr Trp Ser Gly
305                 310                 315                 320

Leu Glu Met Thr Ala Tyr Phe Thr Gly Phe Ala Gly Ala Gln Val Ser
                325                 330                 335

Phe Pro Leu Val Gly Thr Arg Gly Glu Ser Ala Pro Pro Leu Thr Val
            340                 345                 350

Arg Ser Val Asn Asp Gly Ile Tyr Arg Ile Leu Ser Ala Pro Phe Tyr
        355                 360                 365

Ser Ala Pro Phe Leu Gly Thr Ile Val Leu Gly Ser Arg Gly Glu Lys
    370                 375                 380

Phe Asp Phe Ala Leu Asn Asn Ile Ser Pro Pro Pro Ser Thr Ile Tyr
385                 390                 395                 400

Arg His Pro Gly Thr Val Asp Ser Leu Val Ser Ile Pro Pro Gln Asp
                405                 410                 415

Asn Ser Val Pro Pro His Arg Gly Ser Ser His Arg Leu Ser His Val
            420                 425                 430

Thr Met Arg Ala Ser Ser Pro Ile Phe His Trp Thr His Arg Ser Ala
        435                 440                 445

Thr Thr Thr Asn Thr Ile Asn Pro Asn Ala Ile Ile Gln Ile Pro Leu
    450                 455                 460

Val Lys Ala Phe Asn Leu His Ser Gly Ala Thr Val Val Arg Gly Pro
465                 470                 475                 480

Gly Phe Thr Gly Gly Asp Ile Leu Arg Arg Thr Asn Thr Gly Thr Phe
                485                 490                 495

Ala Asp Met Arg Val Asn Ile Thr Gly Pro Leu Ser Gln Arg Tyr Arg
            500                 505                 510

Val Arg Ile Arg Tyr Ala Ser Thr Thr Asp Leu Gln Phe Phe Thr Arg
        515                 520                 525

Ile Asn Gly Thr Ser Val Asn Gln Gly Asn Phe Gln Arg Thr Met Asn
    530                 535                 540

Arg Gly Asp Asn Leu Glu Ser Gly Asn Phe Arg Thr Ala Gly Phe Ser
545                 550                 555                 560

Thr Pro Phe Ser Phe Ser Asn Ala Gln Ser Thr Phe Thr Leu Gly Thr
                565                 570                 575

Gln Ala Phe Ser Asn Gln Glu Val Tyr Ile Asp Arg Ile Glu Phe Val
            580                 585                 590
```

-continued

```
Pro Ala Glu Val Thr Phe Glu Ala Glu Ser Asp Leu Glu Arg Ala Gln
        595                 600                 605

Lys Ala Val Asn Ala Leu Phe Thr Ser Thr Asn Gln Leu Gly Leu Lys
    610                 615                 620

Thr Asp Val Thr Asp Tyr Gln Ile Asp Gln Val Ser Asn Leu Val Glu
625                 630                 635                 640

Cys Leu Ser Asp Glu Phe Cys Leu Asp Glu Lys Arg Glu Leu Ser Glu
                645                 650                 655

Lys Val Lys His Ala Lys Arg Leu Ser Asp Lys Arg Asn Leu Leu Gln
            660                 665                 670

Asp Pro Asn Phe Thr Ser Ile Asn Arg Gln Leu Asp Arg Gly Trp Arg
        675                 680                 685

Gly Ser Thr Asp Ile Thr Ile Gln Gly Gly Asn Asp Val Phe Lys Glu
    690                 695                 700

Asn Tyr Val Thr Leu Pro Gly Thr Phe Asp Glu Cys Tyr Pro Thr Tyr
705                 710                 715                 720

Leu Tyr Gln Lys Ile Asp Glu Ser Lys Leu Lys Ala Tyr Thr Arg Tyr
                725                 730                 735

Glu Leu Arg Gly Tyr Ile Glu Asp Ser Gln Asp Leu Glu Val Tyr Leu
            740                 745                 750

Ile Arg Tyr Asn Ala Lys His Glu Thr Val Asn Val Pro Gly Thr Gly
        755                 760                 765

Ser Leu Trp Pro Leu Ser Val Glu Ser Pro Ile Gly Arg Cys Gly Glu
    770                 775                 780

Pro Asn Arg Cys Val Pro His Ile Glu Trp Asn Pro Asp Leu Asp Cys
785                 790                 795                 800

Ser Cys Arg Asp Gly Glu Lys Cys Ala His His Ser His His Phe Ser
                805                 810                 815

Leu Asp Ile Asp Val Gly Cys Thr Asp Leu Asn Glu Asp Leu Gly Val
            820                 825                 830

Trp Val Ile Phe Lys Ile Lys Thr Gln Asp Gly His Ala Arg Leu Gly
        835                 840                 845

Asn Leu Glu Phe Leu Glu Glu Lys Pro Leu Leu Gly Glu Ala Leu Ala
    850                 855                 860

Arg Val Lys Arg Ala Glu Lys Lys Trp Arg Asp Lys Arg Glu Gln Leu
865                 870                 875                 880

Gln Phe Glu Thr Asn Ile Val Tyr Lys Glu Ala Lys Glu Ser Val Asp
                885                 890                 895

Ala Leu Phe Val Asp Ser His Tyr Asn Arg Leu Gln Ala Asp Thr Asn
            900                 905                 910

Ile Thr Met Ile His Ala Ala Asp Lys Arg Val His Arg Ile Arg Glu
        915                 920                 925

Ala Tyr Leu Pro Glu Leu Ser Val Ile Pro Gly Val Asn Ala Asp Ile
    930                 935                 940

Phe Glu Glu Leu Glu Gly Leu Ile Phe Thr Ala Phe Ser Leu Tyr Asp
945                 950                 955                 960

Ala Arg Asn Ile Ile Lys Asn Gly Asp Phe Asn Asn Gly Leu Ser Cys
                965                 970                 975

Trp Asn Val Lys Gly His Val Asp Ile Gln Gln Asn Asp His Arg Ser
            980                 985                 990

Val Leu Val Val Pro Glu Trp Glu  Ser Glu Val Ser Gln  Glu Val Arg
        995                 1000                1005
```

```
Val Cys  Pro Gly Arg Gly Tyr  Ile Leu Arg Val Thr  Ala Tyr Lys
    1010                 1015                 1020

Glu Gly  Tyr Gly Glu Gly Cys  Val Thr Ile His Glu  Ile Glu Asp
    1025                 1030                 1035

Asn Thr  Asp Glu Leu Lys Phe  Ser Asn Cys Ile Glu  Glu Glu Val
    1040                 1045                 1050

Tyr Pro  Thr Asp Thr Gly Asn  Asp Tyr Thr Ala His  Gln Gly Thr
    1055                 1060                 1065

Thr Gly  Cys Ala Asp Ala Cys  Asn Ser Arg Asn Val  Gly Tyr Glu
    1070                 1075                 1080

Asp Gly  Tyr Glu Ile Asn Thr  Thr Ala Ser Val Asn  Tyr Lys Pro
    1085                 1090                 1095

Thr Tyr  Glu Glu Glu Met Tyr  Thr Asp Val Arg Arg  Asp Asn His
    1100                 1105                 1110

Cys Glu  Tyr Asp Arg Gly Tyr  Gly Asn His Thr Pro  Leu Pro Ala
    1115                 1120                 1125

Gly Tyr  Val Thr Lys Glu Leu  Glu Tyr Phe Pro Glu  Thr Asp Thr
    1130                 1135                 1140

Val Trp  Ile Glu Ile Gly Glu  Thr Glu Gly Thr Phe  Ile Val Asp
    1145                 1150                 1155

Ser Val  Glu Leu Leu Leu Met  Glu Glu
    1160                 1165


<210> SEQ ID NO 10
<211> LENGTH: 1167
<212> TYPE: PRT
<213> ORGANISM: Artificial Sequence
<220> FEATURE:
<223> OTHER INFORMATION: Modfied alpha-helix 3/4 BT0002
<220> FEATURE:
<221> NAME/KEY: MISC_FEATURE
<222> LOCATION: (97)..(150)
<223> OTHER INFORMATION: BT0002 blocks 1 & 2 mutations: A97T; S105N;
      L108I; G110A; K118S; T119D; T123E; R126K; T130I; E131D; I136L;
      A138G; Q139L; V149I & V150I

<400> SEQUENCE: 10

Met Glu Ile Asn Asn Gln Lys Gln Cys Ile Pro Tyr Asn Cys Leu Ser
1               5                   10                  15

Asn Pro Glu Glu Val Leu Leu Asp Gly Glu Arg Ile Leu Pro Asp Ile
            20                  25                  30

Asp Pro Leu Glu Val Ser Leu Ser Leu Leu Gln Phe Leu Leu Asn Asn
        35                  40                  45

Phe Val Pro Gly Gly Gly Phe Ile Ser Gly Leu Val Asp Lys Ile Trp
    50                  55                  60

Gly Ala Leu Arg Pro Ser Glu Trp Asp Leu Phe Leu Ala Gln Ile Glu
65                  70                  75                  80

Arg Leu Ile Asp Gln Arg Ile Glu Ala Thr Val Arg Ala Lys Ala Ile
                85                  90                  95

Thr Glu Leu Glu Gly Leu Gly Arg Asn Tyr Gln Ile Tyr Ala Glu Ala
            100                 105                 110

Phe Lys Glu Trp Glu Ser Cys Pro Asp Asn Glu Ala Ala Lys Ser Arg
        115                 120                 125

Val Ile Asp Arg Phe Arg Ile Leu Asp Gly Ile Ile Glu Ala Asn Ile
    130                 135                 140

Pro Ser Phe Arg Ile Ile Gly Phe Glu Val Pro Leu Leu Leu Val Tyr
145                 150                 155                 160
```

-continued

```
Thr Gln Ala Ala Asn Leu His Leu Ala Leu Leu Arg Asp Ser Val Val
                165                 170                 175

Phe Gly Glu Arg Trp Gly Leu Thr Thr Thr Asn Val Asn Asp Ile Tyr
            180                 185                 190

Asn Arg Gln Val Asn Arg Ile Gly Glu Tyr Ser Asn His Cys Val Asp
        195                 200                 205

Thr Tyr Asn Thr Glu Leu Glu Arg Leu Gly Phe Arg Ser Ile Ala Gln
    210                 215                 220

Trp Arg Ile Tyr Asn Gln Phe Arg Arg Glu Leu Thr Leu Thr Val Leu
225                 230                 235                 240

Asp Ile Val Ala Leu Phe Pro Asn Tyr Asp Ser Arg Leu Tyr Pro Ile
                245                 250                 255

Gln Thr Phe Ser Gln Leu Thr Arg Glu Ile Val Thr Ser Pro Val Ser
            260                 265                 270

Glu Phe Tyr Tyr Gly Val Ile Asn Ser Gly Asn Ile Asn Gly Thr Leu
        275                 280                 285

Thr Glu Gln Gln Ile Arg Arg Pro His Leu Met Asp Phe Phe Asn Ser
    290                 295                 300

Met Ile Met Tyr Thr Ser Asp Asn Arg Arg Glu His Tyr Trp Ser Gly
305                 310                 315                 320

Leu Glu Met Thr Ala Tyr Phe Thr Gly Phe Ala Gly Ala Gln Val Ser
                325                 330                 335

Phe Pro Leu Val Gly Thr Arg Gly Glu Ser Ala Pro Pro Leu Thr Val
            340                 345                 350

Arg Ser Val Asn Asp Gly Ile Tyr Arg Ile Leu Ser Ala Pro Phe Tyr
        355                 360                 365

Ser Ala Pro Phe Leu Gly Thr Ile Val Leu Gly Ser Arg Gly Glu Lys
    370                 375                 380

Phe Asp Phe Ala Leu Asn Asn Ile Ser Pro Pro Pro Ser Thr Ile Tyr
385                 390                 395                 400

Arg His Pro Gly Thr Val Asp Ser Leu Val Ser Ile Pro Pro Gln Asp
                405                 410                 415

Asn Ser Val Pro Pro His Arg Gly Ser Ser His Arg Leu Ser His Val
            420                 425                 430

Thr Met Arg Ala Ser Ser Pro Ile Phe His Trp Thr His Arg Ser Ala
        435                 440                 445

Thr Thr Thr Asn Thr Ile Asn Pro Asn Ala Ile Ile Gln Ile Pro Leu
    450                 455                 460

Val Lys Ala Phe Asn Leu His Ser Gly Ala Thr Val Val Arg Gly Pro
465                 470                 475                 480

Gly Phe Thr Gly Gly Asp Ile Leu Arg Arg Thr Asn Thr Gly Thr Phe
                485                 490                 495

Ala Asp Met Arg Val Asn Ile Thr Gly Pro Leu Ser Gln Arg Tyr Arg
            500                 505                 510

Val Arg Ile Arg Tyr Ala Ser Thr Thr Asp Leu Gln Phe Phe Thr Arg
        515                 520                 525

Ile Asn Gly Thr Ser Val Asn Gln Gly Asn Phe Gln Arg Thr Met Asn
    530                 535                 540

Arg Gly Asp Asn Leu Glu Ser Gly Asn Phe Arg Thr Ala Gly Phe Ser
545                 550                 555                 560

Thr Pro Phe Ser Phe Ser Asn Ala Gln Ser Thr Phe Thr Leu Gly Thr
                565                 570                 575

Gln Ala Phe Ser Asn Gln Glu Val Tyr Ile Asp Arg Ile Glu Phe Val
```

```
            580                 585                 590

Pro Ala Glu Val Thr Phe Glu Ala Glu Ser Asp Leu Glu Arg Ala Gln
        595                 600                 605

Lys Ala Val Asn Ala Leu Phe Thr Ser Thr Asn Gln Leu Gly Leu Lys
    610                 615                 620

Thr Asp Val Thr Asp Tyr Gln Ile Asp Gln Val Ser Asn Leu Val Glu
625                 630                 635                 640

Cys Leu Ser Asp Glu Phe Cys Leu Asp Glu Lys Arg Glu Leu Ser Glu
                645                 650                 655

Lys Val Lys His Ala Lys Arg Leu Ser Asp Lys Arg Asn Leu Leu Gln
            660                 665                 670

Asp Pro Asn Phe Thr Ser Ile Asn Arg Gln Leu Asp Arg Gly Trp Arg
        675                 680                 685

Gly Ser Thr Asp Ile Thr Ile Gln Gly Gly Asn Asp Val Phe Lys Glu
    690                 695                 700

Asn Tyr Val Thr Leu Pro Gly Thr Phe Asp Glu Cys Tyr Pro Thr Tyr
705                 710                 715                 720

Leu Tyr Gln Lys Ile Asp Glu Ser Lys Leu Lys Ala Tyr Thr Arg Tyr
                725                 730                 735

Glu Leu Arg Gly Tyr Ile Glu Asp Ser Gln Asp Leu Glu Val Tyr Leu
            740                 745                 750

Ile Arg Tyr Asn Ala Lys His Glu Thr Val Asn Val Pro Gly Thr Gly
        755                 760                 765

Ser Leu Trp Pro Leu Ser Val Glu Ser Pro Ile Gly Arg Cys Gly Glu
    770                 775                 780

Pro Asn Arg Cys Val Pro His Ile Glu Trp Asn Pro Asp Leu Asp Cys
785                 790                 795                 800

Ser Cys Arg Asp Gly Glu Lys Cys Ala His His Ser His His Phe Ser
                805                 810                 815

Leu Asp Ile Asp Val Gly Cys Thr Asp Leu Asn Glu Asp Leu Gly Val
            820                 825                 830

Trp Val Ile Phe Lys Ile Lys Thr Gln Asp Gly His Ala Arg Leu Gly
        835                 840                 845

Asn Leu Glu Phe Leu Glu Glu Lys Pro Leu Leu Gly Glu Ala Leu Ala
    850                 855                 860

Arg Val Lys Arg Ala Glu Lys Lys Trp Arg Asp Lys Arg Glu Gln Leu
865                 870                 875                 880

Gln Phe Glu Thr Asn Ile Val Tyr Lys Glu Ala Lys Glu Ser Val Asp
                885                 890                 895

Ala Leu Phe Val Asp Ser His Tyr Asn Arg Leu Gln Ala Asp Thr Asn
            900                 905                 910

Ile Thr Met Ile His Ala Ala Asp Lys Arg Val His Arg Ile Arg Glu
        915                 920                 925

Ala Tyr Leu Pro Glu Leu Ser Val Ile Pro Gly Val Asn Ala Asp Ile
    930                 935                 940

Phe Glu Glu Leu Glu Gly Leu Ile Phe Thr Ala Phe Ser Leu Tyr Asp
945                 950                 955                 960

Ala Arg Asn Ile Ile Lys Asn Gly Asp Phe Asn Asn Gly Leu Ser Cys
                965                 970                 975

Trp Asn Val Lys Gly His Val Asp Ile Gln Gln Asn Asp His Arg Ser
            980                 985                 990

Val Leu Val Val Pro Glu Trp Glu  Ser Glu Val Ser Gln  Glu Val Arg
        995                 1000                1005
```

```
Val Cys  Pro Gly Arg Gly Tyr  Ile Leu Arg Val Thr  Ala Tyr Lys
    1010                 1015                 1020

Glu Gly  Tyr Gly Glu Gly Cys  Val Thr Ile His Glu  Ile Glu Asp
    1025                 1030                 1035

Asn Thr  Asp Glu Leu Lys Phe  Ser Asn Cys Ile Glu  Glu Glu Val
    1040                 1045                 1050

Tyr Pro  Thr Asp Thr Gly Asn  Asp Tyr Thr Ala His  Gln Gly Thr
    1055                 1060                 1065

Thr Gly  Cys Ala Asp Ala Cys  Asn Ser Arg Asn Val  Gly Tyr Glu
    1070                 1075                 1080

Asp Gly  Tyr Glu Ile Asn Thr  Thr Ala Ser Val Asn  Tyr Lys Pro
    1085                 1090                 1095

Thr Tyr  Glu Glu Glu Met Tyr  Thr Asp Val Arg Arg  Asp Asn His
    1100                 1105                 1110

Cys Glu  Tyr Asp Arg Gly Tyr  Gly Asn His Thr Pro  Leu Pro Ala
    1115                 1120                 1125

Gly Tyr  Val Thr Lys Glu Leu  Glu Tyr Phe Pro Glu  Thr Asp Thr
    1130                 1135                 1140

Val Trp  Ile Glu Ile Gly Glu  Thr Glu Gly Thr Phe  Ile Val Asp
    1145                 1150                 1155

Ser Val  Glu Leu Leu Leu Met  Glu Glu
    1160                 1165


<210> SEQ ID NO 11
<211> LENGTH: 1167
<212> TYPE: PRT
<213> ORGANISM: Artificial Sequence
<220> FEATURE:
<223> OTHER INFORMATION: Modified alpha-helix 4/5/6 BT0002
<220> FEATURE:
<221> NAME/KEY: MISC_FEATURE
<222> LOCATION: (123)..(200)
<223> OTHER INFORMATION: BT0002 blocks 2 & 3 mutations; T123E; R126K;
      T130I; E131D; I136L; A138G; Q139L; V149I; V150I; L158S; T161V;
      V176I; T186K; V196I; N197R; R198E & G200H

<400> SEQUENCE: 11

Met Glu Ile Asn Asn Gln Lys Gln Cys Ile Pro Tyr Asn Cys Leu Ser
1               5                   10                  15

Asn Pro Glu Glu Val Leu Leu Asp Gly Glu Arg Ile Leu Pro Asp Ile
            20                  25                  30

Asp Pro Leu Glu Val Ser Leu Ser Leu Leu Gln Phe Leu Leu Asn Asn
        35                  40                  45

Phe Val Pro Gly Gly Gly Phe Ile Ser Gly Leu Val Asp Lys Ile Trp
    50                  55                  60

Gly Ala Leu Arg Pro Ser Glu Trp Asp Leu Phe Leu Ala Gln Ile Glu
65                  70                  75                  80

Arg Leu Ile Asp Gln Arg Ile Glu Ala Thr Val Arg Ala Lys Ala Ile
                85                  90                  95

Ala Glu Leu Glu Gly Leu Gly Arg Ser Tyr Gln Leu Tyr Gly Glu Ala
            100                 105                 110

Phe Lys Glu Trp Glu Lys Thr Pro Asp Asn Glu Ala Ala Lys Ser Arg
        115                 120                 125

Val Ile Asp Arg Phe Arg Ile Leu Asp Gly Ile Ile Glu Ala Asn Ile
    130                 135                 140

Pro Ser Phe Arg Ile Ile Gly Phe Glu Val Pro Leu Leu Ser Val Tyr
145                 150                 155                 160
```

```
Val Gln Ala Ala Asn Leu His Leu Ala Leu Leu Arg Asp Ser Val Ile
                165                 170                 175

Phe Gly Glu Arg Trp Gly Leu Thr Thr Glu Asn Val Asn Asp Ile Tyr
            180                 185                 190

Asn Arg Gln Ile Arg Glu Ile His Glu Tyr Ser Asn His Cys Val Asp
        195                 200                 205

Thr Tyr Asn Thr Glu Leu Glu Arg Leu Gly Phe Arg Ser Ile Ala Gln
    210                 215                 220

Trp Arg Ile Tyr Asn Gln Phe Arg Arg Glu Leu Thr Leu Thr Val Leu
225                 230                 235                 240

Asp Ile Val Ala Leu Phe Pro Asn Tyr Asp Ser Arg Leu Tyr Pro Ile
                245                 250                 255

Gln Thr Phe Ser Gln Leu Thr Arg Glu Ile Val Thr Ser Pro Val Ser
            260                 265                 270

Glu Phe Tyr Tyr Gly Val Ile Asn Ser Gly Asn Ile Asn Gly Thr Leu
        275                 280                 285

Thr Glu Gln Gln Ile Arg Arg Pro His Leu Met Asp Phe Phe Asn Ser
    290                 295                 300

Met Ile Met Tyr Thr Ser Asp Asn Arg Arg Glu His Tyr Trp Ser Gly
305                 310                 315                 320

Leu Glu Met Thr Ala Tyr Phe Thr Gly Phe Ala Gly Ala Gln Val Ser
                325                 330                 335

Phe Pro Leu Val Gly Thr Arg Gly Glu Ser Ala Pro Pro Leu Thr Val
            340                 345                 350

Arg Ser Val Asn Asp Gly Ile Tyr Arg Ile Leu Ser Ala Pro Phe Tyr
        355                 360                 365

Ser Ala Pro Phe Leu Gly Thr Ile Val Leu Gly Ser Arg Gly Glu Lys
    370                 375                 380

Phe Asp Phe Ala Leu Asn Asn Ile Ser Pro Pro Pro Ser Thr Ile Tyr
385                 390                 395                 400

Arg His Pro Gly Thr Val Asp Ser Leu Val Ser Ile Pro Pro Gln Asp
                405                 410                 415

Asn Ser Val Pro Pro His Arg Gly Ser Ser His Arg Leu Ser His Val
            420                 425                 430

Thr Met Arg Ala Ser Ser Pro Ile Phe His Trp Thr His Arg Ser Ala
        435                 440                 445

Thr Thr Thr Asn Thr Ile Asn Pro Asn Ala Ile Ile Gln Ile Pro Leu
    450                 455                 460

Val Lys Ala Phe Asn Leu His Ser Gly Ala Thr Val Val Arg Gly Pro
465                 470                 475                 480

Gly Phe Thr Gly Gly Asp Ile Leu Arg Arg Thr Asn Thr Gly Thr Phe
                485                 490                 495

Ala Asp Met Arg Val Asn Ile Thr Gly Pro Leu Ser Gln Arg Tyr Arg
            500                 505                 510

Val Arg Ile Arg Tyr Ala Ser Thr Thr Asp Leu Gln Phe Phe Thr Arg
        515                 520                 525

Ile Asn Gly Thr Ser Val Asn Gln Gly Asn Phe Gln Arg Thr Met Asn
    530                 535                 540

Arg Gly Asp Asn Leu Glu Ser Gly Asn Phe Arg Thr Ala Gly Phe Ser
545                 550                 555                 560

Thr Pro Phe Ser Phe Ser Asn Ala Gln Ser Thr Phe Thr Leu Gly Thr
                565                 570                 575
```

```
Gln Ala Phe Ser Asn Gln Glu Val Tyr Ile Asp Arg Ile Glu Phe Val
            580                 585                 590

Pro Ala Glu Val Thr Phe Glu Ala Glu Ser Asp Leu Glu Arg Ala Gln
        595                 600                 605

Lys Ala Val Asn Ala Leu Phe Thr Ser Thr Asn Gln Leu Gly Leu Lys
    610                 615                 620

Thr Asp Val Thr Asp Tyr Gln Ile Asp Gln Val Ser Asn Leu Val Glu
625                 630                 635                 640

Cys Leu Ser Asp Glu Phe Cys Leu Asp Glu Lys Arg Glu Leu Ser Glu
                645                 650                 655

Lys Val Lys His Ala Lys Arg Leu Ser Asp Lys Arg Asn Leu Leu Gln
            660                 665                 670

Asp Pro Asn Phe Thr Ser Ile Asn Arg Gln Leu Asp Arg Gly Trp Arg
        675                 680                 685

Gly Ser Thr Asp Ile Thr Ile Gln Gly Gly Asn Asp Val Phe Lys Glu
    690                 695                 700

Asn Tyr Val Thr Leu Pro Gly Thr Phe Asp Glu Cys Tyr Pro Thr Tyr
705                 710                 715                 720

Leu Tyr Gln Lys Ile Asp Glu Ser Lys Leu Lys Ala Tyr Thr Arg Tyr
                725                 730                 735

Glu Leu Arg Gly Tyr Ile Glu Asp Ser Gln Asp Leu Glu Val Tyr Leu
            740                 745                 750

Ile Arg Tyr Asn Ala Lys His Glu Thr Val Asn Val Pro Gly Thr Gly
        755                 760                 765

Ser Leu Trp Pro Leu Ser Val Glu Ser Pro Ile Gly Arg Cys Gly Glu
    770                 775                 780

Pro Asn Arg Cys Val Pro His Ile Glu Trp Asn Pro Asp Leu Asp Cys
785                 790                 795                 800

Ser Cys Arg Asp Gly Glu Lys Cys Ala His His Ser His His Phe Ser
                805                 810                 815

Leu Asp Ile Asp Val Gly Cys Thr Asp Leu Asn Glu Asp Leu Gly Val
            820                 825                 830

Trp Val Ile Phe Lys Ile Lys Thr Gln Asp Gly His Ala Arg Leu Gly
        835                 840                 845

Asn Leu Glu Phe Leu Glu Glu Lys Pro Leu Leu Gly Glu Ala Leu Ala
    850                 855                 860

Arg Val Lys Arg Ala Glu Lys Lys Trp Arg Asp Lys Arg Glu Gln Leu
865                 870                 875                 880

Gln Phe Glu Thr Asn Ile Val Tyr Lys Glu Ala Lys Glu Ser Val Asp
                885                 890                 895

Ala Leu Phe Val Asp Ser His Tyr Asn Arg Leu Gln Ala Asp Thr Asn
            900                 905                 910

Ile Thr Met Ile His Ala Ala Asp Lys Arg Val His Arg Ile Arg Glu
        915                 920                 925

Ala Tyr Leu Pro Glu Leu Ser Val Ile Pro Gly Val Asn Ala Asp Ile
    930                 935                 940

Phe Glu Glu Leu Glu Gly Leu Ile Phe Thr Ala Phe Ser Leu Tyr Asp
945                 950                 955                 960

Ala Arg Asn Ile Ile Lys Asn Gly Asp Phe Asn Asn Gly Leu Ser Cys
                965                 970                 975

Trp Asn Val Lys Gly His Val Asp Ile Gln Gln Asn Asp His Arg Ser
            980                 985                 990

Val Leu Val Val Pro Glu Trp Glu  Ser Glu Val Ser Gln  Glu Val Arg
```

```
        995                 1000                1005

Val Cys  Pro Gly Arg Gly Tyr  Ile Leu Arg Val Thr  Ala Tyr Lys
    1010                 1015                 1020

Glu Gly  Tyr Gly Glu Gly Cys  Val Thr Ile His Glu  Ile Glu Asp
    1025                 1030                 1035

Asn Thr  Asp Glu Leu Lys Phe  Ser Asn Cys Ile Glu  Glu Glu Val
    1040                 1045                 1050

Tyr Pro  Thr Asp Thr Gly Asn  Asp Tyr Thr Ala His  Gln Gly Thr
    1055                 1060                 1065

Thr Gly  Cys Ala Asp Ala Cys  Asn Ser Arg Asn Val  Gly Tyr Glu
    1070                 1075                 1080

Asp Gly  Tyr Glu Ile Asn Thr  Thr Ala Ser Val Asn  Tyr Lys Pro
    1085                 1090                 1095

Thr Tyr  Glu Glu Glu Met Tyr  Thr Asp Val Arg Arg  Asp Asn His
    1100                 1105                 1110

Cys Glu  Tyr Asp Arg Gly Tyr  Gly Asn His Thr Pro  Leu Pro Ala
    1115                 1120                 1125

Gly Tyr  Val Thr Lys Glu Leu  Glu Tyr Phe Pro Glu  Thr Asp Thr
    1130                 1135                 1140

Val Trp  Ile Glu Ile Gly Glu  Thr Glu Gly Thr Phe  Ile Val Asp
    1145                 1150                 1155

Ser Val  Glu Leu Leu Leu Met  Glu Glu
    1160                 1165


<210> SEQ ID NO 12
<211> LENGTH: 1167
<212> TYPE: PRT
<213> ORGANISM: Artificial Sequence
<220> FEATURE:
<223> OTHER INFORMATION: Modified alpha-helix 3/5/6 BT0002
<220> FEATURE:
<221> NAME/KEY: MISC_FEATURE
<222> LOCATION: (97)..(200)
<223> OTHER INFORMATION: BT0002 blocks 1 & 3 mutations: A97T; S105N;
      L108I; G110A; K118S; T119D; L158S; T161V; V176I; T186K; V196I;
      N197R; R198E & G200H

<400> SEQUENCE: 12

Met Glu Ile Asn Asn Gln Lys Gln Cys Ile Pro Tyr Asn Cys Leu Ser
1               5                   10                  15

Asn Pro Glu Glu Val Leu Leu Asp Gly Glu Arg Ile Leu Pro Asp Ile
            20                  25                  30

Asp Pro Leu Glu Val Ser Leu Ser Leu Leu Gln Phe Leu Leu Asn Asn
        35                  40                  45

Phe Val Pro Gly Gly Gly Phe Ile Ser Gly Leu Val Asp Lys Ile Trp
    50                  55                  60

Gly Ala Leu Arg Pro Ser Glu Trp Asp Leu Phe Leu Ala Gln Ile Glu
65                  70                  75                  80

Arg Leu Ile Asp Gln Arg Ile Glu Ala Thr Val Arg Ala Lys Ala Ile
                85                  90                  95

Thr Glu Leu Glu Gly Leu Gly Arg Asn Tyr Gln Ile Tyr Ala Glu Ala
            100                 105                 110

Phe Lys Glu Trp Glu Ser Cys Pro Asp Asn Thr Ala Ala Arg Ser Arg
        115                 120                 125

Val Thr Glu Arg Phe Arg Ile Ile Asp Ala Gln Ile Glu Ala Asn Ile
    130                 135                 140

Pro Ser Phe Arg Val Ser Gly Phe Glu Val Pro Leu Leu Ser Val Tyr
```

```
145                 150                 155                 160

Val Gln Ala Ala Asn Leu His Leu Ala Leu Leu Arg Asp Ser Val Ile
                165                 170                 175

Phe Gly Glu Arg Trp Gly Leu Thr Thr Glu Asn Val Asn Asp Ile Tyr
            180                 185                 190

Asn Arg Gln Ile Arg Glu Ile His Glu Tyr Ser Asn His Cys Val Asp
        195                 200                 205

Thr Tyr Asn Thr Glu Leu Glu Arg Leu Gly Phe Arg Ser Ile Ala Gln
    210                 215                 220

Trp Arg Ile Tyr Asn Gln Phe Arg Arg Glu Leu Thr Leu Thr Val Leu
225                 230                 235                 240

Asp Ile Val Ala Leu Phe Pro Asn Tyr Asp Ser Arg Leu Tyr Pro Ile
                245                 250                 255

Gln Thr Phe Ser Gln Leu Thr Arg Glu Ile Val Thr Ser Pro Val Ser
            260                 265                 270

Glu Phe Tyr Tyr Gly Val Ile Asn Ser Gly Asn Ile Asn Gly Thr Leu
        275                 280                 285

Thr Glu Gln Gln Ile Arg Arg Pro His Leu Met Asp Phe Phe Asn Ser
    290                 295                 300

Met Ile Met Tyr Thr Ser Asp Asn Arg Arg Glu His Tyr Trp Ser Gly
305                 310                 315                 320

Leu Glu Met Thr Ala Tyr Phe Thr Gly Phe Ala Gly Ala Gln Val Ser
                325                 330                 335

Phe Pro Leu Val Gly Thr Arg Gly Glu Ser Ala Pro Pro Leu Thr Val
            340                 345                 350

Arg Ser Val Asn Asp Gly Ile Tyr Arg Ile Leu Ser Ala Pro Phe Tyr
        355                 360                 365

Ser Ala Pro Phe Leu Gly Thr Ile Val Leu Gly Ser Arg Gly Glu Lys
    370                 375                 380

Phe Asp Phe Ala Leu Asn Asn Ile Ser Pro Pro Pro Ser Thr Ile Tyr
385                 390                 395                 400

Arg His Pro Gly Thr Val Asp Ser Leu Val Ser Ile Pro Pro Gln Asp
                405                 410                 415

Asn Ser Val Pro Pro His Arg Gly Ser Ser His Arg Leu Ser His Val
            420                 425                 430

Thr Met Arg Ala Ser Ser Pro Ile Phe His Trp Thr His Arg Ser Ala
        435                 440                 445

Thr Thr Thr Asn Thr Ile Asn Pro Asn Ala Ile Ile Gln Ile Pro Leu
    450                 455                 460

Val Lys Ala Phe Asn Leu His Ser Gly Ala Thr Val Val Arg Gly Pro
465                 470                 475                 480

Gly Phe Thr Gly Gly Asp Ile Leu Arg Arg Thr Asn Thr Gly Thr Phe
                485                 490                 495

Ala Asp Met Arg Val Asn Ile Thr Gly Pro Leu Ser Gln Arg Tyr Arg
            500                 505                 510

Val Arg Ile Arg Tyr Ala Ser Thr Thr Asp Leu Gln Phe Phe Thr Arg
        515                 520                 525

Ile Asn Gly Thr Ser Val Asn Gln Gly Asn Phe Gln Arg Thr Met Asn
    530                 535                 540

Arg Gly Asp Asn Leu Glu Ser Gly Asn Phe Arg Thr Ala Gly Phe Ser
545                 550                 555                 560

Thr Pro Phe Ser Phe Ser Asn Ala Gln Ser Thr Phe Thr Leu Gly Thr
                565                 570                 575
```

-continued

Gln Ala Phe Ser Asn Gln Glu Val Tyr Ile Asp Arg Ile Glu Phe Val
580 585 590

Pro Ala Glu Val Thr Phe Glu Ala Glu Ser Asp Leu Glu Arg Ala Gln
595 600 605

Lys Ala Val Asn Ala Leu Phe Thr Ser Thr Asn Gln Leu Gly Leu Lys
610 615 620

Thr Asp Val Thr Asp Tyr Gln Ile Asp Gln Val Ser Asn Leu Val Glu
625 630 635 640

Cys Leu Ser Asp Glu Phe Cys Leu Asp Glu Lys Arg Glu Leu Ser Glu
645 650 655

Lys Val Lys His Ala Lys Arg Leu Ser Asp Lys Arg Asn Leu Leu Gln
660 665 670

Asp Pro Asn Phe Thr Ser Ile Asn Arg Gln Leu Asp Arg Gly Trp Arg
675 680 685

Gly Ser Thr Asp Ile Thr Ile Gln Gly Gly Asn Asp Val Phe Lys Glu
690 695 700

Asn Tyr Val Thr Leu Pro Gly Thr Phe Asp Glu Cys Tyr Pro Thr Tyr
705 710 715 720

Leu Tyr Gln Lys Ile Asp Glu Ser Lys Leu Lys Ala Tyr Thr Arg Tyr
725 730 735

Glu Leu Arg Gly Tyr Ile Glu Asp Ser Gln Asp Leu Glu Val Tyr Leu
740 745 750

Ile Arg Tyr Asn Ala Lys His Glu Thr Val Asn Val Pro Gly Thr Gly
755 760 765

Ser Leu Trp Pro Leu Ser Val Glu Ser Pro Ile Gly Arg Cys Gly Glu
770 775 780

Pro Asn Arg Cys Val Pro His Ile Glu Trp Asn Pro Asp Leu Asp Cys
785 790 795 800

Ser Cys Arg Asp Gly Glu Lys Cys Ala His His Ser His His Phe Ser
805 810 815

Leu Asp Ile Asp Val Gly Cys Thr Asp Leu Asn Glu Asp Leu Gly Val
820 825 830

Trp Val Ile Phe Lys Ile Lys Thr Gln Asp Gly His Ala Arg Leu Gly
835 840 845

Asn Leu Glu Phe Leu Glu Glu Lys Pro Leu Leu Gly Glu Ala Leu Ala
850 855 860

Arg Val Lys Arg Ala Glu Lys Lys Trp Arg Asp Lys Arg Glu Gln Leu
865 870 875 880

Gln Phe Glu Thr Asn Ile Val Tyr Lys Glu Ala Lys Glu Ser Val Asp
885 890 895

Ala Leu Phe Val Asp Ser His Tyr Asn Arg Leu Gln Ala Asp Thr Asn
900 905 910

Ile Thr Met Ile His Ala Ala Asp Lys Arg Val His Arg Ile Arg Glu
915 920 925

Ala Tyr Leu Pro Glu Leu Ser Val Ile Pro Gly Val Asn Ala Asp Ile
930 935 940

Phe Glu Glu Leu Glu Gly Leu Ile Phe Thr Ala Phe Ser Leu Tyr Asp
945 950 955 960

Ala Arg Asn Ile Ile Lys Asn Gly Asp Phe Asn Asn Gly Leu Ser Cys
965 970 975

Trp Asn Val Lys Gly His Val Asp Ile Gln Gln Asn Asp His Arg Ser
980 985 990

-continued

```
Val Leu Val Val Pro Glu Trp Glu  Ser Glu Val Ser Gln  Glu Val Arg
        995                 1000                 1005

Val Cys  Pro Gly Arg Gly Tyr  Ile Leu Arg Val Thr  Ala Tyr Lys
    1010                 1015                 1020

Glu Gly  Tyr Gly Glu Gly Cys  Val Thr Ile His Glu  Ile Glu Asp
    1025                 1030                 1035

Asn Thr  Asp Glu Leu Lys Phe  Ser Asn Cys Ile Glu  Glu Glu Val
    1040                 1045                 1050

Tyr Pro  Thr Asp Thr Gly Asn  Asp Tyr Thr Ala His  Gln Gly Thr
    1055                 1060                 1065

Thr Gly  Cys Ala Asp Ala Cys  Asn Ser Arg Asn Val  Gly Tyr Glu
    1070                 1075                 1080

Asp Gly  Tyr Glu Ile Asn Thr  Thr Ala Ser Val Asn  Tyr Lys Pro
    1085                 1090                 1095

Thr Tyr  Glu Glu Glu Met Tyr  Thr Asp Val Arg Arg  Asp Asn His
    1100                 1105                 1110

Cys Glu  Tyr Asp Arg Gly Tyr  Gly Asn His Thr Pro  Leu Pro Ala
    1115                 1120                 1125

Gly Tyr  Val Thr Lys Glu Leu  Glu Tyr Phe Pro Glu  Thr Asp Thr
    1130                 1135                 1140

Val Trp  Ile Glu Ile Gly Glu  Thr Glu Gly Thr Phe  Ile Val Asp
    1145                 1150                 1155

Ser Val  Glu Leu Leu Leu Met  Glu Glu
    1160                 1165


<210> SEQ ID NO 13
<211> LENGTH: 1167
<212> TYPE: PRT
<213> ORGANISM: Artificial Sequence
<220> FEATURE:
<223> OTHER INFORMATION: Modified alpha-helix 3/4/5/6 BT0002
<220> FEATURE:
<221> NAME/KEY: MISC_FEATURE
<223> OTHER INFORMATION: BT0002 blocks 1,2 &3 mutations: 97T; S105N;
      L108I; G110A; K118S; T119D; T123E; R126K; T130I; E131D; I136L;
      A138G; Q139L; V149I; V150I; L158S; T161V; V176I; T186K; V196I;
      N197R; R198E & G200H
<220> FEATURE:
<221> NAME/KEY: MISC_FEATURE
<223> OTHER INFORMATION: BT0002 blocks 1,2 &3 mutations: 97T; S105N;
      L108I; G110A; K118S; T119D; T123E; R126K; T130I; E131D; I136L;
      A138G; Q139L; V149I; V150I; L158S; T161V; V176I; T186K; V196I;
      N197R; R198E & G200H

<400> SEQUENCE: 13

Met Glu Ile Asn Asn Gln Lys Gln Cys Ile Pro Tyr Asn Cys Leu Ser
1               5                   10                  15

Asn Pro Glu Glu Val Leu Leu Asp Gly Glu Arg Ile Leu Pro Asp Ile
            20                  25                  30

Asp Pro Leu Glu Val Ser Leu Ser Leu Leu Gln Phe Leu Leu Asn Asn
        35                  40                  45

Phe Val Pro Gly Gly Gly Phe Ile Ser Gly Leu Val Asp Lys Ile Trp
    50                  55                  60

Gly Ala Leu Arg Pro Ser Glu Trp Asp Leu Phe Leu Ala Gln Ile Glu
65                  70                  75                  80

Arg Leu Ile Asp Gln Arg Ile Glu Ala Thr Val Arg Ala Lys Ala Ile
                85                  90                  95

Thr Glu Leu Glu Gly Leu Gly Arg Asn Tyr Gln Ile Tyr Ala Glu Ala
            100                 105                 110
```

-continued

```
Phe Lys Glu Trp Glu Ser Asp Pro Asp Asn Glu Ala Ala Lys Ser Arg
        115                 120                 125

Val Ile Asp Arg Phe Arg Ile Leu Asp Gly Ile Ile Glu Ala Asn Ile
    130                 135                 140

Pro Ser Phe Arg Ile Ile Gly Phe Glu Val Pro Leu Leu Ser Val Tyr
145                 150                 155                 160

Val Gln Ala Ala Asn Leu His Leu Ala Leu Leu Arg Asp Ser Val Ile
                165                 170                 175

Phe Gly Glu Arg Trp Gly Leu Thr Thr Glu Asn Val Asn Asp Ile Tyr
            180                 185                 190

Asn Arg Gln Ile Arg Glu Ile His Glu Tyr Ser Asn His Cys Val Asp
        195                 200                 205

Thr Tyr Asn Thr Glu Leu Glu Arg Leu Gly Phe Arg Ser Ile Ala Gln
    210                 215                 220

Trp Arg Ile Tyr Asn Gln Phe Arg Arg Glu Leu Thr Leu Thr Val Leu
225                 230                 235                 240

Asp Ile Val Ala Leu Phe Pro Asn Tyr Asp Ser Arg Leu Tyr Pro Ile
                245                 250                 255

Gln Thr Phe Ser Gln Leu Thr Arg Glu Ile Val Thr Ser Pro Val Ser
            260                 265                 270

Glu Phe Tyr Tyr Gly Val Ile Asn Ser Gly Asn Ile Asn Gly Thr Leu
        275                 280                 285

Thr Glu Gln Gln Ile Arg Arg Pro His Leu Met Asp Phe Phe Asn Ser
    290                 295                 300

Met Ile Met Tyr Thr Ser Asp Asn Arg Arg Glu His Tyr Trp Ser Gly
305                 310                 315                 320

Leu Glu Met Thr Ala Tyr Phe Thr Gly Phe Ala Gly Ala Gln Val Ser
                325                 330                 335

Phe Pro Leu Val Gly Thr Arg Gly Glu Ser Ala Pro Pro Leu Thr Val
            340                 345                 350

Arg Ser Val Asn Asp Gly Ile Tyr Arg Ile Leu Ser Ala Pro Phe Tyr
        355                 360                 365

Ser Ala Pro Phe Leu Gly Thr Ile Val Leu Gly Ser Arg Gly Glu Lys
    370                 375                 380

Phe Asp Phe Ala Leu Asn Asn Ile Ser Pro Pro Pro Ser Thr Ile Tyr
385                 390                 395                 400

Arg His Pro Gly Thr Val Asp Ser Leu Val Ser Ile Pro Pro Gln Asp
                405                 410                 415

Asn Ser Val Pro Pro His Arg Gly Ser Ser His Arg Leu Ser His Val
            420                 425                 430

Thr Met Arg Ala Ser Ser Pro Ile Phe His Trp Thr His Arg Ser Ala
        435                 440                 445

Thr Thr Thr Asn Thr Ile Asn Pro Asn Ala Ile Ile Gln Ile Pro Leu
    450                 455                 460

Val Lys Ala Phe Asn Leu His Ser Gly Ala Thr Val Val Arg Gly Pro
465                 470                 475                 480

Gly Phe Thr Gly Gly Asp Ile Leu Arg Arg Thr Asn Thr Gly Thr Phe
                485                 490                 495

Ala Asp Met Arg Val Asn Ile Thr Gly Pro Leu Ser Gln Arg Tyr Arg
            500                 505                 510

Val Arg Ile Arg Tyr Ala Ser Thr Thr Asp Leu Gln Phe Phe Thr Arg
        515                 520                 525

Ile Asn Gly Thr Ser Val Asn Gln Gly Asn Phe Gln Arg Thr Met Asn
```

```
    530                 535                 540

Arg Gly Asp Asn Leu Glu Ser Gly Asn Phe Arg Thr Ala Gly Phe Ser
545                 550                 555                 560

Thr Pro Phe Ser Phe Ser Asn Ala Gln Ser Thr Phe Thr Leu Gly Thr
                565                 570                 575

Gln Ala Phe Ser Asn Gln Glu Val Tyr Ile Asp Arg Ile Glu Phe Val
            580                 585                 590

Pro Ala Glu Val Thr Phe Glu Ala Glu Ser Asp Leu Glu Arg Ala Gln
        595                 600                 605

Lys Ala Val Asn Ala Leu Phe Thr Ser Thr Asn Gln Leu Gly Leu Lys
    610                 615                 620

Thr Asp Val Thr Asp Tyr Gln Ile Asp Gln Val Ser Asn Leu Val Glu
625                 630                 635                 640

Cys Leu Ser Asp Glu Phe Cys Leu Asp Glu Lys Arg Glu Leu Ser Glu
                645                 650                 655

Lys Val Lys His Ala Lys Arg Leu Ser Asp Lys Arg Asn Leu Leu Gln
            660                 665                 670

Asp Pro Asn Phe Thr Ser Ile Asn Arg Gln Leu Asp Arg Gly Trp Arg
        675                 680                 685

Gly Ser Thr Asp Ile Thr Ile Gln Gly Gly Asn Asp Val Phe Lys Glu
    690                 695                 700

Asn Tyr Val Thr Leu Pro Gly Thr Phe Asp Glu Cys Tyr Pro Thr Tyr
705                 710                 715                 720

Leu Tyr Gln Lys Ile Asp Glu Ser Lys Leu Lys Ala Tyr Thr Arg Tyr
                725                 730                 735

Glu Leu Arg Gly Tyr Ile Glu Asp Ser Gln Asp Leu Glu Val Tyr Leu
            740                 745                 750

Ile Arg Tyr Asn Ala Lys His Glu Thr Val Asn Val Pro Gly Thr Gly
        755                 760                 765

Ser Leu Trp Pro Leu Ser Val Glu Ser Pro Ile Gly Arg Cys Gly Glu
    770                 775                 780

Pro Asn Arg Cys Val Pro His Ile Glu Trp Asn Pro Asp Leu Asp Cys
785                 790                 795                 800

Ser Cys Arg Asp Gly Glu Lys Cys Ala His His Ser His His Phe Ser
                805                 810                 815

Leu Asp Ile Asp Val Gly Cys Thr Asp Leu Asn Glu Asp Leu Gly Val
            820                 825                 830

Trp Val Ile Phe Lys Ile Lys Thr Gln Asp Gly His Ala Arg Leu Gly
        835                 840                 845

Asn Leu Glu Phe Leu Glu Glu Lys Pro Leu Leu Gly Glu Ala Leu Ala
    850                 855                 860

Arg Val Lys Arg Ala Glu Lys Lys Trp Arg Asp Lys Arg Glu Gln Leu
865                 870                 875                 880

Gln Phe Glu Thr Asn Ile Val Tyr Lys Glu Ala Lys Glu Ser Val Asp
                885                 890                 895

Ala Leu Phe Val Asp Ser His Tyr Asn Arg Leu Gln Ala Asp Thr Asn
            900                 905                 910

Ile Thr Met Ile His Ala Ala Asp Lys Arg Val His Arg Ile Arg Glu
        915                 920                 925

Ala Tyr Leu Pro Glu Leu Ser Val Ile Pro Gly Val Asn Ala Asp Ile
    930                 935                 940

Phe Glu Glu Leu Glu Gly Leu Ile Phe Thr Ala Phe Ser Leu Tyr Asp
945                 950                 955                 960
```

```
Ala Arg Asn Ile Ile Lys Asn Gly Asp Phe Asn Asn Gly Leu Ser Cys
                965                 970                 975

Trp Asn Val Lys Gly His Val Asp Ile Gln Gln Asn Asp His Arg Ser
            980                 985                 990

Val Leu Val Val Pro Glu Trp Glu  Ser Glu Val Ser Gln  Glu Val Arg
        995                 1000                1005

Val Cys  Pro Gly Arg Gly Tyr  Ile Leu Arg Val Thr  Ala Tyr Lys
    1010                 1015                 1020

Glu Gly  Tyr Gly Glu Gly Cys  Val Thr Ile His Glu  Ile Glu Asp
    1025                 1030                 1035

Asn Thr  Asp Glu Leu Lys Phe  Ser Asn Cys Ile Glu  Glu Glu Val
    1040                 1045                 1050

Tyr Pro  Thr Asp Thr Gly Asn  Asp Tyr Thr Ala His  Gln Gly Thr
    1055                 1060                 1065

Thr Gly  Cys Ala Asp Ala Cys  Asn Ser Arg Asn Val  Gly Tyr Glu
    1070                 1075                 1080

Asp Gly  Tyr Glu Ile Asn Thr  Thr Ala Ser Val Asn  Tyr Lys Pro
    1085                 1090                 1095

Thr Tyr  Glu Glu Glu Met Tyr  Thr Asp Val Arg Arg  Asp Asn His
    1100                 1105                 1110

Cys Glu  Tyr Asp Arg Gly Tyr  Gly Asn His Thr Pro  Leu Pro Ala
    1115                 1120                 1125

Gly Tyr  Val Thr Lys Glu Leu  Glu Tyr Phe Pro Glu  Thr Asp Thr
    1130                 1135                 1140

Val Trp  Ile Glu Ile Gly Glu  Thr Glu Gly Thr Phe  Ile Val Asp
    1145                 1150                 1155

Ser Val  Glu Leu Leu Leu Met  Glu Glu
    1160                 1165
```

<210> SEQ ID NO 14
<211> LENGTH: 3504
<212> TYPE: DNA
<213> ORGANISM: Bacillus thuringiensis

<400> SEQUENCE: 14

```
atggagataa ataatcagaa gcaatgcata ccatataatt gcttaagtaa tcctgaggaa      60

gtacttttgg atggggagag gatattacct gatatcgatc cactcgaagt ttctttgtcg     120

cttttgcaat ttcttttgaa taactttgtt ccagggggag gctttatttc aggattagtt     180

gataaaatat gggggcttt gagaccatct gaatgggact tatttcttgc acagattgaa     240

cggttgattg atcaaagaat agaagcaaca gtaagagcaa aagcaatcgc tgaattagaa     300

ggtttaggga gaagttatca actatatgga gaggcattta aagagtggga aaaaactcca     360

gataacacag cggctcggtc tagagtaact gagagatttc gtataattga tgctcaaatt     420

gaagcaaata tcccttcgtt tcgggtttcc ggatttgaag tgccacttct attggtttat     480

acccaagcag ctaatttgca tctcgctcta ttaagagatt ctgttgtttt tggagagaga     540

tggggattga cgactacaaa tgtcaatgat atctataata gacaagttaa tagaattggt     600

gaatatagca atcattgcgt agatacgtat aacacagaac tagaacgtct agggtttaga     660

tctatagcgc agtggagaat atataatcag tttagaagag aactaacact aactgtatta     720

gatattgtcg ctcttttccc gaactatgac agtagactgt atccgatcca aacttttct      780

caattgacaa gagaaattgt tacatcccca gtaagcgaat tttattatgg tgttattaat     840
```

```
agtggtaata taaatggtac tcttactgaa cagcagataa ggcgaccaca tcttatggac    900
ttctttaact ccatgatcat gtatacatca gataatagac gggaacatta ttggtcagga    960
cttgaaatga cggcttattt tacaggattt gcaggcgctc aagtgtcatt ccctttagtc   1020
gggactagag gggagtcagc tccaccatta actgttagaa gtgttaatga tggaatttat   1080
agaatattat cggcaccgtt ttattcagcg ccttttctag gcaccattgt attgggaagt   1140
cgtggagaaa aatttgattt tgcgcttaat aatatttcac ctccgccatc tacaatatac   1200
agacatcctg gaacagtaga ttcactagtc agtataccgc cacaggataa tagcgtacca   1260
ccgcacaggg gatctagtca tcgattaagt catgttacaa tgcgcgcaag ttcccctata   1320
ttccattgga cgcatcgcag cgcaaccact acaaatacaa ttaatccaaa tgctattatc   1380
caaataccac tagtaaaagc atttaacctt cattcaggtg ccactgttgt tagaggacca   1440
gggtttacag gtggtgatat ccttcgaaga acgaatactg gcacatttgc agatatgaga   1500
gtaaatatta ctgggccatt atcccaaaga tatcgtgtaa gaattcgcta tgcttctacg   1560
acagatttac aatttttcac gagaatcaat ggaacttctg taaatcaagg taatttccaa   1620
agaactatga atagagggga taatttagaa tctggaaact ttaggactgc aggatttagt   1680
acgcctttta gtttttcaaa tgcgcaaagt acattcacat tgggtactca ggctttttca   1740
aatcaggaag tttatataga tcgaattgaa tttgtcccgg cagaagtaac attcgaggca   1800
gaatctgatt tagaaagagc gcaaaaggcg gtgaatgccc tgtttacttc tacaaaccaa   1860
ctagggctaa aaacagatgt gacggattat cagattgatc aagtgtccaa tttagtagaa   1920
tgtttatcag atgaattttg tctggatgaa aagagagaat tgtccgagaa agtcaaacat   1980
gcaaagcgac ttagtgataa gcggaaccta cttcaagatc caaacttcac atctatcaat   2040
agacaactag accgtggatg gagaggaagt acggatatta ccatccaagg aggaaatgac   2100
gtattcaaag agaattacgt cacactacca ggtacctttg atgagtgtta tccaacgtat   2160
ttgtatcaaa aaatagatga gtcaaaatta aaagcctata ctcgctatga attaagaggg   2220
tatattgaag atagtcaaga tttagaagtc tatttgattc gttacaatgc gaaacatgaa   2280
acagtaaatg ttcccggtac agggtcctta tggccgcttt cagtcgaaag cccaatcgga   2340
aggtgcggag aaccgaatcg atgtgtgcca catattgaat ggaatcctga tttagattgt   2400
tcgtgtaggg atggggagaa gtgtgcccat cattcgcatc atttctctct agatattgat   2460
gttggatgta cagacctaaa tgaggaccta ggtgtatggg tgatctttaa gattaaaacg   2520
caggatggcc atgcaagatt aggaaatcta gagtttctcg aagagaaacc attgttagga   2580
gaagcgttag ctcgtgtgaa aagagcggag aaaaaatgga gagacaaacg cgaacaattg   2640
cagtttgaaa cgaatatcgt ttacaaagag gcaaaagaat ctgtagatgc tttattcgta   2700
gattctcact ataatagatt acaagcggat acgaacatta cgatgattca tgcggcagat   2760
aaacgcgttc atcgaatccg agaggcttat cttccggaat tatccgttat cccaggtgta   2820
aatgcggaca tttttgaaga attagaaggt cttattttca ctgcattctc cctatatgat   2880
gcgagaaata tcattaaaaa cggtgatttc aataatggtt tatcgtgttg gaacgtgaaa   2940
gggcatgtag atatacaaca gaatgatcat cgttctgtcc tcgttgtccc ggaatgggaa   3000
tcagaggtat cacaagaagt ccgcgtatgt ccaggtcgtg gctatattct tcgtgtcaca   3060
gcgtacaaag agggctacgg agaaggatgc gtaacgatcc atgagatcga agacaataca   3120
gacgaattga agtttagtaa ctgcatagaa gaggaagtct atccaacgga tacaggtaat   3180
gattatactg cacaccaagg tacaacagga tgcgcagatg catgtaattc ccgtaatgtt   3240
```

ggatatgagg atggatatga aataaatact acagcatctg ttaattacaa accgacttat 3300
gaagaagaaa tgtatacaga tgtacgaaga gataatcatt gtgaatatga cagaggatat 3360
gggaaccata caccgttacc agctggttat gtaacaaaag aattagagta cttccctgaa 3420
acagatacag tatggataga gattggagaa acggaaggaa cattcatcgt agatagtgtg 3480
gaattactcc tcatggagga ataa 3504

<210> SEQ ID NO 15
<211> LENGTH: 2133
<212> TYPE: DNA
<213> ORGANISM: Bacillus thuringiensis

<400> SEQUENCE: 15
atgaaatcta agaatcaaaa tatgcatcaa agcttgtcta acaatgcgac agttgataaa 60
aactttacag gttcactaga aaataacaca aatacggaat tacaaaactt taatcatgaa 120
ggtatagagc cgtttgttag tgtatcaaca attcaaacgg gtattggtat tgctggtaaa 180
atccttggta acctaggcgt tccctttgct gggcaagtag ctagcctcta tagttttatc 240
ctaggtgagc tttggcccaa agggaaaagc caatgggaaa tttttatgga acatgtagaa 300
gagcttatta atcaaaagat atcgacttat gcaagaaaca aagcacttgc agatttaaaa 360
ggattaggag atgctttggc tgtctaccat gaatcgctgg aaagttggat taaaaatcgc 420
aataacacaa gaactagaag tgttgtcaag agccaataca ttaccttgga acttatgttc 480
gtacaatcat taccttcttt tgcagtgtct ggagaggaag taccactatt accaatatat 540
gctcaagctg caaatttaca cttgttgcta ttaagagatg cgtctatttt tggaaaagaa 600
tggggattat cagactcaga aatttcgaca ttctataatc gtcaagtgga aagaacatca 660
gattattccg atcattgcac gaaatggttt gatacgggct tgaatagatt aaagggctca 720
aatgctgaaa tctgggtaaa gtataatcaa ttccgtagag acatgacttt aatggtacta 780
gatttagtgg cactattcca aagctatgat acacatatgt acccaattaa aactacagcc 840
caacttacta gagaagtata tacaaacgca ttggggacag tacatccgca cccaagtttt 900
acaagtacga cttggtataa taataatgca ccttcgtttt ctgccataga ggctgccgtt 960
atccgaagcc cgcacctact cgattttcta gaacaagtta caatttacag cttattaagc 1020
cgatggagta acactcagta tatgaatatg tggggaggac ataaactaga attccgaaca 1080
ataggaggaa cgttaaatac ctcaacacaa ggatctacta atacttctat taatcctgta 1140
acattaccgt tcacgtctcg agacatctat aggactgaat cattggcagg gctgaatcta 1200
tttttaactc aacctgttaa tggagtacct agggttgatt ttcattggaa attcgtcaca 1260
catccgatcg catctgataa tttctattat ccagggtatg ctggaattgg gacgcaatta 1320
caggattcag aaaatgaatt accacctgaa gcaacaggac agccaaatta tgaatcttat 1380
agtcatagat tatctcatat aggactcatt tcagcatcac atgtgaaagc attggtatat 1440
tcttggacgc atcgtagtgc agatcgtacg aatacaattc attcagatag tataacacaa 1500
ataccactgg taaaagcaca tacccttcag tcaggtacta ctgttgtaaa agggccaggg 1560
tttacaggtg gagatatcct ccgacgaact agtggaggac catttgcttt tagtaatgtt 1620
aatttagact ggaacttgtc acaaagatat cgtgctagaa tacgctatgc ttctactact 1680
aatctaagaa tgtacgtaac gattgcaggg gaacgaattt ttgctggtca atttaataaa 1740
acaatgaata ctggtgatcc attaacattc caatctttta gttacgcaac tattgataca 1800

-continued

```
gcatttacat tcccaacgaa agcgagcagc ttgactgtag gtgctgatac ttttagctca   1860

ggtaatgaag tttatgtaga tagatttgaa ttgatcccag ttactgcaac acttgaggca   1920

gtaactgatt tagaaagagc gcagaaggcg gttcatgaac tgtttacatc tacgaatccg   1980

ggaggattaa aaacggatgt aaaggattat catattgacc aggtatcaaa tttagtagag   2040

tctctatcag ataaattcta tcttgatgaa aagagagaat tattcgagat agttaaatac   2100

gcgaagcaac tccatattga gcgtaacatg tag                                2133
```

<210> SEQ ID NO 16
<211> LENGTH: 3507
<212> TYPE: DNA
<213> ORGANISM: Bacillus thuringiensis

<400> SEQUENCE: 16

```
atggagataa ataatcagaa ccaatgcata ccatataatt gcttaagtaa tcctgaggaa     60

gtatttttgg atggggagag gatattacct gatatcgatc cactcgaagt ttctttgtcg    120

cttttgcaat ttcttttgaa taactttgtt ccaggggggg ggtttatttc aggattactt    180

gataaaatat ggggggcttt gagaccatct gattgggaat tatttcttga acagattgaa    240

cagttgattg atcgaagaat agaaagaaca gtaagagcaa aagcaatcgc tgaattagaa    300

ggtttaggga gaagttatca actatatgga gaggcattta aagagtggga aaaaactcca    360

gataacacag cggctcggtc tagagtaact gagagatttc gtataattga tgctcaaatt    420

gaagcaaata tcccttcgtt tcgggtttcc ggatttgaag tgccacttct attggtttat    480

acccaagcag ctaatttgca tctcgctcta ttaagagatt ctgttgtttt tggagagaga    540

tggggattga cgactacaaa tgtcaatgat atctataata gacaagttaa tagaattggt    600

gaatatagca agcattgtgt agatacgtat aaaacagaat tagaacgtct aggatttaga    660

tctatagcgc aatggagaat atataatcag tttagaaggg aattgacact aacggtatta    720

gatattgtcg ctgttttccc gaactatgat agtagactgt atccgattcg aacaatttct    780

caattgacaa gagaaattta tacatcccca gtaagcgaat tttattatgg tgtcattaat    840

agtaataata taattggtac ccttactgaa cagcaaataa ggcgaccaca tcttatggac    900

ttctttaact ccatgatcat gtatacatca gataatagac gggaacatta ttggtcagga    960

cttgaaatga cggctactaa tactgaggga catcaaaggt cattcccttt agctgggact   1020

atagggaatt cagctccacc agtaactgtt agaaataatg gtgagggaat ttatagaata   1080

ttatcggaac cattttattc agcacctttt ctaggcacaa gtgtgctagg aagtcgtggg   1140

gaagaatttg cttttgcatc taatactact acaagtctgc catctacaat atatagaaat   1200

cgtggaacag tagattcatt agtcagcata ccgccacagg attatagcgt accaccgcac   1260

agggggtata gtcatttatt aagtcacgtt acgatgcgca atagttctcc tatattccac   1320

tggacacatc gtagtgcaac ccctagaaat acaattgatc cagatagtat cactcaaatt   1380

ccagcagtta agggagcgta tatttttaat agtccagtca ttactgggcc aggacataca   1440

ggtggggata taataaggtt taaccctaat actcagaaca acataagaat tccatttcaa   1500

tcaaatgcgg tacagcgtta tcgaattaga atgcgttatg cggcagaagc tgattgtatt   1560

ttagaaagtg gagtaaacat tgttactggg gcaggggtca cctttaggcc aattcctatt   1620

aaagctacaa tgactcctgg aagtccttta acatattaca gcttccagta tgcagattta   1680

aatataaatc ttactgcgcc gataagacct aataattttg tatctattag acgttcaaac   1740

caaccaggaa acctttatat agatagaatt gaattcattc caattgaccc aatccgtgag   1800
```

```
gcagaacatg atttagaaag agcgcaaaag gcggtgaatg cgctgtttac ttcttccaat   1860
caaatcgggt taaaaacaga tgtgacggat tatcatattg atcaagtgtc caatttagtt   1920
gcgtgtttat cggataaatt ctgcctggat gaaaagcgag aattgtccga gaaagttaaa   1980
catgcgaagc gactcagtga tgagagaaat ttactccaag atcaaaactt tacaggcatc   2040
aataggcaag tagaccgtgg gtggagagga agtacggata ttaccatcca aggagggaat   2100
gatgtattca aagagaatta cgtcacacta ccaggtacct ttgatgagtg ttacccaacg   2160
tatttgtatc aaaaaataga tgagtcaaaa ttaaaacctt atactcgcta tgaattaaga   2220
gggtatattg aagatagtca agacttagaa gtctatttga tccgttacaa tgcaaaacac   2280
gaaacgttaa atgtgccagg tacgggttcc ttatggccac ttgcagccga aagttcaatc   2340
gggaggtgcg gcgaaccgaa tcgatgcgcg ccacatattg aatggaatcc tgaactagat   2400
tgttcgtgta gggatggaga aaaatgtgca catcattctc atcatttctc cttggatatt   2460
gatgttggat gtacagactt aaatgaggat ttaggtgtat gggtgatatt taagattaag   2520
acgcaagatg gctatgcaag actaggaaat ttagagtttc tcgaagagaa accattgtta   2580
ggagaagcgc tagctcgtgt gaagagagcg gagaaaaaat ggagagacaa acgcgacaaa   2640
ttggaatggg aaacaaatat tgtttataaa gaggcaaaag aatctgtaga tgctttattc   2700
gtagattctc aatataatag attacaaacg gatacgaaca ttgcgatgat tcatgtggca   2760
gataaacgcg ttcatcgaat ccgagaagcg tatttgccag agttatctgt gattccgggt   2820
gtcaatgcgg ctattttcga agaattagaa ggtcttattt tcactgcatt ctccctatat   2880
gatgcgagaa atgtcattaa aaacggagat ttcaatcatg gtttatcatg ctggaacgtg   2940
aaagggcatg tagatgtaga agaacaaaat aaccaccgtt cggtccttgt tgttccggaa   3000
tgggaagcag aagtgtcaca agaagtccgc gtatgtccag gacgtggcta tatcctgcgt   3060
gttacagcgt acaaagaggg ctacggagaa ggatgcgtaa cgatccatga aattgaagat   3120
catacagacg aactgaaatt tagaaactgt gaagaagagg aagtgtatcc gaataacacg   3180
gtaacgtgta atgattatcc agcaaatcaa gaagaataca gggctgcgga aacttcccgt   3240
aatcgtggat atggcgaatc ttatgaaagt aattcttcca taccagctga gtatgcgcca   3300
atttatgaga aagcatatac agatggaaga aaagagaatt cttgtgaatc taacagagga   3360
tatggaaatt acacaccgtt accagcaggt tatgtgacaa aagaattaga gtacttccca   3420
gaaaccgata aggtatggat agagattgga gaaacggaag gaacattcat cgtagacagt   3480
gtggaattac tcctcatgga ggaatag                                       3507
```

```
<210> SEQ ID NO 17
<211> LENGTH: 3501
<212> TYPE: DNA
<213> ORGANISM: Artificial Sequence
<220> FEATURE:
<223> OTHER INFORMATION: Codon optimized BT0002

<400> SEQUENCE: 17
```

```
atggagatta acaaccaaaa gcaatgcatc ccatataact gtttgtcgaa cccggaggag     60
gttctgttgg acggtgaaag aatattgccc gacatagatc cgcttgaggt ttctttgagc    120
ttgttgcagt ttctgttgaa caacttcgtt cccggcggag gattcatcag cgggcttgtc    180
gataagatct ggggagcgct gagaccatcg gaatgggact tgttcctggc ccagatcgaa    240
cgccttattg accaaaggat agaagccacg gttcgggcca aggctattgc agaacttgaa    300
```

-continued

```
ggactcggcc ggtcctatca actgtatgga gaggcattca aagaatggga aaaaacgcct    360
gacaacactg cagccaggtc gagagtgact gagcgcttta ggataatcga cgcacaaatc    420
gaggcaaaca tcccatcgtt ccgcgtctct ggttttgagg tccccctctt gctcgtctat    480
acacaagctg caaatcttca tttggcattg ttgagggact ccgttgtctt cggggagcgc    540
tggggtctta caacaacgaa cgtgaatgat atctacaaca ggcaggtgaa caggattgga    600
gaatactcta atcattgtgt tgacacatac aacacggagc tggagcgcct cggatttcgg    660
agcattgcgc agtggcggat ttacaatcag ttcaggagag agctcacgct gacagtgctg    720
gacatcgtcg ctctctttcc taactatgac tcgcgcctct atcccatcca gacctttcg     780
cagttgaccc gcgaaatagt cacttcaccc gtgtctgaat tttactacgg cgtcataaat    840
tcagggaaca taaatggaac actgactgag cagcaaatca ggaggcccca tctgatggac    900
ttcttcaatt ccatgattat gtacacatct gacaaccgcc gcgagcatta ttggtcaggc    960
ctggagatga cggcgtactt cacaggtttt gcgggcgcac aggtgtcttt tcctttggtg   1020
gggacgaggg gggagtcagc tcctcctctg acagtccgct cagtgaatga cggcatatat   1080
aggattttga gcgccccttt ctattcggct ccgtttcttg gtactatagt gcttggctca   1140
cggggtgaaa agtttgattt tgcgctgaac aacattagcc cgcctccttc tacaatctac   1200
cggcatccgg gaaccgtcga ttctctcgtg tctattccgc cgcaagataa ctcggtgcca   1260
cctcatcgcg gctcgtccca ccggttgtca cacgttacaa tgagggcttc atccccgatc   1320
ttccactgga ctcatagatc tgccactacg actaatacca tcaatccgaa cgccataata   1380
cagatccccc ttgttaaagc ttttaatctc cactccggtg ccaccgttgt tagagggccg   1440
ggtttcaccg gggagatat acttagaaga actaataccg gcacattcgc tgatatgagg    1500
gtgaatatta ccgggcccct gtcgcagaga tacagggttc ggatcagata cgcctcaaca   1560
actgatttgc aattttttac acgcatcaat gggacctcgg tgaatcaagg aaatttccag   1620
cggacaatga atagagggga taacttggaa tccgggaact ttcggacggc aggtttctca   1680
actcccttta gcttttccaa cgctcaatct accttcaccc tcgggactca ggcattctct   1740
aatcaggaag tctatataga caggattgaa tttgtgccag cggaagttac gttcgaggct   1800
gagagcgatc tcgaaagagc gcaaaaagca gttaatgctc tgttcacctc cacgaatcaa   1860
ctgggcctga agactgatgt tactgattac cagatcgatc aggtgagcaa tctggtcgaa   1920
tgtctctctg atgaattttg tctcgacgag aaaagggaat tgtcagaaaa ggtcaaacat   1980
gccaaaaggc tgtctgataa gcgcaatttg ctccaagatc ccaattttac aagcattaat   2040
cgccagctcg accgcggctg gcggggttct accgacatta ctatacaggg cgggaacgat   2100
gtcttcaaag aaaactacgt gaccttgccg ggcaccttcg atgaatgtta ccctacttac   2160
ttgtatcaaa agatagacga gtccaaattg aaggcgtaca ctcgctatga attgaggggg   2220
tatatcgaag atagccagga tcttgaagtt tatctcatta gatataatgc taagcatgaa   2280
acagtgaacg ttcccggtac aggttctctt tggccactta gcgtcgaatc gccgataggt   2340
aggtgtggcg agccgaacag atgcgttccc cacatcgagt ggaatcctga cttggattgt   2400
tcctgcaggg acggagagaa atgcgcgcac catagccatc acttttcctt ggacatagat   2460
gttggttgta cagacttgaa cgaggatctt ggtgtttggg tgatttttaa aataaagaca   2520
caggatggac acgcaagact tggcaatctc gaatttctgg aggagaagcc cctgttggga   2580
gaagctctcg ctcgggttaa gcgggcggaa aagaaatgga gagacaagcg ggagcagctc   2640
cagttcgaga cgaatatagt ttataaggag gccaaggaga gcgtggacgc cctctttgtt   2700
```

```
gattcccatt acaacagact gcaggccgat actaacatca ctatgattca cgccgcagat   2760

aagagggtcc accggatcag agaagcatac ctgccagaac tctctgtgat accaggggtt   2820

aatgctgata tcttcgaaga gctcgaaggg ctgatcttca cagcattttc actctacgac   2880

gcccgcaaca taataaagaa tggagacttt aataacggtc tgagctgctg gaacgttaaa   2940

ggtcacgttg acatccaaca gaatgaccat cgctctgtgc tcgttgtgcc agaatgggag   3000

agcgaggtgt cccaagaagt ccgcgtctgc ccagggcgcg gttacattct cagagttaca   3060

gcctataagg aaggctacgg cgaggggtgt gttacgatac atgaaatcga ggataatacc   3120

gacgaactca agttctcgaa ctgcatcgag gaagaagttt acccgacgga cactggaaac   3180

gattacaccg ctcatcaagg tacaaccggc tgcgctgacg catgtaactc tcgcaacgtg   3240

gggtatgagg acggctacga aattaatacc accgcttcgg tgaactacaa acccacgtac   3300

gaggaggaga tgtatacgga tgttagacgg gacaatcact gtgagtacga tagaggttac   3360

ggcaaccaca cacctcttcc cgcaggatac gttactaaag aattggagta cttcccagaa   3420

actgatactg tgtggattga gatcggcgaa acggaaggca cattcatcgt ggattccgtg   3480

gaattgctgc tcatggagga a                                             3501
```

<210> SEQ ID NO 18
<211> LENGTH: 2130
<212> TYPE: DNA
<213> ORGANISM: Artificial Sequence
<220> FEATURE:
<223> OTHER INFORMATION: Codon optimized BT0025

<400> SEQUENCE: 18

```
atgaaatcga aaaatcagaa catgcaccaa agcctgtcga acaatgcaac cgtggataag     60

aacttcactg gatcgttgga aaataatacc aatacggagc tgcaaaactt taaccatgaa    120

ggcatcgagc cttttgtgtc agtgagcacg atccagacag gtatcggtat cgccggtaaa    180

attctcggaa atctgggagt gcctttcgcg ggacaagtcg ctagcctgta ttcattcata    240

ctgggtgagc tgtggcccaa aggtaaatcg cagtgggaaa tcttcatgga gcacgttgaa    300

gagcttataa atcaaaagat atccacctac gctcgcaaca aagctctggc cgatttgaaa    360

gggcttggag acgcgctcgc agtgtatcat gaatctctgg agtcatggat aaagaatcgg    420

aataacacga gaacgcggtc tgttgtcaag agccagtaca tcactcttga actcatgttc    480

gtccaatctc tcccgtcctt cgcagtgtcc ggcgaagagg tccctttgct gccgatctat    540

gcacaggcag cgaacctcca cctgcttttg cttcgggatg cgtccatctt tggaaaagag    600

tggggtctta gcgattctga gatatccact ttctataacc ggcaggtgga aaggacctcg    660

gattactccg accactgtac aaaatggttt gacacggggt tgaataggct taaggggtcg    720

aacgccgaaa tctgggttaa gtacaatcaa ttccggagag atatgacact tatggttctc    780

gatctcgtcg cgcttttcca gtcctacgac actcacatgt accctataaa gaccacagcg    840

cagttgacac gggaggtgta tactaatgct ctcgggacgg ttcacccccca tccctctttc    900

actagcacca cttggtataa taataatgcg ccctcatttt ctgcgataga ggccgcagtc    960

atacggagcc cacatctctt ggattttctg gagcaagtca cgatatattc gctcctctct   1020

cgctggtcaa acacacaata tatgaatatg tggggcggtc ataagctgga gtttagaact   1080

attggaggta cgctcaatac gtccacccag ggatcgacaa acacctccat aaaccccgtt   1140

acgctcccat tcacgtctag agacatatat cggactgaga gcctcgccgg cctcaacctc   1200
```

```
tttctgacgc aacccgtgaa cggggtccca cgcgttgatt tccactggaa attcgtgaca   1260

catccgattg cgtcagacaa tttctattac cctgggtacg cgggaatcgg cacgcaactg   1320

caggattcgg agaacgaact tcctccggag gcgacagggc agcccaatta tgaaagctac   1380

agccatcggc tgagccacat cggtctcatc tccgcctctc atgttaaggc gttggtgtat   1440

tcatggacgc acagatccgc agaccggacc aacacgatcc actcggactc gataacccag   1500

attccgctcg ttaaggccca cactctccag agcggaacta ctgtcgtcaa agggccaggg   1560

ttcaccggag gggatatact gaggagaact agcggtggac cgttcgcttt cagcaacgtc   1620

aatctcgact ggaatctctc acagagatac cgcgctcgca taagatatgc ctccaccacg   1680

aatctccgga tgtacgtcac cattgcggga gagcgcatct ttgctggtca gtttaacaag   1740

acaatgaaca ctggcgatcc actgaccttt caatccttct catatgccac aattgacacg   1800

gcgttcacct ttccgaccaa ggcttccagc cttacggttg gtgcggacac cttttctagc   1860

ggcaatgagg tttacgtgga ccgcttcgag ttgattcccg ttaccgctac tctcgaagca   1920

gtgactgatt tggagcgcgc gcaaaaggcg gtgcatgaac ttttcacgag caccaatcct   1980

ggcggcctta aaacggatgt caaagattat catatagacc aggtgtctaa cctggttgag   2040

tcactctcgg ataagtttta tttggatgaa aagcgggaac tttttgagat cgtgaagtac   2100

gctaaacagc tccatatcga acggaatatg                                    2130
```

<210> SEQ ID NO 19
<211> LENGTH: 3504
<212> TYPE: DNA
<213> ORGANISM: Artificial Sequence
<220> FEATURE:
<223> OTHER INFORMATION: Codon optimized BT0053

<400> SEQUENCE: 19

```
atggagatta acaaccagaa ccaatgcata ccttataact gtttgagcaa cccagaagaa     60

gtgttccttg atggggagcg gatactcccc gacatagacc cgctcgaagt cagcttgagc    120

ttgttgcaat tccttctgaa taacttcgtg cctggcgggg gcttcatatc tggtcttctg    180

gataagatct gggggggccct tagaccgagc gattgggaac tcttcctgga gcagatcgag    240

cagctcatag acagaaggat tgagagaact gtgagggcta aagcaattgc agagctggaa    300

ggtttgggca ggagctacca gttgtacggc gaggcgttca aggaatggga aaaaaacaccg    360

gataacacag ctgcccggtc cagagttacg gagaggttcc ggataattga cgctcagatt    420

gaagctaaca taccatcttt tcgcgtgtct ggattcgagg ttcctctgct gcttgtttat    480

acccaagccg ctaatctgca ccttgctctc ttgagggata gcgtcgtgtt cggcgagcgg    540

tggggtttga ccacgaccaa tgtgaatgat atttataatc ggcaggtgaa tcggatcggc    600

gagtactcaa aacattgtgt cgacacgtat aaaacagagc tcgaacgcct tggattccgc    660

agcatagctc agtggaggat ttacaatcag tttcggagag agctcacatt gaccgtcctt    720

gatatagtgg ccgtctttcc caactatgat tctcggctct atcccatccg gactatatca    780

cagcttacca gagagattta tacctcgcct gtctcagaat tttattatgg agtcattaac    840

tctaacaaca taataggaac cctgactgaa cagcagatca gaaggcctca tctgatggac    900

tttttcaact cgatgataat gtatacatcc gacaacaggc gcgagcacta ctggtcgggc    960

ctcgaaatga cagctaccaa cactgaggga catcaacgga gctttccgct tgccggtacc   1020

ataggcaaca gcgctccgcc ggttacagtc cggaacaacg gagaaggaat ataccgcatc   1080

ctcagcgagc cgttctactc tgcacccttt ttggggactt cggtgctggg tagccgcggg   1140
```

```
gaggaatttg cattcgcgtc gaatacgaca acgtccttgc catcaactat atacaggaac   1200
cggggcaccg ttgatagctt ggtgtctata ccaccccagg attactcggt cccccctcat   1260
cggggatatt cacacttgct cagccacgtc acgatgagga actcatcgcc catcttccat   1320
tggactcacc ggtcagcaac acctaggaat acgatcgacc cagattcgat tacccagata   1380
cctgctgtta agggggcata catcttcaac agcccagtca taaccggacc cggccacact   1440
ggaggtgata ttatcaggtt caatcccaat acgcagaata acatcaggat accgttccaa   1500
agcaatgctg tgcagagata tcgcatccgg atgcggtacg cagccgaggc tgactgtatc   1560
cttgaatcgg gcgtgaacat tgttaccgga gccggtgtta cattccgccc gatcccgata   1620
aaagctacga tgactcctgg ttctccattg acttactatt cttttcagta tgccgatctc   1680
aatataaacc tcactgcccc catacgcccg aacaattttg tttccatacg caggtctaac   1740
caacctggga acctctatat cgaccgcatc gaattcattc ctatagatcc catcagggaa   1800
gccgaacacg accttgaacg cgctcagaaa gccgtcaatg cgctttttac gtcgtccaat   1860
caaattggtc tcaaaaccga cgttaccgac taccacatcg atcaagtgtc aaaccttgtc   1920
gcttgcttgt cagataagtt ctgcctcgat gaaaaaaggg agctttcgga aaaagttaag   1980
catgctaaac gcctgtcgga cgaacgcaac ctgctgcagg atcagaattt caccgggatt   2040
aataggcagg tggatagagg ctggcgcggc tccacagaca tcacaatcca agggggggaat  2100
gatgtcttta aggaaaacta cgtcacgttg ccaggaacgt tcgatgagtg ctaccctacg   2160
tatctttacc agaagattga tgaatcgaaa ttgaagccct atactaggta cgagcttcgc   2220
gggtatattg aggatagcca ggaccttgag gtttacctta taaggtacaa cgcgaaacac   2280
gagacgctta acgtgccagg gacaggttct ttgtggcccc tcgccgcaga gtcgtctata   2340
ggccggtgcg gtgaaccaaa ccggtgcgct cctcacattg agtggaatcc ggagctggac   2400
tgtagctgta gggacggaga aaagtgtgcc catcactcgc atcacttttc cctggacata   2460
gacgttgggt gtactgatct taacgaagac cttggagttt gggtgatatt caagatcaag   2520
actcaggatg gctatgctag gctcgggaac ttggagtttc tcgaggagaa acccctcctc   2580
ggggaggctc ttgctagagt caagagagcg gaaaaaaaat ggcgcgataa acgcgacaag   2640
ttggagtggg agacgaacat cgtctacaaa gaagctaaag aatcagtgga cgcccttttt   2700
gtggactctc aatataaccg cctccaaact gacactaaca tcgctatgat tcacgtggcc   2760
gataagcggg tgcataggat aagagaagcg tatttgcccg agctgtcagt tatccctggg   2820
gtgaacgctg caattttcga ggaactggaa ggtctgatat ttaccgcatt ttctctctat   2880
gacgcgcgga atgttattaa gaacggcgat ttcaaccacg gattgtcatg ttggaacgtc   2940
aagggccatg tggatgtcga agaacagaac aaccacagaa gcgttcttgt cgttccggag   3000
tgggaagctg aggtgagcca agaggtccgc gtctgccctg gacgggggta tattttgcgg   3060
gtcaccgctt ataaagaggg gtacggagag gggtgtgtca cgatccacga gattgaagac   3120
cacacagacg agcttaaatt cagaaattgt gaggaagaag aggtctaccc aaataacacc   3180
gttacatgca acgattatcc cgctaatcag gaggaatatc gcgccgcaga aacgagcaga   3240
aatcgcgggt acggcgaatc atacgagtcc aattcttcta tacccgctga atacgcccct   3300
atttatgaga aggcttacac agacgggcgg aaggaaaata gctgcgagtc taataggggg   3360
tacgggaatt acacaccact tccggcaggg tacgttacga aggaactgga gtattttccg   3420
gaaaccgata aggtttggat cgagattggc gagacagaag gaacttttat cgttgactcc   3480
```

gtcgaacttt tgcttatgga agag 3504

<210> SEQ ID NO 20
<211> LENGTH: 3504
<212> TYPE: DNA
<213> ORGANISM: Artificial Sequence
<220> FEATURE:
<223> OTHER INFORMATION: Codon optimized variant BT0002

<400> SEQUENCE: 20
atggagatta acaatcagaa gcagtgcatc ccctacaact gcctgtccaa tccggaggag 60
gtgctcctgg acggcgagcg catcctccct gacattgatc cgctggaggt ctcactctcc 120
ctcctgcagt tcctcctgaa caatttcgtt cccggcgggg gcttcatttc ggggctggtg 180
gacaagatct ggggcgcgct caggccatcc gagtgggatc tcttcctggc tcagatcgag 240
aggctcattg accagaggat cgaggctacc gtgcgcgcta aggccatcgc tgagctggag 300
gggctgggca ggtcctacca gctgtacggc gaggcgttca aggagtggga gaagaccccg 360
gataacaccg cggccaggag cagggtcacg gagcgcttca ggatcattga cgcccagatt 420
gaggcgaaca tccccagctt cagggtgtcg ggcttcgagg tcccactcct gctcgtttac 480
acccaggctg ctaacctcca cctggctctg ctccgcgata gcgtggtctt cggcgagcgc 540
tgggggctca ccacgacaaa cgtgaatgac atctacaacc ggcaggtcaa tcgcatcggc 600
gagtactcta accactgcgt ggacacttac aataccgagc tggagaggct gggcttccgg 660
tcaattgctc agtggcgcat ctacaaccag ttccgcaggg agctgaccct gacggtcctg 720
gatatcgttg ccctcttccc caactacgac tcgcggctgt acccaattca gactttctct 780
cagctcaccc gcgagatcgt gacgtctcct gtctcagagt tctactacgg cgtcattaac 840
tccggcaaca tcaatgggac actgactgag cagcagattc ggcgcccgca cctcatggat 900
ttcttcaact caatgatcat gtacacctcc gacaataggc gggagcatta ctggtcgggc 960
ctcgagatga cggcgtactt cacgggcttc gcgggggcgc aggtgtcttt ccccctggtg 1020
ggcacacgcg gggagtctgc gccgcccctc actgtgcggt cagtcaacga cggcatctac 1080
cgcattctgt cggctccctt ctactctgcc ccattcctgg gcaccatcgt gctgggctcc 1140
cgcggcgaga agttcgactt cgccctgaac aatatttctc cacctccgtc aaccatctac 1200
cgccaccctg gcacggttga ttccctcgtg agcatcccgc cgcaggacaa ctcggtccct 1260
ccgcataggg gctccagcca caggctgtct catgttacca tgagggcgtc gtctccgatc 1320
ttccactgga cccatcggag cgccactacc acgaatacaa tcaaccctaa tgcgatcatt 1380
cagatcccgc tggtcaaggc gttcaacctc cactccggcg ctacggttgt gagggggccc 1440
ggcttcaccg gcggcgacat cctgcgcagg accaacacgg ggacattcgc ggacatgcgg 1500
gtgaatatta ccggcccact gagccagcgc taccgcgtgc gcatccgcta cgctagcaca 1560
actgacctcc agttcttcac acgcatcaac ggcacttccg tgaaccaggg gaatttccag 1620
cgcacgatga acaggggcga caatctcgag tcagggaact tcaggaccgc cggcttctcc 1680
acgcctttca gcttctcgaa tgctcagagc actttcaccc tgggcaccca ggccttctcg 1740
aaccaggagg tctacatcga tcgcattgag ttcgtcccgg cggaggttac gttcgaggct 1800
gagtctgacc tggagagggc ccagaaggcg gtgaacgctc tcttcacgtc aacaaatcag 1860
ctcggcctga agacggacgt cacagattac cagatcgacc aggtgagcaa cctggtcgag 1920
tgcctctcgg acgagttctg cctggatgag aagcgggagc tgtctgagaa ggtgaagcac 1980
gcgaagcggc tgtcagacaa gcgcaacctg ctccaggacc cgaacttcac ctcaatcaat 2040
aggcagctgg acaggggctg gagggggtcc actgatatca ccattcaggg cggcaacgac 2100
gtcttcaagg agaattacgt tacgctgcct ggcacattcg atgagtgcta cccgacatac 2160
ctctaccaga agatcgacga gtcaaagctg aaggcctaca ctcggtacga gctgcgcgga 2220
tacatcgagg actcccagga tctggaggtg tacctcatcc gctacaacgc gaagcacgag 2280
acagtgaatg tgccggggac tggctccctc tggccactgt cggttgagtc tccaattggc 2340
cggtgcgggg agcctaacag gtgcgtgccc catatcgagt ggaatccaga cctggattgc 2400
tcctgcaggg acggcgagaa gtgcgctcac cattcccacc atttcagcct cgacatcgat 2460
gtcgggtgca cagacctgaa cgaggatctc ggcgtttggg tcatcttcaa gatcaagacc 2520
caggacggcc acgctaggct ggggaacctg gagttcctgg aggagaagcc cctgctgggc 2580
gaggctctgg ctagggtgaa gagggcggag aagaagtggc gcgacaagag ggagcagctc 2640
cagttcgaga ccaacatcgt ctacaaggag gccaaggagt ccgttgacgc gctgttcgtg 2700
gatagccact acaacaggct ccaggcggat acgaatatca caatgattca cgcggctgac 2760
aagcgggtgc atcgcattag ggaggcctac ctgcctgagc tgtcggttat tccgggcgtg 2820
aacgcggaca tcttcgagga gctggagggc ctcatcttca ccgctttctc tctgtacgat 2880
gccaggaaca tcattaagaa tggcgacttc aacaatgggc tcagctgctg gaacgtcaag 2940
ggccacgttg acatccagca gaatgatcat cgctcggtcc tcgtcgttcc tgagtgggag 3000
tcagaggttt cccaggaggt cagggtttgc ccccgggaggg gatacatcct gcgcgttacc 3060
gcctacaagg aggggtacgg cgaggggtgc gtgacaatcc acgagattga ggacaacact 3120
gatgagctga agttctccaa ttgcatcgag gaggaggtgt acccgactga caccggcaac 3180
gattacaccg ctcatcaggg caccaccggg tgcgccgatg cttgcaactc caggaatgtc 3240
ggctacgagg acgggtacga gatcaacaca actgcgagcg tgaattacaa gcccacatac 3300
gaggaggaga tgtacactga cgtccggcgc gataaccact gcgagtacga ccgcggctac 3360
gggaatcata ccccgctccc agcgggctac gtgaccaagg agctggagta cttcccagag 3420
acggatacag tctggctcga gattggcgag actgagggga ccttcatcgt tgacagcgtg 3480
gagctgatcc tgatggagga gtga 3504

<210> SEQ ID NO 21
<211> LENGTH: 2133
<212> TYPE: DNA
<213> ORGANISM: Artificial Sequence
<220> FEATURE:
<223> OTHER INFORMATION: Codon optimized variant BT0025

<400> SEQUENCE: 21
atgaagtcca agaatcagaa catgcatcag tcactctcca acaatgcgac ggtcgacaag 60
aatttcacag gcagcctcga gaacaatacc aacacggagc tgcagaattt caaccacgag 120
ggcatcgagc cgttcgtcag cgtttcgaca attcagactg gcatcgggat tgccggcaag 180
atcctcggca acctcggcgt gccgttcgcc ggccaggttg cttcgctcta ctctttcatc 240
ctgggcgagc tgtggcccaa ggggaagtcg cagtgggaga ttttcatgga gcatgtcgag 300
gagctgatca atcagaagat ttctacgtac gcccgcaaca aggccctggc tgacctcaag 360
ggcctggggg atgctctggc cgtgtaccac gagtcactgg agtcctggat caagaacagg 420
aacaatacaa ggactcgctc cgtggtcaag agccagtaca ttaccctcga gctgatgttc 480
gtgcagtcgc tcccctcctt cgccgtttcc ggcgaggagg tgccgctcct gccaatctac 540

```
gcccaggctg cgaatctcca tctcctgctc ctgcgcgacg cttctatctt cggcaaggag    600

tgggggctgt ctgattcaga gatttcaacg ttctacaaca ggcaggtcga gcggacatct    660

gactactcag atcactgcac aaagtggttc gacactggcc tcaataggct gaaggggtcc    720

aacgcggaga tctgggtgaa gtacaaccag ttccgcaggg acatgacgct catggttctc    780

gatctggtgg ccctgttcca gagctacgac acccacatgt accccatcaa gaccacggct    840

cagctcaccc gggaggttta cacgaacgcc ctgggcacag tgcacccaca tccttccttc    900

accagcacaa cttggtacaa caataacgct ccgtccttca gcgccatcga ggctgccgtc    960

attaggagcc cccatctcct ggacttcctc gagcaggtta cgatctactc gctcctgtct   1020

cggtggtcaa atacacaata catgaacatg tggggcgggc acaagctcga gttccgcaca   1080

attggcggga ctctgaacac ttcgacgcag ggctctacaa atacttcaat caacccagtc   1140

accctccctt tcacgtcacg cgacatctac aggactgagt ccctggcggg cctcaatctg   1200

ttcctcacgc agcccgttaa cggggtgccc agggtcgact tccactggaa gttcgtgacc   1260

catccaatcg cgagcgataa cttctactac cctggctacg ctggcattgg gacgcagctc   1320

caggactcgg agaatgagct gccgcccgag gctacaggcc agccaaacta cgagtcgtac   1380

tctcaccgcc tctcccatat cggcctgatt tcagcgtccc acgtcaaggc tctcgtttac   1440

agctggaccc atcgctccgc cgaccgcacc aacacgatcc acagcgattc gatcactcag   1500

attccgctcg tgaaggctca caccctgcag tcgggcacca ccgttgtgaa gggcccaggg   1560

ttcactggcg gggacatcct gaggcgcacc tcgggcgggc ctttcgcgtt ctctaatgtt   1620

aacctcgatt ggaatctgtc ccagcgctac cgcgcccgca tccgctacgc ctccacaact   1680

aacctcagga tgtatgtgac catcgcgggc gagcggattt tcgctgggca gttcaataag   1740

accatgaaca cgggcgaccc actgacgttc cagtctttct catacgctac aatcgatact   1800

gccttcacct tccctaccaa ggcctccagc ctcactgtgg gcgccgacac cttctcgtct   1860

gggaacgagg tctacgtgga taggttcgag ctgatcccgg tgacagccac gctggaggcc   1920

gtcacggacc tggagcgggc tcagaaggcg gtgcatgagc tgttcacctc cacgaatcca   1980

ggcggcctga agaccgacgt caaggattac cacctcgatc aggtgagcaa cctcgtcgag   2040

tccctgagcg acaagttcta cctcgatgag aagcgcgagc tgttcgagct cgtgaagtac   2100

gccaagcagc tgcacattga gaggaacatg tga                               2133
```

<210> SEQ ID NO 22
<211> LENGTH: 3507
<212> TYPE: DNA
<213> ORGANISM: Artificial Sequence
<220> FEATURE:
<223> OTHER INFORMATION: Codon optimized variant BT0053

<400> SEQUENCE: 22

```
atggcgatta acaatcagaa ccagtgcatc ccatacaact gcctgtccaa tcctgaggag     60

gtgttcctgg acggcgagcg catcctcccg gacattgatc cctggaggt gtctctctca    120

ctcctgcagt tcctcctgaa caatttcgtc ccaggcgggg gcttcatttc gggcctcctg    180

gacaagatct ggggcgccct caggccttcg gattgggagc tgttcctcga gcagatcgag    240

cagctcattg acaggaggat cgagcgcacc gtcagggcta aggccatcgc tgagctggag    300

gggctgggcc gctcttacca gctctacggc gaggcgttca aggagtggga gaagacgccc    360

gacaacacgg cggccaggtc aagggtgacg gagcgcttca ggatcattga tgcccagatt    420

gaggcgaaca tcccgtcctt ccgcgtgagc ggcttcgagg tcccccctcct gctcgtttac    480
```

```
acgcaggctg ccaacctcca tctggccctg ctccgggact cggtggtgtt cggcgagagg    540
tgggggctca ccaccacaaa cgtcaatgat atctacaacc ggcaggttaa tcgcatcggc    600
gagtactcaa agcactgcgt cgacacttac aagaccgagc tggagaggct gggcttccgg    660
tccattgcgc agtggaggat ctacaaccag ttccggcgcg agctgacact gactgtgctc    720
gacatcgtcg ctgttttccc aaactacgat tcccggctgt accctatccg cacgattagc    780
cagctcacac gcgagatcta cacttcccca gttagcgagt tctactacgg cgtgatcaac    840
tccaacaata tcattggcac cctcacggag cagcagatta ggcggcctca cctcatggac    900
ttcttcaact cgatgatcat gtacacctct gataatcgca gggagcacta ctggagcggc    960
ctggagatga cagccactaa caccgagggg catcagcgct ccttcccact ggccggcacc   1020
atcgggaatt ctgctccgcc cgtgaccgtg cgcaacaatg ggagagggcat ctacaggatt  1080
ctgtccgagc cattctactc ggcccctttc ctgggcacgt cggtcctggg ctctcgcggg   1140
gaggagttcg ctttcgcgtc gaacactacc acgtcgctgc catctacaat ctacaggaat   1200
cgcggcactg tggactcact cgtctccatc ccacctcagg attactctgt tccgccccac   1260
aggggctact cacacctgct ctcccatgtg acaatgcgca actccagccc gatcttccac   1320
tggactcata ggagcgccac gccacggaat acaatcgacc ctgattcgat cacacagatt   1380
cccgctgtga agggcgccta cattttcaac tcgccggtca tcaccgggcc cggccacacc   1440
ggcggcgaca tcattcgctt caacccaaat acgcagaaca atatcaggat tcctttccag   1500
tccaacgcgg tccagcgcta ccgcatccgc atgcgctacg cggctgaggc tgactgcatt   1560
ctggagagcg gcgttaacat cgtgacaggg gctggcgtga ctttccgccc aatccctatt   1620
aaggccacga tgacaccagg ctcacctctc acctactact ccttccagta cgccgacctg   1680
aacattaatc tcacggcgcc gatccgcccc aacaatttcg tgagcatcag gaggtccaac   1740
cagcccggca atctgtacat cgacaggatt gagttcatcc caattgatcc tatcagggag   1800
gccgagcacg acctcgagcg cgcgcagaag gctgtcaacg ccctgttcac ctcgtctaat   1860
cagattggcc tcaagacgga cgtgacagat taccatatcg accaggttag caacctggtg   1920
gcctgcctct cggacaagtt ctgcctggat gagaagaggg agctgtcaga gaaggtcaag   1980
cacgcgaagc gcctgtccga cgagaggaac ctgctccagg atcagaattt cacgggcatc   2040
aacaggcagg tggatagggg ctggaggggg agcactgaca tcaccattca gggcggcaac   2100
gatgtcttca aggagaatta cgttactctg ccgggcacct tcgacgagtg ctaccccaca   2160
tacctctacc agaagatcga tgagtcgaag ctgaagccgt acactcgcta cgagctgagg   2220
ggatacatcg aggactctca ggatctggag gtctacctca tccgctacaa cgccaagcat   2280
gagaccctca atgtgcccgg gacgggcagc ctctggccgc tggcggccga gtcatccatc   2340
ggcaggtgcg gggagccaaa caggtgcgcc cctcacatcg agtggaatcc ggagctggac   2400
tgctcgtgca gggatggcga gaagtgcgcg caccattctc accatttctc actcgacatc   2460
gatgtgggct gcaccgacct gaacgaggat ctcggggttt gggtcatctt caagatcaag   2520
acccaggacg gctacgctag gctggggaac ctggagttcc tggaggagaa gccgctgctg   2580
ggcgaggctc tggctagggt caagagggcg gagaagaagt ggcgcgacaa gagggataag   2640
ctcgagtggg agaccaacat cgtgtacaag gaggccaagg agtctgtgga cgcgctgttc   2700
gtcgattcac agtacaacag gctccagact gacaccaata tcgcgatgat tcacgttgct   2760
gataagcggg tgcatcgcat ccgcgaggct tacctgcccg agctgtccgt cattcccggc   2820
```

-continued

```
gttaacgctg ccatcttcga ggagctggag gggctcatct tcaccgcttt cagcctgtac   2880

gacgccagga acgtcatcaa gaatggcgat ttcaaccacg ggctctcgtg ctggaacgtg   2940

aagggccacg tcgacgttga ggagcagaac aatcatcgct ctgttctggt tgtgccggag   3000

tgggaggctg aggtgtcaca ggaggtgcgg gtctgcccgg ggaggggata catcctcagg   3060

gtcaccgcct acaaggaggg gtacggcgag gggtgcgtta ccatccacga gattgaggac   3120

catacggatg agctgaagtt ccggaactgc gaggaggagg aggtgtaccc aaacaatacg   3180

gtcacatgca atgactaccc ggccaaccag gaggagtaca gggccgctga gacatccagg   3240

aacaggggct acggggagag ctacgagtcg aatagctcga ttccggcgga gtacgctccc   3300

atctacgaga aggcctacac tgacggcagg aaggagaatt cttgcgagtc aaaccggggc   3360

tacgggaatt acacaccgct gcccgcgggc tacgtcacta aggagctgga gtacttcccg   3420

gagaccgaca aggtttggat cgagattggc gagacggagg ggacattcct cgtcgatagc   3480

gttgagctgc tcctgatgga ggagtga                                         3507
```

<210> SEQ ID NO 23
<211> LENGTH: 3504
<212> TYPE: DNA
<213> ORGANISM: Artificial Sequence
<220> FEATURE:
<223> OTHER INFORMATION: Synthetic sequence encoding modified
      alpha-helix 3 BT0002

<400> SEQUENCE: 23

```
atggagataa ataatcagaa gcaatgcata ccatataatt gcttaagtaa tcctgaggaa     60

gtacttttgg atggggagag gatattacct gatatcgatc cactcgaagt ttctttgtcg    120

cttttgcaat ttcttttgaa taactttgtt ccagggggag gctttatttc aggattagtt    180

gataaaatat ggggggcttt gagaccatct gaatgggact tatttcttgc acagattgaa    240

cggttgattg atcaaagaat agaagcaaca gtaagagcaa aagcaatcac tgaattagaa    300

ggtttaggga gaaattatca aatatatgca gaggcattta aagagtggga aagtgatcca    360

gataacacag cggctcggtc tagagtaact gagagatttc gtataattga tgctcaaatt    420

gaagcaaata tcccttcgtt tcgggtttcc ggatttgaag tgccacttct attggtttat    480

acccaagcag ctaatttgca tctcgctcta ttaagagatt ctgttgtttt tggagagaga    540

tggggattga cgactacaaa tgtcaatgat atctataata gacaagttaa tagaattggt    600

gaatatagca atcattgcgt agatacgtat aacacagaac tagaacgtct agggtttaga    660

tctatagcgc agtggagaat atataatcag tttagaagag aactaacact aactgtatta    720

gatattgtcg ctcttttccc gaactatgac agtagactgt atccgatcca aactttttct    780

caattgacaa gagaaattgt tacatcccca gtaagcgaat tttattatgg tgttattaat    840

agtggtaata taaatggtac tcttactgaa cagcagataa ggcgaccaca tcttatggac    900

ttctttaact ccatgatcat gtatacatca gataatagac gggaacatta ttggtcagga    960

cttgaaatga cggcttattt tacaggattt gcaggcgctc aagtgtcatt ccctttagtc   1020

gggactagag gggagtcagc tccaccatta actgttagaa gtgttaatga tggaatttat   1080

agaatattat cggcaccgtt ttattcagcg ccttttctag gcaccattgt attgggaagt   1140

cgtggagaaa aatttgattt tgcgcttaat aatatttcac ctccgccatc tacaatatac   1200

agacatcctg gaacagtaga ttcactagtc agtataccgc cacaggataa tagcgtacca   1260

ccgcacaggg gatctagtca tcgattaagt catgttacaa tgcgcgcaag ttcccctata   1320
```

-continued

```
ttccattgga cgcatcgcag cgcaaccact acaaatacaa ttaatccaaa tgctattatc   1380
caaataccac tagtaaaagc atttaacctt cattcaggtg ccactgttgt tagaggacca   1440
gggtttacag gtggtgatat ccttcgaaga acgaatactg gcacatttgc agatatgaga   1500
gtaaatatta ctgggccatt atcccaaaga tatcgtgtaa gaattcgcta tgcttctacg   1560
acagatttac aatttttcac gagaatcaat ggaacttctg taaatcaagg taatttccaa   1620
agaactatga atagaggggga taatttagaa tctggaaact ttaggactgc aggatttagt   1680
acgcctttta gtttttcaaa tgcgcaaagt acattcacat tgggtactca ggctttttca   1740
aatcaggaag tttatataga tcgaattgaa tttgtcccgg cagaagtaac attcgaggca   1800
gaatctgatt tagaaagagc gcaaaaggcg gtgaatgccc tgtttacttc tacaaaccaa   1860
ctagggctaa aaacagatgt gacggattat cagattgatc aagtgtccaa tttagtagaa   1920
tgtttatcag atgaattttg tctggatgaa aagagagaat tgtccgagaa agtcaaacat   1980
gcaaagcgac ttagtgataa gcggaaccta cttcaagatc caaacttcac atctatcaat   2040
agacaactag accgtggatg gagaggaagt acggatatta ccatccaagg aggaaatgac   2100
gtattcaaag agaattacgt cacactacca ggtacctttg atgagtgtta tccaacgtat   2160
ttgtatcaaa aaatagatga gtcaaaatta aaagcctata ctcgctatga attaagaggg   2220
tatattgaag atagtcaaga tttagaagtc tatttgattc gttacaatgc gaaacatgaa   2280
acagtaaatg ttcccggtac agggtcctta tggccgcttt cagtcgaaag cccaatcgga   2340
aggtgcggag aaccgaatcg atgtgtgcca catattgaat ggaatcctga tttagattgt   2400
tcgtgtaggg atggggagaa gtgtgcccat cattcgcatc atttctctct agatattgat   2460
gttggatgta cagacctaaa tgaggaccta ggtgtatggg tgatctttaa gattaaaacg   2520
caggatggcc atgcaagatt aggaaatcta gagtttctcg aagagaaacc attgttagga   2580
gaagcgttag ctcgtgtgaa aagagcggag aaaaaatgga gagacaaacg cgaacaattg   2640
cagtttgaaa cgaatatcgt ttacaaagag gcaaaagaat ctgtagatgc tttattcgta   2700
gattctcact ataatagatt acaagcggat acgaacatta cgatgattca tgcggcagat   2760
aaacgcgttc atcgaatccg agaggcttat cttccggaat tatccgttat cccaggtgta   2820
aatgcggaca tttttgaaga attagaaggt cttattttca ctgcattctc cctatatgat   2880
gcgagaaata tcattaaaaa cggtgatttc aataatggtt tatcgtgttg gaacgtgaaa   2940
gggcatgtag atatacaaca gaatgatcat cgttctgtcc tcgttgtccc ggaatgggaa   3000
tcagaggtat cacaagaagt ccgcgtatgt ccaggtcgtg gctatattct tcgtgtcaca   3060
gcgtacaaag agggctacgg agaaggatgc gtaacgatcc atgagatcga agacaataca   3120
gacgaattga agtttagtaa ctgcatagaa gaggaagtct atccaacgga tacaggtaat   3180
gattatactg cacaccaagg tacaacagga tgcgcagatg catgtaattc ccgtaatgtt   3240
ggatatgagg atggatatga aataaatact acagcatctg ttaattacaa accgacttat   3300
gaagaagaaa tgtatacaga tgtacgaaga gataatcatt gtgaatatga cagaggatat   3360
gggaaccata caccgttacc agctggttat gtaacaaaag aattagagta cttccctgaa   3420
acagatacag tatggataga gattggagaa acggaaggaa cattcatcgt agatagtgtg   3480
gaattactcc tcatggagga ataa                                          3504
```

<210> SEQ ID NO 24
<211> LENGTH: 3504
<212> TYPE: DNA
<213> ORGANISM: Artificial Sequence
<220> FEATURE:
<223> OTHER INFORMATION: Synthetic sequence encoding modified
      alpha-helix 4 BT0002

<400> SEQUENCE: 24

```
atggagataa ataatcagaa gcaatgcata ccatataatt gcttaagtaa tcctgaggaa     60

gtacttttgg atggggagag gatattacct gatatcgatc cactcgaagt ttctttgtcg    120

cttttgcaat ttcttttgaa taactttgtt ccagggggag gctttatttc aggattagtt    180

gataaaatat ggggggcttt gagaccatct gaatgggact tatttcttgc acagattgaa    240

cggttgattg atcaaagaat agaagcaaca gtaagagcaa aagcaatcgc tgaattagaa    300

ggtttaggga gaagttatca actatatgga gaggcattta aagagtggga aaaaactcca    360

gataacgaag cggctaagtc tagagtaatt gatagatttc gtatattaga tggtttaatt    420

gaagcaaata tcccttcgtt tcggattatc ggatttgaag tgccacttct attggtttat    480

acccaagcag ctaatttgca tctcgctcta ttaagagatt ctgttgtttt tggagagaga    540

tggggattga cgactacaaa tgtcaatgat atctataata gacaagttaa tagaattggt    600

gaatatagca atcattgcgt agatacgtat aacacagaac tagaacgtct agggtttaga    660

tctatagcgc agtggagaat atataatcag tttagaagag aactaacact aactgtatta    720

gatattgtcg ctcttttccc gaactatgac agtagactgt atccgatcca aacttttct     780

caattgacaa gagaaattgt tacatcccca gtaagcgaat tttattatgg tgttattaat    840

agtggtaata taaatggtac tcttactgaa cagcagataa ggcgaccaca tcttatggac    900

ttctttaact ccatgatcat gtatacatca gataatagac gggaacatta ttggtcagga    960

cttgaaatga cggcttattt tacaggattt gcaggcgctc aagtgtcatt ccctttagtc   1020

gggactagag gggagtcagc tccaccatta actgttagaa gtgttaatga tggaatttat   1080

agaatattat cggcaccgtt ttattcagcg cctttttctag gcaccattgt attgggaagt   1140

cgtggagaaa aatttgattt tgcgcttaat aatatttcac ctccgccatc tacaatatac   1200

agacatcctg gaacagtaga ttcactagtc agtataccgc cacaggataa tagcgtacca   1260

ccgcacaggg gatctagtca tcgattaagt catgttacaa tgcgcgcaag ttcccctata   1320

ttccattgga cgcatcgcag cgcaaccact acaaatacaa ttaatccaaa tgctattatc   1380

caaataccac tagtaaaagc atttaacctt cattcaggtg ccactgttgt tagaggacca   1440

gggtttacag gtggtgatat ccttcgaaga acgaatactg gcacatttgc agatatgaga   1500

gtaaatatta ctgggccatt atcccaaaga tatcgtgtaa gaattcgcta tgcttctacg   1560

acagatttac aatttttcac gagaatcaat ggaacttctg taaatcaagg taatttccaa   1620

agaactatga atagagggga taatttagaa tctggaaact ttaggactgc aggatttagt   1680

acgcctttta gtttttcaaa tgcgcaaagt acattcacat tgggtactca ggctttttca   1740

aatcaggaag tttatataga tcgaattgaa tttgtcccgg cagaagtaac attcgaggca   1800

gaatctgatt tagaaagagc gcaaaaggcg gtgaatgccc tgtttacttc tacaaaccaa   1860

ctagggctaa aaacagatgt gacggattat cagattgatc aagtgtccaa tttagtagaa   1920

tgtttatcag atgaattttg tctggatgaa aagagagaat tgtccgagaa agtcaaacat   1980

gcaaagcgac ttagtgataa gcggaaccta cttcaagatc caaacttcac atctatcaat   2040

agacaactag accgtggatg gagaggaagt acggatatta ccatccaagg aggaaatgac   2100

gtattcaaag agaattacgt cacactacca ggtacctttg atgagtgtta tccaacgtat   2160

ttgtatcaaa aaatagatga gtcaaaatta aaagcctata ctcgctatga attaagaggg   2220
```

```
tatattgaag atagtcaaga tttagaagtc tatttgattc gttacaatgc gaaacatgaa   2280

acagtaaatg ttcccggtac agggtcctta tggccgcttt cagtcgaaag cccaatcgga   2340

aggtgcggag aaccgaatcg atgtgtgcca catattgaat ggaatcctga tttagattgt   2400

tcgtgtaggg atggggagaa gtgtgcccat cattcgcatc atttctctct agatattgat   2460

gttggatgta cagacctaaa tgaggaccta ggtgtatggg tgatctttaa gattaaaacg   2520

caggatggcc atgcaagatt aggaaatcta gagtttctcg aagagaaacc attgttagga   2580

gaagcgttag ctcgtgtgaa aagagcggag aaaaaatgga gagacaaacg cgaacaattg   2640

cagtttgaaa cgaatatcgt ttacaaagag gcaaaagaat ctgtagatgc tttattcgta   2700

gattctcact ataatagatt acaagcggat acgaacatta cgatgattca tgcggcagat   2760

aaacgcgttc atcgaatccg agaggcttat cttccggaat tatccgttat cccaggtgta   2820

aatgcggaca tttttgaaga attagaaggt cttattttca ctgcattctc cctatatgat   2880

gcgagaaata tcattaaaaa cggtgatttc aataatggtt tatcgtgttg gaacgtgaaa   2940

gggcatgtag atatacaaca gaatgatcat cgttctgtcc tcgttgtccc ggaatgggaa   3000

tcagaggtat cacaagaagt ccgcgtatgt ccaggtcgtg gctatattct tcgtgtcaca   3060

gcgtacaaag agggctacgg agaaggatgc gtaacgatcc atgagatcga agacaataca   3120

gacgaattga agtttagtaa ctgcatagaa gaggaagtct atccaacgga tacaggtaat   3180

gattatactg cacaccaagg tacaacagga tgcgcagatg catgtaattc ccgtaatgtt   3240

ggatatgagg atggatatga aataaatact acagcatctg ttaattacaa accgacttat   3300

gaagaagaaa tgtatacaga tgtacgaaga gataatcatt gtgaatatga cagaggatat   3360

gggaaccata caccgttacc agctggttat gtaacaaaag aattagagta cttccctgaa   3420

acagatacag tatggataga gattggagaa acggaaggaa cattcatcgt agatagtgtg   3480

gaattactcc tcatggagga ataa                                          3504
```

<210> SEQ ID NO 25
<211> LENGTH: 3504
<212> TYPE: DNA
<213> ORGANISM: Artificial Sequence
<220> FEATURE:
<223> OTHER INFORMATION: Synthetic sequence encoding modified alpha-helix 5/6 BT0002

<400> SEQUENCE: 25

```
atggagataa ataatcagaa gcaatgcata ccatataatt gcttaagtaa tcctgaggaa     60

gtacttttgg atggggagag gatattacct gatatcgatc cactcgaagt ttctttgtcg    120

cttttgcaat ttcttttgaa taactttgtt ccagggggag gctttatttc aggattagtt    180

gataaaatat ggggggcttt gagaccatct gaatgggact tatttcttgc acagattgaa    240

cggttgattg atcaaagaat agaagcaaca gtaagagcaa aagcaatcgc tgaattagaa    300

ggtttaggga gaagttatca actatatgga gaggcattta aagagtggga aaaaactcca    360

gataacacag cggctcggtc tagagtaact gagagatttc gtataattga tgctcaaatt    420

gaagcaaata tcccttcgtt tcgggtttcc ggatttgaag tgccacttct atcagtttat    480

gttcaagcag ctaatttgca tctcgctcta ttaagagatt ctgttatttt tggagagaga    540

tggggattga cgactaaaaa tgtcaatgat atctataata gacaaataag agaaattcat    600

gaatatagca atcattgcgt agatacgtat aacacagaac tagaacgtct agggtttaga    660

tctatagcgc agtggagaat atataatcag tttagaagag aactaacact aactgtatta    720
```

```
gatattgtcg ctcttttccc gaactatgac agtagactgt atccgatcca aactttttct    780
caattgacaa gagaaattgt tacatcccca gtaagcgaat tttattatgg tgttattaat    840
agtggtaata taaatggtac tcttactgaa cagcagataa ggcgaccaca tcttatggac    900
ttctttaact ccatgatcat gtatacatca gataatagac gggaacatta ttggtcagga    960
cttgaaatga cggcttattt tacaggattt gcaggcgctc aagtgtcatt ccctttagtc   1020
gggactagag gggagtcagc tccaccatta actgttagaa gtgttaatga tggaatttat   1080
agaatattat cggcaccgtt ttattcagcg ccttttctag gcaccattgt attgggaagt   1140
cgtggagaaa aatttgattt tgcgcttaat aatatttcac ctccgccatc tacaatatac   1200
agacatcctg gaacagtaga ttcactagtc agtataccgc cacaggataa tagcgtacca   1260
ccgcacaggg gatctagtca tcgattaagt catgttacaa tgcgcgcaag ttcccctata   1320
ttccattgga cgcatcgcag cgcaaccact acaaatacaa ttaatccaaa tgctattatc   1380
caaataccac tagtaaaagc atttaacctt cattcaggtg ccactgttgt tagaggacca   1440
gggtttacag gtggtgatat ccttcgaaga acgaatactg gcacatttgc agatatgaga   1500
gtaaatatta ctgggccatt atcccaaaga tatcgtgtaa gaattcgcta tgcttctacg   1560
acagatttac aatttttcac gagaatcaat ggaacttctg taaatcaagg taatttccaa   1620
agaactatga atagagggga taatttagaa tctggaaact ttaggactgc aggatttagt   1680
acgcctttta gtttttcaaa tgcgcaaagt acattcacat tgggtactca ggctttttca   1740
aatcaggaag tttatataga tcgaattgaa tttgtcccgg cagaagtaac attcgaggca   1800
gaatctgatt tagaaagagc gcaaaaggcg gtgaatgccc tgtttacttc tacaaaccaa   1860
ctagggctaa aaacagatgt gacggattat cagattgatc aagtgtccaa tttagtagaa   1920
tgtttatcag atgaattttg tctggatgaa aagagagaat tgtccgagaa agtcaaacat   1980
gcaaagcgac ttagtgataa gcggaaccta cttcaagatc caaacttcac atctatcaat   2040
agacaactag accgtggatg gagaggaagt acggatatta ccatccaagg aggaaatgac   2100
gtattcaaag agaattacgt cacactacca ggtacctttg atgagtgtta tccaacgtat   2160
ttgtatcaaa aaatagatga gtcaaaatta aaagcctata ctcgctatga attaagaggg   2220
tatattgaag atagtcaaga tttagaagtc tatttgattc gttacaatgc gaaacatgaa   2280
acagtaaatg ttcccggtac agggtcctta tggccgcttt cagtcgaaag cccaatcgga   2340
aggtgcggag aaccgaatcg atgtgtgcca catattgaat ggaatcctga tttagattgt   2400
tcgtgtaggg atggggagaa gtgtgcccat cattcgcatc atttctctct agatattgat   2460
gttggatgta cagacctaaa tgaggaccta ggtgtatggg tgatctttaa gattaaaacg   2520
caggatggcc atgcaagatt aggaaatcta gagtttctcg aagagaaacc attgttagga   2580
gaagcgttag ctcgtgtgaa aagagcggag aaaaaatgga gagacaaacg cgaacaattg   2640
cagtttgaaa cgaatatcgt ttacaaagag gcaaaagaat ctgtagatgc tttattcgta   2700
gattctcact ataatagatt acaagcggat acgaacatta cgatgattca tgcggcagat   2760
aaacgcgttc atcgaatccg agaggcttat cttccggaat tatccgttat cccaggtgta   2820
aatgcggaca tttttgaaga attagaaggt cttattttca ctgcattctc cctatatgat   2880
gcgagaaata tcattaaaaa cggtgatttc aataatggtt tatcgtgttg gaacgtgaaa   2940
gggcatgtag atatacaaca gaatgatcat cgttctgtcc tcgttgtccc ggaatgggaa   3000
tcagaggtat cacaagaagt ccgcgtatgt ccaggtcgtg gctatattct tcgtgtcaca   3060
```

gcgtacaaag agggctacgg agaaggatgc gtaacgatcc atgagatcga agacaataca 3120
gacgaattga agtttagtaa ctgcatagaa gaggaagtct atccaacgga tacaggtaat 3180
gattatactg cacaccaagg tacaacagga tgcgcagatg catgtaattc ccgtaatgtt 3240
ggatatgagg atggatatga aataaatact acagcatctg ttaattacaa accgacttat 3300
gaagaagaaa tgtatacaga tgtacgaaga gataatcatt gtgaatatga cagaggatat 3360
gggaaccata caccgttacc agctggttat gtaacaaaag aattagagta cttccctgaa 3420
acagatacag tatggataga gattggagaa acggaaggaa cattcatcgt agatagtgtg 3480
gaattactcc tcatggagga ataa 3504

<210> SEQ ID NO 26
<211> LENGTH: 3504
<212> TYPE: DNA
<213> ORGANISM: Artificial Sequence
<220> FEATURE:
<223> OTHER INFORMATION: Synthetic sequence encoding modified alpha-helix 3-4 BT0002

<400> SEQUENCE: 26
atggagataa ataatcagaa gcaatgcata ccatataatt gcttaagtaa tcctgaggaa 60
gtacttttgg atggggagag gatattacct gatatcgatc cactcgaagt ttctttgtcg 120
cttttgcaat ttcttttgaa taactttgtt ccagggggag gctttatttc aggattagtt 180
gataaaatat ggggggcttt gagaccatct gaatgggact tatttcttgc acagattgaa 240
cggttgattg atcaaagaat agaagcaaca gtaagagcaa aagcaatcac tgaattagaa 300
ggtttaggga gaaattatca aatatatgca gaggcattta aagagtggga aagtgatcca 360
gataacgaag cggctaagtc tagagtaatt gatagatttc gtatattaga tggtttaatt 420
gaagcaaata tcccttcgtt tcggattatc ggatttgaag tgccacttct attggtttat 480
acccaagcag ctaatttgca tctcgctcta ttaagagatt ctgttgtttt tggagagaga 540
tggggattga cgactacaaa tgtcaatgat atctataata gacaagttaa tagaattggt 600
gaatatagca atcattgcgt agatacgtat aacacagaac tagaacgtct agggtttaga 660
tctatagcgc agtggagaat atataatcag tttagaagag aactaacact aactgtatta 720
gatattgtcg ctcttttccc gaactatgac agtagactgt atccgatcca aactttttct 780
caattgacaa gagaaattgt tacatcccca gtaagcgaat tttattatgg tgttattaat 840
agtggtaata taaatggtac tcttactgaa cagcagataa ggcgaccaca tcttatggac 900
ttctttaact ccatgatcat gtatacatca gataatagac gggaacatta ttggtcagga 960
cttgaaatga cggcttattt tacaggattt gcaggcgctc aagtgtcatt ccctttagtc 1020
gggactagag gggagtcagc tccaccatta actgttagaa gtgttaatga tggaatttat 1080
agaatattat cggcaccgtt ttattcagcg ccttttctag gcaccattgt attgggaagt 1140
cgtggagaaa aatttgattt tgcgcttaat aatatttcac ctccgccatc tacaatatac 1200
agacatcctg gaacagtaga ttcactagtc agtataccgc cacaggataa tagcgtacca 1260
ccgcacaggg gatctagtca tcgattaagt catgttacaa tgcgcgcaag ttcccctata 1320
ttccattgga cgcatcgcag cgcaaccact acaaatacaa ttaatccaaa tgctattatc 1380
caaataccac tagtaaaagc atttaacctt cattcaggtg ccactgttgt tagaggacca 1440
gggtttacag gtggtgatat ccttcgaaga acgaatactg gcacatttgc agatatgaga 1500
gtaaatatta ctgggccatt atcccaaaga tatcgtgtaa gaattcgcta tgcttctacg 1560

-continued

```
acagatttac aatttttcac gagaatcaat ggaacttctg taaatcaagg taatttccaa   1620

agaactatga atagagggga taatttagaa tctggaaact ttaggactgc aggatttagt   1680

acgcctttta gtttttcaaa tgcgcaaagt acattcacat tgggtactca ggctttttca   1740

aatcaggaag tttatataga tcgaattgaa tttgtcccgg cagaagtaac attcgaggca   1800

gaatctgatt tagaaagagc gcaaaaggcg gtgaatgccc tgtttacttc tacaaaccaa   1860

ctagggctaa aaacagatgt gacggattat cagattgatc aagtgtccaa tttagtagaa   1920

tgtttatcag atgaattttg tctggatgaa aagagagaat tgtccgagaa agtcaaacat   1980

gcaaagcgac ttagtgataa gcggaaccta cttcaagatc caaacttcac atctatcaat   2040

agacaactag accgtggatg gagaggaagt acggatatta ccatccaagg aggaaatgac   2100

gtattcaaag agaattacgt cacactacca ggtacctttg atgagtgtta tccaacgtat   2160

ttgtatcaaa aaatagatga gtcaaaatta aaagcctata ctcgctatga attaagaggg   2220

tatattgaag atagtcaaga tttagaagtc tatttgattc gttacaatgc gaaacatgaa   2280

acagtaaatg ttcccggtac agggtcctta tggccgcttt cagtcgaaag cccaatcgga   2340

aggtgcggag aaccgaatcg atgtgtgcca catattgaat ggaatcctga tttagattgt   2400

tcgtgtaggg atggggagaa gtgtgcccat cattcgcatc atttctctct agatattgat   2460

gttggatgta cagacctaaa tgaggaccta ggtgtatggg tgatctttaa gattaaaacg   2520

caggatggcc atgcaagatt aggaaatcta gagtttctcg aagagaaacc attgttagga   2580

gaagcgttag ctcgtgtgaa aagagcggag aaaaaatgga gagacaaacg cgaacaattg   2640

cagtttgaaa cgaatatcgt ttacaaagag gcaaaagaat ctgtagatgc tttattcgta   2700

gattctcact ataatagatt acaagcggat acgaacatta cgatgattca tgcggcagat   2760

aaacgcgttc atcgaatccg agaggcttat cttccggaat tatccgttat cccaggtgta   2820

aatgcggaca tttttgaaga attagaaggt cttattttca ctgcattctc cctatatgat   2880

gcgagaaata tcattaaaaa cggtgatttc aataatggtt tatcgtgttg gaacgtgaaa   2940

gggcatgtag atatacaaca gaatgatcat cgttctgtcc tcgttgtccc ggaatgggaa   3000

tcagaggtat cacaagaagt ccgcgtatgt ccaggtcgtg gctatattct tcgtgtcaca   3060

gcgtacaaag agggctacgg agaaggatgc gtaacgatcc atgagatcga agacaataca   3120

gacgaattga agtttagtaa ctgcatagaa gaggaagtct atccaacgga tacaggtaat   3180

gattatactg cacaccaagg tacaacagga tgcgcagatg catgtaattc ccgtaatgtt   3240

ggatatgagg atggatatga aataaatact acagcatctg ttaattacaa accgacttat   3300

gaagaagaaa tgtatacaga tgtacgaaga gataatcatt gtgaatatga cagaggatat   3360

gggaaccata caccgttacc agctggttat gtaacaaaag aattagagta cttccctgaa   3420

acagatacag tatggataga gattggagaa acggaaggaa cattcatcgt agatagtgtg   3480

gaattactcc tcatggagga ataa                                          3504
```

<210> SEQ ID NO 27
<211> LENGTH: 3504
<212> TYPE: DNA
<213> ORGANISM: Artificial Sequence
<220> FEATURE:
<223> OTHER INFORMATION: Synthetic sequence encoding modified
      alpha-helix 4/5/6 BT0002

<400> SEQUENCE: 27

```
atggagataa ataatcagaa gcaatgcata ccatataatt gcttaagtaa tcctgaggaa     60
```

-continued

```
gtacttttgg atggggagag gatattacct gatatcgatc cactcgaagt ttctttgtcg    120
cttttgcaat ttcttttgaa taactttgtt ccagggggag gctttatttc aggattagtt    180
gataaaatat ggggggcttt gagaccatct gaatgggact tatttcttgc acagattgaa    240
cggttgattg atcaaagaat agaagcaaca gtaagagcaa aagcaatcgc tgaattagaa    300
ggtttaggga gaagttatca actatatgga gaggcattta aagagtggga aaaaactcca    360
gataacgaag cggctaagtc tagagtaatt gatagatttc gtatattaga tggtttaatt    420
gaagcaaata tcccttcgtt tcggattatc ggatttgaag tgccacttct atcagtttat    480
gttcaagcag ctaatttgca tctcgctcta ttaagagatt ctgttatttt tggagagaga    540
tggggattga cgactaaaaa tgtcaatgat atctataata gacaaataag agaaattcat    600
gaatatagca atcattgcgt agatacgtat aacacagaac tagaacgtct agggtttaga    660
tctatagcgc agtggagaat atataatcag tttagaagag aactaacact aactgtatta    720
gatattgtcg ctcttttccc gaactatgac agtagactgt atccgatcca aacttttttct    780
caattgacaa gagaaattgt tacatcccca gtaagcgaat tttattatgg tgttattaat    840
agtggtaata taaatggtac tcttactgaa cagcagataa ggcgaccaca tcttatggac    900
ttctttaact ccatgatcat gtatacatca gataatagac gggaacatta ttggtcagga    960
cttgaaatga cggcttattt tacaggattt gcaggcgctc aagtgtcatt ccctttagtc   1020
gggactagag gggagtcagc tccaccatta actgttagaa gtgttaatga tggaatttat   1080
agaatattat cggcaccgtt ttattcagcg ccttttctag gcaccattgt attgggaagt   1140
cgtggagaaa aatttgattt tgcgcttaat aatatttcac ctccgccatc tacaatatac   1200
agacatcctg gaacagtaga ttcactagtc agtataccgc cacaggataa tagcgtacca   1260
ccgcacaggg gatctagtca tcgattaagt catgttacaa tgcgcgcaag ttcccctata   1320
ttccattgga cgcatcgcag cgcaaccact acaaatacaa ttaatccaaa tgctattatc   1380
caaataccac tagtaaaagc atttaacctt cattcaggtg ccactgttgt tagaggacca   1440
gggtttacag gtggtgatat ccttcgaaga acgaatactg gcacatttgc agatatgaga   1500
gtaaatatta ctgggccatt atcccaaaga tatcgtgtaa gaattcgcta tgcttctacg   1560
acagatttac aatttttcac gagaatcaat ggaacttctg taaatcaagg taatttccaa   1620
agaactatga atagagggga taatttagaa tctggaaact ttaggactgc aggatttagt   1680
acgcctttta gtttttcaaa tgcgcaaagt acattcacat tgggtactca ggctttttca   1740
aatcaggaag tttatataga tcgaattgaa tttgtcccgg cagaagtaac attcgaggca   1800
gaatctgatt tagaaagagc gcaaaaggcg gtgaatgccc tgtttacttc tacaaaccaa   1860
ctagggctaa aaacagatgt gacggattat cagattgatc aagtgtccaa tttagtagaa   1920
tgtttatcag atgaattttg tctggatgaa aagagagaat tgtccgagaa agtcaaacat   1980
gcaaagcgac ttagtgataa gcggaaccta cttcaagatc caaacttcac atctatcaat   2040
agacaactag accgtggatg gagaggaagt acggatatta ccatccaagg aggaaatgac   2100
gtattcaaag agaattacgt cacactacca ggtacctttg atgagtgtta tccaacgtat   2160
ttgtatcaaa aaatagatga gtcaaaatta aaagcctata ctcgctatga attaagaggg   2220
tatattgaag atagtcaaga tttagaagtc tatttgattc gttacaatgc gaaacatgaa   2280
acagtaaatg ttcccggtac agggtcctta tggccgcttt cagtcgaaag cccaatcgga   2340
aggtgcggag aaccgaatcg atgtgtgcca catattgaat ggaatcctga tttagattgt   2400
tcgtgtaggg atggggagaa gtgtgcccat cattcgcatc atttctctct agatattgat   2460
```

gttggatgta cagacctaaa tgaggaccta ggtgtatggg tgatctttaa gattaaaacg 2520
caggatggcc atgcaagatt aggaaatcta gagtttctcg aagagaaacc attgttagga 2580
gaagcgttag ctcgtgtgaa aagagcggag aaaaaatgga gagacaaacg cgaacaattg 2640
cagtttgaaa cgaatatcgt ttacaaagag gcaaaagaat ctgtagatgc tttattcgta 2700
gattctcact ataatagatt acaagcggat acgaacatta cgatgattca tgcggcagat 2760
aaacgcgttc atcgaatccg agaggcttat cttccggaat tatccgttat cccaggtgta 2820
aatgcggaca tttttgaaga attagaaggt cttattttca ctgcattctc cctatatgat 2880
gcgagaaata tcattaaaaa cggtgatttc aataatggtt tatcgtgttg gaacgtgaaa 2940
gggcatgtag atatacaaca gaatgatcat cgttctgtcc tcgttgtccc ggaatgggaa 3000
tcagaggtat cacaagaagt ccgcgtatgt ccaggtcgtg gctatattct tcgtgtcaca 3060
gcgtacaaag agggctacgg agaaggatgc gtaacgatcc atgagatcga agacaataca 3120
gacgaattga agtttagtaa ctgcatagaa gaggaagtct atccaacgga tacaggtaat 3180
gattatactg cacaccaagg tacaacagga tgcgcagatg catgtaattc ccgtaatgtt 3240
ggatatgagg atggatatga aataaatact acagcatctg ttaattacaa accgacttat 3300
gaagaagaaa tgtatacaga tgtacgaaga gataatcatt gtgaatatga cagaggatat 3360
gggaaccata caccgttacc agctggttat gtaacaaaag aattagagta cttccctgaa 3420
acagatacag tatggataga gattggagaa acggaaggaa cattcatcgt agatagtgtg 3480
gaattactcc tcatggagga ataa 3504

<210> SEQ ID NO 28
<211> LENGTH: 3504
<212> TYPE: DNA
<213> ORGANISM: Artificial Sequence
<220> FEATURE:
<223> OTHER INFORMATION: Synthetic sequence encoding modified
alpha-helix 3/5/6 BT0002

<400> SEQUENCE: 28
atggagataa ataatcagaa gcaatgcata ccatataatt gcttaagtaa tcctgaggaa 60
gtacttttgg atggggagag gatattacct gatatcgatc cactcgaagt ttctttgtcg 120
cttttgcaat ttcttttgaa taactttgtt ccagggggag gctttatttc aggattagtt 180
gataaaatat ggggggcttt gagaccatct gaatgggact tatttcttgc acagattgaa 240
cggttgattg atcaaagaat agaagcaaca gtaagagcaa aagcaatcac tgaattagaa 300
ggtttaggga gaaattatca aatatatgca gaggcattta aagagtggga aagtgatcca 360
gataacacag cggctcggtc tagagtaact gagagatttc gtataattga tgctcaaatt 420
gaagcaaata tcccttcgtt tcgggtttcc ggatttgaag tgccacttct atcagtttat 480
gttcaagcag ctaatttgca tctcgctcta ttaagagatt ctgttatttt tggagagaga 540
tggggattga cgactaaaaa tgtcaatgat atctataata gacaaataag agaaattcat 600
gaatatagca atcattgcgt agatacgtat aacacagaac tagaacgtct agggtttaga 660
tctatagcgc agtggagaat atataatcag tttagaagag aactaacact aactgtatta 720
gatattgtcg ctcttttccc gaactatgac agtagactgt atccgatcca aactttttct 780
caattgacaa gagaaattgt tacatcccca gtaagcgaat tttattatgg tgttattaat 840
agtggtaata taaatggtac tcttactgaa cagcagataa ggcgaccaca tcttatggac 900
ttctttaact ccatgatcat gtatacatca gataatagac gggaacatta ttggtcagga 960
cttgaaatga cggcttattt tacaggattt gcaggcgctc aagtgtcatt ccctttagtc 1020
gggactagag gggagtcagc tccaccatta actgttagaa gtgttaatga tggaatttat 1080
agaatattat cggcaccgtt ttattcagcg ccttttctag gcaccattgt attgggaagt 1140
cgtggagaaa aatttgattt tgcgcttaat aatatttcac ctccgccatc tacaatatac 1200
agacatcctg gaacagtaga ttcactagtc agtataccgc cacaggataa tagcgtacca 1260
ccgcacaggg gatctagtca tcgattaagt catgttacaa tgcgcgcaag ttcccctata 1320
ttccattgga cgcatcgcag cgcaaccact acaaatacaa ttaatccaaa tgctattatc 1380
caaataccac tagtaaaagc atttaacctt cattcaggtg ccactgttgt tagaggacca 1440
gggtttacag gtggtgatat ccttcgaaga acgaatactg gcacatttgc agatatgaga 1500
gtaaatatta ctgggccatt atcccaaaga tatcgtgtaa gaattcgcta tgcttctacg 1560
acagatttac aatttttcac gagaatcaat ggaacttctg taaatcaagg taatttccaa 1620
agaactatga atagagggga taatttagaa tctggaaact ttaggactgc aggatttagt 1680
acgcctttta gtttttcaaa tgcgcaaagt acattcacat tgggtactca ggctttttca 1740
aatcaggaag tttatataga tcgaattgaa tttgtcccgg cagaagtaac attcgaggca 1800
gaatctgatt tagaaagagc gcaaaaggcg gtgaatgccc tgtttacttc tacaaaccaa 1860
ctagggctaa aaacagatgt gacggattat cagattgatc aagtgtccaa tttagtagaa 1920
tgtttatcag atgaattttg tctggatgaa aagagagaat tgtccgagaa agtcaaacat 1980
gcaaagcgac ttagtgataa gcggaaccta cttcaagatc caaacttcac atctatcaat 2040
agacaactag accgtggatg gagaggaagt acggatatta ccatccaagg aggaaatgac 2100
gtattcaaag agaattacgt cacactacca ggtacctttg atgagtgtta tccaacgtat 2160
ttgtatcaaa aaatagatga gtcaaaatta aaagcctata ctcgctatga attaagaggg 2220
tatattgaag atagtcaaga tttagaagtc tatttgattc gttacaatgc gaaacatgaa 2280
acagtaaatg ttcccggtac agggtcctta tggccgcttt cagtcgaaag cccaatcgga 2340
aggtgcggag aaccgaatcg atgtgtgcca catattgaat ggaatcctga tttagattgt 2400
tcgtgtaggg atggggagaa gtgtgcccat cattcgcatc atttctctct agatattgat 2460
gttggatgta cagacctaaa tgaggaccta ggtgtatggg tgatctttaa gattaaaacg 2520
caggatggcc atgcaagatt aggaaatcta gagtttctcg aagagaaacc attgttagga 2580
gaagcgttag ctcgtgtgaa aagagcggag aaaaaatgga gagacaaacg cgaacaattg 2640
cagtttgaaa cgaatatcgt ttacaaagag gcaaaagaat ctgtagatgc tttattcgta 2700
gattctcact ataatagatt acaagcggat acgaacatta cgatgattca tgcggcagat 2760
aaacgcgttc atcgaatccg agaggcttat cttccggaat tatccgttat cccaggtgta 2820
aatgcggaca tttttgaaga attagaaggt cttattttca ctgcattctc cctatatgat 2880
gcgagaaata tcattaaaaa cggtgatttc aataatggtt tatcgtgttg gaacgtgaaa 2940
gggcatgtag atatacaaca gaatgatcat cgttctgtcc tcgttgtccc ggaatgggaa 3000
tcagaggtat cacaagaagt ccgcgtatgt ccaggtcgtg gctatattct tcgtgtcaca 3060
gcgtacaaag agggctacgg agaaggatgc gtaacgatcc atgagatcga agacaataca 3120
gacgaattga agtttagtaa ctgcatagaa gaggaagtct atccaacgga tacaggtaat 3180
gattatactg cacaccaagg tacaacagga tgcgcagatg catgtaattc ccgtaatgtt 3240
ggatatgagg atggatatga aataaatact acagcatctg ttaattacaa accgacttat 3300

-continued gaagaagaaa tgtatacaga tgtacgaaga gataatcatt gtgaatatga cagaggatat 3360
gggaaccata caccgttacc agctggttat gtaacaaaag aattagagta cttccctgaa 3420
acagatacag tatggataga gattggagaa acggaaggaa cattcatcgt agatagtgtg 3480
gaattactcc tcatggagga ataa 3504

<210> SEQ ID NO 29
<211> LENGTH: 3504
<212> TYPE: DNA
<213> ORGANISM: Artificial Sequence
<220> FEATURE:
<223> OTHER INFORMATION: Synthetic sequence encoding modified alpha-helix 3/4/5/6 BT0002

<400> SEQUENCE: 29
atggagataa ataatcagaa gcaatgcata ccatataatt gcttaagtaa tcctgaggaa 60
gtacttttgg atggggagag gatattacct gatatcgatc cactcgaagt ttctttgtcg 120
cttttgcaat ttcttttgaa taactttgtt ccagggggag gctttatttc aggattagtt 180
gataaaatat ggggggcttt gagaccatct gaatgggact tatttcttgc acagattgaa 240
cggttgattg atcaaagaat agaagcaaca gtaagagcaa aagcaatcac tgaattagaa 300
ggtttaggga gaaattatca aatatatgca gaggcattta aagagtggga aagtgatcca 360
gataacgaag cggctaagtc tagagtaatt gatagatttc gtatattaga tggtttaatt 420
gaagcaaata tcccttcgtt tcggattatc ggatttgaag tgccacttct atcagtttat 480
gttcaagcag ctaatttgca tctcgctcta ttaagagatt ctgttatttt tggagagaga 540
tggggattga cgactaaaaa tgtcaatgat atctataata gacaaataag agaaattcat 600
gaatatagca atcattgcgt agatacgtat aacacagaac tagaacgtct agggtttaga 660
tctatagcgc agtggagaat atataatcag tttagaagag aactaacact aactgtatta 720
gatattgtcg ctcttttccc gaactatgac agtagactgt atccgatcca aactttttct 780
caattgacaa gagaaattgt tacatcccca gtaagcgaat tttattatgg tgttattaat 840
agtggtaata taaatggtac tcttactgaa cagcagataa ggcgaccaca tcttatggac 900
ttctttaact ccatgatcat gtatacatca gataatagac gggaacatta ttggtcagga 960
cttgaaatga cggcttattt tacaggattt gcaggcgctc aagtgtcatt ccctttagtc 1020
gggactagag gggagtcagc tccaccatta actgttagaa gtgttaatga tggaatttat 1080
agaatattat cggcaccgtt ttattcagcg ccttttctag gcaccattgt attgggaagt 1140
cgtggagaaa aatttgattt tgcgcttaat aatatttcac ctccgccatc tacaatatac 1200
agacatcctg gaacagtaga ttcactagtc agtataccgc cacaggataa tagcgtacca 1260
ccgcacaggg gatctagtca tcgattaagt catgttacaa tgcgcgcaag ttcccctata 1320
ttccattgga cgcatcgcag cgcaaccact acaaatacaa ttaatccaaa tgctattatc 1380
caaataccac tagtaaaagc atttaacctt cattcaggtg ccactgttgt tagaggacca 1440
gggtttacag gtggtgatat ccttcgaaga acgaatactg gcacatttgc agatatgaga 1500
gtaaatatta ctgggccatt atcccaaaga tatcgtgtaa gaattcgcta tgcttctacg 1560
acagatttac aatttttcac gagaatcaat ggaacttctg taaatcaagg taatttccaa 1620
agaactatga atagagggga taatttagaa tctggaaact ttaggactgc aggatttagt 1680
acgcctttta gtttttcaaa tgcgcaaagt acattcacat tgggtactca ggctttttca 1740
aatcaggaag tttatataga tcgaattgaa tttgtcccgg cagaagtaac attcgaggca 1800

```
gaatctgatt tagaaagagc gcaaaaggcg gtgaatgccc tgtttacttc tacaaaccaa   1860

ctagggctaa aaacagatgt gacggattat cagattgatc aagtgtccaa tttagtagaa   1920

tgtttatcag atgaattttg tctggatgaa aagagagaat tgtccgagaa agtcaaacat   1980

gcaaagcgac ttagtgataa gcggaaccta cttcaagatc caaacttcac atctatcaat   2040

agacaactag accgtggatg gagaggaagt acggatatta ccatccaagg aggaaatgac   2100

gtattcaaag agaattacgt cacactacca ggtacctttg atgagtgtta tccaacgtat   2160

ttgtatcaaa aaatagatga gtcaaaatta aaagcctata ctcgctatga attaagaggg   2220

tatattgaag atagtcaaga tttagaagtc tatttgattc gttacaatgc gaaacatgaa   2280

acagtaaatg ttcccggtac agggtcctta tggccgcttt cagtcgaaag cccaatcgga   2340

aggtgcggag aaccgaatcg atgtgtgcca catattgaat ggaatcctga tttagattgt   2400

tcgtgtaggg atggggagaa gtgtgcccat cattcgcatc atttctctct agatattgat   2460

gttggatgta cagacctaaa tgaggaccta ggtgtatggg tgatctttaa gattaaaacg   2520

caggatggcc atgcaagatt aggaaatcta gagtttctcg aagagaaacc attgttagga   2580

gaagcgttag ctcgtgtgaa aagagcggag aaaaaatgga gagacaaacg cgaacaattg   2640

cagtttgaaa cgaatatcgt ttacaaagag gcaaaagaat ctgtagatgc tttattcgta   2700

gattctcact ataatagatt acaagcggat acgaacatta cgatgattca tgcggcagat   2760

aaacgcgttc atcgaatccg agaggcttat cttccggaat tatccgttat cccaggtgta   2820

aatgcggaca tttttgaaga attagaaggt cttattttca ctgcattctc cctatatgat   2880

gcgagaaata tcattaaaaa cggtgatttc aataatggtt tatcgtgttg gaacgtgaaa   2940

gggcatgtag atatacaaca gaatgatcat cgttctgtcc tcgttgtccc ggaatgggaa   3000

tcagaggtat cacaagaagt ccgcgtatgt ccaggtcgtg gctatattct tcgtgtcaca   3060

gcgtacaaag agggctacgg agaaggatgc gtaacgatcc atgagatcga agacaataca   3120

gacgaattga agtttagtaa ctgcatagaa gaggaagtct atccaacgga tacaggtaat   3180

gattatactg cacaccaagg tacaacagga tgcgcagatg catgtaattc ccgtaatgtt   3240

ggatatgagg atggatatga aataaatact acagcatctg ttaattacaa accgacttat   3300

gaagaagaaa tgtatacaga tgtacgaaga gataatcatt gtgaatatga cagaggatat   3360

gggaaccata caccgttacc agctggttat gtaacaaaag aattagagta cttccctgaa   3420

acagatacag tatggataga gattggagaa acggaaggaa cattcatcgt agatagtgtg   3480

gaattactcc tcatggagga ataa                                          3504
```

<210> SEQ ID NO 30
<211> LENGTH: 9078
<212> TYPE: DNA
<213> ORGANISM: Artificial Sequence
<220> FEATURE:
<223> OTHER INFORMATION: Shuttle vector functional in E. coli and B. thuringiensis

<400> SEQUENCE: 30

```
agaggccatc gtggcctata tatggcctgg gcgagaagta agtagattgt taacaccctg     60

ggtcaaaaat tgatatttag taaaattagt tgcactttgt gcattttttc ataagatgag    120

tcatatgttt taaattgtag taatgaaaaa cagtattata tcataatcaa ttggtatctt    180

aataaaagag atggaggttt aaacggatcc atgaaatcta agaatcaaaa tatgcatcaa    240

agcttgtcta acaatgcgac agttgataaa aactttacag gttcactaga aaataacaca    300
```

-continued

```
aatacggaat tacaaaactt taatcatgaa ggtatagagc cgtttgttag tgtatcaaca    360
attcaaacgg gtattggtat tgctggtaaa atccttggta acctaggcgt tccctttgct    420
gggcaagtag ctagcctcta tagttttatc ctaggtgagc tttggcccaa agggaaaagc    480
caatgggaaa tttttatgga acatgtagaa gagcttatta atcaaaagat atcgacttat    540
gcaagaaaca aagcacttgc agatttaaaa ggattaggag atgctttggc tgtctaccat    600
gaatcgctgg aaagttggat taaaaatcgc aataacacaa gaactagaag tgttgtcaag    660
agccaataca ttaccttgga acttatgttc gtacaatcat taccttcttt tgcagtgtct    720
ggagaggaag taccactatt accaatatat gctcaagctg caaatttaca cttgttgcta    780
ttaagagatg cgtctatttt tggaaaagaa tggggattat cagactcaga aatttcgaca    840
ttctataatc gtcaagtgga aagaacatca gattattccg atcattgcac gaaatggttt    900
gatacgggct tgaatagatt aaagggctca aatgctgaaa tctgggtaaa gtataatcaa    960
ttccgtagag acatgacttt aatggtacta gatttagtgg cactattcca aagctatgat   1020
acacatatgt acccaattaa aactacagcc caacttacta gagaagtata tacaaacgca   1080
ttggggacag tacatccgca cccaagtttt acaagtacga cttggtataa taataatgca   1140
ccttcgtttt ctgccataga ggctgccgtt atccgaagcc cgcacctact cgattttcta   1200
gaacaagtta caatttacag cttattaagc cgatggagta acactcagta tatgaatatg   1260
tggggaggac ataaactaga attccgaaca ataggaggaa cgttaaatac ctcaacacaa   1320
ggatctacta atacttctat taatcctgta acattaccgt tcacgtctcg agacatctat   1380
aggactgaat cattggcagg gctgaatcta tttttaactc aacctgttaa tggagtacct   1440
agggttgatt ttcattggaa attcgtcaca catccgatcg catctgataa tttctattat   1500
ccagggtatg ctggaattgg gacgcaatta caggattcag aaaatgaatt accacctgaa   1560
gcaacaggac agccaaatta tgaatcttat agtcatagat tatctcatat aggactcatt   1620
tcagcatcac atgtgaaagc attggtatat tcttggacgc atcgtagtgc agatcgtacg   1680
aatacaattc attcagatag tataacacaa ataccactgg taaaagcaca tacccttcag   1740
tcaggtacta ctgttgtaaa agggccaggg tttacaggtg gagatatcct ccgacgaact   1800
agtggaggac catttgcttt tagtaatgtt aatttagact ggaacttgtc acaaagatat   1860
cgtgctagaa tacgctatgc ttctactact aatctaagaa tgtacgtaac gattgcaggg   1920
gaacgaattt ttgctggtca atttaataaa acaatgaata ctggtgatcc attaacattc   1980
caatctttta gttacgcaac tattgataca gcatttacat tcccaacgaa agcgagcagc   2040
ttgactgtag gtgctgatac ttttagctca ggtaatgaag tttatgtaga tagatttgaa   2100
ttgatcccag ttactgcaac acttgaggca gtaactgatt tagaaagagc gcagaaggcg   2160
gttcatgaac tgtttacatc tacgaatccg ggaggattaa aaacggatgt aaaggattat   2220
catattgacc aggtatcaaa tttagtagag tctctatcag ataaattcta tcttgatgaa   2280
aagagagaat tattcgagat agttaaatac gcgaagcaac tccatattga gcgtaacatg   2340
taggagctcg aattcgtaat catgtcatag ctgtttcctg tgtgaaattg ttatccgctc   2400
acaattccac acaacatacg agccggaagc ataaagtgta aagcctgggg tgcctaatga   2460
gtgagctaac tcacattaat tgcgttgcgc tcactgcccg ctttccagtc gggaaacctg   2520
tcgtgccagc tgcattaatg aatcggccaa cgcgcgggga gaggcggttt gcgtattggg   2580
cgctcttccg cttcctcgct cactgactcg ctgcgctcgg tcgttcggct gcggcgagcg   2640
gtatcagctc actcaaaggc ggtaatacgg ttatccacag aatcagggga taacgcagga   2700
```

```
aagaacatgt gagcaaaagg ccagcaaaag gccaggaacc gtaaaaaggc cgcgttgctg   2760
gcgtttttcc ataggctccg cccccctgac gagcatcaca aaaatcgacg ctcaagtcag   2820
aggtggcgaa acccgacagg actataaaga taccaggcgt ttccccctgg aagctccctc   2880
gtgcgctctc ctgttccgac cctgccgctt accggatacc tgtccgcctt tctcccttcg   2940
ggaagcgtgg cgctttctca tagctcacgc tgtaggtatc tcagttcggt gtaggtcgtt   3000
cgctccaagc tgggctgtgt gcacgaaccc cccgttcagc ccgaccgctg cgccttatcc   3060
ggtaactatc gtcttgagtc caacccggta agacacgact tatcgccact ggcagcagcc   3120
actggtaaca ggattagcag agcgaggtat gtaggcggtg ctacagagtt cttgaagtgg   3180
tggcctaact acggctacac tagaagaaca gtatttggta tctgcgctct gctgaagcca   3240
gttaccttcg gaaaaagagt tggtagctct tgatccggca aacaaaccac cgctggtagc   3300
ggtggttttt ttgtttgcaa gcagcagatt acgcgcagaa aaaaaggatc tcaagaagat   3360
cctttgatct tttctacggg gtctgacgct cagtggaacg aaaactcacg ttaagggatt   3420
ttggtcatga gattatcaaa aaggatcttc acctagatcc ttttaaatta aaaatgaagt   3480
tttaaatcaa tctaaagtat atatgagtaa acttggtctg acagttacca atgcttaatc   3540
agtgaggcac ctatctcagc gatctgtcta tttcgttcat ccatagttgc ctgactcccc   3600
gtcgtgtaga taactacgat acgggagggc ttaccatctg gccccagtgc tgcaatgata   3660
ccgcgagacc cacgctcacc ggctccagat ttatcagcaa taaaccagcc agccggaagg   3720
gccgagcgca gaagtggtcc tgcaacttta tccgcctcca tccagtctat taattgttgc   3780
cgggaagcta gagtaagtag ttcgccagtt aatagtttgc gcaacgttgt tgccattgct   3840
acaggcatcg tggtgtcacg ctcgtcgttt ggtatggctt cattcagctc cggttcccaa   3900
cgatcaaggc gagttacatg atcccccatg ttgtgcaaaa aagcggttag ctccttcggt   3960
cctccgatcg ttgtcagaag taagttggcc gcagtgttat cactcatggt tatggcagca   4020
ctgcataatt ctcttactgt catgccatcc gtaagatgct tttctgtgac tggtgagtac   4080
tcaaccaagt cattctgaga atagtgtatg cggcgaccga gttgctcttg cccggcgtca   4140
atacgggata ataccgcgcc acatagcaga actttaaaag tgctcatcat tggaaaacgt   4200
tcttcggggc gaaaactctc aaggatctta ccgctgttga gatccagttc gatgtaaccc   4260
actcgtgcac ccaactgatc ttcagcatct tttactttca ccagcgtttc tgggtgagca   4320
aaaacaggaa ggcaaaatgc cgcaaaaaag ggaataaggg cgacacggaa atgttgaata   4380
ctcatactct tcctttttca atgtacccca aattccccgt aggcgctagg gacctcttta   4440
gcttcttgga agctgtcagt agtatatcta ataatttatc tccattccct ttagtaacgt   4500
gtaactttcc aaatttaaaa aagcgactca tagaattatt tcctcccgtt aaataataga   4560
taactattaa aaatagacaa tacttgctca taagtaatgg tacttaaatt gtttactttg   4620
gcgtgtttca ttgcttgatg aaactgattt ttagtaaaca gttgacgata ttctcgattg   4680
acccattttg aaacaaagta cgtatatagc ttccaatatt tatctggaac atctgtggta   4740
tggcgggtaa gttttattaa gacactgttt acttttggtt taggatgaaa gcattccgct   4800
ggcagcttaa gcaattgctg aatcgagact tgagtgtgca agagcaaccc tagtgttcgg   4860
tgaatatcca aggtacgctt gtagaatcct tcttcaacaa tcagatagat gtcagacgca   4920
tggctttcaa aaaccacttt tttaataatt tgtgtgctta aatggtaagg aatactccca   4980
acaattttat acctctgttt gttagggaat tgaaactgta gaatatcttg gtgaattaaa   5040
```

-continued gtgacacgaa tgttcagttt taatttttct gacgataagt tgaatagatg actgtctaat 5100
tcaatagacg ttacctgttt acttatttta gccagtttcg tcgttaaatg ccctttacct 5160
gttccaattt cgtaaacggt atcggtttct tttaaattca attgttttat tatttggttg 5220
agtacttttt cactcgttaa aaagttttga gaatatttta tatttttgtt catgtaatta 5280
ctcctgaagt gattacatct gtaaataaat acagaagtta aacgatttgt ttgtaatttt 5340
agttatctgt ttaaaaagtc ataagattag tcactggtag gaattaatct aacgtattta 5400
tttatctgcg taatcactgt ttttagtctg tttcaaaaca gtagatgttt tatctacatt 5460
acgcatttgg aataccaaca tgacgaatcc ctccttctta attacaaatt tttagcatct 5520
aatttaactt caattcctat tatacacaaa attttaagat actgcactat caacacactc 5580
ttaagtttgc ttcggggatc gatcccacat tagaaataga attggcatca gctaagagtt 5640
gttcagcttc aagaatcttc ctctccaatt gagcgctttt ctcctctagc acagaaactt 5700
tactttctgc ttcttctaat ttctactag cctcgtccat attcttttta gcacgcttat 5760
tagaatatgt aacataagca aacgctgctg taaaaaccgc cgttataatt gccactccaa 5820
tacctactgc tgttaacata ttagatatcg tggtgttcaa aaacgctacc tcatgatcct 5880
gcaatgatat aactttatct tgcaaatcct ttacgacatc agtagatggc gccgctgtaa 5940
atagtatccc cagcatcaat agttccccct gattatataa attcagacga atactattat 6000
ccattatttt tttattaagg taaattaata ttttacctat taaaggaggg acgatttaag 6060
tatggacgtg atgtttggtc aaggtgggaa cataaatttt aattacattg gaacatattg 6120
tggacaagca tctaattcat aatccccact ttccaagcat gaaagtccct tataccatca 6180
attattcaat aaaatatccc tatcataaac ctgtcccgcg cgacggttca aatactcctt 6240
tatgataaaa taaagatata aagagacgag atgagggaga aatttgacgg ctaataaaaa 6300
aaagattgta aataaaccaa ctgttgtggc aaaacttcca caaatcatta tagatacata 6360
taacttgact tgcacttcta acgatgtaaa aatgtttccc ggatttataa agcacgtaaa 6420
gaaacaacat cctggtattt atgaaaaata ttcatcgcac ataaaagata tcgttgaaca 6480
ccccgactat gtcgggcaaa atcctaaaga acctaatagc gttgaattgg taaagatttt 6540
aaatgaccat atactaattg ctataaagtt ggacccaagc ggttatttgt tcttatcaac 6600
tatgttcgat ctaaaaaacg gtcctgcgaa aatccaaaga cgattgaata gtggacgttt 6660
aattgcttac aaagacctgt taagctaacg gggagtttac taaaatataa gaacatggta 6720
tactacctgt agaaagtaac ataataatga tataggatct ttgaggtggg aaaggttccc 6780
cacgcgctta tctaaccgcc gttctcaagc atttgattgg ctaggtaagt taccagagat 6840
gtaggatacg ccgccctacc aacgatccta tgtacggtaa gccatccgtt ttttacggat 6900
ggctttttat attgactttt tcatcgctaa tggttacttt tctatcaaac gacaccgaaa 6960
ggcgatgatt attgtgttaa aaaacccaat attataacat ccactaatgg ataatcttac 7020
ttttagtaag taggttgcct agtgaaatac aataattcca acattgggcc ttaatacata 7080
ttaattagtt ttaaccctct cactataaaa gagttaaata tgactccgca acctctttaa 7140
tatcactatt acattttgta acaacattat tactttcatc ctctgtacca ttaacaaata 7200
aatgaggatt ctttaccata aagtctaaca atagatcaat aaaccgctgc ctttgttctc 7260
tagccatttc ctttctcata gagaaccact cccctatctt tcactattct tttaatttca 7320
tcttgtcttt cacttgattt aaacagctct ggattcttcc tcaatccccc actatcttag 7380
ttaatggtag ttgcttcagt actctacatt ttttgctaat cgaggttaaa atccttcaaa 7440

```
tcccttgact ttaaggtctt aaggttttca tactggcgag tttgttagga aatctgaatg   7500
tagttttggg catagtaacc cctgttgaaa atttacgagg ttaaaacgcc cactcattcg   7560
tactggctta gatgccgagg tctcgaattg agattggttg cattgacgac aaacggttat   7620
agcttacaaa actactatac cgtccgtata tagcttattg gcattgtatt gcgccgtacg   7680
gtgcgtttct cacgcccaac accgttccct ttcgggtgat tcgctatata acccgcatat   7740
ccttgtaata aagcttgtac aagaatagcc gtgaatcagt gtcatgatcg ccgcttacga   7800
gtaactgttt aactccagtc gcacaatcat gtcttatttt gaacccccaa cactttttgc   7860
cgctaacgtc ttggttatca tcattattag gatttacatc ccgtaggctt gttttatgca   7920
aggcttgtgt cctttacctc gcttacgtca gacagttgaa tgcaacgaca actgatatcc   7980
gagtgtactc tcctgcattg gctacactag accatctttt taaagtggta gcttccactg   8040
gaacggaaca caaaaagggc gttctctata tctaaacgcc ctgtacattt acaagacttc   8100
taggtataga aaacgccctt ttatatccgt tttattatgt atatgacaat gctagtaatt   8160
actagttgaa atattcgtag agtaacggta caataggtgt atctaataag ccttgttcgc   8220
gaaaacaagg caaataactt atttgaggtt ggcgcctctt ataagtcgaa gtcctgtatg   8280
gctgtacagg attaagtcat tctcgctaaa ggttggtagc caatagcata tgagagtggc   8340
tttttcatt tccgttctat taagttactg ctaattttac cgctatgttt ctattaaatc   8400
aacgaaaatt tgataaggtt caccagaaac attaatattt gcgacataaa actcactctc   8460
caactttgga ggatggatta ttgaagcatt tatcagggtt attgtctcat gagcggatac   8520
atatttgaat gtatttagaa aaataaacaa ataggggttc cgcgcacatt tccccgaaaa   8580
gtgccacctg acgtctaaga aaccattatt atcatgacat taacctataa aaataggcgt   8640
atcacgaggc cctttcgtct cgcgcgtttc ggtgatgacg gtgaaaacct ctgacacatg   8700
cagctcccgg agacggtcac agcttgtctg taagcggatg ccgggagcag acaagcccgt   8760
cagggcgcgt cagcgggtgt tggcgggtgt cggggctggc ttaactatgc ggcatcagag   8820
cagattgtac tgagagtgca ccatatgcgg tgtgaaatac cgcacagatg cgtaaggaga   8880
aaataccgca tcaggcgcca ttcgccattc aggctgcgca actgttggga agggcgatcg   8940
gtgcgggcct cttcgctatt acgccagctg gcgaaagggg gatgtgctgc aaggcgatta   9000
agttgggtaa cgccagggtt ttcccagtca cgacgttgta aaacgacggc cagtgccaag   9060
cttgcatgcc tgcagtct                                                 9078
```

<210> SEQ ID NO 31
<211> LENGTH: 16384
<212> TYPE: DNA
<213> ORGANISM: Artificial Sequence
<220> FEATURE:
<223> OTHER INFORMATION: Binary vector for plant expression of Cry proteins

<400> SEQUENCE: 31

```
attcctgtgg ttggcatgca catacaaatg gacgaacgga taaacctttt cacgcccttt     60
taaatatccg attattctaa taaacgctct tttctcttag gtttacccgc caatatatcc    120
tgtcaaacac tgatagttta aactggcact agcctaacgg tgttgactaa ctaggccgct    180
tccctaatta gctaacccgg gggcgcgccg ggacccctgc agtgcagcgt gacccggtcg    240
tgcccctctc tagagataat gagcattgca tgtctaagtt ataaaaaatt accacatatt    300
tttttgtca cacttgtttg aagtgcagtt tatctatctt tatacatata tttaaacttt    360
```

```
actctacgaa taatataatc tatagtacta caataatatc agtgttttag agaatcatat    420
aaatgaacag ttagacatgg tctaaaggac aattgagtat tttgacaaca ggactctaca    480
gttttatctt tttagtgtgc atgtgttctc cttttttttt gcaaatagct tcacctatat    540
aatacttcat ccattttatt agtacatcca tttagggttt agggttaatg gtttttatag    600
actaattttt ttagtacatc tattttattc tattttagcc tctaaattaa gaaaactaaa    660
actctatttt agttttttta tttaataatt tagatataaa atagaataaa ataaagtgac    720
taaaaattaa acaaataccc tttaagaaat taaaaaaact aaggaaacat ttttcttgtt    780
tcgagtagat aatgccagcc tgttaaacgc cgccgacgag tctaacggac accaaccagc    840
gaaccagcag cgtcgcgtcg ggccaagcga agcagacggc acggcatctc tgtcgctgcc    900
tctggacccc tctcgagagt tccgctccac cgttggactt gctccgctgt cggcatccag    960
aaattgcgtg gcggagcggc agacgtgagc cggcacggca ggcggcctcc tcctcctctc   1020
acggcaccgg cagctacggg ggattccttt cccaccgctc cttcgctttc ccttcctcgc   1080
ccgccgtaat aaatagacac cccctccaca ccctctttcc ccaacctcgt gttgttcgga   1140
gcgcacacac acacaaccag atctccccca aatccacccg tcggcacctc cgcttcaagg   1200
tacgccgctc gtcctccccc cccccccctc tctaccttct ctagatcggc gttccggtcc   1260
atagttaggg cccggtagtt ctacttctgt tcatgtttgt gttagatccg tgtttgtgtt   1320
agatccgtgc tgttagcgtt cgtacacgga tgcgacctgt acgtcagaca cgttctgatt   1380
gctaacttgc cagtgtttct ctttggggaa tcctgggatg gctctagccg ttccgcagac   1440
gggatcgatt tcatgatttt ttttgtttcg ttgcataggg tttggtttgc cctttttcctt   1500
tatttcaata tatgccgtgc acttgtttgt cgggtcatct tttcatgctt ttttttgtct   1560
tggttgtgat gatgtggtct ggttgggcgg tcgttctaga tcggagtaga attctgtttc   1620
aaactacctg gtggatttat taattttgga tctgtatgtg tgtgccatac atattcatag   1680
ttacgaattg aagatgatgg atggaaatat cgatctagga taggtataca tgttgatgcg   1740
ggttttactg atgcatatac agagatgctt tttgttcgct tggttgtgat gatgtggtgt   1800
ggttgggcgg tcgttcattc gttctagatc ggagtagaat actgtttcaa actacctggt   1860
gtatttatta attttggaac tgtatgtgtg tgtcatacat cttcatagtt acgagtttaa   1920
gatggatgga aatatcgatc taggataggt atacatgttg atgtgggttt tactgatgca   1980
tatacatgat ggcatatgca gcatctattc atatgctcta accttgagta cctatctatt   2040
ataataaaca agtatgtttt ataattattt tgatcttgat atacttggat gatggcatat   2100
gcagcagcta tatgtggatt tttttagccc tgccttcata cgctatttat ttgcttggta   2160
ctgtttcttt tgtcgatgct caccctgttg tttggtgtta cttctgcagg gatcctaaac   2220
catggcgatt aacaatcaga accagtgcat cccatacaac tgcctgtcca atcctgagga   2280
ggtgttcctg gacggcgagc gcatcctccc ggacattgat cccctggagg tgtctctctc   2340
actcctgcag ttcctcctga acaatttcgt cccaggcggg ggcttcattt cgggcctcct   2400
ggacaagatc tggggcgccc tcaggccttc ggattgggag ctgttcctcg agcagatcga   2460
gcagctcatt gacaggagga tcgagcgcac cgtcagggct aaggccatcg ctgagctgga   2520
ggggctgggc cgctcttacc agctctacgg cgaggcgttc aaggagtggg agaagacgcc   2580
cgacaacacg gcggccaggt caagggtgac ggagcgcttc aggatcattg atgcccagat   2640
tgaggcgaac atcccgtcct tccgcgtgag cggcttcgag gtccccctcc tgctcgttta   2700
```

-continued

```
cacgcaggct gccaacctcc atctggccct gctccgggac tcggtggtgt tcggcgagag   2760
gtgggggctc accaccacaa acgtcaatga tatctacaac cggcaggtta atcgcatcgg   2820
cgagtactca aagcactgcg tcgacactta caagaccgag ctggagaggc tgggcttccg   2880
gtccattgcg cagtggagga tctacaacca gttccggcgc gagctgacac tgactgtgct   2940
cgacatcgtc gctgttttcc caaactacga ttcccggctg taccctatcc gcacgattag   3000
ccagctcaca cgcgagatct acacttcccc agttagcgag ttctactacg gcgtgatcaa   3060
ctccaacaat atcattggca ccctcacgga gcagcagatt aggcggcctc acctcatgga   3120
cttcttcaac tcgatgatca tgtacacctc tgataatcgc agggagcact actggagcgg   3180
cctggagatg acagccacta acaccgaggg gcatcagcgc tccttcccac tggccggcac   3240
catcgggaat tctgctccgc ccgtgaccgt gcgcaacaat ggggagggca tctacaggat   3300
tctgtccgag ccattctact cggccccttt cctgggcacg tcggtcctgg gctctcgcgg   3360
ggaggagttc gctttcgcgt cgaacactac cacgtcgctg ccatctacaa tctacaggaa   3420
tcgcggcact gtggactcac tcgtctccat cccacctcag gattactctg ttccgcccca   3480
caggggctac tcacacctgc tctcccatgt gacaatgcgc aactccagcc cgatcttcca   3540
ctggactcat aggagcgcca cgccacggaa tacaatcgac cctgattcga tcacacagat   3600
tcccgctgtg aagggcgcct acattttcaa ctcgccggtc atcaccgggc ccggccacac   3660
cggcggcgac atcattcgct tcaacccaaa tacgcagaac aatatcagga ttcctttcca   3720
gtccaacgcg gtccagcgct accgcatccg catgcgctac gcggctgagg ctgactgcat   3780
tctggagagc ggcgttaaca tcgtgacagg ggctggcgtg actttccgcc caatccctat   3840
taaggccacg atgacaccag gctcacctct cacctactac tccttccagt acgccgacct   3900
gaacattaat ctcacggcgc cgatccgccc caacaatttc gtgagcatca ggaggtccaa   3960
ccagcccggc aatctgtaca tcgacaggat tgagttcatc ccaattgatc ctatcaggga   4020
ggccgagcac gacctcgagc gcgcgcagaa ggctgtcaac gccctgttca cctcgtctaa   4080
tcagattggc ctcaagacgg acgtgacaga ttaccatatc gaccaggtta gcaacctggt   4140
ggcctgcctc tcggacaagt tctgcctgga tgagaagagg gagctgtcag agaaggtcaa   4200
gcacgcgaag cgcctgtccg acgagaggaa cctgctccag gatcagaatt tcacgggcat   4260
caacaggcag gtggataggg gctggagggg gagcactgac atcaccattc agggcggcaa   4320
cgatgtcttc aaggagaatt acgttactct gccgggcacc ttcgacgagt gctaccccac   4380
atacctctac cagaagatcg atgagtcgaa gctgaagccg tacactcgct acgagctgag   4440
gggatacatc gaggactctc aggatctgga ggtctacctc atccgctaca acgccaagca   4500
tgagaccctc aatgtgcccg ggacgggcag cctctggccg ctggcggccg agtcatccat   4560
cggcaggtgc ggggagccaa acaggtgcgc ccctcacatc gagtggaatc cggagctgga   4620
ctgctcgtgc agggatggcg agaagtgcgc gcaccattct caccatttct cactcgacat   4680
cgatgtgggc tgcaccgacc tgaacgagga tctcggggtt tgggtcatct tcaagatcaa   4740
gacccaggac ggctacgcta ggctggggaa cctggagttc ctggaggaga agccgctgct   4800
gggcgaggct ctggctaggg tcaagagggc ggagaagaag tggcgcgaca agagggataa   4860
gctcgagtgg gagaccaaca tcgtgtacaa ggaggccaag gagtctgtgg acgcgctgtt   4920
cgtcgattca cagtacaaca ggctccagac tgacaccaat atcgcgatga ttcacgttgc   4980
tgataagcgg gtgcatcgca tccgcgaggc ttacctgccc gagctgtccg tcattcccgg   5040
cgttaacgct gccatcttcg aggagctgga ggggctcatc ttcaccgctt tcagcctgta   5100
```

```
cgacgccagg aacgtcatca agaatggcga tttcaaccac gggctctcgt gctggaacgt   5160
gaagggccac gtcgacgttg aggagcagaa caatcatcgc tctgttctgg ttgtgccgga   5220
gtgggaggct gaggtgtcac aggaggtgcg ggtctgcccg gggaggggat acatcctcag   5280
ggtcaccgcc tacaaggagg ggtacggcga ggggtgcgtt accatccacg agattgagga   5340
ccatacggat gagctgaagt tccggaactg cgaggaggag gaggtgtacc caaacaatac   5400
ggtcacatgc aatgactacc cggccaacca ggaggagtac agggccgctg agacatccag   5460
gaacaggggc tacggggaga gctacgagtc gaatagctcg attccggcgg agtacgctcc   5520
catctacgag aaggcctaca ctgacggcag gaaggagaat tcttgcgagt caaaccgggg   5580
ctacgggaat tacacaccgc tgcccgcggg ctacgtcact aaggagctgg agtacttccc   5640
ggagaccgac aaggtttgga tcgagattgg cgagacggag gggacattcc tcgtcgatag   5700
cgttgagctg ctcctgatgg aggagtgaga gctcgccatc agtcgttgaa gctgctgctg   5760
tatctgggtt atctagtgtc tctgccattg cccaaggatg gtgctgtctt tcaaagtatt   5820
tgtatggttt gtgtcgtgag tcgtgactga gctggtttca tggaccagtt gtgttctcgt   5880
tacccaaaac tatcgtgcga ccgcatatgg cttaatcatg aataaatgtt gtttgaattt   5940
aaactattcg ctgaatattg ttgtttttg tcatgtcagt taatgttact aaattggttg   6000
ccttctaatt tttgtttact ggtgtttgtc gcaccttatc tttttactgt atgtttactt   6060
caggttctgg cagtctcatt ttttgtgact agttaaaact tacagctaaa aaaatgcagt   6120
ttttcatttt catttgaagt ttgattagag ctattgatac ccggaccatc aggttaggtt   6180
agttgtgcat agaatcataa atattaatca tgttttctat gaattaagtc aaacttgaaa   6240
gtctggctga atatagtttc tatgaatcat attgatatac atgtttgatt atttgttttg   6300
ctattagcta tttactttgg tgaatctata taggcttatg cagaaccttt ttttttgttc   6360
tatatatcca tatcctagta ctcagtagct ctatgttttc tggagactag tggcttgctt   6420
tttcgtatgt ctaatttttt gcttgaccat tgcaaaacaa aaattaccta gtgtaatctc   6480
tttttataat aatcttgtaa tgcgtctacc tataggtcaa agtaggtttt gtttggaacc   6540
cttagagcta actgttagct agttgataaa ttattagctg agttaagcta gctaatgaac   6600
tagttttgat attagctgag gatgtttgaa acctaataat tattttttat tagctaacta   6660
tactaaattt tagtagagag attccaaaca ggagttaaca tgggatcaga ttggctatgc   6720
gtttgcaatc ccatactaat tagctaacgg accgcgatcg cttaattaag cttgcatgcc   6780
tgcagtgcag cgtgacccgg tcgtgcccct ctctagagat aatgagcatt gcatgtctaa   6840
gttataaaaa attaccacat atttttttg tcacacttgt ttgaagtgca gtttatctat   6900
ctttatacat atatttaaac tttactctac gaataatata atctatagta ctacaataat   6960
atcagtgttt tagagaatca tataaatgaa cagttagaca tggtctaaag gacaattgag   7020
tattttgaca acaggactct acagttttat ctttttagtg tgcatgtgtt ctcctttttt   7080
tttgcaaata gcttcaccta tataatactt catccatttt attagtacat ccatttaggg   7140
tttagggtta atggttttta tagactaatt tttttagtac atctatttta ttctatttta   7200
gcctctaaat taagaaaact aaaactctat tttagttttt ttatttaata atttagatat   7260
aaaatagaat aaaataaagt gactaaaaat taaacaaata ccctttaaga aattaaaaaa   7320
actaaggaaa catttttctt gtttcgagta gataatgcca gcctgttaaa cgccgccgac   7380
gagtctaacg gacaccaacc agcgaaccag cagcgtcgcg tcgggccaag cgaagcagac   7440
```

```
ggcacggcat ctctgtcgct gcctctggac ccctctcgag agttccgctc caccgttgga   7500
cttgctccgc tgtcggcatc cagaaattgc gtggcggagc ggcagacgtg agccggcacg   7560
gcaggcggcc tcctcctcct ctcacggcac cggcagctac gggggattcc tttcccaccg   7620
ctccttcgct ttcccttcct cgcccgccgt aataaataga cacccctcc acaccctctt   7680
tccccaacct cgtgttgttc ggagcgcaca cacacacaac cagatctccc ccaaatccac   7740
ccgtcggcac ctccgcttca aggtacgccg ctcgtcctcc cccccccccc ctctctacct   7800
tctctagatc ggcgttccgg tccatagtta gggcccggta gttctacttc tgttcatgtt   7860
tgtgttagat ccgtgtttgt gttagatccg tgctgttagc gttcgtacac ggatgcgacc   7920
tgtacgtcag acacgttctg attgctaact tgccagtgtt tctctttggg gaatcctggg   7980
atggctctag ccgttccgca gacgggatcg atttcatgat tttttttgtt tcgttgcata   8040
gggtttggtt tgccctttc ctttatttca atatatgccg tgcacttgtt tgtcgggtca   8100
tcttttcatg cttttttttg tcttggttgt gatgatgtgg tctggttggg cggtcgttct   8160
agatcggagt agaattctgt ttcaaactac ctggtggatt tattaatttt ggatctgtat   8220
gtgtgtgcca tacatattca tagttacgaa ttgaagatga tggatggaaa tatcgatcta   8280
ggataggtat acatgttgat gcgggtttta ctgatgcata tacagagatg ctttttgttc   8340
gcttggttgt gatgatgtgg tgtggttggg cggtcgttca ttcgttctag atcggagtag   8400
aatactgttt caaactacct ggtgtattta ttaattttgg aactgtatgt gtgtgtcata   8460
catcttcata gttacgagtt taagatggat ggaaatatcg atctaggata ggtatacatg   8520
ttgatgtggg ttttactgat gcatatacat gatggcatat gcagcatcta ttcatatgct   8580
ctaaccttga gtacctatct attataataa acaagtatgt tttataatta ttttgatctt   8640
gatatacttg gatgatggca tatgcagcag ctatatgtgg attttttag ccctgccttc   8700
atacgctatt tatttgcttg gtactgtttc ttttgtcgat gctcaccctg ttgtttggtg   8760
ttacttctgc agggatctcc gatcatgcaa aaactcatta actcagtgca aaactatgcc   8820
tggggcagca aaacggcgtt gactgaactt tatggtatgg aaaatccgtc cagccagccg   8880
atggccgagc tgtggatggg cgcacatccg aaaagcagtt cacgagtgca gaatgccgcc   8940
ggagatatcg tttcactgcg tgatgtgatt gagagtgata aatcgactct gctcggagag   9000
gccgttgcca aacgctttgg cgaactgcct ttcctgttca aagtattatg cgcagcacag   9060
ccactctcca ttcaggttca tccaaacaaa cacaattctg aaatcggttt tgccaaagaa   9120
aatgccgcag gtatcccgat ggatgccgcc gagcgtaact ataaagatcc taaccacaag   9180
ccggagctgg tttttgcgct gacgcctttc cttgcgatga acgcgtttcg tgaattttcc   9240
gagattgtct ccctactcca gccggtcgca ggtgcacatc cggcgattgc tcactttta   9300
caacagcctg atgccgaacg tttaagcgaa ctgttcgcca gcctgttgaa tatgcagggt   9360
gaagaaaaat cccgcgcgct ggcgatttta aaatcggccc tcgatagcca gcagggtgaa   9420
ccgtggcaaa cgattcgttt aatttctgaa ttttacccgg aagacagcgg tctgttctcc   9480
ccgctattgc tgaatgtggt gaaattgaac cctggcgaag cgatgttcct gttcgctgaa   9540
acaccgcacg cttacctgca aggcgtggcg ctggaagtga tggcaaactc cgataacgtg   9600
ctgcgtgcgg gtctgacgcc taaatacatt gatattccgg aactggttgc caatgtgaaa   9660
ttcgaagcca aaccggctaa ccagttgttg acccagccgg tgaaacaagg tgcagaactg   9720
gacttcccga ttccagtgga tgattttgcc ttctcgctgc atgaccttag tgataaagaa   9780
accaccatta gccagcagag tgccgccatt ttgttctgcg tcgaaggcga tgcaacgttg   9840
```

```
tggaaaggtt ctcagcagtt acagcttaaa ccgggtgaat cagcgtttat tgccgccaac   9900
gaatcaccgg tgactgtcaa aggccacggc cgtttagcgc gtgtttacaa caagctgtaa   9960
gagcttactg aaaaaattaa catctcttgc taagctgggt catgggtcgt ttaagctgcc  10020
gatgtgcctg cgtcgtctgg tgccctctct ccatatggag gttgtcaaag tatctgctgt  10080
tcgtgtcatg agtcgtgtca gtgttggttt aataatggac cggttgtgtt gtgtgtgcgt  10140
actacccaga actatgacaa atcatgaata agtttgatgt ttgaaattaa agcctgtgct  10200
cattatgttc tgtctttcag ttgtctccta atatttgcct ccaggtactg gctatctacc  10260
gtttcttact taggaggtgt ttgaatgcac taaaactaat agttagtggc taaaattagt  10320
taaaacatcc aaacaccata gctaatagtt gaactattag ctatttttgg aaaattagtt  10380
aatagtgagg tagttatttg ttagctagct aattcaacta acaattttta gccaactaac  10440
aattagtttc agtgcattca aacaccccct taatgttaac gtggttctat ctaccgtctc  10500
ctaatatatg gttgattgtt cggtttgttg ctatgctatt gggttctgat tgctgctagt  10560
tcttgctgaa tccagaagtt ctcgtagtat agctcagatt catattattt atttgagtga  10620
taagtgatcc aggttattac tatgttagct aggttttttt tacaaggata aattatctgt  10680
gatcataatt cttatgaaag ctttatgttt cctggaggca gtggcatgca atgcatgaca  10740
gcaacttgat cacaccagct gaggtagata cggtaacaag gttcttaaat ctgttcacca  10800
aatcattgga gaacacacat acacattctt gccagtcttg gttagagaaa tttcatgaca  10860
aaatgccaaa gctgtcttga ctcttcactt ttggccatga gtcgtgactt agtttggttt  10920
aatggaccgg ttctcctagc ttgttctact caaaactgtt gttgatgcga ataagttgtg  10980
atggttgatc tctggatttt gttttgctct caatagtgga cgagattaga tagcctgcag  11040
gcccgggggc gcgccctaat tagctaacgg ccaggatcgc cgcgtgagcc tttagcaact  11100
agctagatta attaacgcaa tctgttatta agttgtctaa gcgtcaattt gtttacacca  11160
caatatatcc tgccaccagc cagccaacag ctccccgacc ggcagctcgg cacaaaatca  11220
ccactcgata caggcagccc atcagaatta attctcatgt ttgacagctt atcatcgact  11280
gcacggtgca ccaatgcttc tggcgtcagg cagccatcgg aagctgtggt atggctgtgc  11340
aggtcgtaaa tcactgcata attcgtgtcg ctcaaggcgc actcccgttc tggataatgt  11400
tttttgcgcc gacatcataa cggttctggc aaatattctg aaatgagctg ttgacaatta  11460
atcatccggc tcgtataatg tgtggaattg tgagcggata acaatttcac acaggaaaca  11520
gaccatgagg gaagcgttga tcgccgaagt atcgactcaa ctatcagagg tagttggcgt  11580
catcgagcgc catctcgaac cgacgttgct ggccgtacat ttgtacggct ccgcagtgga  11640
tggcggcctg aagccacaca gtgatattga tttgctggtt acggtgaccg taaggcttga  11700
tgaaacaacg cggcgagctt tgatcaacga ccttttggaa acttcggctt cccctggaga  11760
gagcgagatt ctccgcgctg tagaagtcac cattgttgtg cacgacgaca tcattccgtg  11820
gcgttatcca gctaagcgcg aactgcaatt tggagaatgg cagcgcaatg acattcttgc  11880
aggtatcttc gagccagcca cgatcgacat tgatctggct atcttgctga caaaagcaag  11940
agaacatagc gttgccttgg taggtccagc ggcggaggaa ctctttgatc cggttcctga  12000
acaggatcta tttgaggcgc taaatgaaac cttaacgcta tggaactcgc cgcccgactg  12060
ggctggcgat gagcgaaatg tagtgcttac gttgtcccgc atttggtaca gcgcagtaac  12120
cggcaaaatc gcgccgaagg atgtcgctgc cgactgggca atggagcgcc tgccggccca  12180
```

-continued

```
gtatcagccc gtcatacttg aagctaggca ggcttatctt ggacaagaag atcgcttggc  12240
ctcgcgcgca gatcagttgg aagaatttgt tcactacgtg aaaggcgaga tcaccaaagt  12300
agtcggcaaa taaagctcta gtggatctcc gtacccaggg atctggctcg cggcggacgc  12360
acgacgccgg ggcgagacca taggcgatct cctaaatcaa tagtagctgt aacctcgaag  12420
cgtttcactt gtaacaacga ttgagaattt ttgtcataaa attgaaatac ttggttcgca  12480
tttttgtcat ccgcggtcag ccgcaattct gacgaactgc ccatttagct ggagatgatt  12540
gtacatcctt cacgtgaaaa tttctcaagc gctgtgaaca agggttcaga ttttagattg  12600
aaaggtgagc cgttgaaaca cgttcttctt gtcgatgacg acgtcgctat gcggcatctt  12660
attattgaat accttacgat ccacgccttc aaagtgaccg cggtagccga cagcacccag  12720
ttcacaagag tactctcttc cgcgacggtc gatgtcgtgg ttgttgatct agatttaggt  12780
cgtgaagatg ggctcgagat cgttcgtaat ctggcggcaa agtctgatat tccaatcata  12840
attatcagtg gcgaccgcct tgaggagacg gataaagttg ttgcactcga gctaggagca  12900
agtgatttta tcgctaagcc gttcagtatc agagagtttc tagcacgcat tcgggttgcc  12960
ttgcgcgtgc gccccaacgt tgtccgctcc aaagaccgac ggtctttttg ttttactgac  13020
tggacactta atctcaggca acgtcgcttg atgtccgaag ctggcggtga ggtgaaactt  13080
acggcaggtg agttcaatct tctcctcgcg tttttagaga aaccccgcga cgttctatcg  13140
cgcgagcaac ttctcattgc cagtcgagta cgcgacgagg aggtttatga caggagtata  13200
gatgttctca ttttgaggct gcgccgcaaa cttgaggcag atccgtcaag ccctcaactg  13260
ataaaaacag caagaggtgc cggttatttc tttgacgcgg acgtgcaggt ttcgcacggg  13320
gggacgatgg cagcctgagc caattcccag atccccgagg aatcggcgtg agcggtcgca  13380
aaccatccgg cccggtacaa atcggcgcgg cgctgggtga tgacctggtg gagaagttga  13440
aggccgcgca ggccgcccag cggcaacgca tcgaggcaga agcacgcccc ggtgaatcgt  13500
ggcaagcggc cgctgatcga atccgcaaag aatcccggca accgccggca gccggtgcgc  13560
cgtcgattag gaagccgccc aagggcgacg agcaaccaga tttttcgtt ccgatgctct  13620
atgacgtggg cacccgcgat agtcgcagca tcatggacgt ggccgttttc cgtctgtcga  13680
agcgtgaccg acgagctggc gaggtgatcc gctacgagct tccagacggg cacgtagagg  13740
tttccgcagg gccggccggc atggccagtg tgtgggatta cgacctggta ctgatggcgg  13800
tttcccatct aaccgaatcc atgaaccgat accgggaagg gaagggagac aagcccggcc  13860
gcgtgttccg tccacacgtt gcggacgtac tcaagttctg ccggcgagcc gatggcggaa  13920
agcagaaaga cgacctggta gaaacctgca ttcggttaaa caccacgcac gttgccatgc  13980
agcgtacgaa gaaggccaag aacggccgcc tggtgacggt atccgagggt gaagccttga  14040
ttagccgcta caagatcgta aagagcgaaa ccgggcggcc ggagtacatc gagatcgagc  14100
tggctgattg gatgtaccgc gagatcacag aaggcaagaa cccggacgtg ctgacggttc  14160
accccgatta ctttttgatc gatcccggca tcggccgttt tctctaccgc ctggcacgcc  14220
gcgccgcagg caaggcagaa gccagatggt tgttcaagac gatctacgaa cgcagtggca  14280
gcgccggaga gttcaagaag ttctgtttca ccgtgcgcaa gctgatcggg tcaaatgacc  14340
tgccggagta cgatttgaag gaggaggcgg ggcaggctgg cccgatccta gtcatgcgct  14400
accgcaacct gatcgagggc gaagcatccg ccggttccta atgtacggag cagatgctag  14460
ggcaaattgc cctagcaggg gaaaaaggtc gaaaaggtct ctttcctgtg gatagcacgt  14520
acattgggaa cccaaagccg tacattggga accggaaccc gtacattggg aacccaaagc  14580
```

```
cgtacattgg gaaccggtca cacatgtaag tgactgatat aaaagagaaa aaaggcgatt  14640

tttccgccta aaactcttta aaacttatta aaactcttaa aacccgcctg gcctgtgcat  14700

aactgtctgg ccagcgcaca gccgaagagc tgcaaaaagc gcctaccctt cggtcgctgc  14760

gctccctacg ccccgccgct tcgcgtcggc ctatcgcggc cgctggccgc tcaaaaatgg  14820

ctggcctacg gccaggcaat ctaccagggc gcggacaagc cgcgccgtcg ccactcgacc  14880

gccggcgctg aggtctgcct cgtgaagaag gtgttgctga ctcataccag gcctgaatcg  14940

ccccatcatc cagccagaaa gtgagggagc cacggttgat gagagctttg ttgtaggtgg  15000

accagttggt gattttgaac ttttgctttg ccacggaacg gtctgcgttg tcgggaagat  15060

gcgtgatctg atccttcaac tcagcaaaag ttcgatttat tcaacaaagc cgccgtcccg  15120

tcaagtcagc gtaatgctct gccagtgtta caaccaatta accaattctg attagaaaaa  15180

ctcatcgagc atcaaatgaa actgcaattt attcatatca ggattatcaa taccatattt  15240

ttgaaaaagc cgtttctgta atgaaggaga aaactcaccg aggcagttcc ataggatggc  15300

aagatcctgg tatcggtctg cgattccgac tcgtccaaca tcaatacaac ctattaattt  15360

cccctcgtca aaaataaggt tatcaagtga gaaatcacca tgagtgacga ctgaatccgg  15420

tgagaatggc aaaagctctg cattaatgaa tcggccaacg cgcggggaga ggcggtttgc  15480

gtattgggcg ctcttccgct tcctcgctca ctgactcgct gcgctcggtc gttcggctgc  15540

ggcgagcggt atcagctcac tcaaaggcgg taatacggtt atccacagaa tcaggggata  15600

acgcaggaaa gaacatgtga gcaaaaggcc agcaaaaggc caggaaccgt aaaaaggccg  15660

cgttgctggc gtttttccat aggctccgcc cccctgacga gcatcacaaa aatcgacgct  15720

caagtcagag gtggcgaaac ccgacaggac tataaagata ccaggcgttt ccccctggaa  15780

gctccctcgt gcgctctcct gttccgaccc tgccgcttac cggatacctg tccgcctttc  15840

tcccttcggg aagcgtggcg ctttctcata gctcacgctg taggtatctc agttcggtgt  15900

aggtcgttcg ctccaagctg ggctgtgtgc acgaaccccc cgttcagccc gaccgctgcg  15960

ccttatccgg taactatcgt cttgagtcca acccggtaag acacgactta tcgccactgg  16020

cagcagccac tggtaacagg attagcagag cgaggtatgt aggcggtgct acagagttct  16080

tgaagtggtg gcctaactac ggctacacta gaagaacagt atttggtatc tgcgctctgc  16140

tgaagccagt taccttcgga aaaagagttg gtagctcttg atccggcaaa caaaccaccg  16200

ctggtagcgg tggttttttt gtttgcaagc agcagattac gcgcagaaaa aaaggatctc  16260

aagaagatcc tttgatcttt tctacggggt ctgacgctca gtggaacgaa aactcacgtt  16320

aagggatttt ggtcatgaga ttatcaaaaa ggatcttcac ctagatcctt ttgatccgga  16380

atta                                                              16384

<210> SEQ ID NO 32
<211> LENGTH: 719
<212> TYPE: PRT
<213> ORGANISM: Bacillus thuringiensis

<400> SEQUENCE: 32

Met Lys Leu Lys Asn Gln Asp Lys His Gln Ser Phe Ser Ser Asn Ala
1               5                   10                  15

Lys Val Asp Lys Ile Ser Thr Asp Ser Leu Lys Asn Glu Thr Asp Ile
            20                  25                  30

Glu Leu Gln Asn Ile Asn His Glu Asp Cys Leu Lys Met Ser Glu Tyr
        35                  40                  45
```

```
Glu Asn Val Glu Pro Phe Val Ser Val Ser Thr Ile Gln Thr Gly Ile
    50                  55                  60

Gly Ile Ala Gly Lys Ile Leu Gly Asn Leu Gly Val Pro Phe Ala Gly
65                  70                  75                  80

Gln Val Ala Ser Leu Tyr Ser Phe Ile Leu Gly Glu Leu Trp Pro Lys
                85                  90                  95

Gly Lys Ser Gln Trp Glu Ile Phe Met Glu His Val Glu Glu Leu Ile
            100                 105                 110

Asn Gln Lys Ile Ser Thr Tyr Ala Arg Asn Lys Ala Leu Ala Asp Leu
        115                 120                 125

Lys Gly Leu Gly Asp Ala Leu Ala Val Tyr His Glu Ser Leu Glu Ser
    130                 135                 140

Trp Ile Lys Asn Arg Asn Asn Thr Arg Thr Arg Ser Val Val Lys Ser
145                 150                 155                 160

Gln Tyr Ile Thr Leu Glu Leu Met Phe Val Gln Ser Leu Pro Ser Phe
                165                 170                 175

Ala Val Ser Gly Glu Glu Val Pro Leu Leu Pro Ile Tyr Ala Gln Ala
            180                 185                 190

Ala Asn Leu His Leu Leu Leu Leu Arg Asp Ala Ser Ile Phe Gly Lys
        195                 200                 205

Glu Trp Gly Leu Ser Asp Ser Glu Ile Ser Thr Phe Tyr Asn Arg Gln
    210                 215                 220

Val Glu Arg Thr Ser Asp Tyr Ser Asp His Cys Thr Lys Trp Phe Asp
225                 230                 235                 240

Thr Gly Leu Asn Arg Leu Lys Gly Ser Asn Ala Glu Ile Trp Val Lys
                245                 250                 255

Tyr Asn Gln Phe Arg Arg Asp Met Thr Leu Met Val Leu Asp Leu Val
            260                 265                 270

Ala Leu Phe Gln Ser Tyr Asp Thr His Met Tyr Pro Ile Lys Thr Thr
        275                 280                 285

Ala Gln Leu Thr Arg Glu Val Tyr Thr Asn Ala Ile Gly Thr Val His
    290                 295                 300

Pro His Pro Ser Phe Ala Ser Thr Thr Trp Tyr Asn Asn Asn Ala Pro
305                 310                 315                 320

Ser Phe Ser Ala Ile Glu Ala Ala Val Ile Arg Ser Pro His Leu Leu
                325                 330                 335

Asp Phe Leu Glu Gln Val Thr Ile Tyr Ser Leu Leu Ser Arg Trp Ser
            340                 345                 350

Asn Thr Gln Tyr Met Asn Met Trp Gly Gly His Lys Leu Glu Phe Arg
        355                 360                 365

Thr Ile Gly Gly Thr Leu Asn Thr Ser Thr Gln Gly Ser Thr Asn Thr
    370                 375                 380

Ser Ile Asn Pro Val Thr Leu Pro Phe Thr Ser Arg Asp Ile Tyr Arg
385                 390                 395                 400

Thr Glu Ser Leu Ala Gly Leu Asn Leu Phe Leu Thr Gln Pro Val Asn
                405                 410                 415

Gly Val Pro Arg Val Asp Phe His Trp Lys Phe Val Thr His Pro Ile
            420                 425                 430

Ala Ser Asp Asn Phe Tyr Tyr Pro Gly Tyr Ala Gly Ile Gly Thr Gln
        435                 440                 445

Leu Gln Asp Ser Glu Asn Glu Leu Pro Pro Glu Thr Thr Gly Gln Pro
    450                 455                 460
```

```
Asn Tyr Glu Ser Tyr Ser His Arg Leu Ser His Ile Gly Leu Ile Ser
465                 470                 475                 480

Ala Ser His Val Lys Ala Leu Val Tyr Ser Trp Thr His Arg Ser Ala
                485                 490                 495

Asp Arg Thr Asn Thr Ile His Ser Asp Ser Ile Thr Gln Ile Pro Leu
            500                 505                 510

Val Lys Ala His Thr Leu Gln Ser Gly Thr Thr Val Val Lys Gly Pro
        515                 520                 525

Gly Phe Thr Gly Gly Asp Ile Leu Arg Arg Thr Ser Gly Gly Pro Phe
    530                 535                 540

Ala Phe Ser Asn Val Asn Leu Asp Trp Asn Leu Ser Gln Arg Tyr Arg
545                 550                 555                 560

Ala Arg Ile Arg Tyr Ala Ser Thr Thr Asn Leu Arg Met Tyr Val Thr
                565                 570                 575

Ile Ala Gly Glu Arg Ile Phe Ala Gly Gln Phe Asn Lys Thr Met Asn
            580                 585                 590

Thr Gly Asp Pro Leu Thr Phe Gln Ser Phe Ser Tyr Ala Thr Ile Asp
        595                 600                 605

Thr Ala Phe Thr Phe Pro Thr Lys Ala Ser Ser Leu Thr Val Gly Ala
    610                 615                 620

Asp Thr Phe Ser Ser Gly Asn Glu Val Tyr Val Asp Arg Phe Glu Leu
625                 630                 635                 640

Ile Pro Val Thr Ala Thr Leu Glu Ala Val Thr Asp Leu Glu Arg Ala
                645                 650                 655

Gln Lys Ala Val His Glu Leu Phe Thr Ser Thr Asn Pro Gly Gly Leu
            660                 665                 670

Lys Thr Asp Val Lys Asp Tyr His Ile Asp Gln Val Ser Asn Leu Val
        675                 680                 685

Glu Ser Leu Ser Asp Glu Phe Tyr Leu Asp Glu Lys Arg Glu Leu Phe
    690                 695                 700

Glu Ile Val Lys Tyr Ala Lys Gln Leu His Ile Glu Pro Asn Met
705                 710                 715


<210> SEQ ID NO 33
<211> LENGTH: 1167
<212> TYPE: PRT
<213> ORGANISM: Bacillus thuringiensis

<400> SEQUENCE: 33

Met Glu Ile Asn Asn Gln Lys Gln Cys Ile Pro Tyr Asn Cys Leu Ser
1               5                   10                  15

Asn Pro Glu Glu Val Leu Leu Asp Gly Glu Arg Ile Leu Pro Asp Ile
            20                  25                  30

Asp Pro Leu Glu Val Ser Leu Ser Leu Leu Gln Phe Leu Leu Asn Asn
        35                  40                  45

Phe Val Pro Gly Gly Gly Phe Ile Ser Gly Leu Val Asp Lys Ile Trp
    50                  55                  60

Gly Ala Leu Arg Pro Ser Glu Trp Asp Leu Phe Leu Ala Gln Ile Glu
65                  70                  75                  80

Arg Leu Ile Asp Gln Arg Ile Glu Ala Thr Val Arg Ala Lys Ala Ile
                85                  90                  95

Thr Glu Leu Glu Gly Leu Gly Arg Asn Tyr Gln Ile Tyr Ala Glu Ala
            100                 105                 110

Phe Lys Glu Trp Glu Ser Asp Pro Asp Asn Glu Ala Ala Lys Ser Arg
        115                 120                 125
```

-continued

```
Val Ile Asp Arg Phe Arg Ile Leu Asp Gly Leu Ile Glu Ala Asn Ile
    130                 135                 140

Pro Ser Phe Arg Ile Ile Gly Phe Glu Val Pro Leu Leu Ser Val Tyr
145                 150                 155                 160

Val Gln Ala Ala Asn Leu His Leu Ala Leu Leu Arg Asp Ser Val Ile
                165                 170                 175

Phe Gly Glu Arg Trp Gly Leu Thr Thr Lys Asn Val Asn Asp Ile Tyr
            180                 185                 190

Asn Arg Gln Ile Arg Glu Ile His Glu Tyr Ser Asn His Cys Val Asp
        195                 200                 205

Thr Tyr Asn Thr Glu Leu Glu Arg Leu Gly Phe Arg Ser Ile Ala Gln
    210                 215                 220

Trp Arg Ile Tyr Asn Gln Phe Arg Arg Glu Leu Thr Leu Thr Val Leu
225                 230                 235                 240

Asp Ile Val Ala Leu Phe Pro Asn Tyr Asp Ser Arg Leu Tyr Pro Ile
                245                 250                 255

Gln Thr Phe Ser Gln Leu Thr Arg Glu Ile Val Thr Ser Pro Val Ser
            260                 265                 270

Glu Phe Tyr Tyr Gly Val Ile Asn Ser Gly Asn Ile Ile Gly Thr Leu
        275                 280                 285

Thr Glu Gln Gln Ile Arg Arg Pro His Leu Met Asp Phe Phe Asn Ser
    290                 295                 300

Met Ile Met Tyr Thr Ser Asp Asn Arg Arg Glu His Tyr Trp Ser Gly
305                 310                 315                 320

Leu Glu Met Thr Ala Tyr Phe Thr Gly Phe Ala Gly Ala Gln Val Ser
                325                 330                 335

Phe Pro Leu Val Gly Thr Arg Gly Glu Ser Ala Pro Pro Leu Thr Val
            340                 345                 350

Arg Ser Val Asn Asp Gly Ile Tyr Arg Ile Leu Ser Ala Pro Phe Tyr
        355                 360                 365

Ser Ala Pro Phe Leu Gly Thr Ile Val Leu Gly Ser Arg Gly Glu Lys
    370                 375                 380

Phe Asp Phe Ala Leu Asn Asn Ile Ser Pro Pro Pro Ser Thr Ile Tyr
385                 390                 395                 400

Arg His Pro Gly Thr Val Asp Ser Leu Val Ser Ile Pro Pro Gln Asp
                405                 410                 415

Asn Ser Val Pro Pro His Arg Gly Ser Ser His Arg Leu Ser His Val
            420                 425                 430

Thr Met Arg Ala Ser Ser Pro Ile Phe His Trp Thr His Arg Ser Ala
        435                 440                 445

Thr Thr Thr Asn Thr Ile Asn Pro Asn Ala Ile Ile Gln Ile Pro Leu
    450                 455                 460

Val Lys Ala Phe Asn Leu His Ser Gly Ala Thr Val Val Arg Gly Pro
465                 470                 475                 480

Gly Phe Thr Gly Gly Asp Ile Leu Arg Arg Thr Asn Thr Gly Thr Phe
                485                 490                 495

Ala Asp Met Arg Val Asn Ile Thr Gly Pro Leu Ser Gln Arg Tyr Arg
            500                 505                 510

Val Arg Ile Arg Tyr Ala Ser Thr Thr Asp Leu Gln Phe Phe Thr Arg
        515                 520                 525

Ile Asn Gly Thr Ser Val Asn Gln Gly Asn Phe Gln Arg Thr Met Asn
    530                 535                 540
```

```
Arg Gly Asp Asn Leu Glu Ser Gly Asn Phe Arg Thr Ala Gly Phe Ser
545                 550                 555                 560

Thr Pro Phe Ser Phe Ser Asn Ala Gln Ser Thr Phe Thr Leu Gly Thr
                565                 570                 575

Gln Ala Phe Ser Asn Gln Glu Val Tyr Ile Asp Arg Ile Glu Phe Val
            580                 585                 590

Pro Ala Glu Val Thr Phe Glu Ala Glu Ser Asp Leu Glu Arg Ala Gln
        595                 600                 605

Lys Ala Val Asn Ala Leu Phe Thr Ser Thr Asn Gln Leu Gly Leu Lys
    610                 615                 620

Thr Asp Val Thr Asp Tyr Gln Ile Asp Gln Val Ser Asn Leu Val Glu
625                 630                 635                 640

Cys Leu Ser Asp Glu Phe Cys Leu Asp Glu Lys Arg Glu Leu Ser Glu
                645                 650                 655

Lys Val Lys His Ala Lys Arg Leu Ser Asp Lys Arg Asn Leu Leu Gln
            660                 665                 670

Asp Pro Asn Phe Thr Ser Ile Asn Arg Gln Leu Asp Arg Gly Trp Arg
        675                 680                 685

Gly Ser Thr Asp Ile Thr Ile Gln Gly Gly Asn Asp Val Phe Lys Glu
    690                 695                 700

Asn Tyr Val Thr Leu Pro Gly Thr Phe Asp Glu Cys Tyr Pro Thr Tyr
705                 710                 715                 720

Leu Tyr Gln Lys Ile Asp Glu Ser Lys Leu Lys Ala Tyr Thr Arg Tyr
                725                 730                 735

Glu Leu Arg Gly Tyr Ile Glu Asp Ser Gln Asp Leu Glu Val Tyr Leu
            740                 745                 750

Ile Arg Tyr Asn Ala Lys His Glu Thr Val Asn Val Pro Gly Thr Gly
        755                 760                 765

Ser Leu Trp Pro Leu Ser Val Glu Ser Pro Ile Gly Arg Cys Gly Glu
    770                 775                 780

Pro Asn Arg Cys Val Pro His Ile Glu Trp Asn Pro Asp Leu Asp Cys
785                 790                 795                 800

Ser Cys Arg Asp Gly Glu Lys Cys Ala His His Ser His His Phe Ser
                805                 810                 815

Leu Asp Ile Asp Val Gly Cys Thr Asp Leu Asn Glu Asp Leu Gly Val
            820                 825                 830

Trp Val Ile Phe Lys Ile Lys Thr Gln Asp Gly His Ala Arg Leu Gly
        835                 840                 845

Asn Leu Glu Phe Leu Glu Glu Lys Pro Leu Leu Gly Glu Ala Leu Ala
    850                 855                 860

Arg Val Lys Arg Ala Glu Lys Lys Trp Arg Asp Lys Arg Glu Gln Leu
865                 870                 875                 880

Gln Phe Glu Thr Asn Ile Val Tyr Lys Glu Ala Lys Glu Ser Val Asp
                885                 890                 895

Ala Leu Phe Val Asp Ser His Tyr Asn Arg Leu Gln Ala Asp Thr Asn
            900                 905                 910

Ile Thr Met Ile His Ala Ala Asp Lys Arg Val His Arg Ile Arg Glu
        915                 920                 925

Ala Tyr Leu Pro Glu Leu Ser Val Ile Pro Gly Val Asn Ala Asp Ile
    930                 935                 940

Phe Glu Glu Leu Glu Gly Leu Ile Phe Thr Ala Phe Ser Leu Tyr Asp
945                 950                 955                 960

Ala Arg Asn Ile Ile Lys Asn Gly Asp Phe Asn Asn Gly Leu Ser Cys
```

```
                965                 970                 975

Trp Asn Val Lys Gly His Val Asp Ile Gln Gln Asn Asp His Arg Ser
            980                 985                 990

Val Leu Val Val Pro Glu Trp Glu  Ser Glu Val Ser Gln  Glu Val Arg
        995                 1000                1005

Val Cys  Pro Gly Arg Gly Tyr  Ile Leu Arg Val Thr  Ala Tyr Lys
    1010                1015                1020

Glu Gly  Tyr Gly Glu Gly Cys  Val Thr Ile His Glu  Ile Glu Asp
    1025                1030                1035

Asn Thr  Asp Glu Leu Lys Phe  Ser Asn Cys Ile Glu  Glu Glu Val
    1040                1045                1050

Tyr Pro  Thr Asp Thr Gly Asn  Asp Tyr Thr Ala His  Gln Gly Thr
    1055                1060                1065

Thr Gly  Cys Ala Asp Ala Cys  Asn Ser Arg Asn Val  Gly Tyr Glu
    1070                1075                1080

Asp Gly  Tyr Glu Ile Asn Thr  Thr Ala Ser Val Asn  Tyr Lys Pro
    1085                1090                1095

Thr Tyr  Glu Glu Glu Met Tyr  Thr Asp Val Arg Arg  Asp Asn His
    1100                1105                1110

Cys Glu  Tyr Asp Arg Gly Tyr  Gly Asn His Thr Pro  Leu Pro Ala
    1115                1120                1125

Gly Tyr  Val Thr Lys Glu Leu  Glu Tyr Phe Pro Glu  Thr Asp Thr
    1130                1135                1140

Val Trp  Ile Glu Ile Gly Glu  Thr Glu Gly Thr Phe  Ile Val Asp
    1145                1150                1155

Ser Val  Glu Leu Leu Leu Met  Glu Glu
    1160                1165


<210> SEQ ID NO 34
<211> LENGTH: 1168
<212> TYPE: PRT
<213> ORGANISM: Bacillus thuringiensis
<220> FEATURE:
<221> NAME/KEY: misc_feature
<222> LOCATION: (124)..(124)
<223> OTHER INFORMATION: Xaa can be any naturally occurring amino acid
<220> FEATURE:
<221> NAME/KEY: misc_feature
<222> LOCATION: (139)..(139)
<223> OTHER INFORMATION: Xaa can be any naturally occurring amino acid
<220> FEATURE:
<221> NAME/KEY: misc_feature
<222> LOCATION: (882)..(882)
<223> OTHER INFORMATION: Xaa can be any naturally occurring amino acid
<220> FEATURE:
<221> NAME/KEY: misc_feature
<222> LOCATION: (884)..(884)
<223> OTHER INFORMATION: Xaa can be any naturally occurring amino acid
<220> FEATURE:
<221> NAME/KEY: misc_feature
<222> LOCATION: (892)..(892)
<223> OTHER INFORMATION: Xaa can be any naturally occurring amino acid
<220> FEATURE:
<221> NAME/KEY: misc_feature
<222> LOCATION: (900)..(900)
<223> OTHER INFORMATION: Xaa can be any naturally occurring amino acid

<400> SEQUENCE: 34

Met Glu Ile Asn Asn Gln Asn Gln Cys Ile Pro Tyr Asn Cys Leu Ser
1               5                   10                  15

Asn Pro Glu Glu Val Phe Leu Asp Gly Glu Arg Ile Leu Pro Asp Ile
            20                  25                  30
```

```
Asp Pro Leu Glu Val Ser Leu Ser Leu Leu Gln Phe Leu Leu Asn Asn
        35                  40                  45

Phe Val Pro Gly Gly Gly Phe Ile Ser Gly Leu Leu Asp Lys Ile Trp
    50                  55                  60

Gly Ala Leu Arg Pro Ser Asp Trp Glu Leu Phe Leu Glu Gln Ile Glu
65                  70                  75                  80

Gln Leu Ile Asp Arg Arg Ile Glu Arg Thr Val Arg Ala Lys Ala Ile
                85                  90                  95

Ala Glu Leu Glu Gly Leu Gly Arg Ser Tyr Gln Leu Tyr Gly Glu Ala
            100                 105                 110

Phe Lys Glu Trp Glu Lys Thr Pro Asp Asn Thr Xaa Ala Arg Ser Arg
        115                 120                 125

Val Thr Glu Arg Phe Arg Ile Ile Asp Ala Xaa Ile Glu Ala Asn Ile
    130                 135                 140

Pro Ser Phe Arg Val Ser Gly Phe Glu Val Pro Leu Leu Leu Val Tyr
145                 150                 155                 160

Thr Gln Ala Ala Asn Leu His Leu Ala Leu Leu Arg Asp Ser Val Val
                165                 170                 175

Phe Gly Glu Arg Trp Gly Leu Thr Thr Thr Asn Val Asn Asp Ile Tyr
            180                 185                 190

Asn Arg Gln Val Asn Arg Ile Gly Glu Tyr Ser Lys His Cys Val Asp
        195                 200                 205

Thr Tyr Lys Thr Glu Leu Glu Arg Leu Gly Phe Arg Ser Ile Ala Gln
    210                 215                 220

Trp Arg Ile Tyr Asn Gln Phe Arg Arg Glu Leu Thr Leu Thr Val Leu
225                 230                 235                 240

Asp Ile Val Ala Val Phe Pro Asn Tyr Asp Ser Arg Leu Tyr Pro Ile
                245                 250                 255

Arg Thr Ile Ser Gln Leu Thr Arg Glu Ile Tyr Thr Ser Pro Val Ser
            260                 265                 270

Glu Phe Tyr Tyr Gly Val Ile Asn Ser Asn Asn Ile Ile Gly Thr Leu
        275                 280                 285

Thr Glu Gln Gln Ile Arg Arg Pro His Leu Met Asp Phe Phe Asn Ser
    290                 295                 300

Met Ile Met Tyr Thr Ser Asp Asn Arg Arg Glu His Tyr Trp Ser Gly
305                 310                 315                 320

Leu Glu Met Thr Ala Thr Asn Thr Glu Gly His Gln Arg Ser Phe Pro
                325                 330                 335

Leu Ala Gly Thr Ile Gly Asn Ser Ala Pro Pro Val Thr Val Arg Asn
            340                 345                 350

Asn Gly Glu Gly Ile Tyr Arg Ile Leu Ser Glu Pro Phe Tyr Ser Ala
        355                 360                 365

Pro Phe Leu Gly Thr Ser Val Leu Gly Ser Arg Gly Glu Glu Phe Ala
    370                 375                 380

Phe Ala Ser Asn Thr Thr Thr Ser Leu Pro Ser Thr Ile Tyr Arg Asn
385                 390                 395                 400

Arg Gly Thr Val Asp Ser Leu Val Ser Ile Pro Pro Gln Asp Tyr Ser
                405                 410                 415

Val Pro Pro His Arg Gly Tyr Ser His Leu Leu Ser His Val Thr Met
            420                 425                 430

Arg Asn Ser Ser Pro Ile Phe His Trp Thr His Arg Ser Ala Thr Pro
        435                 440                 445

Arg Asn Thr Ile Asp Pro Asp Ser Ile Thr Gln Ile Pro Ala Val Lys
```

```
    450                 455                 460

Gly Ala Tyr Ile Phe Asn Ser Pro Val Ile Thr Gly Pro Gly His Thr
465                 470                 475                 480

Gly Gly Asp Ile Ile Arg Phe Asn Pro Asn Thr Gln Asn Asn Ile Arg
                485                 490                 495

Ile Pro Phe Gln Ser Asn Ala Val Gln Arg Tyr Arg Ile Arg Met Arg
            500                 505                 510

Tyr Ala Ala Glu Ala Asp Cys Ile Leu Glu Ser Gly Val Asn Ile Val
        515                 520                 525

Thr Gly Ala Gly Val Thr Phe Arg Pro Ile Pro Ile Lys Ala Thr Met
    530                 535                 540

Thr Pro Gly Ser Pro Leu Thr Tyr Tyr Ser Phe Gln Tyr Ala Asp Leu
545                 550                 555                 560

Asn Ile Asn Leu Thr Ala Pro Ile Arg Pro Asn Asn Phe Val Ser Ile
                565                 570                 575

Arg Arg Ser Asn Gln Pro Gly Asn Leu Tyr Ile Asp Arg Ile Glu Phe
            580                 585                 590

Ile Pro Ile Asp Pro Ile Arg Glu Ala Glu His Asp Leu Glu Arg Ala
        595                 600                 605

Gln Lys Ala Val Asn Ala Leu Phe Thr Ser Ser Asn Gln Leu Gly Leu
    610                 615                 620

Lys Thr Asp Val Thr Asp Tyr His Ile Asp Gln Val Ser Asn Leu Val
625                 630                 635                 640

Ala Cys Leu Ser Asp Lys Phe Cys Leu Asp Glu Lys Arg Glu Leu Ser
                645                 650                 655

Glu Lys Val Lys His Ala Lys Arg Leu Ser Asp Glu Arg Asn Leu Leu
            660                 665                 670

Gln Asp Gln Asn Phe Thr Gly Ile Asn Arg Gln Val Asp Arg Gly Trp
        675                 680                 685

Arg Gly Ser Thr Asp Ile Thr Thr Gln Gly Gly Asn Asp Val Phe Lys
    690                 695                 700

Glu Asn Tyr Val Thr Leu Pro Gly Thr Phe Asp Glu Cys Tyr Pro Thr
705                 710                 715                 720

Tyr Leu Tyr Gln Lys Ile Asp Glu Ser Lys Leu Lys Pro Tyr Thr Arg
                725                 730                 735

Tyr Glu Leu Arg Gly Tyr Ile Glu Asp Ser Gln Asp Leu Glu Val Tyr
            740                 745                 750

Leu Ile Arg Tyr Asn Ala Lys His Glu Thr Leu Asn Val Pro Gly Thr
        755                 760                 765

Gly Ser Leu Trp Pro Leu Ala Ala Glu Ser Ser Ile Gly Arg Cys Gly
    770                 775                 780

Glu Pro Asn Arg Cys Ala Pro His Ile Glu Trp Asn Pro Glu Leu Asp
785                 790                 795                 800

Cys Ser Cys Arg Asp Gly Glu Lys Cys Ala His His Ser His His Phe
                805                 810                 815

Ser Leu Asp Ile Asp Val Gly Cys Thr Asp Leu Asn Glu Asp Leu Gly
            820                 825                 830

Val Trp Val Ile Phe Lys Ile Lys Thr Gln Asp Gly Tyr Ala Arg Leu
        835                 840                 845

Gly Asn Leu Glu Phe Leu Glu Glu Lys Pro Leu Leu Gly Glu Ala Leu
    850                 855                 860

Ala Arg Val Lys Arg Ala Glu Lys Lys Trp Arg Asp Lys Arg Asp Lys
865                 870                 875                 880
```

-continued

```
Leu Xaa Trp Xaa Thr Asn Ile Val Tyr Lys Glu Xaa Lys Glu Ser Val
                885                 890                 895

Asp Ala Leu Xaa Val Asp Ser Gln Tyr Asn Arg Leu Gln Pro Asp Thr
            900                 905                 910

Asn Ile Ala Met Ile His Val Ala Asp Lys Arg Val His Arg Ile Arg
        915                 920                 925

Glu Ala Tyr Leu Pro Glu Leu Ser Val Ile Pro Gly Val Asn Ala Ala
    930                 935                 940

Ile Phe Glu Glu Leu Glu Gly Leu Ile Phe Thr Ala Phe Ser Leu Tyr
945                 950                 955                 960

Asp Ala Arg Asn Val Ile Lys Asn Gly Asp Phe Asn His Gly Leu Ser
                965                 970                 975

Cys Trp Asn Val Lys Gly His Val Asp Val Glu Glu Gln Asn Asn His
            980                 985                 990

Arg Ser Val Leu Val Val Pro Glu  Trp Glu Ala Glu Val  Ser Gln Glu
        995                 1000                1005

Val Arg  Val Cys Pro Gly Arg  Gly Tyr Ile Leu Arg  Val Thr Ala
    1010                 1015                 1020

Tyr Lys  Glu Gly Tyr Gly Glu  Gly Cys Val Thr Ile  His Glu Ile
    1025                 1030                 1035

Glu Asp  His Thr Asp Glu Leu  Lys Phe Arg Asn Cys  Glu Glu Glu
    1040                 1045                 1050

Glu Val  Tyr Pro Asn Asn Thr  Val Thr Cys Asn Asp  Tyr Pro Ala
    1055                 1060                 1065

Asn Gln  Glu Glu Tyr Arg Ala  Ala Glu Thr Ser Arg  Asn Arg Gly
    1070                 1075                 1080

Tyr Gly  Glu Ser Tyr Glu Ser  Asn Ser Ser Ile Pro  Ala Glu Tyr
    1085                 1090                 1095

Ala Pro  Ile Tyr Glu Lys Ala  Tyr Thr Asp Gly Arg  Lys Glu Asn
    1100                 1105                 1110

Ser Cys  Glu Ser Asn Arg Gly  Tyr Gly Asn Tyr Thr  Pro Leu Pro
    1115                 1120                 1125

Ala Gly  Tyr Val Thr Lys Glu  Leu Glu Tyr Phe Pro  Glu Thr Asp
    1130                 1135                 1140

Lys Val  Trp Ile Glu Ile Gly  Glu Thr Glu Gly Thr  Phe Ile Val
    1145                 1150                 1155

Asp Ser  Val Glu Leu Leu Leu  Met Glu Glu
    1160                 1165
```

COMPOSITIONS AND METHODS FOR CONTROL OF INSECT PESTS

RELATED APPLICATION INFORMATION

This application is a 371 of International Application No. PCT/US2017/64897, filed Dec. 6, 2017, which claims priority to U.S. Provisional Application No. 62/442,155, filed Jan. 4, 2017, the contents of which are incorporated herein by reference herein.

STATEMENT REGARDING ELECTRONIC SUBMISSION OF A SEQUENCE LISTING

A Sequence Listing in ASCII text format, submitted under 37 C.F.R. § 1.821, entitled "81065-US-ORG-NAT-1_SeqList_ST25.txt", created on Nov. 23, 2021, and having a size of 250 kilobytes and filed via EFS-Web is provided in lieu of a paper copy. This Sequence Listing is hereby incorporated by reference into the specification for its disclosures.

FIELD OF THE INVENTION

This invention relates to pesticidal proteins and the polynucleotides that encode them, as well as compositions and methods for controlling plant pests.

BACKGROUND

Plant pests are a major factor in the loss of the world's important agricultural crops. About $8 billion are lost every year in the U.S. alone due to infestations of invertebrate pests including insects. In addition to losses in field crops, insect pests are also an economic problem in commodities derived from crop plants, in vegetable and fruit production, and in home gardens.

Insect pests are mainly controlled by intensive applications of chemical pesticides, which are active through inhibition of insect growth, prevention of insect feeding or reproduction, or cause death. Biological pest control agents, such as *Bacillus thuringiensis* strains expressing pesticidal toxins such as Cry proteins, have also been applied to crop plants with satisfactory results, offering an alternative or compliment to chemical pesticides. The genes coding for some of these Cry proteins have been isolated and their expression in heterologous hosts such as transgenic plants have been shown to provide another tool for the control of economically important insect pests.

Good insect control can thus be reached, but certain chemicals can sometimes also affect non-target beneficial insects and certain biologicals have a very narrow spectrum of activity. In addition, the continued use of certain chemical and biological control methods heightens the chance for insect pests to develop resistance to such control measures. This has been partially alleviated by various resistance management practices, but there remains a need to develop new and effective pest control agents that provide an economic benefit to farmers and that are environmentally acceptable. Particularly needed are control agents that can target different spectrums of economically important insect pests and that efficiently control insect strains that are or could become resistant to existing insect control agents.

SUMMARY

In view of these needs, it is an object of the present invention to provide new pest control agents by providing new *Bacillus thuringiensis* (Bt) isolates as well as novel genes and pesticidal proteins that may be used to control a variety of plant and commodity pests.

The invention provides compositions and methods for conferring pesticidal activity to bacteria, plants, plant parts, plant cells, tissues and seeds. In particular, novel polynucleotides that encode Cry proteins isolated from Bt and sequences substantially identical thereto are provided. The invention is further drawn to chimeric genes comprising the novel polynucleotides whose expression results in Cry proteins with toxicity to economically important insect pests, particularly insect pests that infest plants or commodities derived from plants. The invention is further drawn to the novel Cry proteins resulting from the expression of the polynucleotides, and to compositions and formulations containing the Cry proteins, which are toxic to insects by inhibiting the ability of insect pests to survive, grow and reproduce, or of limiting insect-related damage or loss to crop plants or commodities derived from crop plants. Cry proteins of the invention include native Cry proteins and their variants as well as modified Cry proteins that have one or more amino acid substitutions, additions or deletions. Examples of modified Cry proteins include without limitation those that are mutated to modulate their biological activity. Such modulation may, for example, broaden or narrow their spectrum of activity, or increase or decrease their specificity compared to their native Cry protein counterparts. Cry proteins of the invention may be mutated to introduce an epitope to generate antibodies that differentially recognize the modified protein from the native protein or they may be mutated to modify expression in a transgenic organism, such as a plant or bacteria. The Cry proteins of the invention are highly active against economically important insect pests, for example, insect pests of crop plants such as black cutworm (BCW; *Agrotis ipsilon*), European corn borer (ECB; *Ostrinia nubilalis*), fall armyworm (FAW; *Spodoptera frugiperda*), corn earworm (CEW; *Helicoverpa zea*), sugarcane borer (SCB; *Diatraea saccharalis*), velvetbean caterpillar (VBC; *Anticarsia gemmatalis*), soybean looper (SBL; *Chrysodeixis includes*), southwest corn borer (SWCB; *Diatraea grandiosella*), western bean cutworm (WBC; *Richia albicosta*), tobacco budworm (TBW; *Heliothis virescens*), Asian corn borer (ACB; *Ostrinia furnacalis*), cotton bollworm (CBW; *Helicoverpa armigera*), striped stem borer (SSB; *Chilo suppressalis*), pink stem borer (PSB; *Sesamia calamistis*), rice leaffolder (RLF; *Cnaphalocrocis medinalis*), and the like, or economically important insect pests of stored-products or commodity products derived from crop plants such as whiteshouldered house moth (WHM; *Endrosis sarcitrella*), brown hose moth (BHM; *Hofmannophila pseudospretella*), Angoumois grain moth (AGM; *Sitotroga cerealella*), almond moth (ADM; *Cadra cautella*), Mediterranean flour moth (MFM; *Ephestia kuehniella*), Indianmeal moth (IMM; *Plodia interpunctella*), European grain moth (EGM; *Nemapogon granella*), and the like.

The invention also provides synthetic polynucleotides that encode the Cry proteins of the invention that have one or more codons optimized for expression in transgenic organisms such as transgenic bacteria or transgenic plants.

The invention is further drawn to expression cassettes and recombinant vectors comprising a polynucleotide that encodes a Cry protein of the invention. The invention also provides transformed bacteria, plants, plant parts, plant cells, tissues, and seeds comprising a chimeric gene, or an expression cassette or a recombinant vector which are useful in expressing a Cry protein of the invention in the transformed bacteria, plants, plant cells, tissues and seeds.

The invention is also drawn to isolated *Bacillus thuringiensis* (Bt) strains that produce the Cry proteins of the invention. Such Bt strains may be a naturally occurring isolate or a recombinant Bt strain which produces one or more of the Cry proteins of the invention.

The invention is also drawn to methods of using polynucleotides of the invention, for example in DNA constructs or chimeric genes or expression cassettes or recombinant vectors for transformation and expression in organisms, including plants and microorganisms, such as bacteria. The nucleotide or amino acid sequences may be native or synthetic sequences that have been designed for expression in an organism such as a plant or bacteria or in making hybrid Cry toxins with enhanced pesticidal activity. The invention is further drawn to methods of making the Cry proteins and to methods of using the polynucleotide sequences and Cry proteins, for example in microorganisms to control insects or in transgenic plants to confer protection from insect damage.

Another aspect of the invention includes insecticidal compositions and formulations comprising the Cry proteins or the *Bacillus thuringiensis* strains of the invention, and methods of using the compositions or formulations to control insect pest populations, for example by applying the compositions or formulations to insect-infested areas, or to prophylactically treat insect-susceptible areas or plants to confer protection against the insect pests. Optionally, the compositions or formulations of the invention may, in addition to the Cry protein or Bt strain of the invention, comprise other pesticidal agents such as chemical or biological pesticides in order to augment or enhance the insect-controlling capability of the compositions or formulations of the invention.

The compositions and methods of the invention are useful for controlling insect pests that attack plants, particularly crop plants or commodity products derived from crop plants. The compositions of the invention are also useful for generating altered or improved Cry proteins that have pesticidal activity, or for detecting the presence of a Cry protein or polynucleotides in commercial products or transgenic organisms.

These and other features, aspects, and advantages of the invention will become better understood with reference to the following detailed description and claims.

BRIEF DESCRIPTION OF THE SEVERAL DRAWINGS

FIG. 1A-E shows an alignment of a BT2Cry1J protein and various embodiments of modified BT2Cry1J proteins. BT-0002 is SEQ ID NO: 1, mBT02BLK-1 is SEQ ID NO: 7, mBT0002BLK-2 is SEQ ID NO: 8, mBT02BLK-3 is SEQ ID NO: 9, mBTO2BLK-1&2 is SEQ ID NO: 10, mBT02BLK-2&3 is SEQ ID NO: 11, mBT02B1k-1&3 is SEQ ID NO: 12, mBT02BLK-1-2 is SEQ ID NO: 13, and mBT-0002pro is SEQ ID NO: 4.

FIG. 2A-B shows an alignment of a Cry1Ig1 protein (SEQ ID NO: 32), a BT25Cry1I protein (SEQ ID NO: 2) and a variant BT25Cry1I protein (SEQ ID NO: 5).

FIG. 3A-B shows an alignment of a Cry1Ja1 protein (SEQ ID NO: 33), a BT2Cry1J protein (SEQ ID NO: 1) and a variant BT2Cry1J protein (SEQ ID NO: 4).

FIG. 4A-B shows an alignment of a Cry1Jc1 protein (SEQ ID NO: 34), a BT53Cry1J protein (SEQ ID NO: 3) and a variant BT53Cry1J protein (SEQ ID NO: 6).

BRIEF DESCRIPTION OF THE SEQUENCES IN THE SEQUENCE LISTING

SEQ ID NO:1 is a BT2Cry1J amino acid sequence.

SEQ ID NO:2 is a BT25Cry1I amino acid sequence.

SEQ ID NO:3 is a BT53Cry1J amino acid sequence.

SEQ ID NO:4 is a variant BT2Cry1J amino acid sequence.

SEQ ID NO:5 is a variant BT25Cry1I amino acid sequence.

SEQ ID NO:6 is a variant BT53Cry1J amino acid sequence.

SEQ ID NO:7 is a α-helix3 modified BT2Cry1J amino acid sequence.

SEQ ID NO:8 is a α-helix4 modified BT2Cry1J amino acid sequence.

SEQ ID NO:9 is a α-helix5/6 modified BT2Cry1J amino acid sequence.

SEQ ID NO:10 is a α-helix3/4 modified BT2Cry1J amino acid sequence.

SEQ ID NO:11 is a α-helix4/5/6 modified BT2Cry1J amino acid sequence.

SEQ ID NO:12 is a α-helix 3/5/6 modified BT2Cry1J amino acid sequence.

SEQ ID NO:13 is a α-helix 3/4/5/6 modified BT2Cry1J amino acid sequence.

SEQ ID NO:14 is a nucleotide sequence encoding SEQ ID NO:1.

SEQ ID NO:15 is a nucleotide sequence encoding SEQ ID NO:2.

SEQ ID NO:16 is a nucleotide sequence encoding SEQ ID NO:3.

SEQ ID NO:17 is a codon optimized sequence encoding SEQ ID NO:1.

SEQ ID NO:18 is a codon optimized sequence encoding SEQ ID NO:2.

SEQ ID NO:19 is a codon optimized sequence encoding SEQ ID NO:3.

SEQ ID NO:20 is a nucleotide sequence encoding SEQ ID NO: 4.

SEQ ID NO:21 is a nucleotide sequence encoding SEQ ID NO:5.

SEQ ID NO:22 is a nucleotide sequence encoding SEQ ID NO:6.

SEQ ID NO: 23 is a nucleotide sequence encoding SEQ ID NO:7.

SEQ ID NO: 24 is a nucleotide sequence encoding SEQ ID NO:8.

SEQ ID NO: 25 is a nucleotide sequence encoding SEQ ID NO:9.

SEQ ID NO: 26 is a nucleotide sequence encoding SEQ ID NO:10.

SEQ ID NO: 27 is a nucleotide sequence encoding SEQ ID NO:11.

SEQ ID NO: 28 is a nucleotide sequence encoding SEQ ID NO:12.

SEQ ID NO: 29 is a nucleotide sequence encoding SEQ ID NO:13.

SEQ ID NO:30 is a nucleotide sequence of a shuttle vector.

SEQ ID NO:31 is a nucleotide sequence of a binary transformation vector.

SEQ ID NO:32 is a Cry1Ig1 amino acid sequence.

SEQ ID NO:33 is a Cry1Ja1 amino acid sequence.

SEQ ID NO:34 is a Cry1Jc1 amino acid sequence.

DETAILED DESCRIPTION

This description is not intended to be a detailed catalog of all the different ways in which the invention may be implemented, or all the features that may be added to the instant invention. For example, features illustrated with respect to one embodiment may be incorporated into other embodiments, and features illustrated with respect to a particular embodiment may be deleted from that embodiment. Thus, the invention contemplates that in some embodiments of the invention, any feature or combination of features set forth herein can be excluded or omitted. In addition, numerous variations and additions to the various embodiments suggested herein will be apparent to those skilled in the art in light of the instant disclosure, which do not depart from the instant invention. Hence, the following descriptions are intended to illustrate some particular embodiments of the invention, and not to exhaustively specify all permutations, combinations and variations thereof.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention.

Definitions

As used herein and in the appended claims, the singular forms "a," "and," and "the" include plural reference unless the context clearly dictates otherwise. Thus, for example, reference to "a plant" is a reference to one or more plants and includes equivalents thereof known to those skilled in the art, and so forth. As used herein, the word "or" means any one member of a particular list and also includes any combination of members of that list (i.e., includes also "and").

The term "about" is used herein to mean approximately, roughly, around, or in the region of. When the term "about" is used in conjunction with a numerical range, it modifies that range by extending the boundaries above and below the numerical values set forth. In general, the term "about" is used herein to modify a numerical value above and below the stated value by a variance of 20 percent, preferably 10 percent up or down (higher or lower). With regard to a temperature the term "about" means±1° C., preferably ±0.5° C. Where the term "about" is used in the context of this invention (e.g., in combinations with temperature or molecular weight values) the exact value (i.e., without "about") is preferred.

An "active" Cry protein or the "activity" of a Cry protein of the invention is meant that the Cry protein functions as an insect control agent, has a toxic effect, or is able to disrupt or deter insect feeding, which may or may not cause death of the insect. When a Cry protein of the invention is delivered to the insect, the result is typically death of the insect, or the insect does not feed upon the source that makes the Cry protein available to the insect.

As used herein, the term "amplified" means the construction of multiple copies of a polynucleotide or multiple copies complementary to the polynucleotide using at least one of the polynucleotides as a template. Amplification systems include the polymerase chain reaction (PCR) system, ligase chain reaction (LCR) system, nucleotide sequence based amplification (NASBA, Cangene, Mississauga, Ontario), Q-Beta Replicase systems, transcription-based amplification system (TAS), and strand displacement amplification (SDA). See, e.g., Diagnostic Molecular Microbiology: Principles and Applications, PERSING et al., Ed., American Society for Microbiology, Washington, D.C. (1993). The product of amplification is termed an "amplicon."

The term "chimeric construct" or "chimeric gene" or "chimeric polynucleotide" or "chimeric nucleic acid" (or similar terms) as used herein refers to a construct or molecule comprising two or more polynucleotides of different origin assembled into a single polynucleotide. The term "chimeric construct", "chimeric gene", "chimeric polynucleotide" or "chimeric nucleic acid" refers to any construct or molecule that contains, without limitation, (1) polynucleotides (e.g., DNA), including regulatory and coding polynucleotides that are not found together in nature (i.e., at least one of the polynucleotides in the construct is heterologous with respect to at least one of its other polynucleotides), or (2) polynucleotides encoding parts of proteins not naturally adjoined, or (3) parts of promoters that are not naturally adjoined. Further, a chimeric construct, chimeric gene, chimeric polynucleotide or chimeric nucleic acid may comprise regulatory polynucleotides and coding polynucleotides that are derived from different sources, or comprise regulatory polynucleotides and coding polynucleotides derived from the same source, but arranged in a manner different from that found in nature. In some embodiments of the invention, the chimeric construct, chimeric gene, chimeric polynucleotide or chimeric nucleic acid comprises an expression cassette comprising a polynucleotide of the invention under the control of regulatory polynucleotides, particularly under the control of regulatory polynucleotides functional in plants or bacteria.

A "coding sequence" is a nucleotide sequence that is transcribed into RNA such as mRNA, rRNA, tRNA, snRNA, sense RNA or antisense RNA. Preferably the RNA is then translated in an organism to produce a protein.

As used herein, a "codon optimized" sequence means a nucleotide sequence of a recombinant, transgenic, or synthetic polynucleotide wherein the codons are chosen to reflect the particular codon bias that a host cell or organism may have. This is typically done in such a way so as to preserve the amino acid sequence of the polypeptide encoded by the nucleotide sequence that is codon optimized. In certain embodiments, the DNA sequence of the recombinant DNA construct includes sequence that has been codon optimized for the cell (e.g., an animal, plant, or fungal cell) in which the construct is to be expressed. For example, a construct to be expressed in a plant cell can have all or parts of its sequence (e.g., the first gene suppression element or the gene expression element) codon optimized for expression in a plant. See, for example, U.S. Pat. No. 6,121,014, incorporated herein by reference.

To "control" insects means to inhibit, through a toxic effect, the ability of insect pests to survive, grow, feed, or reproduce, or to limit insect-related damage or loss in crop plants or to protect the yield potential of a crop when grown in the presence of insect pests. To "control" insects may or may not mean killing the insects, although it preferably means killing the insects.

The terms "comprises" or "comprising," when used in this specification, specify the presence of stated features, integers, steps, operations, elements, or components, but do not preclude the presence or addition of one or more other features, integers, steps, operations, elements, components, or groups thereof.

As used herein, the transitional phrase "consisting essentially of (and grammatical variants) means that the scope of a claim is to be interpreted to encompass the specified materials or steps recited in the claim" and those that do not materially alter the basic and novel characteristic(s)" of the claimed invention. Thus, the term "consisting essentially of"

when used in a claim of this invention is not intended to be interpreted to be equivalent to "comprising."

In the context of the invention, "corresponding to" or "corresponds to" means that when the amino acid sequences of variant or modified Cry proteins are aligned with each other, the amino acids that "correspond to" certain enumerated positions in the variant or modified protein are those that align with these positions in a reference protein but that are not necessarily in these exact numerical positions relative to the particular reference amino acid sequence of the invention. For example, if SEQ ID NO:1 is the reference sequence and is aligned with SEQ ID NO:3, Pro419 of SEQ ID NO:3 "corresponds to" Pro421 of SEQ ID NO:1 or Tyr417 of SEQ ID NO:3 "corresponds to" Asn419 of SEQ ID NO:1.

As used herein, the term "Cry protein" means an insecticidal protein of a *Bacillus thuringiensis* crystal delta-endotoxin type. The term "Cry protein" can refer to the protoxin form or any insecticidally active fragment or toxin thereof. Cry proteins from *Bacillus thuringiensis* have potent insecticidal activity against predominantly lepidopteran, dipteran, and coleopteran pest insects. These proteins also have shown activity against pests in the Orders Hymenoptera, Homoptera, Phthiraptera, Mallophaga, and Acari pest orders, as well as other invertebrate orders such as Nemathelminthes, Platyhelminthes, and Sarcomastigorphora (Feitelson, J. 1993. The *Bacillus Thuringiensis* family tree. In Advanced Engineered Pesticides. Marcel Dekker, Inc., New York, N.Y.). These proteins were originally classified based primarily on their insecticidal activity. The major classes were Lepidoptera-specific (CryI), Lepidoptera- and Diptera-specific (CryII), Coleoptera-specific (CryIII), Diptera-specific (CryIV), and nematode-specific (CryV) and (CryVI). The proteins were further classified into subfamilies; more highly related proteins within each family were assigned divisional letters such as CryIA, CryIB, CryIC, etc. Even more closely related proteins within each division were given names such as CryIC(a), CryIC(b), etc. The terms "Cry toxin" and "delta-endotoxin" have been used interchangeably with the term "Cry protein." Current nomenclature for Cry proteins and genes is based upon amino acid sequence homology rather than insect target specificity (Crickmore et al. (1998) Microbiol. Mol. Biol. Rev. 62:807-813). In this more accepted classification, each Cry protein is assigned a unique name incorporating a primary rank (an Arabic number) if it has <45% sequence identity to known named Cry proteins, for example Cry1 or Cry2 and the like; a secondary rank (an uppercase letter) if it has >45% and <75% sequence identity to known named Cry proteins, for example Cry1I or Cry1J and the like; a tertiary rank (a lowercase letter) if it has from 75% to 95% sequence identity to known named Cry proteins, for example Cry1Ja or Cry1Jc and the like; and a quaternary rank (another Arabic number) if it has >95% sequence identity to known named Cry proteins, for example Cry1Ja1 or Cry1Ja2 and the like. In the current classification, Roman numerals have been exchanged for Arabic numerals in the primary rank. For example, "CryIA(a)" under the older nomenclature is now "Cry1Aa" under the current nomenclature. According to Ibrahim et al. (2010, Bioeng. Bugs, 1:31-50), the Cry toxins can still be separated into six major classes according to their insect host specificities and include: Group 1—lepidopteran e.g., Cry1, Cry9 and Cry15); group 2—lepidopteran and dipteran (e.g., Cry2); group 3—coleopteran (Cry3, Cry7 and Cry8); group 4—dipteran (Cry4, Cry10, Cry11, Cry16, Cry17, Cry19 and Cry20); group 5—lepidopteran and coleopteran (Cry1I); and group 6—nematodes (Cry6). The Cry1I, Cry2, Cry3, Cry10 and Cry11 toxins (73-82 kDa) are unique because they appear to be natural truncations of the larger Cry1 and Cry4 proteins (130-140 kDa).

Cry proteins are globular protein molecules which accumulate as protoxins in crystalline form during the sporulation stage of Bt. After ingestion by a pest, the crystals are typically solubilized to release protoxins, which can range in size, for example, from 130-140 kDa for many of the lepidopteran-active Cry proteins, such as Cry1 and Cry9, and 60-80 kDa for the coleopteran-active Cry3 proteins and the lepidopteran/dipteran-active Cry2 proteins. After the crystals are solubilized by a susceptible insect the released protoxins are processed by proteases in the insect gut, for example trypsin and chymotrypsin, to produce a protease-resistant core Cry protein toxin. This proteolytic processing involves the removal of amino acids from different regions of the various Cry protoxins. For example, Cry protoxins that are 130-140 kDa are typically activated through the proteolytic removal of an N-terminal peptide of 25-30 amino acids and approximately half of the remaining protein from the C-terminus resulting in an approximately 60-70 kDa mature Cry toxin. The protoxins that are 60-80 kDa, e.g. Cry2 and Cry3, are also processed but not to the same extent as the larger protoxins. The smaller protoxins typically have equal or more amino acids removed from the N-terminus than the larger protoxins but less amino acids removed from the C-terminus. For example, proteolytic activation of Cry2 family members typically involves the removal of approximately 40-50 N-terminal amino acids. Many of the Cry proteins are quite toxic to specific target insects, but many have narrow spectrums of activity.

Cry proteins generally have five conserved sequence domains, and three conserved structural domains (see, for example, de Maagd et al. (2001) Trends Genetics 17:193-199). The first conserved structural domain, called Domain I, typically consists of seven alpha helices and is involved in membrane insertion and pore formation. Domain II typically consists of three beta-sheets arranged in a Greek key configuration, and domain III typically consists of two antiparallel beta-sheets in 'jelly-roll' formation (de Maagd et al., 2001, supra). Domains II and III are involved in receptor recognition and binding, and are therefore considered determinants of toxin specificity.

The term "Cry1I" refers to any member of a group of Cry proteins having at least 75% sequence identity to the holotype Cry1I protein (NCBI Accession No. CAA44633) and the term "Cry1Ig" refers to any member of a family of Cry1I proteins having at least 95% sequence identity to the holotype Cry1Ig protein (NCBI Accession No. KC156701) according to Crickmore et al. supra., incorporated herein by reference.

The term "Cry1J" refers to any member of a group of Cry proteins having at least 75% sequence identity to the holotype Cry1J protein (NCBI Accession No. AA22341) and the term "Cry1Ja" refers to any member of a family of Cry proteins having at least 95% sequence identity to the above identified holotype Cry1Ja protein, according to Crickmore et al. supra., incorporated herein by reference. The term "Cry1Jc" refers to any member of a family of Cry proteins having at least 95% sequence identity to the holotype Cry1Jc1 protein (NCBI Accession No. AAC31092).

To "deliver" a composition or toxic protein means that the composition or toxic protein comes in contact with an insect, which facilitates the oral ingestion of the composition or toxic Cry protein, resulting in a toxic effect and control of the insect. The composition or toxic Cry protein can be delivered in many recognized ways, including but not limited to, transgenic plant expression, formulated protein composition(s), sprayable protein composition(s), a bait matrix, or any other art-recognized protein delivery system.

The term "domain" refers to a set of amino acids conserved at specific positions along an alignment of sequences of evolutionarily related proteins. While amino acids at other positions can vary between homologues, amino acids that are highly conserved at specific positions indicate amino acids that are likely essential in the structure, stability or function of a protein. Identified by their high degree of conservation in aligned sequences of a family of protein homologues, they can be used as identifiers to determine if any polypeptide in question belongs to a previously identified polypeptide group.

"Effective insect-controlling amount" means that concentration of a Cry protein that inhibits, through a toxic effect, the ability of insects to survive, grow, feed or reproduce, or limits insect-related damage or loss in crop plants or protects the yield potential of a crop when grown in the presence of insect pests. "Effective insect-controlling amount" may or may not mean an amount that kills the insects, although it preferably means an amount that kills insects.

"Expression cassette" as used herein means a polynucleotide capable of directing expression of at least one polynucleotide of interest, such as a polynucleotide that encodes a Cry protein of the invention, in an appropriate host cell, comprising a promoter operably linked to the polynucleotide of interest which is operably linked to a termination signal. An "expression cassette" also typically comprises additional polynucleotides required for proper translation of the polynucleotide of interest. The expression cassette may also comprise other polynucleotides not necessary in the direct expression of a polynucleotide of interest but which are present due to convenient restriction sites for removal of the cassette from an expression vector. The expression cassette comprising the polynucleotide(s) of interest may be chimeric, meaning that at least one of its components is heterologous with respect to at least one of its other components. The expression cassette may also be one that is naturally occurring but has been obtained in a recombinant form useful for heterologous expression. Typically, however, the expression cassette is heterologous with respect to the host, i.e. the polynucleotide of interest in the expression cassette does not occur naturally in the host cell and must have been introduced into the host cell or an ancestor of the host cell by a transformation process or a breeding process. The expression of the polynucleotide(s) of interest in the expression cassette is generally under the control of a promoter. In the case of a multicellular organism, such as a plant, the promoter can also be specific or preferential to a particular tissue, or organ, or stage of development. An expression cassette, or fragment thereof, can also be referred to as "inserted polynucleotide" or "insertion polynucleotide" when transformed into a plant.

A "gene" is defined herein as a hereditary unit comprising one or more polynucleotides that occupies a specific location on a chromosome or plasmid and that contains the genetic instruction for a particular characteristic or trait in an organism.

A "gut protease" is a protease naturally found in the digestive tract of an insect. The gut protease is typically involved in the digestion of ingested proteins. Examples of insect gut proteases include trypsin, which typically cleaves peptides on the C-terminal side of lysine (K) or arginine (R) residues, and chymotrypsin, which typically cleaves peptides on the C-terminal side of phenylalanine (F), tryptophan (W) or tyrosine (Y).

The term "heterologous" when used in reference to a gene or a polynucleotide or a polypeptide refers to a gene or a polynucleotide or a polypeptide that is or contains a part thereof not in its natural environment (i.e., has been altered by the hand of man). For example, a heterologous gene may include a polynucleotide from one species introduced into another species. A heterologous gene may also include a polynucleotide native to an organism that has been altered in some way (e.g., mutated, added in multiple copies, linked to a non-native promoter or enhancer polynucleotide, etc.). Heterologous genes further may comprise plant gene polynucleotides that comprise cDNA forms of a plant gene; the cDNAs may be expressed in either a sense (to produce mRNA) or anti-sense orientation (to produce an anti-sense RNA transcript that is complementary to the mRNA transcript). In one aspect of the invention, heterologous genes are distinguished from endogenous plant genes in that the heterologous gene polynucleotide are typically joined to polynucleotides comprising regulatory elements such as promoters that are not found naturally associated with the gene for the protein encoded by the heterologous gene or with plant gene polynucleotide in the chromosome, or are associated with portions of the chromosome not found in nature (e.g., genes expressed in loci where the gene is not normally expressed). Further, a "heterologous" polynucleotide refers to a polynucleotide not naturally associated with a host cell into which it is introduced, including non-naturally occurring multiple copies of a naturally occurring polynucleotide.

"Homologous recombination" is the exchange ("crossing over") of DNA fragments between two DNA molecules or chromatids of paired chromosomes in a region of identical polynucleotides. A "recombination event" is herein understood to mean a meiotic crossing-over.

A nucleotide sequence is "isocoding" with a reference nucleotide sequence when the nucleotide sequence encodes a polypeptide having the same amino acid sequence as the polypeptide encoded by the reference nucleotide sequence. For example, SEQ ID NO:17 is isocoding with SEQ ID NO: 14 because they both encode the amino acid sequence represented by SEQ ID NO:1.

The term "isolated" polynucleotide or protein is a polynucleotide or protein that no longer exists in its natural environment. An isolated polynucleotide or protein of the invention may exist in a purified form or may exist in a recombinant host such as in a transgenic bacteria or a transgenic plant. Therefore, it is intended that a claim directed to an "isolated polynucleotide" encompasses that polynucleotide when the polynucleotide is comprised within a plant.

"Operably linked" refers to the association of polynucleotides on a single polynucleotide fragment so that the function of one affects the function of the other. For example, a promoter is operably linked with a coding polynucleotide or functional RNA when it is capable of affecting the expression of that coding polynucleotide or functional RNA (i.e., that the coding polynucleotide or functional RNA is under the transcriptional control of the promoter). Coding polynucleotide in sense or antisense orientation can be operably linked to regulatory polynucleotides.

As used herein "pesticidal," insecticidal," and the like, refer to the ability of a Cry protein of the invention to control a pest organism or an amount of a Cry protein that can control a pest organism as defined herein. Thus, a pesticidal Cry protein can kill or inhibit the ability of a pest organism (e.g., insect pest) to survive, grow, feed, or reproduce.

A "plant" is any plant at any stage of development, particularly a seed plant.

A "plant cell" is a structural and physiological unit of a plant, comprising a protoplast and a cell wall. The plant cell may be in the form of an isolated single cell or a cultured cell, or as a part of a higher organized unit such as, for example, plant tissue, a plant organ, or a whole plant.

"Plant cell culture" means cultures of plant units such as, for example, protoplasts, cell culture cells, cells in plant tissues, pollen, pollen tubes, ovules, embryo sacs, zygotes and embryos at various stages of development.

"Plant material" refers to leaves, stems, roots, flowers or flower parts, fruits, pollen, egg cells, zygotes, seeds, cuttings, cell or tissue cultures, or any other part or product of a plant.

A "plant organ" is a distinct and visibly structured and differentiated part of a plant such as a root, stem, leaf, flower bud, or embryo.

"Plant tissue" as used herein means a group of plant cells organized into a structural and functional unit. Any tissue of a plant in planta or in culture is included. This term includes, but is not limited to, whole plants, plant organs, plant seeds, tissue culture and any groups of plant cells organized into structural or functional units. The use of this term in conjunction with, or in the absence of, any specific type of plant tissue as listed above or otherwise embraced by this definition is not intended to be exclusive of any other type of plant tissue.

A "polynucleotide" refers to a polymer composed of many nucleotide monomers covalently bonded in a chain. Such "polynucleotides" includes DNA, RNA, modified oligo nucleotides (e.g., oligonucleotides comprising bases that are not typical to biological RNA or DNA, such as 2'-O-methylated oligonucleotides), and the like. In some embodiments, a polynucleotide can be single-stranded, double-stranded, multi-stranded, or combinations thereof. Unless otherwise indicated, a particular polynucleotide of the present invention optionally comprises or encodes complementary polynucleotides, in addition to any polynucleotide explicitly indicated.

"Polynucleotide of interest" refers to any polynucleotide which, when transferred to an organism, e.g., a plant, confers upon the organism a desired characteristic such as insect resistance, disease resistance, herbicide tolerance, antibiotic resistance, improved nutritional value, improved performance in an industrial process, production of commercially valuable enzymes or metabolites or altered reproductive capability.

The term "promoter" refers to a polynucleotide, usually upstream (5') of its coding polynucleotide, which controls the expression of the coding polynucleotide by providing the recognition for RNA polymerase and other factors required for proper transcription.

A "protoplast" is an isolated plant cell without a cell wall or with only parts of the cell wall.

As used herein, the term "recombinant" refers to a form of polynucleotide (e.g., DNA or RNA) or protein or an organism that would not normally be found in nature and as such was created by human intervention. As used herein, a "recombinant polynucleotide" is a polynucleotide comprising a combination of polynucleotides that would not naturally occur together and is the result of human intervention, e.g., a polynucleotide that is comprised of a combination of at least two polynucleotides heterologous to each other, or a polynucleotide that is artificially synthesized and comprises a polynucleotide that deviates from the polynucleotide that would normally exist in nature, or a polynucleotide that comprises a transgene artificially incorporated into a host cell's genomic DNA and the associated flanking DNA of the host cell's genome. An example of a recombinant polynucleotide is a DNA molecule resulting from the insertion of a transgene into a plant's genomic DNA, which may ultimately result in the expression of a recombinant RNA or protein molecule in that organism. A "recombinant protein" is a protein encoded by a recombinant polynucleotide that has been cloned in a system that supports expression of the polynucleotide and translation of mRNA. For example, a Cry protein having a native amino acid sequence or a mutated amino acid sequence and expressed in a plant is a recombinant Cry protein. As used herein, a "recombinant plant" is a plant that would not normally exist in nature, is the result of human intervention, and contains a transgene or heterologous polynucleotide incorporated into its genome. As a result of such genomic alteration, the recombinant plant is distinctly different from the related wild-type plant.

"Regulatory elements" refer to sequences involved in controlling the expression of a nucleotide sequence. Regulatory elements comprise a promoter operably linked to the nucleotide sequence of interest and termination signals. They also typically encompass sequences required for proper translation of the nucleotide sequence.

The term "identity" or "identical" or "substantially identical," in the context of two nucleotide or amino acid sequences, refers to two or more sequences or subsequences that have at least 60%, preferably at least 80%, more preferably at least 90%, even more preferably at least 95%, and most preferably at least 99% nucleotide or amino acid residue identity, when compared and aligned for maximum correspondence, as measured using one of the following sequence comparison algorithms or by visual inspection. Preferably, the substantial identity exists over a region of the sequences that is at least about 50 residues or bases in length, more preferably over a region of at least about 100 residues or bases, and most preferably the sequences are substantially identical over at least about 150 residues or bases. In an especially preferred embodiment, the sequences are substantially identical over the entire length of the coding regions. Furthermore, substantially identical nucleotide or amino acid sequences perform substantially the same function.

For sequence comparison, typically one sequence acts as a reference sequence to which test sequences are compared. When using a sequence comparison algorithm, test and reference sequences are input into a computer, subsequence coordinates are designated if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, Adv. Appl. Math. 2: 482 (1981), by the homology alignment algorithm of Needleman & Wunsch, J. Mol. Biol. 48: 443 (1970), by the search for similarity method of Pearson & Lipman, Proc. Nat'l. Acad Sci. USA 85: 2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally, Ausubel et al., infra).

One example of an algorithm that is suitable for determining percent sequence identity and sequence similarity is the BLAST algorithm, which is described in Altschul et al., J. Mol. Biol. 215: 403-410 (1990). Software for performing BLAST analyses is publicly available through the National Center for Biotechnology Information (National Center for Biotechnology Information, U.S. National Library of Medicine, 8600 Rockville Pike, Bethesda, Md. 20894 USA). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., 1990). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always>0) and N (penalty score for mismatching residues; always <0). For amino acid sequences, a scoring matrix is used to calculate the cumulative score. Extension of the word hits in each direction are halted when the cumulative alignment score falls off by the quantity X from its maximum achieved value, the cumulative score goes to zero or below due to the accumulation of one or more negative-scoring residue alignments, or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff, Proc. Natl. Acad Sci. USA 89: 10915 (1989)).

In addition to calculating percent sequence identity, the BLAST algorithm also performs a statistical analysis of the similarity between two sequences (see, e.g., Karlin & Altschul, Proc. Nat'l. Acad. Sci. USA 90: 5873-5787 (1993)). One measure of similarity provided by the BLAST algorithm is the smallest sum probability (P(N)), which provides an indication of the probability by which a match between two nucleotide or amino acid sequences would occur by chance. For example, a test nucleotide sequence is considered similar to a reference sequence if the smallest sum probability in a comparison of the test nucleotide sequence to the reference nucleotide sequence is less than about 0.1, more preferably less than about 0.01, and most preferably less than about 0.001.

Another indication that two nucleotide sequences are substantially identical is that the two molecules hybridize to each other under stringent conditions. The phrase "hybridizing specifically to" refers to the binding, duplexing, or hybridizing of a molecule only to a particular nucleotide sequence under stringent conditions when that sequence is present in a complex mixture (e.g., total cellular) DNA or RNA. "Bind(s) substantially" refers to complementary hybridization between a probe nucleotide and a target nucleotide and embraces minor mismatches that can be accommodated by reducing the stringency of the hybridization media to achieve the desired detection of the target nucleotide sequence.

"Stringent hybridization conditions" and "stringent hybridization wash conditions" in the context of polynucleotide hybridization experiments such as Southern and Northern hybridizations are sequence dependent, and are different under different environmental parameters. Longer sequences hybridize specifically at higher temperatures. An extensive guide to the hybridization of nucleotides is found in Tijssen (1993) Laboratory Techniques in Biochemistry and Molecular Biology-Hybridization with Nucleic Acid Probes part I chapter 2 "Overview of principles of hybridization and the strategy of nucleic acid probe assays" Elsevier, New York. Generally, highly stringent hybridization and wash conditions are selected to be about 5° C. lower than the thermal melting point ($T_m$) for the specific sequence at a defined ionic strength and pH. Typically, under "stringent conditions" a probe will hybridize to its target subsequence, but not to other sequences.

The $T_m$ is the temperature (under defined ionic strength and pH) at which 50% of the target sequence hybridizes to a perfectly matched probe. Very stringent conditions are selected to be equal to the $T_m$ for a particular probe. An example of stringent hybridization conditions for hybridization of complementary polynucleotides which have more than 100 complementary residues on a filter in a Southern or northern blot is 50% formamide with 1 mg of heparin at 42° C., with the hybridization being carried out overnight. An example of highly stringent wash conditions is 0.15M NaCl at 72° C. for about 15 minutes. An example of stringent wash conditions is a 0.2×SSC wash at 65° C. for 15 minutes (see, Sambrook, infra, for a description of SSC buffer). Often, a high stringency wash is preceded by a low stringency wash to remove background probe signal. An example medium stringency wash for a duplex of, e.g., more than 100 nucleotides, is 1×SSC at 45° C. for 15 minutes. An example low stringency wash for a duplex of, e.g., more than 100 nucleotides, is 4-6×SSC at 40° C. for 15 minutes. For short probes (e.g., about 10 to 50 nucleotides), stringent conditions typically involve salt concentrations of less than about 1.0 M Na ion, typically about 0.01 to 1.0 M Na ion concentration (or other salts) at pH 7.0 to 8.3, and the temperature is typically at least about 30° C. Stringent conditions can also be achieved with the addition of destabilizing agents such as formamide. In general, a signal to noise ratio of 2× (or higher) than that observed for an unrelated probe in the particular hybridization assay indicates detection of a specific hybridization. Polynucleotides that do not hybridize to each other under stringent conditions are still substantially identical if the proteins that they encode are substantially identical. This occurs, e.g., when a copy of a polynucleotide is created using the maximum codon degeneracy permitted by the genetic code.

The following are examples of sets of hybridization/wash conditions that may be used to clone homologous nucleotide sequences that are substantially identical to reference nucleotide sequences of the present invention: a reference nucleotide sequence preferably hybridizes to the reference nucleotide sequence in 7% sodium dodecyl sulfate (SDS), 0.5 M $NaPO_4$, 1 mM EDTA at 50° C. with washing in 2×SSC, 0.1% SDS at 50° C., more desirably in 7% sodium dodecyl sulfate (SDS), 0.5 M $NaPO_4$, 1 mM EDTA at 50° C. with washing in 1×SSC, 0.1% SDS at 50° C., more desirably still in 7% sodium dodecyl sulfate (SDS), 0.5 M $NaPO_4$, 1 mM EDTA at 50° C. with washing in 0.5×SSC, 0.1% SDS at 50° C., preferably in 7% sodium dodecyl sulfate (SDS), 0.5 M $NaPO_4$, 1 mM EDTA at 50° C. with washing in 0.1×SSC, 0.1% SDS at 50° C., more preferably in 7% sodium dodecyl sulfate (SDS), 0.5 M $NaPO_4$, 1 mM EDTA at 50° C. with washing in 0.1×SSC, 0.1% SDS at 65° C.

A further indication that two proteins are substantially identical is that an antibody raised against a protein encoded by a first polynucleotide is immunologically cross reactive with, or specifically binds to, a protein encoded by a second polynucleotide. Thus, a protein is typically substantially identical to a second protein, for example, where the two proteins differ only by conservative substitutions.

"Synthetic" refers to a nucleotide sequence comprising bases or structural features that are not present in the natural sequence. For example, an artificial sequence encoding a Cry protein of the invention that resembles more closely the G+C content and the normal codon distribution of dicot or monocot plant genes is said to be synthetic.

As used herein, "toxic" is synonymous with "insecticidal" and is meant that a Cry protein of the invention has a negative effect on an insect pest by killing the insect pest, or by disrupting or deterring feeding of the insect pest, or causing growth inhibition to the insect pest, both of which may or may not cause death of the insect. When a Cry protein of the invention is delivered to an insect or an insect comes into oral contact with the Cry protein, the toxic effect is typically death of the insect, or the insect's growth is slowed, or the insect stops feeding upon the source that makes the toxic Cry protein available to the insect.

"Transformation" is a process for introducing a heterologous polynucleotide into a host cell or organism. In particular, "transformation" means the stable integration of a DNA molecule into the genome of an organism of interest.

"Transformed/transgenic/recombinant" refer to a host organism such as a bacterium or a plant into which a heterologous polynucleotide has been introduced. The polynucleotide can be stably integrated into the genome of the host or the polynucleotide can also be present as an extra-chromosomal molecule. Such an extrachromosomal molecule can be auto-replicating. Transformed cells, tissues, or plants are understood to encompass not only the end product of a transformation process, but also transgenic progeny thereof. A "non-transformed", "non-transgenic", or "non-recombinant" host refers to a wild-type organism, e.g., a bacterium or plant, which does not contain the heterologous polynucleotide.

Nucleotides are indicated herein by their bases by the following standard abbreviations: adenine (A), cytosine (C), thymine (T), and guanine (G). Amino acids are likewise indicated by the following standard abbreviations: alanine (Ala; A), arginine (Arg; R), asparagine (Asn; N), aspartic acid (Asp; D), cysteine (Cys; C), glutamine (Gln; Q), glutamic acid (Glu; E), glycine (Gly; G), histidine (His; H), isoleucine (Ile; 1), leucine (Leu; L), lysine (Lys; K), methionine (Met; M), phenylalanine (Phe; F), proline (Pro; P), serine (Ser; S), threonine (Thr; T), tryptophan (Trp; W), tyrosine (Tyr; Y), and valine (Val; V).

This invention provides compositions and methods for controlling harmful pests of crop plants and commodities derived from crop plants. Particularly, the invention relates to Cry proteins that may be isolated from bacteria, such as *Bacillus thuringiensis*, that are toxic to insect pests and to polynucleotides that comprise nucleotide sequences that encode the Cry proteins, and to the making and using of the polynucleotides and Cry proteins to control insect pests.

Polynucleotides that are fragments of Cry protein protoxin-encoding polynucleotides are also encompassed by the invention. By "fragment" is intended a portion of the nucleotide sequence encoding a Cry protein. A fragment of a nucleotide sequence may encode a biologically active portion of a Cry protein, the so called "toxin fragment," or it may be a fragment that can be used as a hybridization probe or PCR primer using methods disclosed below. Polynucleotides that are fragments of a Cry protein encoding nucleotide sequence comprise at least about 15, 20, 50, 75, 100, 200, 300, 350, 400, 450, 500, 550, 600, 650, 700, 750, 800, 850, 900, 950, 1000, 1050, 1100, 1150, 1200, 1250, 1300, 1350, 1400, 1450 contiguous nucleotides, or up to the number of nucleotides present in a full-length Cry protein encoding nucleotide sequence disclosed herein (for example, 3504 nucleotides for SEQ ID NO:14) depending upon the intended use. By "contiguous" nucleotides is intended nucleotide residues that are immediately adjacent to one another. Some fragments of the nucleotide sequences of the invention will encode toxin fragments that retain the biological activity of the Cry protein and, hence, retain insecticidal activity. By "retains insecticidal activity" is intended that the fragment will have at least about 30%, preferably at least about 50%, more preferably at least about 70%, even more preferably at least about 80% of the insecticidal activity of the Cry protein. Methods for measuring insecticidal activity are well known in the art. See, for example, Czapla and Lang (1990) J. Econ. Entomol. 83:2480-2485; Andrews et al. (1988) Biochem. J. 252:199-206; Marrone et al. (1985) J. of Economic Entomology 78:290-293; and U.S. Pat. No. 5,743,477, all of which are herein incorporated by reference in their entirety.

A toxin fragment of a Cry protein of the invention will encode at least about 15, 25, 30, 50, 75, 100, 125, 150, 175, 200, 250, 300, 350, 400, and 450 contiguous amino acids, or up to the total number of amino acids present in a full-length Cry protein of the invention (for example, 1167 amino acids for SEQ ID NO:1). Thus, in some embodiments, Cry proteins which have been activated by means of proteolytic processing, for example, by proteases prepared from the gut of an insect, may be characterized and the N-terminal or C-terminal amino acids of the activated toxin fragment identified. In this aspect of the invention, the skilled person can determine that, for example, a toxin fragment of SEQ ID NO:1 may comprise amino acids from about position 28, 30, 36, 41, 43, 44, 45, 47 or 48 to about position 610, 615, 616, 622, 623, 624 or 625 of SEQ ID NO:1, or a toxin fragment of SEQ ID NO:2 may comprise amino acids from about position 21, 23, 28, 35, 38, 46 or 61 to about position 607, 611, 618, 625 or 628 of SEQ ID NO:2, or a toxin fragment of SEQ ID NO:3 may comprise amino acids from about position 23, 24, 28, 30, 32, 33, 35, 36, 37 or 40 to about position 611, 616, 617, 625, 626, 647, 653 or 654 of SEQ ID NO:3. Cry protein variants produced by introduction or elimination of protease processing sites at appropriate positions in the coding sequence to allow, or eliminate, proteolytic cleavage of a larger variant protein by insect, plant or microorganism proteases are also within the scope of the invention. The end result of such manipulation is understood to be the generation of toxin fragment molecules having the same or different activity as the intact protoxin Cry protein.

According to some embodiments, the invention provides a polynucleotide or optionally an isolated polynucleotide comprising a nucleotide sequence encoding a Cry protein in its protoxin form or a toxin fragment thereof that is toxic to a lepidopteran pest, wherein the nucleotide sequence (a) has at least 80% to at least 99% sequence identity with any of SEQ ID NOs:14-16 or a toxin-encoding fragment of any of SEQ ID NOs:14-16; or (b) encodes a protein comprising an amino acid sequence that has at least 80% to at least 99% sequence identity with any of SEQ ID NOs:1-3 or a toxin fragment of any of SEQ ID NOs:1-3; or (c) is a synthetic sequence of (a) or (b) that has codons optimized for expression in a transgenic organism.

In other embodiments, the lepidopteran pest is selected from the group consisting of European corn borer (*Ostrinia nubilalis*), fall armyworm (*Spodoptera frugiperda*), corn earworm (*Helicoverpa zea*), sugarcane borer (*Diatraea saccharalis*), velvetbean caterpillar (*Anticarsia gemmatalis*), soybean looper (*Chrysodeixis includes*), southwest corn borer (*Diatraea grandiosella*), western bean cutworm (*Richia albicosta*), tobacco budworm (*Heliothis virescens*), Asian corn borer (*Ostrinia furnacalis*), cotton bollworm (*Helicoverpa armigera*), striped stem borer (*Chilo suppressalis*), pink stem borer (*Sesamia calamistis*) and rice leaffolder (*Cnaphalocrocis medinalis*).

In still other embodiments, the nucleotide sequence or the synthetic nucleotide sequence comprises any of SEQ ID NOs:14-29 or a toxin-encoding fragment of any of SEQ ID NOs:14-29. In other embodiments, the synthetic nucleotide sequence comprises any of SEQ ID NOs:17-22 or a toxin-encoding fragment of any of SEQ ID NOs:17-22.

In some embodiments, a polynucleotide of the invention comprises, consists essentially of or consists of a nucleotide sequence encoding a Cry protein comprising an amino acid sequence that has at least 80% to at least 99% sequence identity with any of SEQ ID NOs:1-3 or a toxin fragment of any of SEQ ID NOs:1-3. In some other embodiments, the amino acid sequence comprises, consists essentially of or consists of any of SEQ ID NOs:1-13 or a toxin fragment of any of SEQ ID NOs:1-13.

In some embodiments, the polynucleotide of the invention encodes a Cry protein that is a Cry1I or a Cry1J protein. In other embodiments the Cry1I protein is a Cry1Ig protein. In still other embodiments, the Cry1Ig protein comprises SEQ ID NO:2, SEQ ID NO:5, or a toxin fragment of SEQ ID NO:2 or SEQ ID NO:5. In other embodiments, the Cry1Ig protein is toxic to a lepidopteran pest selected from the group consisting of European corn borer (*Ostrinia nubilalis*), sugarcane borer (*Diatraea saccharalis*), soybean looper (*Chrysodeixis includes*) and southwest corn borer (*Diatraea grandiosella*). In still other embodiments, the synthetic sequence comprises, consists essentially of or consists of SEQ ID NO:18, or a toxin-encoding fragment thereof.

In some embodiments, the polynucleotide of the invention encodes a Cry1J protein that is a Cry1Ja or a Cry1Jc protein. In other embodiments, the Cry1Ja protein comprises, consists essentially of or consists of an amino acid sequence selected from the group consisting of SEQ ID NO:1, SEQ ID NO:4, SEQ ID NOs:7-13 and a toxin fragment of SEQ ID NO:1, SEQ ID NO:4 or any of SEQ ID NOs:7-13. In other embodiments, the Cry1Ja protein is toxic to a lepidopteran pest selected from the group consisting of European corn borer (*Ostrinia nubilalis*), fall armyworm (*Spodoptera frugiperda*), corn earworm (*Helicoverpa zea*), sugarcane borer (*Diatraea saccharalis*), velvetbean caterpillar (*Anticarsia gemmatalis*), soybean looper (*Chrysodeixis includes*), southwest corn borer (*Diatraea grandiosella*) and tobacco budworm (*Heliothis virescens*). In still other embodiments, the synthetic sequence comprises SEQ ID NO:17 or a toxin-encoding fragment thereof.

In other embodiments, the Cry1Jc protein comprises, consists essentially of or consists of SEQ ID NO:3, SEQ ID NO:6, or a toxin fragment of SEQ ID NO:3 or SEQ ID NO:6. In still other embodiments, the Cry1Jc protein is toxic to a lepidopteran pest selected from the group consisting of European corn borer (*Ostrinia nubilalis*), corn earworm (*Helicoverpa zea*), sugarcane borer (*Diatraea saccharalis*), velvetbean caterpillar (*Anticarsia gemmatalis*), soybean looper (*Chrysodeixis includes*), southwest corn borer (*Diatraea grandiosella*) and tobacco budworm (*Heliothis virescens*). In other embodiments, the synthetic sequence comprises, consists essentially of or consists of SEQ ID NO:19 or a toxin-encoding fragment thereof.

In some embodiments of the invention, a chimeric gene is provided that comprises a heterologous promoter operably linked to a polynucleotide comprising, consisting essentially of or consisting of a nucleotide sequence that encodes a Cry protein toxic to a lepidopteran pest, wherein the nucleotide sequence (a) has at least 80% (e.g., 80%, 81%, 82%, 83%, 84%, 85%, 86%, 87%, 88%, 89%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9%) to at least 99% (99%, 99.1%, 99.2%, 99.3%, 99.4%, 99.5%, 99.6%, 99.7%, 99.8%, 99.9%) sequence identity with any one of SEQ ID NOs:14-16, or a toxin-encoding fragment of any of SEQ ID NOs:14-16; or (b) encodes a protein comprising an amino acid sequence that has at least 80% (e.g., 80%, 81%, 82%, 83%, 84%, 85%, 86%, 87%, 88%, 89%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9%) to at least 99% (99%, 99.1%, 99.2%, 99.3%, 99.4%, 99.5%, 99.6%, 99.7%, 99.8%, 99.9%) sequence identity with any one of SEQ ID NOs:1-3, or a toxin fragment of any of SEQ ID NOs:1-3; or (c) is a synthetic sequence of (a) or (b) that has codons optimized for expression in a transgenic organism.

In other embodiments, the heterologous promoter in the chimeric gene of the invention is operable in multiple bacterial species. In other embodiments, the bacterial species is *Bacillus thuringiensis* or *Escherichia coli*. In still other embodiments, the heterologous promoter is a Cry1Ac promoter or variant thereof. In further embodiments, the Cry1Ac promoter comprises, consists essentially of or consists of nucleotides 12-197 of SEQ ID NO:30 or a fragment thereof. In still other embodiments, the heterologous promoter is a Cry1Ac promoter and the polynucleotide comprises, consists essentially of or consists of any of SEQ ID NOs:1-3 or a toxin fragment of any of SEQ ID NOs:1-3.

In other embodiments, the heterologous promoter in the chimeric gene of the invention is a plant-expressible promoter. For example, without limitation, the plant-expressible promoter can be selected from the group of promoters consisting of ubiquitin, cestrum yellow virus, corn TrpA, OsMADS 6, maize H3 histone, bacteriophage T3 gene 9 5' UTR, corn sucrose synthetase 1, corn alcohol dehydrogenase 1, corn light harvesting complex, corn heat shock protein, maize mtl, pea small subunit RuBP carboxylase, rice actin, rice cyclophilin, Ti plasmid mannopine synthase, Ti plasmid nopaline synthase, *petunia* chalcone isomerase, bean glycine rich protein 1, potato patatin, lectin, CaMV 35S and S-E9 small subunit RuBP carboxylase promoter.

In additional embodiments, the protein encoded by the chimeric gene is toxic to one or more lepidopteran pests selected from the group consisting of European corn borer (ECB; *Ostrinia nubilalis*), black cutworm (BCW; *Agrotis ipsilon*), fall armyworm (FAW; *Spodoptera frugiperda*), corn earworm (CEW; *Helicoverpa zea*), sugarcane borer (SCB; *Diatraea saccharalis*), velvetbean caterpillar (VBC; *Anticarsia gemmatalis*), soybean looper (SBL; *Chrysodeixis includes*), southwest corn borer (SWCB; *Diatraea grandiosella*), western bean cutworm (WBC; *Richia albicosta*), tobacco budworm (TBW; *Heliothis virescens*), Asian corn borer (ACB; *Ostrinia furnacalis*), cotton bollworm (CBW; *Helicoverpa armigera*), striped stem borer (SSB; *Chilo suppressalis*), pink stem borer (PSB; *Sesamia calamistis*) and rice leaffolder (RLF; *Cnaphalocrocis medinalis*).

In further embodiments, the chimeric gene comprises a polynucleotide that comprises, consists essentially of or consists of a nucleotide sequence that has at least 99%, or at least 99.1%, or at least 99.2%, or at least 99.3%, or at least 99.4%, or at least 99.5% or at least 99.6%, or at least 99.7%, or at least 99.8%, or at least 99.9% sequence identity with SEQ ID NO:14, or a toxin-encoding fragment thereof, or has at least 96%, or at least 97%, or at least 98%, or at least 99%, or at least 99.1%, or at least 99.2%, or at least 99.3%, or at least 99.4%, or at least 99.5% or at least 99.6%, or at least 99.7%, or at least 99.8%, or at least 99.9% sequence identity with SEQ ID NO:15, or a toxin-encoding fragment thereof, or has at least 99.1%, or at least 99.2%, or at least 99.3%, or at least 99.4%, or at least 99.5% or at least 99.6%, or at least 99.7%, or at least 99.8%, or at least 99.9% sequence identity with SEQ ID NO:16, or a toxin-encoding fragment thereof.

In other embodiments, the polynucleotide comprises, consists essentially of or consists of any of SEQ ID NOs:14-29, or a toxin-encoding fragment of any of SEQ ID NOs:14-29.

In still other embodiments, the polynucleotide comprises, consists essentially of or consists of a nucleotide sequence that encodes a protein comprising, consisting essentially of or consisting of an amino acid sequence that has at least 80% to at least 99% sequence identity with any one of SEQ ID NOs:1-3, or a toxin fragment of any of SEQ ID NOs:1-3.

In still other embodiments, the amino acid sequence has at least 99%, or at least 99.1%, or at least 99.2%, or at least 99.3%, or at least 99.4%, or at least 99.5% or at least 99.6%, or at least 99.7%, or at least 99.8%, or at least 99.9% sequence identity with SEQ ID NO:1, or a toxin fragment thereof.

In further embodiments, the amino acid sequence has at least 96%, or at least 97%, or at least 98%, or at least 99%, or at least 99.1%, or at least 99.2%, or at least 99.3%, or at least 99.4%, or at least 99.5% or at least 99.6%, or at least 99.7%, or at least 99.8%, or at least 99.9% sequence identity with SEQ ID NO:2, or a toxin fragment thereof.

In still further embodiments, the amino acid sequence has at least 99.1%, or at least 99.2%, or at least 99.3%, or at least 99.4%, or at least 99.5% or at least 99.6%, or at least 99.7%, or at least 99.8%, or at least 99.9% sequence identity with SEQ ID NO:3, or a toxin fragment thereof.

In other embodiments, the amino acid sequence comprises, consists essentially of or consists of any of SEQ ID NOs:1-13, or a toxin fragment of any of SEQ ID NOs:1-13.

In some embodiments, the chimeric gene of the invention comprises a polynucleotide comprising a synthetic nucleotide sequence that has at least 80%, or at least 81%, or at least 82%, or at least 83%, or at least 84%, or at least 85%, or at least 86%, or at least 87%, or at least 88%, or at least 89%, or at least 90%, or at least 91%, or at least 92%, or at least 93%, or at least 94%, or at least 95%, or at least 96%, or at least 97%, or at least 98%, or at least 99%, or at least 99.1%, or at least 99.2%, or at least 99.3%, or at least 99.4%, or at least 99.5% or at least 99.6%, or at least 99.7%, or at least 99.8%, or at least 99.9% sequence identity over the entire length of any of SEQ ID NOs:14-22, wherein the synthetic sequence has codons optimized for expression is a transgenic organism. In other embodiments, the chimeric gene of the invention comprises a polynucleotide comprising a synthetic sequence of a nucleotide sequence that encodes a protein comprising an amino acid sequence that has at least 80%, or at least 81%, or at least 82%, or at least 83%, or at least 84%, or at least 85%, or at least 86%, or at least 87%, or at least 88%, or at least 89%, or at least 90%, or at least 91%, or at least 92%, or at least 93%, or at least 94%, or at least 95%, or at least 96%, or at least 97%, or at least 98%, or at least 99%, or at least 99.1%, or at least 99.2%, or at least 99.3%, or at least 99.4%, or at least 99.5% or at least 99.6%, or at least 99.7%, or at least 99.8%, or at least 99.9% sequence identity over the entire length of any of SEQ ID NOs:1-13, or a toxin fragment of any of SEQ ID NOs:1-13, wherein the synthetic sequence has codons optimized for expression is a transgenic organism. In other embodiments, the protein comprises, consists essentially of or consists of any of SEQ ID NOs:1-13, or a toxin fragment of any of SEQ ID NOs:1-13. In further embodiments, the transgenic organism is a transgenic bacteria or a transgenic plant. In still other embodiments, the transgenic bacteria is *Escherichia coli* or *Bacillus thuringiensis*. In other embodiments, the transgenic plant is *Zea mays*.

In some embodiments, the chimeric gene of the invention comprises a polynucleotide that encodes a Cry1I or a Cry1J protein. In other embodiments, the Cry1I protein is a Cry1Ig protein. In other embodiments, the Cry1Ig protein comprises SEQ ID NO:2, SEQ ID NO:5, or a toxin fragment of SEQ ID NO:2 or SEQ ID NO:5. In still other embodiments, the Cry1Ig is toxic to European corn borer (*Ostrinia nubilalis*), sugarcane borer (*Diatraea saccharalis*), soybean looper (*Chrysodeixis includes*) and southwest corn borer (*Diatraea grandiosella*). In other embodiments, the Cry1Ig protein is encoded by a synthetic polynucleotide comprising, consisting essentially of or consisting of SEQ ID NO:18 or a toxin-encoding fragment thereof.

In some embodiments, the chimeric gene encodes a Cry1J protein that is a Cry1Ja or a Cry1Jc protein. In other embodiments, the Cry1Ja protein comprises an amino acid sequence selected from the group consisting of SEQ ID NO:1, SEQ ID NO:4, SEQ ID NOs:7-13 and a toxin fragment of SEQ ID NO:1, SEQ ID NO:4 or any of SEQ ID NOs:7-13. In other embodiments, the Cry1Ja protein is toxic to European corn borer (*Ostrinia nubilalis*), fall armyworm (*Spodoptera frugiperda*), corn earworm (*Helicoverpa zea*), sugarcane borer (*Diatraea saccharalis*), velvetbean caterpillar (*Anticarsia gemmatalis*), soybean looper (*Chrysodeixis includes*), southwest corn borer (*Diatraea grandiosella*) and tobacco budworm (*Heliothis virescens*). In other embodiments, the Cry1Ja protein is encoded by a synthetic polynucleotide comprising, consisting essentially of or consisting of SEQ ID NO:17 or a toxin-encoding fragment thereof.

In some embodiments, the chimeric gene encodes a Cry1J protein that is a Cry1Jc protein. In other embodiments, the Cry1Jc protein comprises SEQ ID NO:3, SEQ ID NO:6, or a toxin fragment of SEQ ID NO:3 or SEQ ID NO:6. In still other embodiments, the Cry1Jc protein is toxic to European corn borer (*Ostrinia nubilalis*), corn earworm (*Helicoverpa zea*), sugarcane borer (*Diatraea saccharalis*), velvetbean caterpillar (*Anticarsia gemmatalis*), soybean looper (*Chrysodeixis includes*), southwest corn borer (*Diatraea grandiosella*) and tobacco budworm (*Heliothis virescens*). In other embodiments, the Cry1Jc protein is encoded by a synthetic polynucleotide comprising, consisting essentially of or consisting of SEQ ID NO:19 or a toxin-encoding fragment thereof.

In some embodiments, the invention provides a synthetic polynucleotide comprising, consisting essentially of or consisting of a nucleotide sequence that encodes a protein that is toxic to a lepidopteran pest, wherein the nucleotide sequence has at least 80%, or at least 81%, or at least 82%, or at least 83%, or at least 84%, or at least 85%, or at least 86%, or at least 87%, or at least 88%, or at least 89%, or at least 90%, or at least 91%, or at least 92%, or at least 93%, or at least 94%, or at least 95%, or at least 96%, or at least 97%, or at least 98%, or at least 99%, or at least 99.1%, or at least 99.2%, or at least 99.3%, or at least 99.4%, or at least 99.5% or at least 99.6%, or at least 99.7%, or at least 99.8%, or at least 99.9% sequence identity with any of SEQ ID NOs:14-22, or a toxin-encoding fragment of any of SEQ ID NOs:14-22.

In other embodiments, the invention provides a synthetic polynucleotide comprising, consisting essentially of or consisting of a nucleotide sequence that encodes a protein that is toxic to a lepidopteran pest, wherein the nucleotide sequence encodes an amino acid sequence that has at least 80%, or at least 81%, or at least 82%, or at least 83%, or at least 84%, or at least 85%, or at least 86%, or at least 87%, or at least 88%, or at least 89%, or at least 90%, or at least 91%, or at least 92%, or at least 93%, or at least 94%, or at least 95%, or at least 96%, or at least 97%, or at least 98%, or at least 99%, or at least 99.1%, or at least 99.2%, or at least 99.3%, or at least 99.4%, or at least 99.5% or at least 99.6%, or at least 99.7%, or at least 99.8%, or at least 99.9% sequence identity over the entire length of any one of SEQ ID NOs:1-13, or a toxin fragment of any of SEQ ID NOs:1-13. In other embodiments, the synthetic polynucleotide encodes a protein comprising, consisting essentially of or consisting of any of SEQ ID NOs:1-13, or a toxin fragment of any of SEQ ID NOs:1-13.

Cry proteins of the invention may be isolated from certain *Bacillus thuringiensis* (Bt) strains such as SC0532, SC0705 and SC0666 described herein. It will be recognized that Cry proteins of the invention may also be isolated from other Bt strains and that such Bt strains can be isolated by standard techniques and tested for the presence of the Cry proteins of the invention or for toxicity to a lepidopteran pest of the invention. Generally Bt strains can be isolated from any environmental sample, including soil, plant, insect, grain elevator dust, and other sample material by methods known in the art. See, for example, Travers et al. (1987) Appl. Environ. Microbiol. 53:1263-1266; Saleh et al. (1969) Can J. Microbiol. 15:1101-1104; DeLucca et al. (1981) Can J. Microbiol. 27:865-870; and Norris, et al. (1981) "The genera *Bacillus* and *Sporolactobacillus*," In Starr et al. (eds.), The Prokaryotes: A Handbook on Habitats, Isolation, and Identification of Bacteria, Vol. II, Springer-Verlog Berlin Heidelberg; all incorporated herein by reference. After isolation, Bt strains can be tested for toxicity to a lepidopteran pest and one or more Cry proteins encompassed by the invention can be identified using, for example, the nucleotide or amino acid sequences disclosed herein, and molecular techniques standard in the art. Therefore, in some embodiments, the invention encompasses a *Bacillus thuringiensis* (Bt) strain that produces a Cry protein or a recombinant Cry protein comprising, consisting essentially of or consisting of an amino acid sequence having at least 80% to at least 99% sequence identity to any of SEQ ID NOs: 1-13, or a toxin fragment of any of SEQ ID NOs:1-13. In other embodiments, the Bt strain is selected from the group consisting of SC0532, SC0705 and SC0666. In still further embodiments, the Cry protein or recombinant Cry protein comprises, consists essentially of or consists of any of SEQ ID NOs:1-13, or a toxin fragment of any of SEQ ID NOs:1-13.

According to some embodiments, the invention provides a Cry protein or an optionally isolated Cry protein or a recombinant Cry protein that is toxic to a lepidopteran pest, wherein the Cry protein, optionally isolated Cry protein or recombinant Cry protein comprises, consists essentially of or consists of (a) an amino acid sequence that has at least 80% sequence identity to at least 99% sequence identity with any one of SEQ ID NOs:1-6, or a toxin fragment of any of SEQ ID NOs:1-6; or (b) an amino acid sequence that is encoded by a nucleotide sequence that has at least 80% sequence identity to at least 99% sequence identity with a nucleotide sequence represented by any one of SEQ ID NOs:14-19, or a toxin-encoding fragment of any of SEQ ID NOs:14-19.

In other embodiments, the Cry protein or optionally isolated Cry protein or recombinant Cry protein comprises, consists essentially of or consists of an amino acid sequence that has at least 80% to at least 99% sequence identity with any one of SEQ ID NOs:1-6., or a toxin fragment of any of SEQ ID NOs:1-6. In still other embodiments, the amino acid sequence has at least 98%, or at least 99%, or at least 99.1%, or at least 99.2%, or at least 99.3%, or at least 99.4%, or at least 99.5% or at least 99.6%, or at least 99.7%, or at least 99.8%, or at least 99.9% sequence identity with SEQ ID NO:1, or a toxin fragment thereof.

In further embodiments, the amino acid sequence has at least 96%, or at least 97%, or at least 98%, or at least 99%, or at least 99.1%, or at least 99.2%, or at least 99.3%, or at least 99.4%, or at least 99.5% or at least 99.6%, or at least 99.7%, or at least 99.8%, or at least 99.9% sequence identity with SEQ ID NO:2, or a toxin fragment thereof.

In still further embodiments, the amino acid sequence has at least 99.1%, or at least 99.2%, or at least 99.3%, or at least 99.4%, or at least 99.5% or at least 99.6%, or at least 99.7%, or at least 99.8%, or at least 99.9% sequence identity with SEQ ID NO:3, or a toxin fragment thereof.

In some embodiments, the amino acid sequence comprises, consists essentially of or consists of any one of SEQ ID NOs:1-13, or a toxin fragment thereof. In other embodiments, the amino acid sequence is encoded by a nucleotide sequence comprising, consisting essentially of or consisting of any of SEQ ID NOs:14-29, or a toxin-encoding fragment of any of SEQ ID NOs: 14-29.

In other embodiments, the Cry protein or optionally isolated Cry protein or recombinant Cry protein of the invention is toxic to a lepidopteran pest selected from the group consisting of European corn borer (*Ostrinia nubilalis*), black cutworm (*Agrotis ipsilon*), fall armyworm (*Spodoptera frugiperda*), corn earworm (*Helicoverpa zea*), sugarcane borer (*Diatraea saccharalis*), velvetbean caterpillar (*Anticarsia gemmatalis*), soybean looper (*Chrysodeixis includes*), southwest corn borer (*Diatraea grandiosella*), western bean cutworm (*Richia albicosta*), tobacco budworm (*Heliothis virescens*), Asian corn borer (*Ostrinia furnacalis*), cotton bollworm (*Helicoverpa armigera*), striped stem borer (*Chilo suppressalis*), pink stem borer (*Sesamia calamistis*) and rice leaffolder (*Cnaphalocrocis medinalis*).

In other embodiments, the Cry protein, the optionally isolated Cry protein or recombinant Cry protein comprises, consists essentially of or consists of an amino acid sequence that has at least 80% to at least 99% sequence identity with any one of SEQ ID NOs:1-13, or a toxin fragment of any of SEQ ID NOs;1-13.

In still other embodiments, the amino acid sequence of the Cry protein, optionally isolated Cry protein or recombinant Cry protein has at least 80%, or at least 81%, or at least 82%, or at least 83%, or at least 84%, or at least 85%, or at least 86%, or at least 87%, or at least 88%, or at least 89%, or at least 90%, or at least 91%, or at least 92%, or at least 93%, or at least 94%, or at least 95%, or at least 96%, or at least 97%, or at least 98%, or at least 99%, or at least 99.1%, or at least 99.2%, or at least 99.3%, or at least 99.4%, or at least 99.5% or at least 99.6%, or at least 99.7%, or at least 99.8%, or at least 99.9% sequence identity with SEQ ID NO:1, or a toxin fragment thereof.

In still other embodiments, the amino acid sequence of the Cry protein, optionally isolated Cry protein or recombinant Cry protein has at least 80%, or at least 81%, or at least 82%, or at least 83%, or at least 84%, or at least 85%, or at least 86%, or at least 87%, or at least 88%, or at least 89%, or at least 90%, or at least 91%, or at least 92%, or at least 93%, or at least 94%, or at least 95%, or at least 96%, or at least 97%, or at least 98%, or at least 99%, or at least 99.1%, or at least 99.2%, or at least 99.3%, or at least 99.4%, or at least 99.5% or at least 99.6%, or at least 99.7%, or at least 99.8%, or at least 99.9% sequence identity with SEQ ID NO:2, or a toxin fragment thereof.

In still other embodiments, the amino acid sequence of the Cry protein, optionally isolated Cry protein or recombinant Cry protein has at least 80%, or at least 81%, or at least 82%, or at least 83%, or at least 84%, or at least 85%, or at least 86%, or at least 87%, or at least 88%, or at least 89%, or at least 90%, or at least 91%, or at least 92%, or at least 93%, or at least 94%, or at least 95%, or at least 96%, or at least 97%, or at least 98%, or at least 99%, or at least 99.1%, or at least 99.2%, or at least 99.3%, or at least 99.4%, or at least 99.5% or at least 99.6%, or at least 99.7%, or at least 99.8%, or at least 99.9% sequence identity with SEQ ID NO:3, or a toxin fragment thereof.

In still other embodiments, the amino acid sequence of the Cry protein, optionally isolated Cry protein or recombinant Cry protein has at least 80%, or at least 81%, or at least 82%, or at least 83%, or at least 84%, or at least 85%, or at least 86%, or at least 87%, or at least 88%, or at least 89%, or at least 90%, or at least 91%, or at least 92%, or at least 93%, or at least 94%, or at least 95%, or at least 96%, or at least 97%, or at least 98%, or at least 99%, or at least 99.1%, or at least 99.2%, or at least 99.3%, or at least 99.4%, or at least 99.5% or at least 99.6%, or at least 99.7%, or at least 99.8%, or at least 99.9% sequence identity with SEQ ID NO:4, or a toxin fragment thereof.

In still other embodiments, the amino acid sequence of the Cry protein, optionally isolated Cry protein or recombinant Cry protein has at least 80%, or at least 81%, or at least 82%, or at least 83%, or at least 84%, or at least 85%, or at least 86%, or at least 87%, or at least 88%, or at least 89%, or at least 90%, or at least 91%, or at least 92%, or at least 93%, or at least 94%, or at least 95%, or at least 96%, or at least 97%, or at least 98%, or at least 99%, or at least 99.1%, or at least 99.2%, or at least 99.3%, or at least 99.4%, or at least 99.5% or at least 99.6%, or at least 99.7%, or at least 99.8%, or at least 99.9% sequence identity with SEQ ID NO:5, or a toxin fragment thereof.

In still other embodiments, the amino acid sequence of the Cry protein, optionally isolated Cry protein or recombinant Cry protein has at least 80%, or at least 81%, or at least 82%, or at least 83%, or at least 84%, or at least 85%, or at least 86%, or at least 87%, or at least 88%, or at least 89%, or at least 90%, or at least 91%, or at least 92%, or at least 93%, or at least 94%, or at least 95%, or at least 96%, or at least 97%, or at least 98%, or at least 99%, or at least 99.1%, or at least 99.2%, or at least 99.3%, or at least 99.4%, or at least 99.5% or at least 99.6%, or at least 99.7%, or at least 99.8%, or at least 99.9% sequence identity with SEQ ID NO:6, or a toxin fragment thereof.

In still other embodiments, the amino acid sequence of the Cry protein, optionally isolated Cry protein or recombinant Cry protein has at least 80%, or at least 81%, or at least 82%, or at least 83%, or at least 84%, or at least 85%, or at least 86%, or at least 87%, or at least 88%, or at least 89%, or at least 90%, or at least 91%, or at least 92%, or at least 93%, or at least 94%, or at least 95%, or at least 96%, or at least 97%, or at least 98%, or at least 99%, or at least 99.1%, or at least 99.2%, or at least 99.3%, or at least 99.4%, or at least 99.5% or at least 99.6%, or at least 99.7%, or at least 99.8%, or at least 99.9% sequence identity with SEQ ID NO:7, or a toxin fragment thereof.

In still other embodiments, the amino acid sequence of the Cry protein, optionally isolated Cry protein or recombinant Cry protein has at least 80%, or at least 81%, or at least 82%, or at least 83%, or at least 84%, or at least 85%, or at least 86%, or at least 87%, or at least 88%, or at least 89%, or at least 90%, or at least 91%, or at least 92%, or at least 93%, or at least 94%, or at least 95%, or at least 96%, or at least 97%, or at least 98%, or at least 99%, or at least 99.1%, or at least 99.2%, or at least 99.3%, or at least 99.4%, or at least 99.5% or at least 99.6%, or at least 99.7%, or at least 99.8%, or at least 99.9% sequence identity with SEQ ID NO:8, or a toxin fragment thereof.

In still other embodiments, the amino acid sequence of the Cry protein, optionally isolated Cry protein or recombinant Cry protein has at least 80%, or at least 81%, or at least 82%, or at least 83%, or at least 84%, or at least 85%, or at least 86%, or at least 87%, or at least 88%, or at least 89%, or at least 90%, or at least 91%, or at least 92%, or at least 93%, or at least 94%, or at least 95%, or at least 96%, or at least 97%, or at least 98%, or at least 99%, or at least 99.1%, or at least 99.2%, or at least 99.3%, or at least 99.4%, or at least 99.5% or at least 99.6%, or at least 99.7%, or at least 99.8%, or at least 99.9% sequence identity with SEQ ID NO:9, or a toxin fragment thereof.

In still other embodiments, the amino acid sequence of the Cry protein, optionally isolated Cry protein or recombinant Cry protein has at least 80%, or at least 81%, or at least 82%, or at least 83%, or at least 84%, or at least 85%, or at least 86%, or at least 87%, or at least 88%, or at least 89%, or at least 90%, or at least 91%, or at least 92%, or at least 93%, or at least 94%, or at least 95%, or at least 96%, or at least 97%, or at least 98%, or at least 99%, or at least 99.1%, or at least 99.2%, or at least 99.3%, or at least 99.4%, or at least 99.5% or at least 99.6%, or at least 99.7%, or at least 99.8%, or at least 99.9% sequence identity with SEQ ID NO:10, or a toxin fragment thereof.

In still other embodiments, the amino acid sequence of the Cry protein, optionally isolated Cry protein or recombinant Cry protein has at least 80%, or at least 81%, or at least 82%, or at least 83%, or at least 84%, or at least 85%, or at least 86%, or at least 87%, or at least 88%, or at least 89%, or at least 90%, or at least 91%, or at least 92%, or at least 93%, or at least 94%, or at least 95%, or at least 96%, or at least 97%, or at least 98%, or at least 99%, or at least 99.1%, or at least 99.2%, or at least 99.3%, or at least 99.4%, or at least 99.5% or at least 99.6%, or at least 99.7%, or at least 99.8%, or at least 99.9% sequence identity with SEQ ID NO:11, or a toxin fragment thereof.

In still other embodiments, the amino acid sequence of the Cry protein, optionally isolated Cry protein or recombinant Cry protein has at least 80%, or at least 81%, or at least 82%, or at least 83%, or at least 84%, or at least 85%, or at least 86%, or at least 87%, or at least 88%, or at least 89%, or at least 90%, or at least 91%, or at least 92%, or at least 93%, or at least 94%, or at least 95%, or at least 96%, or at least 97%, or at least 98%, or at least 99%, or at least 99.1%, or at least 99.2%, or at least 99.3%, or at least 99.4%, or at least 99.5% or at least 99.6%, or at least 99.7%, or at least 99.8%, or at least 99.9% sequence identity with SEQ ID NO:12, or a toxin fragment thereof.

In still other embodiments, the amino acid sequence of the Cry protein, optionally isolated Cry protein or recombinant Cry protein has at least 80%, or at least 81%, or at least 82%, or at least 83%, or at least 84%, or at least 85%, or at least 86%, or at least 87%, or at least 88%, or at least 89%, or at least 90%, or at least 91%, or at least 92%, or at least 93%, or at least 94%, or at least 95%, or at least 96%, or at least 97%, or at least 98%, or at least 99%, or at least 99.1%, or at least 99.2%, or at least 99.3%, or at least 99.4%, or at least 99.5% or at least 99.6%, or at least 99.7%, or at least 99.8%, or at least 99.9% sequence identity with SEQ ID NO:13, or a toxin fragment thereof.

In still further embodiments, the Cry protein, optionally isolated Cry protein or recombinant Cry protein comprises, consists essentially of or consists of an amino acid sequence of any of SEQ ID NOs:4-13, or a toxin fragment thereof. In other embodiments, the recombinant Cry protein is encoded by a nucleotide sequence that comprises, consists essentially of or consists of any of SEQ ID NOs:17-29, or a toxin-encoding fragment thereof.

In some embodiments, the Cry protein, optionally isolated Cry protein or recombinant Cry protein of the invention is a Cry1I or a Cry1J protein. In other embodiments, the Cry1I protein is a Cry1Ig protein. In other embodiments, the Cry1Ig protein comprises SEQ ID NO:2, SEQ ID NO:5, or a toxin fragment of SEQ ID NO:2 or SEQ ID NO:5. In still other embodiments, the Cry1Ig is toxic to European corn borer (*Ostrinia nubilalis*), sugarcane borer (*Diatraea saccharalis*), soybean looper (*Chrysodeixis includes*) and southwest corn borer (*Diatraea grandiosella*). In other embodiments, the Cry1Ig protein is encoded by a synthetic polynucleotide comprising, consisting essentially of or consisting of SEQ ID NO:18 or a toxin-encoding fragment thereof.

In some embodiments, the Cry1J protein, optionally isolated Cry1J protein or recombinant Cry1J protein is a Cry1Ja or a Cry1Jc protein. In other embodiments, the Cry1Ja protein comprises an amino acid sequence selected from the group consisting of SEQ ID NO:1, SEQ ID NO:4, SEQ ID NOs:7-13 and a toxin fragment of SEQ ID NO:1, SEQ ID NO:4 or any of SEQ ID NOs:7-13. In other embodiments, the Cry1Ja protein is toxic to European corn borer (*Ostrinia nubilalis*), fall armyworm (*Spodoptera frugiperda*), corn earworm (*Helicoverpa zea*), sugarcane borer (*Diatraea saccharalis*), velvetbean caterpillar (*Anticarsia gemmatalis*), soybean looper (*Chrysodeixis includes*), southwest corn borer (*Diatraea grandiosella*) and tobacco budworm (*Heliothis virescens*). In other embodiments, the Cry1Ja protein is encoded by a synthetic polynucleotide comprising, consisting essentially of or consisting of SEQ ID NO:17 or a toxin-encoding fragment thereof.

In some embodiments, the Cry1J protein, optionally isolated Cry1J protein or recombinant Cry1J protein that is a Cry1Jc protein. In other embodiments, the Cry1Jc protein comprises SEQ ID NO:3, SEQ ID NO:6, or a toxin fragment of SEQ ID NO:3 or SEQ ID NO:6. In still other embodiments, the Cry1Jc protein is toxic to European corn borer (*Ostrinia nubilalis*), corn earworm (*Helicoverpa zea*), sugarcane borer (*Diatraea saccharalis*), velvetbean caterpillar (*Anticarsia gemmatalis*), soybean looper (*Chrysodeixis includes*), southwest corn borer (*Diatraea grandiosella*) and tobacco budworm (*Heliothis virescens*). In other embodiments, the Cry1Jc protein is encoded by a synthetic polynucleotide comprising, consisting essentially of or consisting of SEQ ID NO:19 or a toxin-encoding fragment thereof.

Antibodies raised in response to immune challenge by a native or mutant BT2Cry1J, BT25Cry1I and BT53Cry1J Cry protein or related Cry proteins are also encompassed by the invention. Such antibodies may be produced using standard immunological techniques for production of polyclonal antisera and, if desired, immortalizing the antibody-producing cells of the immunized host for sources of monoclonal antibody production. Techniques for producing antibodies to any substance of interest are well known, e.g., as in Harlow and Lane (1988. Antibodies a laboratory manual. pp. 726. Cold Spring Harbor Laboratory) and as in Goding (Monoclonal Antibodies: Principles & practice. 1986. Academic Press, Inc., Orlando, Fla.), both of which are incorporated herein by reference. The present invention encompasses insecticidal proteins that cross-react with antibodies, particularly monoclonal antibodies, raised against one or more of the insecticidal Cry proteins of the present invention.

The antibodies produced in the invention are also useful in immunoassays for determining the amount or presence of a native or mutant BT2Cry1J, BT25Cry1I and BT53Cry1J or related Cry protein in a biological sample. Such assays are also useful in quality-controlled production of compositions containing one or more of the Cry proteins of the invention or related Cry proteins. In addition, the antibodies can be used to assess the efficacy of recombinant production of one or more of the Cry proteins of the invention or a related protein, as well as for screening expression libraries for the presence of a nucleotide sequence encoding one or more of the Cry proteins of the invention or related protein coding sequences. Antibodies are useful also as affinity ligands for purifying or isolating any one or more of the proteins of the invention and related proteins. The Cry proteins of the invention and proteins containing related antigenic epitopes may be obtained by over expressing full or partial lengths of a sequence encoding all or part of a Cry protein of the invention or a related protein in a preferred host cell.

It is recognized that DNA sequences that encode a native Cry protein of the invention may be altered by various methods, and that these alterations may result in DNA sequences encoding proteins with amino acid sequences different than that encoded by a native Cry protein of the invention. A Cry protein may be altered in various ways to make a mutant Cry protein including amino acid substitutions, deletions, truncations, and insertions of one or more amino acids of any of SEQ ID NOs:1-3, or a toxin fragment of any of SEQ ID NOs:1-3, including up to about 2, about 3, about 4, about 5, about 6, about 7, about 8, about 9, about 10, about 15, about 20, about 25, about 30, about 35, about 40, about 45, about 50, about 55, about 60, about 65, about 70, about 75, about 80, about 85, about 90, about 100, about 105, about 110, about 115, about 120, about 125, about 130, about 135, about 140, about 145, about 150, about 155, or more amino acid substitutions, deletions or insertions. Methods for such manipulations are generally known in the art. For example, amino acid sequence variants of a native Cry protein can be prepared by mutations in a polynucleotide that encodes the protein. This may also be accomplished by one of several forms of mutagenesis or in directed evolution. In some aspects, the changes encoded in the amino acid sequence will not substantially affect the function of the protein. Such variants will possess a desired insecticidal activity. In some embodiments of the invention, nucleotide sequences represented by SEQ ID NOs: 14-16 are altered to introduce amino acid substitutions in the encoded protein resulting in a mutant protein having essentially the same insecticidal properties as the native protein. In other embodiments, the resulting mutant protein is encoded by a synthetic mutant polynucleotide comprising a nucleotide sequence represented by any one of SEQ ID NOs:17-29, or a toxin-encoding fragment of any of SEQ ID NOs:17-29. In other embodiments, the mutant proteins comprise, consist essentially of or consist of an amino acid sequence represented by any one of SEQ ID NOs:4-13, or a toxin fragment of any of SEQ ID NOs:4-13.

In other embodiments, the insecticidal activity of a native Cry protein of the invention can be modulated by inserting, deleting or substituting amino acids in the native Cry protein amino acid sequence resulting in a modified Cry protein of the invention. For example, a Cry protein's insecticidal activity is modulated where the modified Cry protein is toxic to a wider or narrower range of insects compared to the range of insects that is affected by a native Cry protein. It may be desirable to create a modified Cry protein with toxicity to a wider range of insect pests than the native Cry protein where multiple pests feed on a single crop plant of interest, while a modified Cry protein with toxicity to a narrower range of insects may be desirable where, for example, a particular insect pest that a native Cry protein is active against does not feed on the crop plant into which the modified Cry protein will be expressed. This reduction in target pest range may help to mitigate insect resistance development in multiple cropping system environments, for example, where transgenic corn, transgenic soybean and transgenic cotton are grown in close proximity to each other.

In some other embodiments the insecticidal activity of a native Cry protein can be modulated by substituting at least one amino acid in alpha-helix 3, alpha-helix 4, alpha-helix 5 or alpha-helix 6 of domain I of the native Cry amino acid sequence with a different amino acid than the one at that position in the native Cry protein. In other embodiments, the native Cry protein is a Cry1J protein. In other embodiments, the Cry1J protein is a Cry1Ja or a Cry1Jc protein. In still other embodiments, the amino acids in alpha-helix 3 of a native Cry1J protein corresponding to amino acid positions 97, 105, 108, 110, 118 and 119 of SEQ ID NO:1 or SEQ ID NO:3 are substituted with an amino acid different from the amino acid that is present at these positions in the native Cry1J protein resulting in a modified Cry1J protein. In some embodiments, the amino acid substitutions in alpha-helix 3 of a Cry1Ja protein result in a modified Cry1Ja protein that is toxic is a narrower range of insects than a native Cry1Ja protein. In other embodiments the native Cry1Ja protein comprises SEQ ID NO:1 and the modified Cry1Ja has an A97T, an S105N, an L108I, a G110A, a K118S and a T119D substitution in alpha-helix 3. In still other embodiments, the modified Cry1Ja comprises SEQ ID NO:7 or a toxin fragment thereof. In still other embodiments, the modified Cry1Ja has activity against soybean looper and tobacco budworm but little or no activity against European corn borer, sugarcane borer, southwest corn borer, black cutworm, fall armyworm, corn earworm or velvetbean caterpillar compared to a native Cry1Ja protein.

In some embodiments, the amino acids in alpha-helix 4 of a native Cry1Ja protein corresponding to amino acid positions 123, 126, 130, 131, 136, 138, 139, 149 and 150 of SEQ ID NO:1 are substituted with an amino acid different from the amino acid that is present at these positions in the native Cry1Ja protein resulting in a modified Cry1Ja protein. In other embodiments, the amino acid substitutions in alpha-helix 4 of the Cry1Ja protein result in a modified Cry1Ja protein that is toxic is a narrower range of insects than a native Cry1Ja protein. In other embodiments the native Cry1Ja protein comprises SEQ ID NO:1 or a toxin fragment thereof and the modified Cry1Ja has a T123E, an R126K, a T130I, an E131D, an I136L, an A138G, a Q139L, a V149I and a V150I substitution in alpha-helix 4. In still other embodiments, the modified Cry1Ja comprises SEQ ID NO:8 or a toxin fragment thereof. In still other embodiments, the modified Cry1Ja has activity against soybean looper, velvetbean caterpillar and tobacco budworm but little or no activity against European corn borer, sugarcane borer, southwest corn borer, black cutworm, fall armyworm and corn earworm compared to a native Cry1Ja protein.

In some embodiments, the amino acids in alpha-helix 5/6 of a native Cry1Ja protein corresponding to amino acid positions 158, 161, 176, 186, 196, 197, 198 and 200 of SEQ ID NO:1 are substituted with an amino acid different from the amino acid that is present at these positions in the native Cry1Ja protein resulting in a modified Cry1Ja protein. In other embodiments, the amino acid substitutions in alpha-helix 5/6 of the Cry1Ja protein result in a modified Cry1Ja protein having essentially the same insecticidal spectrum of activity as a native Cry1Ja. In other embodiments the native Cry1Ja protein comprises SEQ ID NO:1 or a toxin fragment thereof and the modified Cry1Ja has an L158S; a T161V; a V176I; a T186K; a V196I; an N197R; an R198E and a G200H substitution in alpha-helix 5/6. In still other embodiments, the modified Cry1Ja comprises SEQ ID NO:9 or a toxin fragment thereof.

In some embodiments, the amino acids in alpha-helix 3 and alpha-helix 4 of a native Cry1Ja protein corresponding to amino acid positions 97, 105, 108, 110, 118, 119, 123, 126, 130, 131, 136, 138, 139, 149 and 150 of SEQ ID NO:1 are substituted with an amino acid different from the amino acid that is present at these positions in the native Cry1Ja protein resulting in a modified Cry1Ja protein. In some embodiments, the amino acid substitutions in alpha-helix 3 and alpha-helix 4 of the Cry1Ja protein result in a modified Cry1Ja protein that is toxic is a narrower range of insects than a native Cry1Ja protein. In other embodiments, the native Cry1Ja protein comprises SEQ ID NO:1 or a toxin fragment thereof and the modified Cry1Ja has an A97T, an S105N, an L1081, a G110A, a K118S, a T119D, a T123E, an R126K, a T1301, an E131D, an I136L, an A138G, a Q139L, a V1491 and a V1501 substitution in alpha-helix 3 and alpha-helix 4. In still other embodiments, the modified Cry1Ja comprises SEQ ID NO:10 or a toxin fragment thereof. In still other embodiments, the modified Cry1I has no or reduced activity against sugarcane borer, FAW and CEW and essentially the same activity against European corn borer, southwest corn borer, black cutworm, soybean looper, velvet bean caterpillar and tobacco budworm compared to a native Cry1Ja protein.

In some embodiments, the amino acids in alpha-helix 4 and alpha-helix 5/6 of a native Cry1Ja protein corresponding to amino acid positions 123, 126, 130, 131, 136, 138, 139, 149, 150, 158, 161, 176, 186, 196, 197, 198 and 200 of SEQ ID NO:1 are substituted with an amino acid different from the amino acid that is present at these positions in the native Cry1Ja protein resulting in a modified Cry1Ja protein. In other embodiments, the amino acid substitutions in alpha-helix 4 and alpha-helix 5/6 of the Cry1Ja protein result in a modified Cry1Ja protein that is toxic to a narrower range of insects than a native Cry1Ja protein. In other embodiments, the modified Cry1Ja protein is active against insect pests in the Family Noctuidae but not active against insect pests in the Family Crambidae. In other embodiments the native Cry1Ja protein comprises SEQ ID NO:1 or a toxin fragment thereof and the modified Cry1Ja has a T123E, an R126K, a T130I, an E131D, an I136L, an A138G, a Q139L, a V1491, a V150I, an L158S; a T161V; a V1761; a T186K; a V1961; an N197R; an R198E and a G200H substitution in alpha-helix 4 and alpha-helix 5/6. In still other embodiments, the modified Cry1Ja comprises SEQ ID NO:11 or a toxin fragment thereof. In still other embodiments, the modified Cry1Ja protein has no activity against the Crambidae Family members European corn borer, sugarcane borer and SWCB. In other embodiments, the modified Cry1Ja protein has activity against the Noctuidae members black cutworm, fall armyworm, corn earworm, soybean looper, velvetbean caterpillar and tobacco budworm. In still other embodiments, the modified Cry1Ja protein has reduced activity against black cutworm, fall armyworm and corn earworm compared to the native Cry1Ja protein. In still other embodiments, the modified Cry1Ja protein has no activity against European corn borer, sugarcane borer and southwest corn borer and has activity against black cutworm, fall armyworm, corn earworm, soybean looper, velvetbean caterpillar and tobacco budworm.

In some embodiments, the amino acids in alpha-helix 3 and alpha-helix 5/6 of a native Cry1Ja protein corresponding to amino acid positions 97, 105, 108, 110, 118, 119, 158, 161, 176, 186, 196, 197, 198 and 200 of SEQ ID NO:1 are substituted with an amino acid different from the amino acid that is present at these positions in the native Cry1Ja protein resulting in a modified Cry1Ja protein. In some embodiments, the amino acid substitutions in alpha-helix 3 and alpha-helix 5/6 of the Cry1Ja protein result in a modified Cry1Ja protein with no insecticidal activity compared to the native Cry1Ja protein. In other embodiments, the native Cry1Ja protein comprises SEQ ID NO:1 or a toxin fragment thereof and the modified Cry1Ja has an A97T, an S105N, an L108I, a G110A, a K118S, a T119D, an L158S; a T161V; a V176I; a T186K; a V196I; an N197R; an R198E and a G200H substitution in alpha-helix 3 and alpha-helix 5/6. In still other embodiments, the modified Cry1Ja comprises SEQ ID NO:12 or a toxin fragment thereof.

In some embodiments, the amino acids in alpha-helix 3, alpha-helix 4 and alpha-helix 5/6 of a native Cry1Ja protein corresponding to amino acid positions 97, 105, 108, 110, 118, 119, 123, 126, 130, 131, 136, 138, 139, 149, 150, 158, 161, 176, 186, 196, 197, 198 and 200 of SEQ ID NO:1 are substituted with an amino acid different from the amino acid that is present at these positions in the native Cry1Ja protein resulting in a modified Cry1Ja protein. In some embodiments, the amino acid substitutions in alpha-helix 3, alpha-helix 4 and alpha-helix 5/6 of the Cry1Ja protein result in a modified Cry1Ja protein with the same insecticidal activity as a native Cry1Ja protein. In other embodiments, the native Cry1Ja protein comprises SEQ ID NO:1 or a toxin fragment thereof and the modified Cry1Ja has an A97T, an S105N, an L108I, a G110A, a K118S, a T119D, a T123E, an R126K, a T130I, an E131D, an I136L, an A138G, a Q139L, a V149I, a V150I, an L158S; a T161V; a V176I; a T186K; a V196I; an N197R; an R198E and a G200H substitution in alpha-helix 3, alpha-helix 4 and alpha-helix 5/6. In still other embodiments, the modified Cry1Ja comprises SEQ ID NO:13 or a toxin fragment thereof.

It is understood that the ability of an insecticidal protein to confer insecticidal activity may be improved by the use of such techniques upon the compositions of this invention. For example, one may express a Cry protein in host cells that exhibit high rates of base mis-incorporation during DNA replication, such as XL-1 Red (Stratagene, La Jolla, Calif.). After propagation in such strains, one can isolate the DNA (for example by preparing plasmid DNA, or by amplifying by PCR and cloning the resulting PCR fragment into a vector), culture the Cry protein mutations in a non-mutagenic strain, and identify mutated genes with insecticidal activity, for example by performing an assay to test for insecticidal activity. Generally, the protein is mixed and used in feeding assays. See, for example Marrone et al. (1985) J. of Economic Entomology 78:290-293. Such assays can include contacting plants with one or more pests and determining the plant's ability to survive or cause the death of the pests. Examples of mutations that result in increased toxicity are found in Schnepf et al. (1998) Microbiol. Mol. Biol. Rev. 62:775-806.

Alternatively, alterations may be made to an amino acid sequence of the invention at the amino or carboxy terminus without substantially affecting activity. This can include insertions, deletions, or alterations introduced by modern molecular methods, such as PCR, including PCR amplifications that alter or extend the protein coding sequence by virtue of inclusion of amino acid encoding sequences in the oligonucleotides utilized in the PCR amplification. Alternatively, the protein sequences added can include entire protein-coding sequences, such as those used commonly in the art to generate protein fusions. Such fusion proteins are often used to (1) increase expression of a protein of interest (2) introduce a binding domain, enzymatic activity, or epitope to facilitate either protein purification, protein detection, or other experimental uses known in the art (3) target secretion or translation of a protein to a subcellular organelle, such as the periplasmic space of Gram-negative bacteria, or the endoplasmic reticulum of eukaryotic cells, the latter of which often results in glycosylation of the protein.

A Cry protein of the invention can also be mutated to introduce an epitope to generate antibodies that recognize the mutated protein. Therefore, in some embodiments, the invention provides a mutated Cry protein, wherein an amino acid substitution in a native Cry protein produces a mutant Cry protein having an antigenic region that allows the mutant Cry protein to be distinguished from the native Cry protein in a protein detection assay.

In some embodiments, the invention provides a method of making an antibody that differentially recognizes a mutated Cry protein from the native Cry protein from which the mutated Cry protein is derived, the method comprising the steps of substituting amino acids in an antigenic loop of a native Cry protein and raising antibodies that specifically recognize the mutated antigenic loop in the mutated Cry protein and does not recognize the native Cry protein. In one embodiment, the antigenic loop is identified in non-conserved regions outside of domain I of the native Cry protein. In another embodiment, the antigenic loop is not a loop involved in the Cry protein's insect gut receptor recognition or involved in the protease activation of the Cry protein.

Variant nucleotide and amino acid sequences of the invention also encompass sequences derived from mutagenic and recombinogenic procedures such as DNA shuffling. With such a procedure, one or more different toxic protein coding regions can be used to create a new toxic protein possessing the desired properties. In this manner, libraries of recombinant polynucleotides are generated from a population of related sequence polynucleotides comprising sequence regions that have substantial sequence identity and can be homologously recombined in vitro or in vivo. For example, using this approach, sequence motifs encoding a domain of interest may be shuffled between a pesticidal gene of the invention and other known pesticidal genes to obtain a new gene coding for a protein with an improved property of interest, such as an increased insecticidal activity. Strategies for such DNA shuffling are known in the art. See, for example, Stemmer (1994) Proc. Natl. Acad. Sci. USA 91:10747-10751; Stemmer (1994) Nature 370:389-391; Crameri et al. (1997) Nature Biotech. 15:436-438; Moore et al. (1997) J. Mol. Biol. 272:336-347; Zhang et al. (1997)

Proc. Natl. Acad. Sci. USA 94:4504-4509; Crameri et al. (1998) Nature 391:288-291; and U.S. Pat. Nos. 5,605,793 and 5,837,458.

Domain swapping or shuffling is another mechanism for generating altered Cry proteins of the invention. Domains may be swapped between Cry proteins, resulting in hybrid or chimeric toxic proteins with improved pesticidal activity or target spectrum. Methods for generating recombinant proteins and testing them for pesticidal activity are well known in the art (see, for example, Naimov et al. (2001) Appl. Environ. Microbiol. 67:5328-5330; de Maagd et al. (1996) Appl. Environ. Microbiol. 62:1537-1543; Ge et al. (1991) J. Biol. Chem. 266:17954-17958; Schnepf et al. (1990) J. Biol. Chem. 265:20923-20930; Rang et al. 91999) Appl. Environ. Microbiol. 65:2918-2925). In some embodiments, the invention provides hybrid Cry proteins comprising at a C-terminus, amino acids from a first Cry protein of the invention and at an N-terminus, amino acids from a second Cry protein different from the first Cry protein of the invention. In other embodiments, the invention provides hybrid Cry proteins comprising at an N-terminus, amino acids from a Cry protein of the invention and at a C-terminus, amino acids from a second Cry protein different from the first Cry protein of the invention.

When a heterologous polynucleotide sequence encoding a Cry protein encompassed by the invention is introduced into a plant the introduced polynucleotide is stably integrated into the genome of the now transgenic plant. Thus, according to the invention, the encoded Cry protein can be mutated in situ by targeted DNA editing using various genome editing techniques such as zinc finger nucleases (ZNFs), transcription activator-like effector nucleases (TALENS), meganucleases and Clustered Regularly Interspaced Short Palindromic Repeats (CRISPR) (U.S. Pat. No. 8,697,359; Ran et al., incorporated by reference). The CRISPR system can be used to introduce specific nucleotide modifications at the target sequence. Originally discovered in bacteria, where several different CRISPR cascades function as innate immune systems and natural defense mechanisms, the engineered CRISPR-Cas9 system can be programmed to target specific stretches of genetic code and to make cuts at precise locations. Over the past few years, those capabilities have been harnessed and used as genome editing tools, enabling researchers to permanently modify genes in plant cells.

Thus, the invention encompasses a method for generating a mutant polynucleotide encoding a modified Cry protein wherein said method comprises modifying a plant genome comprising a polynucleotide encoding a Cry protein using CRISPR. The method involves targeting of Cas9 to the specific genomic locus, in this case a Cry protein-encoding polynucleotide, via a 20 nt guide sequence of the single-guide RNA. An online CRISPR Design Tool can identify suitable target sites (world wide web at tools.genome-engineering.org. Ran et al. Genome engineering using the CRISPR-Cas9 system nature protocols, VOL. 8 NO. 11, 2281-2308, 2013). Target plants for the mutagenesis/genome editing methods according to the invention are any monocot or dicot plants into which a Cry protein-encoding polynucleotide of the invention has been introduced.

In an exemplary embodiment, the activity of a Cry1J protein can be modulated by mutating a cry1J gene, for example a gene encoding BT2Cry1Ja (SEQ ID NO:1) or BT53Cry1J (SEQ ID NO:3), comprised in a transgenic maize genome by engineering recombinant DNA restriction enzymes by fusing a nuclease, for example FokI, with a structure that binds to a site in the cry1J gene to make a double strand cut within the cry1J gene and replace with an engineered polynucleotide that comprises the mutations of interest. FokI is a bacterial type IIS restriction endonuclease consisting of an N-terminal DNA-binding domain, which can be made to bind to specific DNA sequences in the genome and a non-specific DNA cleavage domain at the C-terminus. Plants expressing the mutated Cry1J protein with modulated activity can be selected using insect bioassays as disclosed herein.

In some embodiments, the invention provides a recombinant vector comprising a polynucleotide, an expression cassette or a chimeric gene of the invention. In other embodiments, the vector is further defined as a plasmid, cosmid, phagemid, artificial chromosome, phage or viral vector. Certain vectors comprising on or more expression cassettes for use in transformation of plants and other organisms are known in the art.

Thus, some embodiments of the invention are directed to expression cassettes designed to express the Cry protein-encoding polynucleotides of the invention. As used herein, "expression cassette" means a polynucleotide having at least a control sequence operatively linked to a nucleotide sequence of interest. In this manner, for example, plant promoters operably linked to the nucleotide sequences to be expressed are provided in expression cassettes for expression in a plant, plant part or plant cell.

An expression cassette comprising a polynucleotide of interest may be chimeric, meaning that at least one of its components is heterologous with respect to at least one other of its other components. An expression cassette may also be one that is naturally occurring but has been obtained in a recombinant form useful for heterologous expression. Typically, however, the expression cassette is heterologous with respect to the host, i.e., the particular nucleotide sequence of the expression cassette does not occur naturally in the host cell and must have been introduced into the host cell or an ancestor of the host cell by a transformation event.

In addition to the promoters operatively linked to the nucleotide sequences of the invention, an expression cassette of this invention also can include other regulatory sequences. As used herein, "regulatory sequences" means nucleotide sequences located upstream (5' non-coding sequences), within or downstream (3' non-coding sequences) of a coding sequence, and which influence the transcription, RNA processing or stability, or translation of the associated coding sequence. Regulatory sequences include, but are not limited to, enhancers, introns, translation leader sequences, termination signals, and polyadenylation signal sequences.

In some embodiments, an expression cassette of the invention also can include polynucleotides that encode other desired traits in addition to the Cry proteins of the invention. Such expression cassettes comprising the stacked traits may be used to create plants, plant parts or plant cells having a desired phenotype with the stacked traits (i.e., molecular stacking). Such stacked combinations in plants can also be created by other methods including, but not limited to, cross breeding plants by any conventional methodology. If stacked by genetically transforming the plants, the nucleotide sequences of interest can be combined at any time and in any order. For example, a transgenic plant comprising one or more desired traits can be used as the target to introduce further traits by subsequent transformation. The additional nucleotide sequences can be introduced simultaneously in a co-transformation protocol with a nucleotide sequence, polynucleotide, polynucleotide construct, or composition of this invention, provided by any combination of expression cassettes. For example, if two nucleotide sequences will be introduced, they can be incorporated in separate cassettes (trans) or can be incorporated on the same cassette (cis). Expression of polynucleotides can be driven by the same promoter or by different promoters. It is further recognized that polynucleotides can be stacked at a desired genomic location using a site-specific recombination system. See, e.g., Int'l Patent Application Publication Nos. WO 99/25821; WO 99/25854; WO 99/25840; WO 99/25855 and WO 99/25853.

The expression cassette also can include an additional coding sequence for one or more polypeptides or double stranded RNA molecules (dsRNA) of interest for agronomic traits that primarily are of benefit to a seed company, grower or grain processor. A polypeptide of interest can be any polypeptide encoded by a nucleotide sequence of interest. Non-limiting examples of polypeptides of interest that are suitable for production in plants include those resulting in agronomically important traits such as herbicide resistance (also sometimes referred to as "herbicide tolerance"), virus resistance, bacterial pathogen resistance, insect resistance, nematode resistance, or fungal resistance. See, e.g., U.S. Pat. Nos. 5,569,823; 5,304,730; 5,495,071; 6,329,504; and 6,337,431. The polypeptide also can be one that increases plant vigor or yield (including traits that allow a plant to grow at different temperatures, soil conditions and levels of sunlight and precipitation), or one that allows identification of a plant exhibiting a trait of interest (e.g., a selectable marker, seed coat color, etc.). Various polypeptides of interest, as well as methods for introducing these polypeptides into a plant, are described, for example, in U.S. Pat. Nos. 4,761,373; 4,769,061; 4,810,648; 4,940,835; 4,975,374; 5,013,659; 5,162,602; 5,276,268; 5,304,730; 5,495,071; 5,554,798; 5,561,236; 5,569,823; 5,767,366; 5,879,903, 5,928,937; 6,084,155; 6,329,504 and 6,337,431; as well as US Patent Publication No. 2001/0016956. See also, on the World Wide Web at lifesci.sussex.ac.uk/home/Neil_Crickmore/Bt/.

Polynucleotides conferring resistance/tolerance to an herbicide that inhibits the growing point or meristem, such as an imidazalinone or a sulfonylurea can also be suitable in some embodiments of the invention. Exemplary polynucleotides in this category code for mutant ALS and AHAS enzymes as described, e.g., in U.S. Pat. Nos. 5,767,366 and 5,928,937. U.S. Pat. Nos. 4,761,373 and 5,013,659 are directed to plants resistant to various imidazalinone or sulfonamide herbicides. U.S. Pat. No. 4,975,374 relates to plant cells and plants containing a polynucleotide encoding a mutant glutamine synthetase (GS) resistant to inhibition by herbicides that are known to inhibit GS, e.g., phosphinothricin and methionine sulfoximine. U.S. Pat. No. 5,162,602 discloses plants resistant to inhibition by cyclohexanedione and aryloxyphenoxypropanoic acid herbicides. The resistance is conferred by an altered acetyl coenzyme A carboxylase (ACCase).

Polypeptides encoded by nucleotides sequences conferring resistance to glyphosate are also suitable for the invention. See, e.g., U.S. Pat. Nos. 4,940,835 and 4,769,061. U.S. Pat. No. 5,554,798 discloses transgenic glyphosate resistant maize plants, which resistance is conferred by an altered 5-enolpyruvyl-3-phosphoshikimate (EPSP) synthase gene.

Polynucleotides coding for resistance to phosphono compounds such as glufosinate ammonium or phosphinothricin, and pyridinoxy or phenoxy propionic acids and cyclohexones are also suitable. See, European Patent Application No. 0 242 246. See also, U.S. Pat. Nos. 5,879,903, 5,276,268 and 5,561,236.

Other suitable polynucleotides include those coding for resistance to herbicides that inhibit photosynthesis, such as a triazine and a benzonitrile (nitrilase) See, U.S. Pat. No. 4,810,648. Additional suitable polynucleotides coding for herbicide resistance include those coding for resistance to 2,2-dichloropropionic acid, sethoxydim, haloxyfop, imidazolinone herbicides, sulfonylurea herbicides, triazolopyrimidine herbicides, s-triazine herbicides and bromoxynil. Also suitable are polynucleotides conferring resistance to a protox enzyme, or that provide enhanced resistance to plant diseases; enhanced tolerance of adverse environmental conditions (abiotic stresses) including but not limited to drought, excessive cold, excessive heat, or excessive soil salinity or extreme acidity or alkalinity; and alterations in plant architecture or development, including changes in developmental timing. See, e.g., U.S. Patent Publication No. 2001/0016956 and U.S. Pat. No. 6,084,155.

Additional suitable polynucleotides include those coding for pesticidal (e.g., insecticidal) polypeptides. These polypeptides may be produced in amounts sufficient to control, for example, insect pests (i.e., insect controlling amounts). It is recognized that the amount of production of a pesticidal polypeptide in a plant necessary to control insects or other pests may vary depending upon the cultivar, type of pest, environmental factors and the like. Polynucleotides useful for additional insect or pest resistance include, for example, those that encode toxins identified in *Bacillus* organisms. Polynucleotides comprising nucleotide sequences encoding *Bacillus thuringiensis* (Bt) Cry proteins from several subspecies have been cloned and recombinant clones have been found to be toxic to lepidopteran, dipteran and coleopteran insect larvae. Examples of such Bt insecticidal proteins include the Cry proteins such as Cry1Aa, Cry1Ab, Cry1Ac, Cry1B, Cry1C, Cry1D, Cry1Ea, Cry1Fa, Cry3A, Cry9A, Cry9B, Cry9C, and the like, as well as vegetative insecticidal proteins such as Vip1, Vip2, Vip3, and the like. A full list of Bt-derived proteins can be found on the worldwide web at *Bacillus thuringiensis* Toxin Nomenclature Database maintained by the University of Sussex (see also, Crickmore et al. (1998) *Microbiol. Mol. Biol. Rev.* 62:807-813).

Polypeptides that are suitable for production in plants further include those that improve or otherwise facilitate the conversion of harvested plants or plant parts into a commercially useful product, including, for example, increased or altered carbohydrate content or distribution, improved fermentation properties, increased oil content, increased protein content, improved digestibility, and increased nutraceutical content, e.g., increased phytosterol content, increased tocopherol content, increased stanol content or increased vitamin content. Polypeptides of interest also include, for example, those resulting in or contributing to a reduced content of an unwanted component in a harvested crop, e.g., phytic acid, or sugar degrading enzymes. By "resulting in" or "contributing to" is intended that the polypeptide of interest can directly or indirectly contribute to the existence of a trait of interest (e.g., increasing cellulose degradation by the use of a heterologous cellulase enzyme).

In some embodiments, the polypeptide contributes to improved digestibility for food or feed. Xylanases are hemicellulolytic enzymes that improve the breakdown of plant cell walls, which leads to better utilization of the plant nutrients by an animal. This leads to improved growth rate and feed conversion. Also, the viscosity of the feeds containing xylan can be reduced. Heterologous production of xylanases in plant cells also can facilitate lignocellulosic conversion to fermentable sugars in industrial processing.

Numerous xylanases from fungal and bacterial microorganisms have been identified and characterized (see, e.g., U.S. Pat. No. 5,437,992; Coughlin et al. (1993) "Proceedings of the Second TRICEL Symposium on *Trichoderma reesei* Cellulases and Other Hydrolases" Espoo; Souminen and Reinikainen, eds. (1993) *Foundation for Biotechnical and Industrial Fermentation Research* 8:125-135; U.S. Patent Publication No. 2005/0208178; and PCT Publication No. WO 03/16654). In particular, three specific xylanases (XYL-I, XYL-II, and XYL-III) have been identified in *T. reesei* (Tenkanen et al. (1992) *Enzyme Microb. Technol.* 14:566; Torronen et al. (1992) *Bio/Technology* 10:1461; and Xu et al. (1998) *Appl. Microbiol. Biotechnol.* 49:718).

In other embodiments, a polypeptide useful for the invention can be a polysaccharide degrading enzyme. Plants of this invention producing such an enzyme may be useful for generating, for example, fermentation feedstocks for bioprocessing. In some embodiments, enzymes useful for a fermentation process include alpha amylases, proteases, pullulanases, isoamylases, cellulases, hemicellulases, xylanases, cyclodextrin glycotransferases, lipases, phytases, laccases, oxidases, esterases, cutinases, granular starch hydrolyzing enzyme and other glucoamylases.

Polysaccharide-degrading enzymes include: starch degrading enzymes such as α-amylases (EC 3.2.1.1), glucuronidases (E.C. 3.2.1.131); exo-1,4-α-D glucanases such as amyloglucosidases and glucoamylase (EC 3.2.1.3), β-amylases (EC 3.2.1.2), α-glucosidases (EC 3.2.1.20), and other exo-amylases; starch debranching enzymes, such as a) isoamylase (EC 3.2.1.68), pullulanase (EC 3.2.1.41), and the like; b) cellulases such as exo-1,4-3-cellobiohydrolase (EC 3.2.1.91), exo-1,3-β-D-glucanase (EC 3.2.1.39), β-glucosidase (EC 3.2.1.21); c) L-arabinases, such as endo-1,5-α-L-arabinase (EC 3.2.1.99), α-arabinosidases (EC 3.2.1.55) and the like; d) galactanases such as endo-1,4-β-D-galactanase (EC 3.2.1.89), endo-1,3-β-D-galactanase (EC 3.2.1.90), α-galactosidase (EC 3.2.1.22), β-galactosidase (EC 3.2.1.23) and the like; e) mannanases, such as endo-1,4-β-D-mannanases (EC 3.2.1.78), β-mannosidase (EC 3.2.1.25), α-mannosidase (EC 3.2.1.24) and the like; f) xylanases, such as endo-1,4-β-xylanase (EC 3.2.1.8), β-D-xylosidase (EC 3.2.1.37), 1,3-β-D-xylanase, and the like; and g) other enzymes such as α-L-fucosidase (EC 3.2.1.51), α-L-rhamnosidase (EC 3.2.1.40), levanase (EC 3.2.1.65), inulanase (EC 3.2.1.7), and the like. In one embodiment, the α-amylase is the synthetic α-amylase, Amy797E, described is U.S. Pat. No. 8,093,453, herein incorporated by reference in its entirety.

Further enzymes which may be used with the invention include proteases, such as fungal and bacterial proteases. Fungal proteases include, but are not limited to, those obtained from *Aspergillus, Trichoderma, Mucor* and *Rhizopus*, such as *A. niger, A. awamori, A. oryzae* and *M. miehei*. In some embodiments, the polypeptides of this invention can be cellobiohydrolase (CBH) enzymes (EC 3.2.1.91). In one embodiment, the cellobiohydrolase enzyme can be CBH1 or CBH2.

Other enzymes useful with the invention include, but are not limited to, hemicellulases, such as mannases and arabinofuranosidases (EC 3.2.1.55); ligninases; lipases (e.g., E.C. 3.1.1.3), glucose oxidases, pectinases, xylanases, transglucosidases, alpha 1,6 glucosidases (e.g., E.C. 3.2.1.20); esterases such as ferulic acid esterase (EC 3.1.1.73) and acetyl xylan esterases (EC 3.1.1.72); and cutinases (e.g. E.C. 3.1.1.74).

Double stranded RNA molecules useful with the invention include, but are not limited to those that suppress target insect genes. As used herein the words "gene suppression", when taken together, are intended to refer to any of the well-known methods for reducing the levels of protein produced as a result of gene transcription to mRNA and subsequent translation of the mRNA. Gene suppression is also intended to mean the reduction of protein expression from a gene or a coding sequence including posttranscriptional gene suppression and transcriptional suppression. Posttranscriptional gene suppression is mediated by the homology between of all or a part of a mRNA transcribed from a gene or coding sequence targeted for suppression and the corresponding double stranded RNA used for suppression, and refers to the substantial and measurable reduction of the amount of available mRNA available in the cell for binding by ribosomes. The transcribed RNA can be in the sense orientation to effect what is called co-suppression, in the anti-sense orientation to effect what is called anti-sense suppression, or in both orientations producing a dsRNA to effect what is called RNA interference (RNAi). Transcriptional suppression is mediated by the presence in the cell of a dsRNA, a gene suppression agent, exhibiting substantial sequence identity to a promoter DNA sequence or the complement thereof to effect what is referred to as promoter trans suppression. Gene suppression may be effective against a native plant gene associated with a trait, e.g., to provide plants with reduced levels of a protein encoded by the native gene or with enhanced or reduced levels of an affected metabolite. Gene suppression can also be effective against target genes in plant pests that may ingest or contact plant material containing gene suppression agents, specifically designed to inhibit or suppress the expression of one or more homologous or complementary sequences in the cells of the pest. Such genes targeted for suppression can encode an essential protein, the predicted function of which is selected from the group consisting of muscle formation, juvenile hormone formation, juvenile hormone regulation, ion regulation and transport, digestive enzyme synthesis, maintenance of cell membrane potential, amino acid biosynthesis, amino acid degradation, sperm formation, pheromone synthesis, pheromone sensing, antennae formation, wing formation, leg formation, development and differentiation, egg formation, larval maturation, digestive enzyme formation, hemolymph synthesis, hemolymph maintenance, neurotransmission, cell division, energy metabolism, respiration, and apoptosis.

In some embodiments, the invention provides a transgenic non-human host cell comprising a polynucleotide, a chimeric gene, an expression cassette or a recombinant vector of the invention. The transgenic non-human host cell can include, but is not limited to, a plant cell, a yeast cell, a bacterial cell or an insect cell. Accordingly, in some embodiments, the invention provides a bacterial cell selected from the genera *Bacillus, Brevibacillus, Clostridium, Xenorhabdus, Photorhabdus, Pasteuria, Escherichia, Pseudomonas, Erwinia, Serratia, Klebsiella, Salmonella, Pasteurella, Xanthomonas, Streptomyces, Rhizobium, Rhodopseudomonas, Methylophilius, Agrobacterium, Acetobacter, Lactobacillus, Arthrobacter, Azotobacter, Leuconostoc*, or *Alcaligenes*. Thus, for example, as biological insect control agents, the Cry proteins of the invention can be produced by expression of a chimeric gene encoding the Cry proteins of the invention in a bacterial cell. For example, in some embodiments, a *Bacillus thuringiensis* cell comprising a chimeric gene of the invention is provided.

In further embodiments, the invention provides a transgenic plant cell that is a dicot plant cell or a monocot plant cell. In additional embodiments, the dicot plant cell is selected from the group consisting of a soybean cell, sunflower cell, tomato cell, cole crop cell, cotton cell, sugar beet cell and tobacco cell. In further embodiments, the monocot cell is selected from the group consisting of a barley cell, maize cell, oat cell, rice cell, sorghum cell, sugar cane cell and wheat cell. In some embodiments, the invention provides a plurality of dicot cells or monocot cells expressing a Cry protein of the invention that is encoded by a chimeric gene of the invention. In other embodiments the plurality of cells are juxtaposed to form an apoplast and are grown in natural sunlight.

In other embodiments of the invention, an insecticidal Cry protein of the invention is expressed in a higher organism, for example, a plant. In this case, transgenic plants expressing effective amounts of the insecticidal protein protect themselves from plant pests such as insect pests. When an insect starts feeding on such a transgenic plant, it ingests the expressed insecticidal Cry protein. This can deter the insect from further biting into the plant tissue or may even harm or kill the insect. A polynucleotide of the invention is inserted into an expression cassette, which is then stably integrated in the genome of the plant. In other embodiments, the polynucleotide is included in a non-pathogenic self-replicating virus. Plants transformed in accordance with the invention may be monocots or dicots and include, but are not limited to, corn (maize), soybean, rice, wheat, barley, rye, oats, sorghum, millet, sunflower, safflower, sugar beet, cotton, sugarcane, oilseed rape, alfalfa, tobacco, peanuts, vegetables, including, sweet potato, bean, pea, chicory, lettuce, cabbage, cauliflower, broccoli, turnip, carrot, eggplant, cucumber, radish, spinach, potato, tomato, asparagus, onion, garlic, melons, pepper, celery, squash, pumpkin, zucchini, fruits, including, apple, pear, quince, plum, cherry, peach, nectarine, apricot, strawberry, grape, raspberry, blackberry, pineapple, avocado, *papaya*, mango, banana, and specialty plants, such as *Arabidopsis*, and woody plants such as coniferous and deciduous trees. Preferably, plants of the of the invention are crop plants such as maize, sorghum, wheat, sunflower, tomato, crucifers, peppers, potato, cotton, rice, soybean, sugar beet, sugarcane, tobacco, barley, oilseed rape, and the like.

Once a desired polynucleotide has been transformed into a particular plant species, it may be propagated in that species or moved into other varieties of the same species, particularly including commercial varieties, using traditional breeding techniques.

A polynucleotide of the invention is expressed in transgenic plants, thus causing the biosynthesis of the corresponding Cry protein, either in protoxin or mature toxin form, in the transgenic plants. In this way, transgenic plants with enhanced yield protection in the presence of insect pressure are generated. For their expression in transgenic plants, the nucleotide sequences of the invention may require modification and optimization. Although in many cases genes from microbial organisms can be expressed in plants at high levels without modification, low expression in transgenic plants may result from microbial nucleotide sequences having codons that are not preferred in plants. It is known in the art that living organisms have specific preferences for codon usage, and the codons of the nucleotide sequences described in this invention can be changed to conform with plant preferences, while maintaining the amino acids encoded thereby. Furthermore, high expression in plants, for example corn plants, is best achieved from coding sequences that have at least about 35% GC content, or at least about 45%, or at least about 50%, or at least about 60%. Microbial nucleotide sequences that have low GC contents may express poorly in plants due to the existence of ATTTA motifs that may destabilize messages, and AATAAA motifs that may cause inappropriate polyadenylation. Although certain gene sequences may be adequately expressed in both monocotyledonous and dicotyledonous plant species, sequences can be modified to account for the specific codon preferences and GC content preferences of monocotyledons or dicotyledons as these preferences have been shown to differ (Murray et al. Nucl. Acids Res. 17:477-498 (1989)). In addition, the nucleotide sequences are screened for the existence of illegitimate splice sites that may cause message truncation. All changes required to be made within the nucleotide sequences such as those described above are made using well known techniques of site directed mutagenesis, PCR, and synthetic gene construction using the methods described for example in U.S. Pat. Nos. 5,625,136; 5,500,365 and 6,013,523.

In some embodiments, the invention provides synthetic coding sequences or polynucleotide made according to the procedure disclosed in U.S. Pat. No. 5,625,136, herein incorporated by reference. In this procedure, maize preferred codons, i.e., the single codon that most frequently encodes that amino acid in maize, are used. The maize preferred codon for a particular amino acid can be derived, for example, from known gene sequences from maize. For example, maize codon usage for 28 genes from maize plants is found in Murray et al., Nucleic Acids Research 17:477-498 (1989), the disclosure of which is incorporated herein by reference. Specifically exemplified synthetic sequences of the present invention made with maize optimized codons are represented by any one of SEQ ID NOs: 17-22. It is recognized that codons optimized for expression in one plant species will also function in other plant species but possibly not at the same level as the plant species for which the codons were optimized. In this manner, the nucleotide sequences can be optimized for expression in any plant. It is recognized that all or any part of a nucleotide sequence may be optimized or synthetic. That is, a polynucleotide may comprise a nucleotide sequence that is part native sequence and part codon optimized sequence.

For efficient initiation of translation, sequences adjacent to the initiating methionine may require modification. For example, they can be modified by the inclusion of sequences known to be effective in plants. Joshi has suggested an appropriate consensus for plants (NAR 15:6643-6653 (1987)) and Clonetech suggests a further consensus translation initiator (1993/1994 catalog, page 210). These consensuses are suitable for use with the nucleotide sequences of this invention. The sequences are incorporated into constructions comprising the nucleotide sequences, up to and including the ATG (while leaving the second amino acid unmodified), or alternatively up to and including the GTC subsequent to the ATG (with the possibility of modifying the second amino acid of the transgene).

The novel Cry protein coding sequences of the invention, either as their native sequence or as synthetic sequences as described above, can be operably fused to a variety of promoters for expression in plants including constitutive, inducible, temporally regulated, developmentally regulated, chemically regulated, tissue-preferred and tissue-specific promoters to prepare recombinant DNA molecules, i.e., chimeric genes. The choice of promoter will vary depending on the temporal and spatial requirements for expression, and also depending on the target species. Thus, expression of the nucleotide sequences of this invention in leaves, in stalks or stems, in ears, in inflorescences (e.g. spikes, panicles, cobs, etc.), in roots, or seedlings is preferred. In many cases, however, protection against more than one type of insect pest is sought, and thus expression in multiple tissues is desirable. Although many promoters from dicotyledons have been shown to be operational in monocotyledons and vice versa, ideally dicotyledonous promoters are selected for expression in dicotyledons, and monocotyledonous promoters for expression in monocotyledons. However, there is no restriction to the provenance of selected promoters; it is sufficient that they are operational in driving the expression of the nucleotide sequences in the desired cell.

Suitable constitutive promoters include, for example, CaMV 35S promoter (Odell et al., Nature 313:810-812, 1985); *Arabidopsis* At6669 promoter (see PCT Publication No. W004081173A2); maize Ubi 1 (Christensen et al., Plant Mol. Biol. 18:675-689, 1992); rice actin (McElroy et al., Plant Cell 2:163-171, 1990); pEMU (Last et al., Theor. Appl. Genet. 81:581-588, 1991); CaMV 19S (Nilsson et al., Physiol. Plant 100:456-462, 1997); GOS2 (de Pater et al., Plant J November; 2(6):837-44, 1992); ubiquitin (Christensen et al., Plant Mol. Biol. 18: 675-689, 1992); Rice cyclophilin (Bucholz et al., Plant Mol Biol. 25(5):837-43, 1994); Maize H3 histone (Lepetit et al., Mol. Gen. Genet. 231: 276-285, 1992); Actin 2 (An et al., Plant J. 10(1);107-121, 1996), constitutive root tip CT2 promoter (PCT application No. IL/2005/000627) and Synthetic Super MAS (Ni et al., The Plant Journal 7: 661-76, 1995). Other constitutive promoters include those in U.S. Pat. Nos. 5,659,026, 5,608,149; 5,608,144; 5,604,121; 5,569,597: 5,466,785; 5,399,680; 5,268,463; and 5,608,142.

Tissue-specific or tissue-preferential promoters useful for the expression of the novel cry protein coding sequences of the invention in plants, particularly maize, are those that direct expression in root, pith, leaf or pollen. Suitable tissue-specific promoters include, but not limited to, leaf-specific promoters [such as described, for example, by Yamamoto et al., Plant J. 12:255-265, 1997; Kwon et al., Plant Physiol. 105:357-67, 1994; Yamamoto et al., Plant Cell Physiol. 35:773-778, 1994; Gotor et al., Plant J. 3:509-18, 1993; Orozco et al., Plant Mol. Biol. 23:1129-1138, 1993; and Matsuoka et al., Proc. Natl. Acad. Sci. USA 90:9586-9590, 1993], seed-preferred promoters [e.g., from seed specific genes (Simon, et al., Plant Mol. Biol. 5. 191, 1985; Scofield, et al., J. Biol. Chem. 262: 12202, 1987; Baszczynski, et al., Plant Mol. Biol. 14: 633, 1990), Brazil Nut albumin (Pearson' et al., Plant Mol. Biol. 18: 235-245, 1992), legumin (Ellis, et al. Plant Mol. Biol. 10: 203-214, 1988), Glutelin (rice) (Takaiwa, et al., Mol. Gen. Genet. 208: 15-22, 1986; Takaiwa, et al., FEBS Letts. 221: 43-47, 1987), Zein (Matzke et al., Plant Mol Biol, 143). 323-32 1990), napA (Stalberg, et al., Planta 199: 515-519, 1996), Wheat SPA (Albani et al, Plant Cell, 9: 171-184, 1997), sunflower oleosin (Cummins, et al., Plant Mol. Biol. 19: 873-876, 1992)], endosperm specific promoters [e.g., wheat LMW and UMW, glutenin-1 (Mol Gen Genet 216:81-90, 1989; NAR 17:461-2), wheat a, b and g gliadins (EMB03:1409-15, 1984), Barley ltrl promoter, barley B1, C, D hordein (Theor Appl Gen 98:1253-62, 1999; Plant J 4:343-55, 1993; Mol Gen Genet 250:750-60, 1996), Barley DOF (Mena et al., The Plant Journal, 116(1): 53-62, 1998), Biz2 (EP99106056.7), Synthetic promoter (Vicente-Carbajosa et al., Plant J. 13: 629-640, 1998), rice prolamin NRP33, rice-globulin Glb-1 (Wu et al., Plant Cell Physiology 39(8) 885-889, 1998), rice alpha-globulin REB/OHP-1 (Nakase et al. Plant Mol. Biol. 33: 513-S22, 1997), rice ADP-glucose PP (Trans Res 6:157-68, 1997), maize ESR gene family (Plant J 12:235-46, 1997), sorgum gamma-kafirin (Plant Mol. Biol 32:1029-35, 1996)], embryo specific promoters [e.g., rice OSH1 (Sato et al., Proc. Nati. Acad. Sci. USA, 93: 8117-8122), KNOX (Postma-Haarsma of al, Plant Mol. Biol. 39:257-71, 1999), rice oleosin (Wu et at, J. Biochem., 123:386, 1998)], flower-specific promoters [e.g., AtPRP4, chalene synthase (chsA) (Van der Meer, et al., Plant Mol. Biol. 15, 95-109, 1990), LAT52 (Twell et al., Mol. Gen Genet. 217:240-245; 1989), apetala-3, plant reproductive tissues [e.g., OsMADS promoters (U.S. Patent Application publication No. 2007/0006344)].

The nucleotide sequences of this invention can also be expressed under the regulation of promoters that are chemically regulated. This enables the Cry proteins of the invention to be synthesized only when the crop plants are treated with the inducing chemicals. Examples of such technology for chemical induction of gene expression is detailed in the published application EP 0 332 104 and U.S. Pat. No. 5,614,395. In one embodiment, the chemically regulated promoter is the tobacco PR-la promoter.

Another category of promoters useful in the invention is that which is wound inducible. Numerous promoters have been described which are expressed at wound sites and also at the sites of phytopathogen infection. Ideally, such a promoter should only be active locally at the sites of insect invasion, and in this way the insecticidal proteins only accumulate in cells that need to synthesize the insecticidal proteins to kill the invading insect pest. Examples of promoters of this kind include those described by Stanford et al. Mol. Gen. Genet. 215:200-208 (1989), Xu et al. Plant Molec. Biol. 22:573-588 (1993), Logemann et al. Plant Cell 1:151-158 (1989), Rohrmeier & Lehle, Plant Molec. Biol. 22:783-792 (1993), Firek et al. Plant Molec. Biol. 22:129-142 (1993), and Warner et al. Plant J. 3:191-201 (1993).

Non-limiting examples of promoters that cause tissue specific expression patterns that are useful in the invention include green tissue specific, root specific, stem specific, or flower specific. Promoters suitable for expression in green tissue include many that regulate genes involved in photosynthesis and many of these have been cloned from both monocotyledons and dicotyledons. One such promoter is the maize PEPC promoter from the phosphoenol carboxylase gene (Hudspeth & Grula, Plant Molec. Biol. 12:579-589 (1989)). Another promoter for root specific expression is that described by de Framond (FEBS 290:103-106 (1991) or U.S. Pat. No. 5,466,785). Another promoter useful in the invention is the stem specific promoter described in U.S. Pat. No. 5,625,136, which naturally drives expression of a maize trpA gene.

In addition to the selection of a suitable promoter, constructs for expression of an insecticidal toxin in plants require an appropriate transcription terminator to be operably linked downstream of the heterologous nucleotide sequence. Several such terminators are available and known in the art (e.g. tml from CaMV, E9 from rbcS). Any available terminator known to function in plants can be used in the context of this invention.

Numerous other sequences can be incorporated into expression cassettes described in this invention. These include sequences that have been shown to enhance expression such as intron sequences (e.g. from Adhl and bronzel) and viral leader sequences (e.g. from TMV, MCMV and AMV).

It may be preferable to target expression of the nucleotide sequences of the present invention to different cellular localizations in the plant. In some cases, localization in the cytosol may be desirable, whereas in other cases, localization in some subcellular organelle may be preferred. Any mechanism for targeting gene products, e.g., in plants, can be used to practice this invention, and such mechanisms are known to exist in plants and the sequences controlling the functioning of these mechanisms have been characterized in some detail. Sequences have been characterized which cause the targeting of gene products to other cell compartments Amino terminal sequences can be responsible for targeting a protein of interest to any cell compartment, such as, a vacuole, mitochondrion, peroxisome, protein bodies, endoplasmic reticulum, chloroplast, starch granule, amyloplast, apoplast or cell wall of a plant (e.g. Unger et. al. Plant Molec. Biol. 13: 411-418 (1989); Rogers et. al. (1985) Proc. Natl. Acad. Sci. USA 82: 6512-651; U.S. Pat. No. 7,102,057; WO 2005/096704, all of which are hereby incorporated by reference. Optionally, the signal sequence may be an N-terminal signal sequence from waxy, an N-terminal signal sequence from gamma-zein, a starch binding domain, a C-terminal starch binding domain, a chloroplast targeting sequence, which imports the mature protein to the chloroplast (Comai et. al. (1988) J. Biol. Chem. 263: 15104-15109; van den Broeck, et. al. (1985) Nature 313: 358-363; U.S. Pat. No. 5,639,949) or a secretion signal sequence from aleurone cells (Koehler & Ho, Plant Cell 2: 769-783 (1990)). Additionally, amino terminal sequences in conjunction with carboxy terminal sequences are responsible for vacuolar targeting of gene products (Shinshi et. al. (1990) Plant Molec. Biol. 14: 357-368). In one embodiment, the signal sequence selected includes the known cleavage site, and the fusion constructed takes into account any amino acids after the cleavage site(s), which are required for cleavage. In some cases this requirement may be fulfilled by the addition of a small number of amino acids between the cleavage site and the transgene ATG or, alternatively, replacement of some amino acids within the transgene sequence. These construction techniques are well known in the art and are equally applicable to any cellular compartment.

It will be recognized that the above-described mechanisms for cellular targeting can be utilized not only in conjunction with their cognate promoters, but also in conjunction with heterologous promoters so as to effect a specific cell-targeting goal under the transcriptional regulation of a promoter that has an expression pattern different to that of the promoter from which the targeting signal derives.

Plant Transformation

Procedures for transforming plants are well known and routine in the art and are described throughout the literature. Non-limiting examples of methods for transformation of plants include transformation via bacterial-mediated polynucleotide delivery (e.g., via *Agrobacterium*), viral-mediated polynucleotide delivery, silicon carbide or whisker-mediated polynucleotide delivery, liposome mediated polynucleotide delivery, microinjection, microparticle bombardment, calcium-phosphate-mediated transformation, cyclodextrin-mediated transformation, electroporation, nanoparticle-mediated transformation, sonication, infiltration, PEG-mediated polynculeotide uptake, as well as any other electrical, chemical, physical (mechanical) or biological mechanism that results in the introduction of polynucleotide into the plant cell, including any combination thereof. General guides to various plant transformation methods known in the art include Miki et al. ("Procedures for Introducing Foreign DNA into Plants" in *Methods in Plant Molecular Biology and Biotechnology*, Glick, B. R. and Thompson, J. E., Eds. (CRC Press, Inc., Boca Raton, 1993), pages 67-88) and Rakowoczy-Trojanowska (*Cell. Mol. Biol. Lett.* 7:849-858 (2002)).

For *Agrobacterium*-mediated transformation, binary vectors or vectors carrying at least one T-DNA border sequence are suitable, whereas for direct gene transfer (e.g., particle bombardment and the like) any vector is suitable and linear DNA containing only the construction of interest can be used. In the case of direct gene transfer, transformation with a single DNA species or co-transformation can be used (Schocher et al., *Biotechnology* 4:1093-1096 (1986)). For both direct gene transfer and *Agrobacterium*-mediated transfer, transformation is usually (but not necessarily) undertaken with a selectable marker that may be a positive selection (Phosphomannose Isomerase), provide resistance to an antibiotic (kanamycin, hygromycin or methotrexate) or a herbicide (glyphosate or glufosinate). However, the choice of selectable marker is not critical to the invention.

*Agrobacterium*-mediated transformation is a commonly used method for transforming plants because of its high efficiency of transformation and because of its broad utility with many different species. *Agrobacterium*-mediated transformation typically involves transfer of the binary vector carrying the foreign DNA of interest to an appropriate *Agrobacterium* strain that may depend on the complement of vir genes carried by the host *Agrobacterium* strain either on a co-resident Ti plasmid or chromosomally (Uknes et al. (1993) *Plant Cell* 5:159-169). The transfer of the recombinant binary vector to *Agrobacterium* can be accomplished by a triparental mating procedure using *Escherichia coli* carrying the recombinant binary vector, a helper *E. coli* strain that carries a plasmid that is able to mobilize the recombinant binary vector to the target *Agrobacterium* strain. Alternatively, the recombinant binary vector can be transferred to *Agrobacterium* by polynucleotide transformation (Hagen & Willmitzer (1988) *Nucleic Acids Res.* 16:9877).

Dicots as well as monocots may be transformed using *Agrobacterium*. Methods for *Agrobacterium*-mediated transformation of rice include well known methods for rice transformation, such as those described in any of the following: European patent application EP 1198985 A1, Aldemita and Hodges (Planta 199: 612-617, 1996); Chan et al. (Plant Mol Biol 22 (3): 491-506, 1993), Hiei et al. (Plant J 6 (2): 271-282, 1994), which disclosures are incorporated by reference herein as if fully set forth. In the case of corn transformation, the preferred method is as described in either Ishida et al. (Nat. Biotechnol 14(6): 745-50, 1996) or Frame et al. (Plant Physiol 129(1): 13-22, 2002), which disclosures are incorporated by reference herein as if fully set forth. Said methods are further described by way of example in B. Jenes et al., Techniques for Gene Transfer, in: Transgenic Plants, Vol. 1, Engineering and Utilization, eds. S. D. Kung and R. Wu, Academic Press (1993) 128-143 and in Potrykus Annu. Rev. Plant Physiol. Plant Molec. Biol. 42 (1991) 205-225). The polynucleotides or the construct to be expressed is preferably cloned into a vector, which is suitable for transforming *Agrobacterium tumefaciens*, for example pBin19 (Bevan et al., Nucl. Acids Res. 12 (1984) 8711). Agrobacteria transformed by such a vector can then be used in known manner for the transformation of plants, such as plants used as a model, like *Arabidopsis* or crop plants such as, by way of example, tobacco plants, for example by immersing bruised leaves or chopped leaves in an agrobacterial solution and then culturing them in suitable media. The transformation of plants by means of *Agrobacterium tumefaciens* is described, for example, by Hagen and Willmitzer in Nucl. Acid Res. (1988) 16, 9877 or is known inter alia from F. F. White, Vectors for Gene Transfer in Higher Plants; in Transgenic Plants, Vol. 1, Engineering and Utilization, eds. S. D. Kung and R. Wu, Academic Press, 1993, pp. 15-38.

Transformation of a plant by recombinant *Agrobacterium* usually involves co-cultivation of the *Agrobacterium* with explants from the plant and follows methods well known in the art. Transformed tissue is regenerated on selection medium carrying an antibiotic or herbicide resistance marker between the binary plasmid T-DNA borders.

As discussed previously, another method for transforming plants, plant parts and plant cells involves propelling inert or biologically active particles at plant tissues and cells. See, e.g., U.S. Pat. Nos. 4,945,050; 5,036,006 and 5,100,792. Generally, this method involves propelling inert or biologically active particles at the plant cells under conditions effective to penetrate the outer surface of the cell and afford incorporation within the interior thereof. When inert particles are utilized, the vector can be introduced into the cell by coating the particles with the vector containing the polynucleotide of interest. Alternatively, a cell or cells can be surrounded by the vector so that the vector is carried into the cell by the wake of the particle. Biologically active particles (e.g., a dried yeast cell, a dried bacterium or a bacteriophage, each containing one or more polynucleotides sought to be introduced) also can be propelled into plant tissue.

In other embodiments, a polynucleotide of the invention can be directly transformed into the plastid genome. A major advantage of plastid transformation is that plastids are generally capable of expressing bacterial genes without substantial modification, and plastids are capable of expressing multiple open reading frames under control of a single promoter. Plastid transformation technology is extensively described in U.S. Pat. Nos. 5,451,513, 5,545,817, and 5,545,818, in PCT application no. WO 95/16783, and in McBride et al. (1994) Proc. Nati. Acad. Sci. USA 91, 7301-7305. The basic technique for chloroplast transformation involves introducing regions of cloned plastid DNA flanking a selectable marker together with the gene of interest into a suitable target tissue, e.g., using biolistics or protoplast transformation (e.g., calcium chloride or PEG mediated transformation). The 1 to 1.5 kb flanking regions, termed targeting sequences, facilitate homologous recombination with the plastid genome and thus allow the replacement or modification of specific regions of the plastome. Initially, point mutations in the chloroplast 16S rRNA and rps12 genes conferring resistance to spectinomycin or streptomycin can be utilized as selectable markers for transformation (Svab, Z., Hajdukiewicz, P., and Maliga, P. (1990) *Proc. Natl. Acad. Sci. USA* 87, 8526-8530; Staub, J. M., and Maliga, P. (1992) *Plant Cell* 4, 39-45). The presence of cloning sites between these markers allows creation of a plastid targeting vector for introduction of foreign genes (Staub, J. M., and Maliga, P. (1993) *EMBO J.* 12, 601-606). Substantial increases in transformation frequency can be obtained by replacement of the recessive rRNA or r-protein antibiotic resistance genes with a dominant selectable marker, the bacterial aadA gene encoding the spectinomycin-detoxifying enzyme aminoglycoside-3'-adenyltransferase (Svab, Z., and Maliga, P. (1993) *Proc. Natl. Acad. Sci. USA* 90, 913-917). Previously, this marker had been used successfully for high-frequency transformation of the plastid genome of the green alga *Chlamydomonas reinhardtii* (Goldschmidt-Clermont, M. (1991) *Nucl. Acids Res.* 19:4083-4089). Other selectable markers useful for plastid transformation are known in the art and encompassed within the scope of the invention. Typically, approximately 15-20 cell division cycles following transformation are required to reach a homoplastidic state. Plastid expression, in which genes are inserted by homologous recombination into all of the several thousand copies of the circular plastid genome present in each plant cell, takes advantage of the enormous copy number advantage over nuclear-expressed genes to permit expression levels that can readily exceed 10% of the total soluble plant protein. In one embodiment, a polynucleotide of the invention can be inserted into a plastid-targeting vector and transformed into the plastid genome of a desired plant host. Thus, plants homoplastic for plastid genomes containing a nucleotide sequence of the invention can be obtained, which are capable of high expression of the polynucleotide.

Methods of selecting for transformed, transgenic plants, plant cells or plant tissue culture are routine in the art and can be employed in the methods of the invention provided herein. For example, a recombinant vector of the invention also can include an expression cassette comprising a nucleotide sequence for a selectable marker, which can be used to select a transformed plant, plant part or plant cell. As used herein, "selectable marker" means a nucleotide sequence that when expressed imparts a distinct phenotype to the plant, plant part or plant cell expressing the marker and thus allows such transformed plants, plant parts or plant cells to be distinguished from those that do not have the marker. Such a nucleotide sequence may encode either a selectable or screenable marker, depending on whether the marker confers a trait that can be selected for by chemical means, such as by using a selective agent (e.g., an antibiotic, herbicide, or the like), or on whether the marker is simply a trait that one can identify through observation or testing, such as by screening (e.g., the R-locus trait). Of course, many examples of suitable selectable markers are known in the art and can be used in the expression cassettes described herein.

Examples of selectable markers include, but are not limited to, a nucleotide sequence encoding neo or nptII, which confers resistance to kanamycin, G418, and the like (Potrykus et al. (1985) *Mol. Gen. Genet.* 199:183-188); a nucleotide sequence encoding bar, which confers resistance to phosphinothricin; a nucleotide sequence encoding an altered 5-enolpyruvylshikimate-3-phosphate (EPSP) synthase, which confers resistance to glyphosate (Hinchee et al. (1988) *Biotech.* 6:915-922); a nucleotide sequence encoding a nitrilase such as bxn from *Klebsiella ozaenae* that confers resistance to bromoxynil (Stalker et al. (1988) *Science* 242:419-423); a nucleotide sequence encoding an altered acetolactate synthase (ALS) that confers resistance to imidazolinone, sulfonylurea or other ALS-inhibiting chemicals (EP Patent Application No. 154204); a nucleotide sequence encoding a methotrexate-resistant dihydrofolate reductase (DHFR) (Thillet et al. (1988) *J. Biol. Chem.* 263:12500-12508); a nucleotide sequence encoding a dalapon dehalogenase that confers resistance to dalapon; a nucleotide sequence encoding a mannose-6-phosphate isomerase (also referred to as phosphomannose isomerase (PMI)) that confers an ability to metabolize mannose (U.S. Pat. Nos. 5,767,378 and 5,994,629); a nucleotide sequence encoding an altered anthranilate synthase that confers resistance to 5-methyl tryptophan; or a nucleotide sequence encoding hph that confers resistance to hygromycin. One of skill in the art is capable of choosing a suitable selectable marker for use in an expression cassette of this invention.

Additional selectable markers include, but are not limited to, a nucleotide sequence encoding β-glucuronidase or uidA (GUS) that encodes an enzyme for which various chromogenic substrates are known; an R-locus nucleotide sequence that encodes a product that regulates the production of anthocyanin pigments (red color) in plant tissues (Dellaporta et al., "Molecular cloning of the maize R-nj allele by transposon-tagging with Ac" 263-282 In: *Chromosome Structure and Function: Impact of New Concepts,* 18th Stadler Genetics Symposium (Gustafson & Appels eds., Plenum Press 1988)); a nucleotide sequence encoding β-lactamase, an enzyme for which various chromogenic substrates are known (e.g., PADAC, a chromogenic cephalosporin) (Sutcliffe (1978) *Proc. Natl. Acad. Sci. USA* 75:3737-3741); a nucleotide sequence encoding xylE that encodes a catechol dioxygenase (Zukowsky et al. (1983) *Proc. Natl. Acad. Sci. USA* 80:1101-1105); a nucleotide sequence encoding tyrosinase, an enzyme capable of oxidizing tyrosine to DOPA and dopaquinone, which in turn condenses to form melanin (Katz et al. (1983) *J. Gen. Microbiol.* 129:2703-2714); a nucleotide sequence encoding β-galactosidase, an enzyme for which there are chromogenic substrates; a nucleotide sequence encoding luciferase (lux) that allows for bioluminescence detection (Ow et al. (1986) *Science* 234:856-859); a nucleotide sequence encoding aequorin which may be employed in calcium-sensitive bioluminescence detection (Prasher et al. (1985) *Biochem. Biophys. Res. Comm.* 126:1259-1268); or a nucleotide sequence encoding green fluorescent protein (Niedz et al. (1995) *Plant Cell Reports* 14:403-406). One of skill in the art is capable of choosing a suitable selectable marker for use in an expression cassette of this invention.

Further, as is well known in the art, intact transgenic plants can be regenerated from transformed plant cells, plant tissue culture or cultured protoplasts using any of a variety of known techniques. Plant regeneration from plant cells, plant tissue culture or cultured protoplasts is described, for example, in Evans et al. (*Handbook of Plant Cell Cultures*, Vol. 1, Macmillan Publishing Co. New York (1983)); and Vasil I. R. (ed.) (*Cell Culture and Somatic Cell Genetics of Plants*, Acad. Press, Orlando, Vol. I (1984), and Vol. II (1986)).

Additionally, the genetic properties engineered into the transgenic seeds and plants, plant parts, or plant cells of the invention described above can be passed on by sexual reproduction or vegetative growth and therefore can be maintained and propagated in progeny plants. Generally, maintenance and propagation make use of known agricultural methods developed to fit specific purposes such as harvesting, sowing or tilling.

A polynucleotide therefore can be introduced into the plant, plant part or plant cell in any number of ways that are well known in the art, as described above. Therefore, no particular method for introducing one or more polynucleotides into a plant is relied upon, rather any method that allows the one or more polynucleotides to be stably integrated into the genome of the plant can be used. Where more than one polynucleotide is to be introduced, the respective polynucleotides can be assembled as a single polynucleotide, or as separate polynucleotides, and can be located on the same or different expression cassettes or vectors. Accordingly, the polynucleotides can be introduced into the cell of interest in a single transformation event, in separate transformation events, or, for example, in plants, as part of a breeding protocol.

Additional embodiments of the invention encompasses harvested products produced from the transgenic plants or parts thereof comprising a Cry protein-encoding polynucleotide of the invention, as well as a processed product produced from the harvested products. A harvested product can be a whole plant or any plant part, as described herein. Thus, in some embodiments, non-limiting examples of a harvested product include a seed, a fruit, a flower or part thereof (e.g., an anther, a stigma, and the like), a leaf, a stem, and the like. In other embodiments, a processed product includes, but is not limited to, flour, meal, oil, starch, cereal, and the like produced from a harvested seed or other plant part of the invention, wherein the seed or other plant part comprises a polynucleotide or nucleotide sequence of the invention. In some embodiments, the invention encompasses harvested products and processed products, such as meal or flour that comprise a Cry protein of the invention, where the Cry protein continues to perform the insecticidal function it had in the transgenic plant from which the harvested product or processed product was derived.

In other embodiments, the invention provides an extract from a transgenic seed or a transgenic plant of the invention, wherein the extract comprises a polynucleotide or a Cry protein of the invention. Extracts from plants or plant parts can be made according to procedures well known in the art (See, de la Torre et al., *Food, Agric. Environ.* 2(1):84-89 (2004); Guidet, *Nucleic Acids Res.* 22(9): 1772-1773 (1994); Lipton et al., *Food Agric. Immun.* 12:153-164 (2000)).

Insecticidal Compositions

In some embodiments, the invention provides an insecticidal composition comprising a Cry protein of the invention in an agriculturally acceptable carrier. As used herein an "agriculturally-acceptable carrier" can include natural or synthetic, organic or inorganic material which is combined with the active Cry protein to facilitate its application to or in the plant, or part thereof. Examples of agriculturally acceptable carriers include, without limitation, powders, dusts, pellets, granules, sprays, emulsions, colloids, and solutions. Agriculturally-acceptable carriers further include, but are not limited to, inert components, dispersants, surfactants, adjuvants, tackifiers, stickers, binders, or combinations thereof, that can be used in agricultural formulations. Such compositions can be applied in any manner that brings the pesticidal proteins or other pest control agents in contact with the pests. Accordingly, the compositions can be applied to the surfaces of plants or plant parts, including seeds, leaves, flowers, stems, tubers, roots, and the like. In other embodiments, a plant producing a Cry protein of the invention in planta is an agricultural-carrier of the expressed Cry protein.

In further embodiments, the insecticidal composition comprises a bacterial cell or a transgenic bacterial cell of the invention, wherein the bacterial cell or transgenic bacterial cell produces a Cry protein of the invention. Such an insecticidal composition can be prepared by desiccation, lyophilization, homogenization, extraction, filtration, centrifugation, sedimentation, or concentration of a culture of *Bacillus thuringiensis* (Bt). Such Bt cultures can be selected from the group of Bt strains consisting of SC0532, SC0705, SC0666 described below in the Examples or transgenic Bt cultures. In additional embodiments, the composition comprises from about 1% to about 99% by weight of the Cry protein of the invention.

The Cry proteins of the invention can be used in combination with other pest control agents to increase pest target range or for the prevention or management of insect resistance. Therefore, in some embodiments, the invention provides a composition that controls one or more plant pests, wherein the composition comprises a first Cry protein of the invention and a second pest control agent different from the first Cry protein. In other embodiments, the composition is a formulation for topical application to a plant. In still other embodiments, the composition is a transgenic plant. In further embodiments, the composition is a combination of a formulation topically applied to a transgenic plant. In some embodiments, the formulation comprises the first Cry protein of the invention when the transgenic plant comprises the second pest control agent. In other embodiments, the formulation comprises the second pest control agent when the transgenic plant comprises the first Cry protein of the invention.

In some embodiments, the second pest control agent can be an agent selected from the group consisting of a chemical pesticide, such as an insecticide, a *Bacillus thuringiensis* (Bt) insecticidal protein, a Xenorhabdus insecticidal protein, a *Photorhabdus* insecticidal protein, a *Brevibacillus laterosporus* insecticidal protein, a *Bacillus sphaericus* insecticidal protein, a protease inhibitors (both serine and cysteine types), lectins, alpha-amylase, peroxidase, cholesterol oxidase and a double stranded RNA (dsRNA) molecule.

In other embodiments, the second pest control agent is a chemical pesticide selected from the group consisting of pyrethroids, carbamates, neonicotinoids, neuronal sodium channel blockers, insecticidal macrocyclic lactones, gamma-aminobutyric acid (GABA) antagonists, insecticidal ureas and juvenile hormone mimics. In other embodiments, the chemical pesticide is selected from the group consisting of abamectin, acephate, acetamiprid, amidoflumet (S-1955), avermectin, azadirachtin, azinphos-methyl, bifenthrin, binfenazate, buprofezin, carbofuran, chlorfenapyr, chlorfluazuron, chlorpyrifos, chlorpyrifos-methyl, chromafenozide, clothianidin, cyfluthrin, beta-cyfluthrin, cyhalothrin, lambda-cyhalothrin, cypermethrin, cyromazine, deltamethrin, diafenthiuron, diazinon, diflubenzuron, dimethoate, diofenolan, emamectin, endosulfan, esfenvalerate, ethiprole, fenothicarb, fenoxycarb, fenpropathrin, fenproximate, fenvalerate, fipronil, flonicamid, flucythrinate, tau-fluvalinate, flufenerim (UR-50701), flufenoxuron, fonophos, halofenozide, hexaflumuron, imidacloprid, indoxacarb, isofenphos, lufenuron, malathion, metaldehyde, methamidophos, methidathion, methomyl, methoprene, methoxychlor, monocrotophos, methoxyfenozide, nithiazin, novaluron, noviflumuron (XDE-007), oxamyl, parathion, parathion-methyl, permethrin, phorate, phosalone, phosmet, phosphamidon, pirimicarb, profenofos, pymetrozine, pyridalyl, pyriproxyfen, rotenone, spinosad, spiromesifin (BSN 2060), sulprofos, tebufenozide, teflubenzuron, tefluthrin, terbufos, tetrachlorvinphos, thiacloprid, thiamethoxam, thiodicarb, thiosultap-sodium, tralomethrin, trichlorfon and triflumuron, aldicarb, oxamyl, fenamiphos, amitraz, chinomethionat, chlorobenzilate, cyhexatin, dicofol, dienochlor, etoxazole, fenazaquin, fenbutatin oxide, fenpropathrin, fenpyroximate, hexythiazox, propargite, pyridaben and tebufenpyrad. In still other embodiments, the chemical pesticide is selected from the group consisting of cypermethrin, cyhalothrin, cyfluthrin and beta-cyfluthrin, esfenvalerate, fenvalerate, tralomethrin, fenothicarb, methomyl, oxamyl, thiodicarb, clothianidin, imidacloprid, thiacloprid, indoxacarb, spinosad, abamectin, avermectin, emamectin, endosulfan, ethiprole, fipronil, flufenoxuron, triflumuron, diofenolan, pyriproxyfen, pymetrozine and amitraz.

In additional embodiments, the second pest control agent can be one or more of any number of *Bacillus thuringiensis* insecticidal proteins including but not limited to a Cry protein, a vegetative insecticidal protein (VIP) and insecticidal chimeras of any of the preceding insecticidal proteins. In other embodiments, the second pest control agent is a Cry protein selected from the group consisting of Cry1Aa, Cry1Ab, Cry1Ac, Cry1Ad, Cry1Ae, Cry1Af, Cry1Ag, Cry1Ah, Cry1Ai, Cry1Aj, Cry1Ba, Cry1Bb, Cry1Bc, Cry1Bd, Cry1Be, Cry1Bf, Cry1Bg, Cry1Bh, Cry1Bi, Cry1Ca, Cry1Cb, Cry1Da, Cry1db, Cry1Dc, Cry1Dd, Cry1Ea, Cry1Eb, Cry1Fa, Cry1Fb, Cry1Ga, Cry1Gb, Cry1Gc, Cry1Ha, Cry1Hb, Cry1Hc, Cry1Ia, Cry1Ib, Cry1Ic, Cry1Id, Cry1Ie, Cry1If, Cry1Ig, Cry1Ja, Cry1Jb, Cry1Jc, Cry1Jd, Cry1Ka, Cry1La, Cry1Ma, Cry1Na, Cry1Nb, Cry2Aa, Cry2Ab, Cry2Ac, Cry2Ad, Cry2Ae, Cry2Af, Cry2Ag, Cry2Ah, Cry2Ai, Cry2Aj, Cry2Ak, Cry2A1, Cry2Ba, Cry3Aa, Cry3Ba, Cry3Bb, Cry3Ca, Cry4Aa, Cry4Ba, Cry4Ca, Cry4Cb, Cry4Cc, Cry5Aa, Cry5Ab, Cry5Ac, Cry5Ad, Cry5Ba, Cry5Ca, Cry5 Da, Cry5Ea, Cry6Aa, Cry6Ba, Cry7Aa, Cry7Ab, Cry7Ac, Cry7Ba, Cry7Bb, Cry7Ca, Cry7Cb, Cry7 Da, Cry7Ea, Cry7Fa, Cry7Fb, Cry7Ga, Cry7Gb, Cry7Gc, Cry7Gd, Cry7Ha, Cry7Ia, Cry7Ja, Cry7Ka, Cry7Kb, Cry7La, Cry8Aa, Cry8Ab, Cry8Ac, Cry8Ad, Cry8Ba, Cry8Bb, Cry8Bc, Cry8Ca, Cry8 Da, Cry8db, Cry8Ea, Cry8Fa, Cry8Ga, Cry8Ha, Cry8Ia, Cry8Ib, Cry8Ja, Cry8Ka, Cry8Kb, Cry8La, Cry8Ma, Cry8Na, Cry8 Pa, Cry8Qa, Cry8Ra, Cry8Sa, Cry8Ta, Cry9Aa, Cry9Ba, Cry9Bb, Cry9Ca, Cry9 Da, Cry9db, Cry9Dc, Cry9Ea, Cry9Eb, Cry9Ec, Cry9Ed, Cry9Ee, Cry9Fa, Cry9Ga, Cry10Aa, Cry11Aa, Cry11Ba, Cry11Bb, Cry12Aa, Cry13Aa, Cry14Aa, Cry14Ab, Cry15Aa, Cry16Aa, Cry17Aa, Cry18Aa, Cry18Ba, Cry18Ca, Cry19Aa, Cry19Ba, Cry19Ca, Cry20Aa, Cry20Ba, Cry21Aa, Cry21Ba, Cry21Ca, Cry21 Da, Cry21Ea, Cry21Fa, Cry21Ga, Cry21Ha, Cry22Aa, Cry22Ab, Cry22Ba, Cry22Bb, Cry23Aa, Cry24Aa, Cry24Ba, Cry24Ca, Cry25Aa, Cry26Aa, Cry27Aa, Cry28Aa, Cry29Aa, Cry29Ba, Cry30Aa, Cry30Ba, Cry30Ca, Cry30 Da, Cry30db, Cry30Ea, Cry30Fa, Cry30Ga, Cry31Aa, Cry31Ab, Cry31Ac, Cry31Ad, Cry32Aa, Cry32Ab, Cry32Ba, Cry32Ca, Cry32Cb, Cry32 Da, Cry32Ea, Cry32Eb, Cry32Fa, Cry32Ga, Cry32Ha, Cry32Hb, Cry32Ia, Cry32Ja, Cry32Ka, Cry32La, Cry32Ma, Cry32 Mb, Cry32Na, Cry320a, Cry32 Pa, Cry32Qa, Cry32Ra, Cry32Sa, Cry32Ta, Cry32Ua, Cry33Aa, Cry34Aa, Cry34Ab, Cry34Ac, Cry34Ba, Cry35Aa, Cry35Ab, Cry35Ac, Cry35Ba, Cry36Aa, Cry37Aa, Cry38Aa, Cry39Aa, Cry40Aa, Cry40Ba, Cry40Ca, Cry40 Da, Cry41Aa, Cry41Ab, Cry41Ba, Cry42Aa, Cry43Aa, Cry43Ba, Cry43Ca, Cry43Cb, Cry43Cc, Cry44Aa, Cry45Aa, Cry46Aa Cry46Ab, Cry47Aa, Cry48Aa, Cry48Ab, Cry49Aa, Cry49Ab, Cry50Aa, Cry50Ba, Cry51Aa, Cry52Aa, Cry52Ba, Cry53Aa, Cry53Ab, Cry54Aa, Cry54Ab, Cry54Ba, Cry55Aa, Cry56Aa, Cry57Aa, Cry57Ab, Cry58Aa, Cry59Aa, Cry59Ba, Cry60Aa, Cry60Ba, Cry61Aa, Cry62Aa, Cry63Aa, Cry64Aa, Cry65Aa, Cry66Aa, Cry67Aa, Cry68Aa, Cry69Aa, Cry69Ab, Cry70Aa, Cry70Ba, Cry70Bb, Cry71Aa, Cry72Aa and Cry73Aa.

In further embodiments, the second pest control agent is a Vip3 vegetative insecticidal protein selected from the group consisting of Vip3Aa1, Vip3Aa2, Vip3Aa3, Vip3Aa4, Vip3Aa5, Vip3Aa6, Vip3Aa7, Vip3Aa8, Vip3Aa9, Vip3Aa10, Vip3Aa11, Vip3Aa12, Vip3Aa13, Vip3Aa14, Vip3Aa15, Vip3Aa16, Vip3Aa17, Vip3Aa18, Vip3Aa19, Vip3Aa20, Vip3Aa21, Vip3Aa22, Vip3Aa2, Vip3Aa24, Vip3Aa25, Vip3Aa26, Vip3Aa27, Vip3Aa28, Vip3Aa29, Vip3Aa30, Vip3Aa31, Vip3Aa32, Vip3Aa33, Vip3Aa34, Vip3Aa35, Vip3Aa36, Vip3Aa37, Vip3Aa38, Vip3Aa39, Vip3Aa40, Vip3Aa41, Vip3Aa42, Vip3Aa43, Vip3Aa44, Vip3Ab1, Vip3Ab2, Vip3Ac1, Vip3Ad1, Vip3Ad2, Vip3Ae1, Vip3Af1, Vip3Af2, Vip3Af3, Vip3Ag1, Vip3Ag2, Vip3Ag3 HM117633, Vip3Ag4, Vip3Ag5, Vip3Ah1, Vip3Ba1, Vip3Ba2, Vip3Bb1, Vip3Bb2 and Vip3Bb3.

In still further embodiments, the first Cry protein of the invention and the second pest control agent are co-expressed in a transgenic plant. This co-expression of more than one pesticidal principle in the same transgenic plant can be achieved by genetically engineering a plant to contain and express all the genes necessary. Alternatively, a plant, Parent 1, can be genetically engineered for the expression of the Cry protein of the invention. A second plant, Parent 2, can be genetically engineered for the expression of a second pest control agent. By crossing Parent 1 with Parent 2, progeny plants are obtained which express all the genes introduced into Parents 1 and 2.

In other embodiments, the invention provides a stacked transgenic plant resistant to plant pest infestation comprising a DNA sequence encoding a dsRNA for suppression of an essential gene in a target pest and a DNA sequence encoding a Cry protein of the invention exhibiting biological activity against the target pest. It has been reported that dsRNAs are ineffective against certain lepidopteran pests (Rajagopol et al. 2002. J. Biol. Chem. 277:468-494), likely due to the high pH of the midgut which destabilizes the dsRNA. Therefore, in some embodiments where the target pest is a lepidopteran pest, a Cry protein of the invention acts to transiently reduce the midgut pH which serves to stabilize the co-ingested dsRNA rendering the dsRNA effective in silencing the target genes.

In addition to providing compositions, the invention provides methods of producing a Cry protein toxic to a lepidopteran pest. Such a method comprises, culturing a transgenic non-human host cell that comprises a polynucleotide or a chimeric gene or a recombinant vector of the invention under conditions in which the host cell produces a protein toxic to the lepidopteran pest. In some embodiments, the transgenic non-human host cell is a plant cell. In some other embodiments, the plant cell is a maize cell. In other embodiments, the conditions under which the plant cell or maize cell are grown include natural sunlight. In other embodiments, the transgenic non-human host cell is a bacterial cell. In still other embodiments, the transgenic non-human host cell is a yeast cell.

In other embodiments of the method, the lepidopteran pest is selected from the group consisting of European corn borer (*Ostrinia nubilalis*), black cutworm (*Agrotis ipsilon*), fall armyworm (*Spodoptera frugiperda*), corn earworm (*Helicoverpa zea*), sugarcane borer (*Diatraea saccharalis*), velvetbean caterpillar (*Anticarsia gemmatalis*), soybean looper (*Chrysodeixis includes*), southwest corn borer (*Diatraea grandiosella*), western bean cutworm (*Richia albicosta*), tobacco budworm (*Heliothis virescens*), Asian corn borer (*Ostrinia furnacalis*), cotton bollworm (*Helicoverpa armigera*), striped stem borer (*Chilo suppressalis*), pink stem borer (*Sesamia calamistis*), rice leaffolder (*Cnaphalocrocis medinalis*), and any combination thereof.

In further embodiments of the method, the chimeric gene comprises any of SEQ ID NOs:14-29, or a toxin-encoding fragment thereof. In still other embodiments, the produced protein comprises an amino acid sequence of any of SEQ ID NOs: 1-13, or a toxin fragment thereof.

In some embodiments of the method, the chimeric gene comprises a nucleotide sequence that is codon optimized for expression in a plant. In other embodiments, the chimeric gene comprises any of SEQ ID NOs:17-22, or a toxin-encoding fragment thereof. In further embodiments, the produced protein comprises an amino acid sequence of any of SEQ ID NOs:1-6, or a toxin fragment thereof.

In further embodiments, the invention provides a method of producing a pest-resistant (e.g., an insect-resistant) transgenic plant, comprising: introducing into a plant a polynucleotide, a chimeric gene, a recombinant vector, an expression cassette or a polynucleotide of the invention comprising a nucleotide sequence that encodes a Cry protein of the invention, wherein the encoded Cry protein is expressed in the plant, thereby conferring to the plant resistance to at least a lepidopteran insect pest, and producing a pest-resistant transgenic plant. In some embodiments the polynucleotide, chimeric gene, recombinant vector, expression cassette or polynucleotide comprises a nucleotide sequence that encodes any of SEQ ID NOs: 1-13. In other embodiments, the polynucleotide, chimeric gene, recombinant vector, expression cassette or polynucleotide comprises any of SEQ ID NOs:17-22. In still other embodiments, the pest-resistant transgenic plant is resistant to at least European corn borer (*Ostrinia nubilalis*) or black cutworm (*Agrotis ipsilon*) as compared to a control plant lacking the polynucleotide, chimeric gene, recombinant vector, expression cassette or polynucleotide of the invention. In some embodiments, the introducing is achieved by transforming the plant. In other embodiments, the introducing is achieved by crossing a first plant comprising the polynucleotide, chimeric gene, recombinant vector, expression cassette or polynucleotide of the invention with a different second plant resulting in progeny seed and plants having the polynucleotide, chimeric gene, recombinant vector, expression cassette or polynucleotide incorporated into their genome.

In some embodiments, a transgenic plant of the invention that is resistant to at least European corn borer (*Ostrinia nubilalis*) or black cutworm (*Agrotis ipsilon*) is further resistant to at least one additional insect, wherein the additional insect includes, but is not limited to, fall armyworm (*Spodoptera frugiperda*), corn earworm (*Helicoverpa zea*), sugarcane borer (*Diatraea saccharalis*), velvetbean caterpillar (*Anticarsia gemmatalis*), soybean looper (*Chrysodeixis includes*), southwest corn borer (*Diatraea grandiosella*), western bean cutworm (*Richia albicosta*), tobacco budworm (*Heliothis virescens*), Asian corn borer (*Ostrinia furnacalis*), cotton bollworm (*Helicoverpa armigera*), striped stem borer (*Chilo suppressalis*), pink stem borer (*Sesamia calamistis*) or rice leaffolder (*Cnaphalocrocis medinalis*), and any combination thereof.

In further embodiments, a method of controlling at least a lepidopteran insect pest such as European corn borer (*Ostrinia nubilalis*) or black cutworm (*Agrotis ipsilon*) is provided, the method comprising delivering to the insects an effective amount of a Cry protein of the invention. To be effective, the Cry protein is first orally ingested by the insect. However, the Cry protein can be delivered to the insect in many recognized ways. The ways to deliver a protein orally to an insect include, but are not limited to, providing the protein (1) in a transgenic plant, wherein the insect eats (ingests) one or more parts of the transgenic plant, thereby ingesting the polypeptide that is expressed in the transgenic plant; (2) in a formulated protein composition(s) that can be applied to or incorporated into, for example, insect growth media; (3) in a protein composition(s) that can be applied to the surface, for example, sprayed, onto the surface of a plant part, which is then ingested by the insect as the insect eats one or more of the sprayed plant parts; (4) a bait matrix; or (5) any other art-recognized protein delivery system. Thus, any method of oral delivery to an insect can be used to deliver the toxic Cry proteins of the invention. In some particular embodiments, the Cry protein of the invention is delivered orally to an insect, wherein the insect ingests one or more parts of a transgenic plant.

In other embodiments, the Cry protein of the invention is delivered orally to an insect, wherein the insect ingests one or more parts of a plant sprayed with a composition comprising the Cry proteins of the invention. Delivering the compositions of the invention to a plant surface can be done using any method known to those of skill in the art for applying compounds, compositions, formulations and the like to plant surfaces. Some non-limiting examples of delivering to or contacting a plant or part thereof include spraying, dusting, sprinkling, scattering, misting, atomizing, broadcasting, soaking, soil injection, soil incorporation, drenching (e.g., root, soil treatment), dipping, pouring, coating, leaf or stem infiltration, side dressing or seed treatment, and the like, and combinations thereof. These and other procedures for contacting a plant or part thereof with compound(s), composition(s) or formulation(s) are well-known to those of skill in the art.

In some embodiments, the invention encompasses a method of providing a farmer with a means of controlling a lepidopteran pest, the method comprising supplying or selling to the farmer plant material such as a seed, the plant material comprising a polynucleotide, chimeric gene, expression cassette or a recombinant vector capable of expressing a Cry protein of the invention in a plant grown from the seed, as described above.

Embodiments of this invention can be better understood by reference to the following examples. The foregoing and following description of embodiments of the invention and the various embodiments are not intended to limit the claims, but are rather illustrative thereof. Therefore, it will be understood that the claims are not limited to the specific details of these examples. It will be appreciated by those skilled in the art that other embodiments of the invention may be practiced without departing from the spirit and the scope of the disclosure, the scope of which is defined by the appended claims.

EXAMPLES

Example 1. Identification of Bt Strains Containing Novel Cry Proteins

*Bacillus thuringiensis* isolates present in current collections were cultured from spores and maintained on T3+penicillin agar plates. Each isolate was grown aerobically in 24 well deep blocks for about 10 days at 28° C. until sporulation, which was verified by staining with Coomasie blue/acetic acid and visualization with a microscope. After sporulation both the soluble and insoluble fractions were tested for activity against lepidopteran species of interest. Fractions were tested in a surface contamination bioassay, where the fractions were overlaid onto a multispecies artificial diet. Each isolate was screened against at least four lepidopteran species, including *Helicoverpa zea* (corn earworm), *Agrotis ipsilon* (black cutworm), *Ostrinia nubilalis* (European corn borer), and *Spodoptera frugiperda* (fall armyworm) with a sample size of 12 neonate larvae. The duration of each assay was about 7 days at room temperature; the plates were scored for mortality as well as larval growth inhibition. Observed mortality at an increase of 30% over the negative control was considered active. Based on the initial insect testing, three Bt strains, designated SC0532, SC0666 and SC0705, were selected for further analysis.

Example 2. Genome Assembly and Analysis

Bt cry genes of the invention were isolated from the strains identified in Example 1 using a whole genome sequencing approach. Briefly, *Bacillus* DNA was sheared using a Covaris S2 ultrasonic device (Covaris, Inc., Woburn, Mass.) with the program DNA_400 bp set at duty cycle: 10%; intensity: 4; cycles/burst: 200. The DNA was treated with the NEBNext® Ultra™ End Repair/dA-tailing module (New England Biolabs, Inc. Ipswich, Mass.). Bioscience indexes 1-57 adapters (1-27 Brazil, 28-57 USA, UK and Switzerland) were ligated using NEB Quick Ligation™ as described by the supplier (New England Biolabs, Inc. Ipswich, Mass.). Ligations were cleaned up using Agencourt AMPure XP beads as described by the supplier (Beckman Coulter, Inc., Indianapolis, Ind.).

The library was size fractionated as follows: A 50 μl sample was mixed with 45 μl 75% bead mix (25% AMPure beads plus 75% NaCl/PEG solution; TekNova, Inc. Hollister, Calif., USA; cat #P4136). The mix was stirred and placed on a magnetic rack. The resulting supernatant was transferred to a new well and 45 μl 50% bead mix (50% AMPure beads plus 50% NaCl/PEG solution; TekNova cat #P4136) was added. This mix was stirred and placed on a magnetic rack. The resulting supernatant was removed and the beads were washed with 80% ethanol. 25 μl of elution buffer (EB) buffer was added and the mix placed on a magnetic rack. The final resulting supernatant was removed and placed in 1.5 ml tube. This method yielded libraries in the 525 DNA base pairs (bp) (insert plus adapter) size range.

The sized DNA library was amplified using KAPA Biosystem HiFi Hot Start (Kapa Biosystems, Inc., Wilmington, Mass.) using the following cycle conditions: [98° C., 45s]; 12×[98° C., 15s, 60° C., 30s, 72° C., 30s]; [72° C., 1 min]. Each reaction contained: 5 μl DNA library, 1 μl Bioscience universal primer (25 μM), 18 μl sterile water, 1 μl Bioscience indexed primer (25 μM), 25 μl 2X KAPA HiFi polymerase.

Libraries were run on the Agilent 2100 Bioanalyzer (Agilent Technologies, Santa Clara, Calif.) using High Sensitivity chips to determine the library size range and average insert size. All libraries were processed for paired end (PE) sequencing (100 cycles per read; 12-24 libraries per lane) on a HiSeq 2500 sequencing system using standard manufacturer's sequencing protocols (Illumina, Inc., San Diego, Calif.).

A *Bacillus* computational analysis tool developed to identify and characterize Cry-like genes was used for prioritization of leads for further laboratory testing.

The genome assembly and analysis as well as the genomic library analysis described above led to the identification of three Cry1-like genes in the *Bacillus thuringiensis* strains with toxicity to at least European corn borer (*Ostrinia nubilalis*) or corn earworm (*Helicoverpa zea*). Identifying characteristics of the Cry1-like genes and proteins are shown in Table 1.

TABLE 1

Cry genes/proteins identified in *Bacillus thuringiensis* strains.

| Strain | Protein/ Gene Name | Nearest Cry Family Member | Molecular Weight (kD) | Amino Acid SEQ ID NO: | Nucleotide SEQ ID NO: |
|---|---|---|---|---|---|
| SC0532 | BT2Cry1J | Cry1Ja | 132.6 | 1 | 14 |
| SC0705 | BT25Cry1I | Cry1Ig | 79.8 | 2 | 15 |
| SC0666 | BT53Cry1J | Cry1Jc | 133.3 | 3 | 16 |

Example 3. Homology of BT2Cry1J, BT25Cry1I and BT53Cry1J to Known Bt Cry Proteins Comparison of the amino acid sequences of the proteins in Table 1 to the non-redundant (nr) database maintained by the National Center for Biotechnology Information (NCBI)

(world wide web at ncbi.nlm.nih.gov) using the BLAST algorithm revealed that the proteins have the highest identity to Cry proteins, particularly those in the Cry1 family. More specifically, BT2Cry1J has about 98% identity to Cry1Ja proteins, example sequences of which may be found at NCBI under accession numbers AAA22341 (Cry1Ja1), HM070030 (Cry1Ja2) and JQ228425 (Cry1Ja3). BT25Cry1I has about 95% identity to Cry1Ig proteins, an example sequence of which may be found at NCBI under accession number KC156701 (cry1Ig1). BT53Cry1J has about 99% identity to Cry1Jc proteins, examples of which may be found at NCBI under accession numbers AAC31092 (Cry1Jc1) and AAQ52372 (Cry1Jc2).

Example 4. Bt Protein Expression in Recombinant Host Cells

The Cry proteins described in Examples 2 and 3 were expressed in recombinant bacterial host cells via a shuttle vector designated pCIB5634', designed for expression in both *E. coli* and *Bacillus thuringiensis*. Vector pCIB5634' comprises a variant modified Cry1Ac promoter (bp 12-97 of SEQ ID NO:30) that improves expression of the cloned Bt Cry gene and a erythromycin resistance marker over the native Cry1Ac promoter. For example, a BT25Cry1I coding sequence was cloned into the pCIB5634' vector using BamHI and SacI restriction sites resulting in an Cry expression shuttle vector comprising the sequence of SEQ ID NO:30.

*Bacillus* Expression. Expression cassettes comprising the Cry protein coding sequence of interest were transformed into a crystal-minus *Bacillus thuringiensis* (Bt) strain having no observable background insecticidal activity via electroporation and transgenic Bt strains were selected on erythromycin containing agar plates. Selected transgenic Bt strains were grown to the sporulation phase in T3 media at 28° C. for 4-5 days. Cell pellets were harvested and washed iteratively before solubilization of the expressed protein in high pH carbonate buffer (50 mM) containing 2 mM DTT.

*E. coli* Expression. Cry proteins were expressed in *E. coli* strains using pET28a or pET29a vectors (Merck KGaA, Darmstadt, Germany). Constructs were transformed by electroporation and transgenic *E. coli* clones were selected on kanamycin-containing agar plates. Selected transgenic *E. coli* strains were grown and Cry protein expression induced using IPTG induction at 28° C. Cells were resuspended in high pH carbonate buffer (50 mM) containing 2 mM DTT and then broken using a Microfluidics LV-1 homogenizer.

Expression Analysis. Resulting cell lysates from either transgenic Bt or *E. coli* strains were then clarified via centrifugation and samples were analyzed for purity via SDS-PAGE and electropherogram using a BioRad Experion system (Biorad, Hercules, Calif.). Total protein concentrations were determined via Bradford or Thermo 660 assay. Purified Cry proteins were then tested in bioassays described below.

Example 5. Activity of Cry Proteins in Bioassays

The Cry proteins produced in Example 4 were tested against one or more of the following insect pest species using an art-recognized artificial diet bioassay method: fall armyworm (FAW; *Spodoptera frugiperda*), corn earworm (CEW; *Helicoverpa zea*), European corn borer (ECB; *Ostrinia nubilalis*), black cutworm (BCW; *Agrotis ipsilon*), sugarcane borer (SCB; *Diatraea saccharlis*), velvet bean caterpillar (VBC; *Anticarsia gemmatalis*), soybean looper (SBL; *Pseudoplusia includens*), southwest corn borer (SWCB; *Diatraea grandiosella*), western bean cutworm (WBCW; *Striacosta albicosta*), tobacco budworm (TBW; *Heliothis virescens*), Asian corn borer (ACB; *Ostrinia furnacalis*), cotton bollworm (CBW; *Helicoverpa armigera*), striped stem borer (SSB; *Chilo suppressalis*), pink stem borer (PSB; *Sesamia inferens*) or rice leaf folder (RLF; *Cnaphalocrocis medinails*).

An equal amount of protein in solution was applied to the surface of an artificial insect diet (Bioserv, Inc., Frenchtown, N.J.) in 24 well plates. After the diet surface dried, larvae of the insect species being tested were added to each well. The plates were sealed and maintained at ambient laboratory conditions with regard to temperature, lighting and relative humidity. A positive-control group consisted of larvae exposed to a very active and broad-spectrum wild-type *Bacillus* strain. Negative control groups consisted of larvae exposed to insect diet treated with only the buffer solution or empty vector and larvae on untreated insect diet; i.e. diet alone. Mortality was assessed after about 120 hours and scored relative to the controls.

Results are shown in Table 2, where a "–" means no mortality compared to the control group, a "+/–" means 0-10% mortality compared to the control group (this category also includes 0% mortality with strong larval growth inhibition), a "+" means 10-25% activity compared to the control group, a "++" means 26-75% mortality compared to the control group, and a "+++" means 76-100% mortality compared to the control group.

TABLE 2

Results of bioassays with Cry Proteins.

| BT | Insect Species | | | | | | | | |
|---|---|---|---|---|---|---|---|---|---|
| Proteins | FAW | CEW | ECB | BCW | SCB | VBC | SBL | SWCB | TBW |
| BT2Cry1J | +/– | + | +++ | +++ | +++ | +++ | +++ | ++ | +++ |
| BT25Cry1I | – | – | + | – | ++ | – | +/– | +/– | – |
| BT53Cry1J | – | +++ | ++ | +++ | +++ | +++ | +++ | +/– | +++ |

Example 6. Mutagenesis of the BT2Cry1J Protein

The BT2Cry1J protein has 98% identity to the known Cry1Ja proteins, Cry1Ja1 (NCBI Accession No. AAA22341), Cry1Ja2 (NCBI Accession No. HM070030) and Cry1Ja3 (NCBI Accession No. JQ228425). Based on standard Bt Cry protein nomenclature (Crickmore et al. 1998. Microbiol. Molecular Biol. Rev. 62:807-813), BT2Cry1J most likely would be designated a Cry1Ja protein. Given the very high identity between BT2Cry1Ja and Cry1Ja1, having only 24 amino acid differences over 1167 total amino acids, one may expect that the two proteins would have the same spectrum of activity and specificity. Surprisingly, BT2Cry1Ja appears to have a broader spectrum of activity or higher specific activity than the known Cry1Ja proteins. For example, results of some research suggest that Cry1Ja1 has minimal activity against fall armyworm (*Spodoptera frugiperda*), corn earworm (*Helicoverpa zea*) and European corn borer (*Ostrinia nubilalis*) and no activity against black cutworm (*Agrotis ipsilon*) (U.S. Pat. Nos. 5,322,687 and 6,593,293), whereas BT2Cry1Ja has high activity against fall armyworm, corn earworm, European corn borer and black cutworm. Other reports suggest that Cry1Ja1 has some activity against cotton bollworm (*Helicoverpa armigera*), but no activity against diamondback moth or beet armyworm (*Spodoptera exigua*) (Choi et al. 2007. J. Microbiol. Biotechnol. 17:1498-1503). Still other reports suggest that Cry1Ja2 is active against diamondback moth and that Cry1Ja3 is active against Asian corn borer (*Ostrinia furnacalis*) (Hai-Shou et al. 2015. Genetics 11:1145-1451.

Twenty-three of the twenty-four amino acid differences between BT2Cry1J of the invention and Cry1Ja1 are in the region of domain I spanning alpha-helices 3 to 6. The last amino acid difference is in a region in domain II known as Loop alpha-8, which is a region that is believed to be important in insect gut receptor binding. To determine which of the domain I amino acids may be important in modulating the activity of Cry1J proteins, mutations were made in the BT2Cry1J amino acid sequence (SEQ ID NO:1) in three blocks, which essentially correspond to regions spanning alpha-helix 3, alpha-helix 4 and alpha-helices 5&6, respectively. The three mutation blocks were designated: BLK-1 comprising the following amino acid substitutions, A97T, S105N, L108I, G110A, K118S and T119D, which spans alpha-helix 3 and one additional amino acid in the loop between alpha-helices 3 and 4; BLK-2 comprising the following amino acid substitutions, T123E, R126K, T130I, E131D, I136L, A138G, Q139L, V1491 and V1501, which spans alpha-helix 4 and two amino acids in the loop between alpha-helices 4 and 5; and BLK-3 comprising the following amino acid substitutions, L158S, T161V, V176I, T186K, V1961, N197R, R198E and G200H, which spans alpha-helix 5 and a portion of alpha-helix 6. BT2Cry1J proteins comprising combinations of the three mutation blocks were also made resulting in a total of seven modified BT2Cry1J proteins that were tested against target insects Constructs comprising each of the mutation blocks and combinations of the mutation blocks were made by synthesizing approximately 663 bp NcoI-BglII 5' polynucleotide fragments of SEQ ID NO:14 encoding the substituted amino acids in the desired region of the BT2Cry1J amino acid sequence. Each polynucleotide fragment was cloned into a vector comprising the full-length native BT2Cry1J coding sequence cut with NcoI-BglII enzymes. Each fragment then replaced the 5' end of the full-length gene resulting in a modified full-length coding sequence (SEQ ID NOs:23-29) encoding a modified BT2Cry1J protein (SEQ ID NOs:7-13). Each vector was cloned into a crystal-minus *Bacillus thuringiensis* strain as described above.

Modified BT2Cry1J proteins were expressed as described above and tested against three insect pest species in the Family Crambidae, European corn borer (*Ostrinia nubilalis*), sugarcane borer (*Diatraea saccharalis*) and southwest corn borer (*Diatraea grandiosella*), and six insect pest species in the Family Noctuidae, black cutworm (*Agrotis ipsilon*), fall armyworm (*Spodoptera frugiperda*), corn earworm (*Helicoverpa zea*), soybean looper (*Chrysodeixis includens*), velvetbean caterpillar (*Anticarsia gemmatalis*) and tobacco budworm (*Heliothis virescens*). The presence of each modified BT2Cry1J protein was confirmed by Coomassie-stained SDS-PAGE using the Bt cells carrying the empty vector as a negative control. The insecticidal activity, as corrected percent mortality, of the seven modified BT2Cry1J proteins compared to a native BT2Cry1J protein (SEQ ID NO:1) and an empty-vector control are shown in Table 3.

TABLE 3

Insecticidal activity of modified BT2Cry1J proteins.

| Modified Protein or | Corrected Percent Mortality | | | | | | | | |
|---|---|---|---|---|---|---|---|---|---|
| Controls | ECB | SCB | SWCB | BCW | FAW | CEW | SBL | VBC | TBW |
| BT0002Cry1Ja | 83 | 100 | 75 | 75 | 100 | 75 | 100 | 100 | 100 |
| BT21J-BLK-1 | 0 | 0 | 0 | 0 | 0 | 8 | 42 | 0 | 92 |
| BT21J-BLK-2 | 8 | 0 | 0 | 8 | 0 | 8 | 100 | 67 | 42 |
| BT21J-BLK-3 | 75 | 92 | 75 | 92 | 83 | 100 | 100 | 100 | 100 |
| BT21J-BLK-1/2 | 83 | 75 | 75 | 67 | 25 | 42 | 100 | 100 | 92 |
| BT21J-BLK-2/3 | 8 | 8 | 0 | 42 | 83 | 50 | 100 | 100 | 92 |
| BT21J-BLK-1/3 | 0 | 0 | 0 | 0 | 0 | 8 | 0 | 0 | 0 |
| BT21J-BLK-1/2/3 | 83 | 100 | 75 | 92 | 92 | 92 | 100 | 100 | 100 |
| Empty Vector | 0 | 0 | 0 | 0 | 0 | 0 | 0 | 0 | 0 |

Example 7. Vectoring of Genes for Plant Expression

Prior to expression in plants, a synthetic polynucleotide comprising a nucleotide sequence having codons optimized for expression in the plant and encoding a Cry protein of the invention, such as a BT2Cry1J (SEQ ID NO:1 or SEQ ID NO) or a variant sequence (SEQ ID NO:4), BT25Cry1I (SEQ ID NO:2) or a variant sequence (SEQ ID NO:5) or BT53Cry1J (SEQ ID NO:3) or a variant sequence (SEQ ID NO:6), is synthesized by methods known in the art. For this example, a first expression cassette was made comprising a maize ubiquitin promoter (Ubi1) operably linked to a BT53Cry1J synthetic coding sequence (SEQ ID NO:19) which is operably linked to a maize ubiquitin (Ubi361) terminator and a second expression cassette was made comprising a maize ubiquitin 1 (Ubi1) promoter operably linked to a phosphomannose isomerase (PMI) coding sequence which is operably linked to a maize Ubi1 terminator. Expression of PMI allows for positive selection of transgenic plants on mannose. Both expression cassettes were cloned into a binary vector (SEQ ID NO:31) for use in *Agrobacterium*-mediated maize transformation.

Example 8. Expression and Activity of Cry Proteins in Maize Plants

Transformation of immature maize embryos was performed essentially as described in Negrotto et al., 2000, Plant Cell Reports 19: 798 803. Briefly, *Agrobacterium* strain LBA4404 (pSB1) comprising a binary vector described in Example 7 was grown on YEP (yeast extract (5 g/L), peptone (10 g/L), NaCl (5 g/L), 15 g/l agar, pH 6.8) solid medium for 2-4 days at 28° C. Approximately $0.8\times10^9$ *Agrobacterium* cells were suspended in LS-inf media supplemented with 100 μM As. Bacteria were pre-induced in this medium for approximately 30-60 minutes.

Immature embryos from an inbred maize line were excised from about 8-12 day old ears into liquid LS-inf+100 μM As. Embryos were rinsed once with fresh infection medium. *Agrobacterium* solution was then added and embryos were vortexed for about 30 seconds and allowed to settle with the bacteria for 5 minutes. The embryos were then transferred scutellum side up to LSAs medium and cultured in the dark for two to three days. Subsequently, between approximately 20 and 25 embryos per petri plate were transferred to LSDc medium supplemented with cefotaxime (250 mg/1) and silver nitrate (1.6 mg/1) and cultured in the dark at approximately 28° C. for 10 days.

Immature embryos, producing embryogenic callus were transferred to LSD1M0.5S medium. The cultures were selected on this medium for approximately 6 weeks with a subculture step at about 3 weeks. Surviving calli were transferred to Reg1 medium supplemented with mannose. Following culturing in the light (16 hour light/8 hour dark regiment), green tissues were then transferred to Reg2 medium without growth regulators and incubated for about 1-2 weeks. Plantlets were transferred to Magenta GA-7 boxes (Magenta Corp, Chicago Ill.) containing Reg3 medium and grown in the light. After about 2-3 weeks, plants were tested for the presence of the PMI genes and the Bt53cry1J gene by PCR. Positive plants from the PCR assay were transferred to a greenhouse for further evaluation.

Transgenic plants from multiple independent events were evaluated for copy number (determined by Taqman analysis), protein expression level (determined by ELISA), and efficacy against insect pest species of interest in leaf excision bioassays. Specifically, plant tissue was excised from 25 single copy events (V3-V4 stage) and infested with neonate larvae of a target pest, then incubated at room temperature for about 5 days. Leaf disks from transgenic plants expressing the variant BT53Cry1J protein (SEQ ID NO:6) were tested against corn earworm (*Helicoverpa zea*; CEW), black cutworm (*Agrotis ipsilon*; BCW), and sugarcane borer (*Diatraea saccharalis*; SCB).

The expression levels of the BT53Cry1J protein in the 25 transgenic events ranged from about 3 ng/mg TSP to about 11 ng/mg TSP. Results of the plant bioassay confirmed that stably transformed maize plants expressing a BT53Cry1J protein are toxic to one or more lepidopteran insect pests with 15/25 plants having activity against CEW, 7/25 plants having activity against BCW and 11/25 plants having activity against SCB.

Example 9. Mutation of a Cry Protein-Encoding Gene Comprised in a Transgenic Plant The following example illustrates the use of genome editing to incorporate mutations into a gene encoding a Cry1J protein of the invention, including but not limited to SEQ ID NO:1, SEQ ID NO:3, SEQ ID NO:4 and SEQ ID NO:6, comprised in a transgenic maize plant.

Targeted genome modification, also known as genome editing, is useful for introducing mutations in specific DNA sequences. These genome editing technologies, which include zinc finger nucleases (ZNFs), transcription activator-like effector nucleases (TALENS), meganucleases and clustered regularly interspaced short palindromic repeats (CRISPR) have been successfully applied to over 50 different organisms including crop plants. See, e.g., Belhaj, K., et al., Plant Methods 9, 39 (2013); Jiang, W., et al., Nucleic Acids Res, 41, e188 (2013)). The CRISPR/Cas system for genome editing is based on transient expression of Cas9 nuclease and an engineered single guide RNA (sgRNA) that specifies the targeted polynucleotide sequence.

Cas9 is a large monomeric DNA nuclease guided to a DNA target sequence with the aid of a complex of two 20-nucleotide (nt) non-coding RNAs: CRIPSR RNA (crRNA) and trans-activating crRNA (tracrRNA), which are functionally available as single synthetic RNA chimera. The Cas9 protein contains two nuclease domains homologous to RuvC and HNH nucleases. The HNH nuclease domain cleaves the complementary DNA strand whereas the RuvC-like domain cleaves the non-complementary strand and, as a result, a blunt cut is introduced in the target cry1J DNA.

When the Cas9 and the sgRNA are transiently expressed in living maize cells, double strand breaks (DSBs) in the specific targeted cry1J DNA is created in the transgenic maize. Mutation at the break site is introduced through the non-homologous end joining and homology-directed DNA repair pathways.

Specific mutations, for example the BLK1 mutations described above, are introduced into the gene encoding BT2Cry1J or a variant thereof, such as SEQ ID NO:1 or SEQ ID NO:4, through the use of recombinant plasmids expressing the Cas9 nuclease and the sgRNA target that is codon optimized for the cry1J sequence in the transgenic maize. Implementation of the method is by an agroinfiltration method with *Agrobacterium tumufaciens* carrying the binary plasmid harboring the specified target sequence of interest of cry1J After the sgRNA binds to the cry1J coding sequence, the Cas9 nuclease makes specific cuts into the coding sequence and introduces the BLK1 mutations during DNA repair. Thus, the now mutated cry1J gene will encode a modified Cry1J protein, such as SEQ ID NO:7, where a mutation at position 97 replaces Ala (A) with Thr (T); a mutation at position 105 replaces Ser (S) with Asn (N); a mutation at position 108 replaces Leu (L) with Ile (I); a mutation at position 110 replaces Gly (G) with Ala (A); a mutation at position 118 replaces the Lys (K) with Ser (S) and a mutation at position 119 replaces Thr (T) with Asp (D). Plant cells comprising mutated cry1J polynucleotides are screened by PCR and sequencing. Callus that harbor mutations in the cry1J gene are induced to regenerate plants for phenotype evaluation for modulated insecticidal activity of the expressed modified Cry1J protein.

What is claimed is:

1. A chimeric gene comprising a heterologous promoter that functions in a plant or bacteria operably linked to a polynucleotide that encodes a recombinant Cry protein that is toxic to a lepidopteran pest, wherein the recombinant Cry protein comprises an amino acid sequence that has at least 99% sequence identity with the amino acid sequence of SEQ ID NO: 1.

2. The chimeric gene of claim 1, wherein the recombinant Cry protein comprises an amino acid sequence selected from the group consisting of SEQ ID NO:1, SEQ ID NO:4, SEQ ID NO: 9, and a toxin fragment of SEQ ID NO:1, SEQ ID NO:4 or SEQ ID NO: 9.

3. The chimeric gene of claim 1, wherein a) the plant expressible promoter is a ubiquitin, cestrum yellow virus, corn TrpA, OsMADS 6, maize H3 histone, bacteriophage T3 gene 9 5' UTR, corn sucrose synthetase 1, corn alcohol dehydrogenase 1, corn light harvesting complex, corn heat shock protein, maize mtl, pea small subunit RuBP carboxylase, rice actin, rice cyclophilin, Ti plasmid mannopine synthase, Ti plasmid nopaline synthase, petunia chalcone isomerase, bean glycine rich protein 1, potato patatin, lectin, CaMV 35S or a S-E9 small subunit RuBP carboxylase promoter; or b) the bacteria expressible promoter comprises nucleotides 12-197 of SEQ ID NO:30.

4. A transgenic bacterial cell or plant cell comprising the chimeric gene of claim 1.

5. The transgenic plant cell of claim 4, wherein the plant cell is a) a dicot plant cell; or b) a monocot plant cell; or c) a dicot plant cell selected from the group consisting of a soybean cell, sunflower cell, tomato cell, cole crop cell, cotton cell, sugar beet cell and tobacco cell; or d) a monocot plant cell selected from the group consisting of a barley cell, maize cell, oat cell, rice cell, sorghum cell, sugar cane cell and wheat cell.

6. A transgenic plant comprising the transgenic plant cell of claim 5.

7. A transgenic seed of the transgenic plant of claim 6, wherein the transgenic seed comprises the polynucleotide.

8. A harvested product derived from the transgenic plant of claim 6, wherein the harvested product comprises the recombinant Cry protein.

9. A processed product derived from the harvested product of claim 8, wherein the processed product is selected from the group consisting of flour, meal, oil, and starch, or a product derived therefrom, and wherein the processed product comprises the recombinant Cry protein.

10. A method of producing a Cry protein that is toxic to a lepidopteran pest, the method comprising: culturing the transgenic cell of claim 4 under conditions in which the transgenic cell produces the recombinant Cry protein.

11. A method of producing an insect-resistant transgenic plant, the method comprising: introducing into a plant the chimeric gene of claim 1, wherein the recombinant Cry protein is expressed in the plant, thereby producing an insect-resistant transgenic plant.

12. The method of claim 11, wherein the introducing step is achieved by a) transforming the plant with the chimeric gene; or b) crossing a first plant comprising the chimeric gene with a different second plant; or c) genome editing a chimeric gene preexisting in a transgenic plant.

13. A method of controlling a lepidopteran pest, the method comprising delivering to the lepidopteran pest the transgenic plant of claim 6, wherein the lepidopteran pests ingests the recombinant Cry protein in the transgenic plant.

* * * * *